US012747296B2

(12) United States Patent
Lan et al.

(10) Patent No.: US 12,747,296 B2
(45) Date of Patent: Sep. 29, 2026

(54) ANTI-CCR8 ANTIBODIES FOR TREATING CANCER

(71) Applicant: BRISTOL-MYERS SQUIBB COMPANY, Princeton, NJ (US)

(72) Inventors: Ruth Yin-Zong Lan, Fremont, CA (US); Olufemi A. Adelakun, Kendall Park, NJ (US); Ishita Barman, Millbrae, CA (US); Joseph Richard Campbell, Stanford, CA (US); SJ Jian Zhe Diong, San Mateo, CA (US); Felix Findeisen, San Francisco, CA (US); Danielle M. Greenawalt, Philadelphia, PA (US); Renu Jain, Redwood City, CA (US); Amy D. Jhatakia, Freemont, CA (US); John K. Lee, Alameda, CA (US); Peter Sung Keun Lee, Millbrae, CA (US); Linda Liang, Mountain View, CA (US); Kai Lu, Foster City, CA (US); Bryan McDonald, San Diego, CA (US); Paul Blaine Mesko, Redwood City, CA (US); Arvind Rajpal, San Francisco, CA (US); Sharmila Sambanthamoorthy, Belmont, CA (US); Mark J. Selby, San Francisco, CA (US); Nathan O. Siemers, Pacific Grove, CA (US); Pavel Strop, San Mateo, CA (US); Gaby A. Terracina, Metuchen, NJ (US); Xi-Tao Wang, Princeton, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 1042 days.

(21) Appl. No.: 17/914,257

(22) PCT Filed: Mar. 22, 2021

(86) PCT No.: PCT/US2021/023430

§ 371 (c)(1),
(2) Date: Sep. 23, 2022

(87) PCT Pub. No.: WO2021/194942

PCT Pub. Date: Sep. 30, 2021

(65) Prior Publication Data

US 2023/0119066 A1 Apr. 20, 2023

Related U.S. Application Data

(60) Provisional application No. 63/157,618, filed on Mar. 5, 2021, provisional application No. 63/041,992, filed on Jun. 21, 2020, provisional application No. 62/993,570, filed on Mar. 23, 2020.

(51) Int. Cl.

| | |
|---|---|
| ***C07K 16/28*** | (2006.01) |
| ***A61K 39/00*** | (2006.01) |
| ***A61P 35/00*** | (2006.01) |

(52) U.S. Cl.
CPC .......... *C07K 16/2866* (2013.01); *A61P 35/00* (2018.01); *C07K 16/2818* (2013.01); *A61K 2039/505* (2013.01); *A61K 2039/507* (2013.01); *A61K 2039/545* (2013.01); *C07K 2317/21* (2013.01); *C07K 2317/24* (2013.01); *C07K 2317/33* (2013.01); *C07K 2317/34* (2013.01); *C07K 2317/41* (2013.01); *C07K 2317/52* (2013.01); *C07K 2317/55* (2013.01); *C07K 2317/565* (2013.01); *C07K 2317/732* (2013.01); *C07K 2317/76* (2013.01); *C07K 2317/92* (2013.01)

(58) Field of Classification Search
CPC ................................................ A61K 2039/505
See application file for complete search history.

(56) References Cited

U.S. PATENT DOCUMENTS

| | | | |
|---|---|---|---|
| 10,087,259 | B1 | 10/2018 | Rudensky et al. |
| 10,550,191 | B2 | 2/2020 | Yoshida et al. |
| 11,427,640 | B1 | 8/2022 | Berndt et al. |

(Continued)

FOREIGN PATENT DOCUMENTS

| | | | |
|---|---|---|---|
| AU | 2014201371 A1 * | 4/2014 | |
| CN | 110835371 A | 2/2020 | |

(Continued)

OTHER PUBLICATIONS

Villarreal et. al. Cancer Res. 78(18):5340-5348. (2018) (Year: 2018).*

(Continued)

*Primary Examiner* — Meera Natarajan
*Assistant Examiner* — Francesca Edgingtongiordano
(74) *Attorney, Agent, or Firm* — Ashton J. Delauney

(57) ABSTRACT

This disclosure provides isolated antibodies, for example, monoclonal antibodies, that specifically bind to the C-C Motif Chemokine Receptor 8 (CCR8) expressed on the surface of a cell and mediate depletion of the CCR8-expressing cell by anti-body-dependent cellular cytotoxicity (ADCC). The disclosure provides methods for treating a subject afflicted with a cancer comprising administering to the subject a therapeutically effective amount of an anti-CCR8 antibody as monotherapy or in combination with an anti-cancer agent such as an immune checkpoint inhibitor, for example, an anti-PD-1 or anti-PD-L1 antibody.

36 Claims, 57 Drawing Sheets

Specification includes a Sequence Listing.

(56) References Cited

U.S. PATENT DOCUMENTS

| | | | |
|---|---|---|---|
| 11,639,393 | B2 | 5/2023 | Mccluskey et al. |
| 11,692,038 | B2 | 7/2023 | Mcgrath et al. |
| 2004/0110704 | A1 | 6/2004 | Yamane et al. |
| 2014/0288275 | A1 | 9/2014 | Moore et al. |
| 2019/0382490 | A1 | 12/2019 | Loffredo et al. |
| 2021/0238292 | A1 | 8/2021 | Holland et al. |
| 2022/0064312 | A1 | 3/2022 | Yoshikawa et al. |
| 2022/0195057 | A1 | 6/2022 | Li et al. |

FOREIGN PATENT DOCUMENTS

| | | | |
|---|---|---|---|
| CN | 110835374 | | 2/2020 |
| CN | 110835374 | A | 2/2020 |
| WO | 2007/044756 | A2 | 4/2007 |
| WO | 2013131010 | A2 | 9/2013 |
| WO | 2014044686 | A1 | 3/2014 |
| WO | 2015161311 | A2 | 10/2015 |
| WO | 2017120599 | A1 | 7/2017 |
| WO | 2018112032 | A1 | 6/2018 |
| WO | 2018112033 | A1 | 6/2018 |
| WO | 2019040727 | A1 | 2/2019 |
| WO | 2019157098 | A1 | 8/2019 |
| WO | 2020138489 | A1 | 7/2020 |
| WO | 2021163064 | A2 | 8/2021 |
| WO | 2021178749 | A2 | 9/2021 |
| WO | 2021260206 | A2 | 12/2021 |
| WO | 2021260208 | A2 | 12/2021 |
| WO | 2021260209 | A2 | 12/2021 |
| WO | 2021260210 | A2 | 12/2021 |
| WO | 2022003156 | A1 | 1/2022 |
| WO | 2022004760 | | 1/2022 |
| WO | 2022004760 | A1 | 1/2022 |
| WO | 2022042690 | | 3/2022 |
| WO | 2022042690 | A1 | 3/2022 |
| WO | 2022081718 | A1 | 4/2022 |
| WO | 2022117569 | A1 | 6/2022 |
| WO | 2022117572 | A2 | 6/2022 |
| WO | 2022136647 | A1 | 6/2022 |
| WO | 2022136649 | A1 | 6/2022 |
| WO | 2022216965 | A1 | 10/2022 |
| WO | 2023098888 | A1 | 6/2023 |

OTHER PUBLICATIONS

Almagro et. al., Front. Immunol. 2018; 8:1751 (Year: 2018).*
Rudikoff et al., Proc. Nat'l Acad. Sci. USA, 79:1979-83 (1982) (Year: 1982).*
Brown et al., J. Immunol., 156(9):3285-91 (1996) (Year: 1996).*
Marvin et. al., Biochemistry, 42(23):7077-7083 (2003) (Year: 2003).*
Chiu et al., Antibodies, 8(55):1-80. (2019) (Year: 2019).*
Villarreal DO, et al. "Targeting CCR8 Induces Protective Antitumor Immunity and Enhances Vaccine-Induced Responses in Colon Cancer" Cancer Res. Sep. 15, 2018 vol. 78(18) pp. 5340-5348.
R&D Systems: "Human CCR8 Antibody," Retrieved from the Internet: URL:http://www.rndsystems.com, 2020.
Lazar, Greg A., et al., "Engineered Antibody FC Variants with Enhanced Effector Function", PNAS, vol. 103, No. 11, pp. 4005-4010, Mar. 14, 2006.
Pereira NA, et al. "The 'less-is-more' in therapeutic antibodies: Afucosylated anti-cancer antibodies with enhanced antibody-dependent cellular cytotoxicity" MAbs. Jul. 2018 vol. 10(5) pp. 693-711.
Wang X, et al. "IgG Fc engineering to modulate antibody effector functions" Protein Cell. Jan. 2018 vol. 9(1) pp. 63-73.
Akinleye, et al. "Immune checkpoint inhibitors of PD-L1 as cancer therapeutics" J Hematol Oncol vol. 12(92) pp. 1-13 (2019).
Anonymous, "Purified anti-mouse CD198 (CCR8) Antibody," Biolegend—Product sheet Catalog No. 150302, Dec. 16, 2015, pp. 1-2, XP055768629, Retrieved from the Internet: URL:https://www.biolegend.com/en-us/products/purified-anti-mouse-cd198-ccr8-antibody-12025.
Arce Vargas, et al. "Fc-optimized anti-CD25 depletes tumor-infiltrating regulatory T cells and synergizes with PD-1 blockade to eradicate established tumors" Immunity vol. 46(4) pp. 577-586 (2017).
Campbell, et al. "Fc-Optimized Anti-CCR8 Antibody Depletes Regulatory T Cells in Human Tumor Models" Cancer Res vol. 81 (11) pp. 2983-2994 (2021).
De Simone M., et al. "Transcriptional landscape of human tissue lymphocytes unveils uniqueness of tumor-infiltrating T regulatory cells" Immunity vol. 45(5) pp. 1135-1147 (2016).
Dépis F, et al. "Preclinical evaluation of JTX-1811, an anti-CCR8 antibody with enhanced ADCC activity, for preferential depletion of tumor-infiltrating regulatory T cells" Cancer Res vol. 80(16_ Supplement) Abstract No. 4532 (2020).
Finotello F., et al. "New strategies for cancer immunotherapy: targeting regulatory T cells" Genome Medicine vol. 9:10 pp. 1-3 (2017).
Hagemann U., et al. "Fully human antagonistic antibodies against CCR4 potently inhibit cell signaling and chemotaxis" PLoS One vol. 9(7) p. e103776 (2014).
Han S., et al. "Turning the tide against regulatory T cells" Front Oncol vol. 9 article 279 (2019).
Harbour BioMed "Harbour BioMed presented its newly discovered anti-human CCR8 novel monoclonal antibodies" Press Release presented at the 16th PEGS Sep. 2, 2020.
Ishida T, et al. "Defucosylated anti-CCR4 monoclonal antibody (KW-0761) for relapsed adult T-cell leukemia-lymphoma: a multi-center phase II study" J Clin Oncol vol. 30(8) pp. 837-842 (2012).
Kamada T., et al. "PD-1+ regulatory T cells amplified by PD-1 blockade promote hyperprogression of cancer" Proc Natl Acad Sci USA vol. 116(20) pp. 9999-10008 (2019).
Kavanagh, Brian, et al., "CTLA-4 Blockade Expands FoxP3 Regulatory and Activated Effector CD4 . . . ", Blood, vol. 112, No. 4, pp. 1175-1183, (2008).
Korman A. et al. "Next-generation anti-CTLA-4 antibodies" Cancer Res vol. 77(13_Supplemental) Abstract No. SY09-01 (2017).
Kuehn H., et al. "Immune dysregulation in human subjects with heterozygous germline mutations in CTLA4" Science vol. 345(6204) pp. 1623-1627 (2014).
Kumar P., et al. "A comprehensive review on the role of co-signaling receptors and Treg homeostasis in autoimmunity and tumor immunity" J Autoimmun vol. 95 pp. 77-99 (2018).
Kurose K., et al. "Phase Ia study of FoxP3+ CD4 Treg depletion by infusion of a humanized anti-CCR4 antibody, KW-0761, in cancer patients" Clin Cancer Res vol. 21(19) pp. 4327-4336 (2015).
Lake A, et al. "SRF114 is a fully human, CCR8 selective IgG1 antibody that induces destruction of tumor Tregs through ADCC" Poster No. 726 presented at the Society for Immunotherapy of Cancer 35th Anniversary Annual Meeting & Pre-Conference Programs (SITC 2020), Nov. 11, 2020.
Lake A, et al. Abstract 726: SRF114 is a fully human, CCR8 selective IgG1 antibody that induces destruction of tumor Tregs through ADCC Immunother Cancer vol. 8(Suppl 3) pp. A434-A435 (2020).
Lu, S. et al. "HBM1022, A Novel Anti-CCR8 Antibody Depletes Tumor-Infiltrating Regulatory T Cells via Enhanced ADCC Activity, Mediates Potent Anti-Tumor Activity with Keytruda" J Immunother Cancer, vol. 8, Supp. 3, p. A426 (2020).
Maurin AGT, et al. (2023) Poster #2945: Depleting anti-hCCR8 mAb Therapy #2: Selection of candidates for the development of innovative depleting anti-CCR8 therapeutic antibodies to control the immunosuppressive tumor microenvironment. American Association for Cancer Research (AACR) Annual Meeting, Orlando, Florida, Apr. 14-19, 2023.
Muroyama Y., et al. "Stereotactic radiotherapy increases functionally suppressive regulatory T cells in the tumor microenvironment" Cancer Immunol Res vol. 5(11) pp. 992-1004 (2017).
Naik E, Norris B et al. (2020) Development of FPA157, an anti-CCR8 depleting antibody engineered to preferentially eliminate tumor-infiltrating T regulatory cells. Poster No. 861 presented at the Society for Immunotherapy of Cancer 35th Anniversary Annual Meeting & Pre-Conference Programs (SITC 2020), Nov. 11, 2020.

(56) References Cited

OTHER PUBLICATIONS

Ni X., et al. "YAP is essential for Treg-mediated suppression of antitumor immunity" Cancer Discov vol. 8(8) pp. 1026-1043 (2018).
Pianko et al., "Immune checkpoint blockade for hematologic malignancies: a review". Stem Cell Investig 4:32. (2017).
Plitas, G., et al. "Regulatory T cells exhibit distinct features in human breast cancer" Immunity vol. 45(5) pp. 1122-1134 (2016).
Rankin A, et al. "Abstract 861: Development of FPA157, an anti-CCR8 depleting antibody engineered to preferentially eliminate tumor-infiltrating T regulatory cells" J Immunother Cancer vol. 8(Suppl 3) pp. A512-A513 (2020).
Richert I, et al. (2023) Poster #2946: Depleting anti-hCCR8 mAb Therapy #1: Characterization of a broad collection of anti-hCCR8 mAbs. American Association for Cancer Research (AACR) Annual Meeting, Orlando, Florida, Apr. 14-19, 2023.
Saleh R., et al. "FoxP3+ T regulatory cells in cancer: prognostic biomarkers and therapeutic targets" Cancer Lett vol. 490 pp. 174-185 (2020).
Scortegagna M, et al. "Siah2 control of T-regulatory cells limits anti-tumor immunity" Nat Commun vol. 11 article 99 (2020).
Selby, Mark et al., "Anti-CTLA-4 Antibodies of IgG2a Isotype Enhance Antitumor . . . ", Cancer Immunology Research, vol. 1, pp. 32-42, Apr. 7, 2013.
Shah W, et al. "A reversed CD4/CD8 ratio of tumor-infiltrating lymphocytes and a high percentage of CD4+FOXP3+ regulatory T cells are significantly associated with clinical outcome in squamous cell carcinoma of the cervix" Cell Mol Immunol vol. 8(1) pp. 59-66 (2011).
Sharma A, et al. "Anti-CTLA-4 immunotherapy does not deplete foxp3+ regulatory t cells (tregs) in human cancers—Response" Clin Cancer Res vol. 25(11) pp. 3469-3470 (2019).
Sharma A, et al. "Anti-CTLA-4 immunotherapy does not deplete FOXP3+ regulatory T cells (Tregs) in human cancers" Clin Cancer Res vol. 25(4) pp. 1233-1238 (2019).
Shitara K, et al. "Regulatory T cells: a potential target in cancer immunotherapy" Ann N Y Acad Sci vol. 1417(1) pp. 104-115 (2018).
Siemers N., et al. "Genome-wide association analysis identifies genetic correlates of immune infiltrates in solid tumors" PLoS One vol. 12(7) p. e0179726 (2017).
Simpson, Tyler, R. et al., "Fc-Dependent Depletion of Tumor-infiltrating Regulatory T Cells . . . ", Journal of Experimental Medicine, Rockefeller Press, vol. 210, pp. 1695-1710, Aug. 26, 2013.
Tao H, et al. "Prognostic potential of FOXP3 expression in non-small cell lung cancer cells combined with tumor-infiltrating regulatory T cells" Lung Cancer vol. 75(1) pp. 95-101 (2012).
Teng M., et al. "Conditional regulatory T-cell depletion releases adaptive immunity preventing carcinogenesis and suppressing established tumor growth" Cancer Research vol. 70(20) pp. 7800-7809 (2010).
Tivol E., et al. "Loss of CTLA-4 leads to massive lymphoproliferation and fatal multiorgan tissue destruction, revealing a critical negative regulatory role of CTLA-4" Immunity vol. 3(5) pp. 541-547 (1995).
Vila-Caballer, M., et al. "Disruption of the CCL1-CCR8 axis inhibits vascular Treg recruitment and function and promotes atherosclerosis in mice" J Mol Cell Cardiol vol. 132 pp. 154-163 (2019).
Wang L., et al. "Connecting blood and intratumoral Treg cell activity in predicting future relapse in breast cancer" Nature Immunol vol. 20 pp. 1220-1230 (2019).
Xu K., et al. "A novel prognostic risk score model based on immune-related genes in patients with stage IV colorectal cancer" Biosci Rep vol. 40(10) article 1725 (2020).
Yi J, et al. "Dysregulation of CCL18/CCR8 axis predicts poor prognosis in patients with gastric cancer" Eur J Inflamm vol. 16 pp. 1-7 (2018).
Zhang J, et al. "ZL-1218, a novel anti-CCR8 antibody, exerts potent antitumor effect by depleting intratumoral regulatory T cells" In: Proceedings of the American Association for Cancer Research Annual Meeting 2022; Apr. 8-13, 2022. Philadelphia. Cancer Res 2022; vol. 82(12_Suppl) Abstract nr 3590 (2022).
Zhao, S., et al. "Clinicopathological and prognostic significance of regulatory T cells in patients with non-small cell lung cancer: a systematic review with meta-analysis" Oncotarget vol. 7(24) pp. 36065-36073 (2016).
Zheng C, et al. "Landscape of infiltrating T cells in liver cancer revealed by single-cell sequencing" Cell vol. 169(7) pp. 1342-1356 (2017).
Trimble, A. "A Later-Filed, Later-Expiring Unrelated Patent is Not a Proper Reference Patent for an Obviousness-Type Double Patenting Rejection" Mintz Blog, Nov. 20, 2024 retrieved from the internet Dec. 23, 2025 https://www.mintz.com/insights-center/viewpoints/2231/2024-11-20-later-filed-later-expiring-unrelated-patent-not-proper.
Ahamadi-Fesharaki R, et al. "Single-Chain Variable Fragment-Based Bispecific Antibodies: Hitting Two Targets with One Sophisticated Arrow" Mol Ther Oncolytics. Mar. 23, 2019 vol. 14 pp. 38-56.
Bujak E, et al. "Reformatting of scFv antibodies into the scFv-Fc format and their downstream purification" Methods Mol Biol. 2014 vol. 1131 pp. 315-334.
Spiess C, et al. "Alternative molecular formats and therapeutic applications for bispecific antibodies" Mol Immunol. Oct. 2015 vol. 67(2 Pt A) pp. 95-106.

* cited by examiner

ANTI-CCR8 ANTIBODIES FOR TREATING CANCER

CROSS REFERENCE TO RELATED APPLICATIONS

This application claims the benefit of U.S. Provisional Application Nos. 63/157,618, filed Mar. 5, 2021; 63/041,992, filed Jun. 21, 2020; and 62/993,570, filed Mar. 23, 2020, the content of each of which is hereby incorporated herein by reference in its entirety.

This application is a 35 U.S.C. § 371 national stage application of International Application No. PCT/US21/23430, filed Mar. 22, 2021, which claims the benefit of U.S. Provisional Application Nos. 63/157,618, filed Mar. 5, 2021; 63/041,992, filed Jun. 21, 2020; and 62/993,570, filed Mar. 23, 2020, the content of each of which is hereby incorporated herein by reference in its entirety.

Throughout this application, various publications are referenced in parentheses by author name and date, or by Patent No. or Patent Publication No. Full citations for these publications may be found at the end of the specification immediately preceding the claims. The disclosures of these publications are hereby incorporated in their entireties by reference into this application in order to more fully describe the state of the art as known to those skilled therein as of the date of the invention described and claimed herein. However, these disclosures are incorporated into the present application only to the extent that no conflict exists between the information incorporated by reference and the information provided by explicit disclosure in the present application. Moreover, the citation of a reference herein should not be construed as an acknowledgement that such reference is prior art to the present invention.

SEQUENCE LISTING

The present application contains a Sequence Listing which has been submitted electronically in ASCII format and is hereby incorporated herein by reference in its entirety. The ASCII copy was created on Mar. 19, 2021, is named 20210319_SEQL_13358WOPCT.txt, and is 81,920 bytes in size.

FIELD OF THE INVENTION

The disclosed invention relates to isolated antibodies (Abs), e.g., monoclonal antibodies (mAbs), that bind specifically to C-C Motif Chemokine Receptor 8 (CCR8), and methods for treating a cancer in a subject comprising administering to the subject an anti-CCR8 Ab as monotherapy or in combination with an anticancer agent such as an immune checkpoint inhibitor.

BACKGROUND OF THE INVENTION

Human cancers harbor numerous genetic and epigenetic alterations, generating neoantigens potentially recognizable by the immune system (Chakravarthi et al., 2016). Harnessing the attributes of the adaptive immune system to treat cancer makes immunotherapy unique among all cancer treatment modalities in its applicability to a broad range of cancers and in inducing durable anti-tumor effects.

Considerable success has already been achieved in treating diverse solid tumors and hematological malignancies by stimulating the activity of cytotoxic T cells using checkpoint inhibitors such as the anti-PD-1 Ab, nivolumab (OPDIVO®)

and the anti-CTLA-4 Ab, ipilimumab (YERVOY®). However, typically less than around 15% of patients benefit long-term from treatment with a checkpoint inhibitor in cancers amenable to this treatment (Haslam and Prasad, 2019), and checkpoint inhibitors have proven to be less effective in certain cancers, including breast and prostate cancers. The persistence of immunosuppressive mechanisms, especially those mediated by regulatory T cells (Tregs), may contribute to the observed resistance of certain cancers or certain patients to treatment with checkpoint inhibitors (Fares et al., 2019; Han et al., 2019). As one means of overcoming this resistance, the present application discloses methods of stimulating the immune system by reducing the immunosuppressive effects of Tregs.

Tumor-infiltrating $CD4^+$ $CD25^+$ $FOXP3^+$ Tregs, a subset of $CD4^+$ T cells, are mediators of immunological self-tolerance. Deficiency of genes involved in Treg development and function result in systemic autoimmunity in both mice (Fontenot et al., 2003; Khattri et al., 2003; Tivol et al., 1995) and humans (Yagi et al., 2004; Kuehn et al., 2014), revealing an important non-redundant role for Tregs in maintaining immune homeostasis. Tregs suppress the immune system via multiple mechanisms including down-regulating the induction and proliferation of effector T cells, secretion of chemokines and inhibitory cytokines, and suppression of dendritic cell maturation and function (Shitara and Nishikawa, 2018; Han et al., 2019). Mechanisms utilized by Tregs to promote self-tolerance may be co-opted in the tumor microenvironment to suppress the anti-tumor immune response. Indeed, systemic depletion of Tregs in mice is sufficient to enable immune-mediated tumor regression (Teng et al., 2010). Thus, Tregs are thought to play a role in mediating peripheral tolerance to self-antigens, preventing autoimmune disease, and suppressing anti-tumor immune responses.

Consequently, reducing the activity or numbers of tumor-infiltrating Tregs has been identified as an attractive approach to reversing immunosuppressive activity in the tumor microenvironment and augmenting anti-tumor immunity (Finotello and Trajanoski, 2017; Han et al., 2019). A variety of methods have been and are being pursued to target Tregs in cancer immunotherapy, including ADCC-mediated depletion of Tregs using antibodies (Abs) to antigens expressed on Tregs such as CD25 (Arce Vargas et al., 2017), CCR4 (Ishida et al., 2012; Hagemann et al., 2014) and CTLA-4 (Korman et al., 2017), and inhibition of E3 ubiquitin ligase Siah2 (Scortegagna et al., 2020) and Yes-associated protein (YAP; Ni et al., 2018). However, clinical attempts to specifically target or deplete Treg from the tumor microenvironment have been unsuccessful. Diphtheria toxin fused to IL-2 (denileukin diftitox) failed to effectively reduce Treg numbers in melanoma patients (Luke et al., (2016), and despite documented anti-CTLA-4 mediated Treg depletion in mouse tumor models (Selby et al., 2013; Simpson et al., 2013), clear evidence for Treg depletion by ipilimumab or tremelimumab (anti-human CTLA-4 Abs) in human cancer is unclear (Sharma et al., 2019a; Sharma et al., 2019b). Treg depletion was achieved with the nonfucosylated (nf) anti-CCR4 Ab mogamulizumab, but significant depletion of conventional $CD4^+$ T cells and modest reductions in $CD8^+$ T cell numbers were also observed (Kurose et al., 2015), limiting its utility in the treatment of solid tumors. Thus, there remains a need for a safe and effective Treg depleting agent that also spares T effector cells (Teffs) for optimal anti-tumor responses.

CCR8 is a chemokine receptor that has recently been identified as a potential specific marker for tumor-infiltrating Tregs, as CCR8 expression is selectively upregulated in these Tregs in multiple cancers, including breast, colorectal, and lung (Plitas et al., 2016; De Simone et al., 2016; Wang et al., 2019), and as a core member of the IRF4-dependent 'effector' Treg gene program (Alvisi et al., 2020). These CCR8$^+$ Tregs represent a highly activated and suppressive subpopulation of Tregs, and high abundance of CCR8$^+$ Tregs in these tumor types is associated with poor prognosis (Wang et al., 2019; De Simone et al., 2016). Therefore, CCR8 may be a promising therapeutic target to effect the depletion of tumor-resident Tregs in order to augment anti-tumor immunity. Targeting CCR8, while depleting suppressive Tregs, may also have the advantage of not depleting cytolytic effector cells that drive anti-tumor immune responses. Moreover, because CCR8 is rarely expressed on Tregs and Teffs in peripheral blood or in other tissues, targeting CCR8$^+$ tumor Tregs may pose minimal toxicity risks.

CCR8 is a seven-transmembrane G-protein-coupled chemokine receptor (GPCR) expressed primarily on intratumoral FOXP3$^{hi}$ Tregs (Wang et al., 2019; Plitas et al., 2016; De Simone et al., 2016). The N-terminus and ECL2 regions of CCR8 are important for binding to its functional ligand C-C Motif Chemokine Ligand 1 (CCL1), which is produced by intratumoral myeloid cells and T cells. In addition to affecting the migration of Tregs to the tumor microenvironment (TME), the CCL1:CCR8 interaction also potentiates the immunosuppressive capacity of Tregs through upregulation of CCR8, FOXP3, IL-10, and other suppressive factors (Vila-Caballer et al., 2019).

Recently issued U.S. Pat. No. 10,087,259 claims a method of treating cancer by administering to a cancer patient an Ab agent that binds specifically to CCR8 so that tumor-infiltrating Treg cells are specifically depleted in the patient to a greater extent than are normal-tissue infiltrating T cells. However, this patent does not exemplify any Ab agent that binds specifically to CCR8 nor does it demonstrate any method of treating any cancer by administering an anti-CCR8 Ab to a subject.

U.S. Pat. No. 10,550,191 claims a method for treating a cancer comprising administering an Ab against CCR8. The Examples demonstrate that a single Ab, a commercially available rat IgG2b anti-mouse CCR8 (anti-mCCR8) Ab (Clone SA214G2; BioLegend, San Diego, CA), reduces the volume of a variety of tumors in mouse tumor models. No anti-human CCR8 (anti-hCCR8) Ab, or any chimeric, humanized or human Ab suitable for use in human therapy is disclosed.

PCT Publication No. WO 2018/112033 relates to methods for treating cancer by administering to a subject an agent that induces cytotoxicity in tumor-infiltrating Treg cells that express a specified gene product included in Table 1 or 2 and thereby decreases the number or activity of tumor-infiltrating Treg cells in the subject. CCR8 is not a gene product included in Table 1 or 2, but Example 8 demonstrates a moderate level of anti-tumor activity of an anti-mCCR8 Ab in a mouse MC38 colon adenocarcinoma model.

PCT Publication No. WO 2019/157098 relates to an immunogenic composition comprising a recombinant Listeria strain and an anti-CCR8 Ab, and a method of treating a tumor in a subject comprising administering this immunogenic composition to the subject. Similar to U.S. Pat. No. 10,550,191, WO 2019/157098 does not report generating any anti-CCR8 Ab but instead demonstrates the use of the commercial SA214G2 anti-mCCR8 Ab, in combination with Listeria-based immunotherapy, to treat implanted colon carcinoma tumors in a mouse model.

More recently, various groups have reported the generation of humanized anti-CCR8 Abs for use in depleting tumor-associated Tregs and treating cancer (see, e.g., Dépis et al., 2020; WO 2020/138489; Harbour BioMed, 2020).

The invention disclosed herein demonstrates that CCR8 expression is highly restricted to tumor Tregs from diverse tumor types. The invention comprises the production of anti-CCR8 Abs, specifically anti-CCR8 mAbs, including human, humanized and chimeric anti-hCCR8 mAbs, and demonstrates that anti-CCR8-mediated Treg depletion in mouse tumor models requires Fc engagement. The present disclosure also describes the development of nf anti-hCCR8 Abs that mediate tumor-specific Treg depletion in ex vivo human tumor culture systems. Anti-CCR8 Ab treatment as monotherapy or in combination with checkpoint blockade, for example, inhibition of the PD-1/PD-L1 signaling pathway, induces potent anti-tumor responses and may provide clinical benefit to patients who do not respond to anti-PD-1 monotherapy. The combination of the mechanisms of action of anti-CCR8-mediated Treg depletion and checkpoint blockade offers a unique opportunity to increase the killing of tumor cells and thereby treat a wide range of cancers.

SUMMARY OF THE INVENTION

The present invention provides isolated Abs, preferably mAbs, that specifically bind to CCR8, such as human CCR8 (hCCR8), expressed on the surface of a cell and exhibit various functional properties, including properties that are desirable in a therapeutic Ab. These properties include binding with high affinity to CCR8-expressing cells, such as tumor-infiltrating, activated CD4$^+$FOXP3$^{high}$ Tregs; other than Tregs, binding only to rare and scattered immune cells in the medulla of the thymus and dermis of the skin but not binding to many other tissues; mediating depletion of the CCR8-expressing cells, such as tumor-infiltrating, activated CD4$^+$FOXP3$^{high}$ Tregs, by ADCC; mediating depletion specifically of tumor-infiltrating Tregs but not of CCR8$^+$ T cells in normal tissues; inhibiting binding of CCL1 to CCR8 and inhibiting CCR8/CCL1 signaling; not causing internalization of CCR8 when bound to CCR8 on the surface of a cell either in the presence or absence of a cross-linking Ab; mediating specific depletion of CCR8$^+$ Tregs in vitro and in human tumor ex-vivo tissue samples; and inhibiting growth of tumor cells in a subject, preferably a human subject, when administered to the subject as monotherapy or in combination with another anti-cancer agent. In preferred embodiments, the anti-CCR8 Ab is a modified mAb comprising a modified heavy chain constant region, such as a hypofucosylated or nonfucosylated (nf) heavy chain constant region, that binds with higher affinity to an Fcγ receptor (FcγR) and mediates enhanced ADCC compared to an unmodified mAb.

Specifically, this disclosure provides an isolated Ab, preferably a mAb, or an antigen-binding portion thereof, that specifically binds to CCR8 expressed on the surface of a cell and mediates depletion of the CCR8-expressing cell by ADCC. In certain embodiments, the CCR8 is hCCR8 having the amino acid sequence set forth in SEQ ID NO: 1. In certain other embodiments, the Ab, e.g., the mAb, or antigen-binding portion thereof comprises a heavy chain constant region which is of a human IgG1 or IgG3 isotype.

The disclosure also provides a modified anti-hCCR8 mAb, or an antigen-binding portion thereof, which comprises a modified heavy chain constant region that binds with higher affinity to an Fcγ receptor (FcγR) and mediates enhanced ADCC compared to an unmodified mAb or antigen-binding portion thereof. In preferred embodiments, the modified mAb or antigen-binding portion thereof comprises a modified IgG1 heavy chain constant region which exhibits reduced fucosylation. In certain embodiments, the mAb or antigen-binding portion thereof binds to a N-terminal peptide of hCCR8, wherein the epitope comprises at least one amino acid within a peptide having the sequence $Y_{15}Y_{16}Y_{17}P_{18}D_{19}I_{20}F_{21}$(SEQ ID NO: 2) and further comprises sulfated tyr-15 and/or sulfated tyr-17 residues. In certain preferred embodiments, the mAb or antigen-binding portion thereof binds to a N-terminal peptide of hCCR8, wherein the epitope comprises at least one amino acid within a peptide having the sequence $V_{12}T_{13}D_{14}Y_{15}Y_{16}Y_{17}P_{18}D_{19}I_{20}F_{21}S_{22}$ (SEQ ID NO: 109) and further comprises sulfated tyr-15 and sulfated tyr-17 residues.

In certain embodiments, the anti-CCR8 mAb or antigen-binding portion thereof exhibits at least one, e.g., at least 2, 3, 4, 5, 6, 7 or all of the following properties: (a) specifically binds to CCR8 expressed on the surface of a cell with an $EC_{50}$ of about 1 nM or lower or an $EC_{50}$ of about 2 nM or lower; (b) binds to rare and scattered immune cells in the medulla of the thymus and dermis of the skin but does not bind to human cerebrum, cerebellum, heart, liver, lung, kidney, tonsil, spleen, thymus, colon, stomach, pancreas, adrenal, pituitary, skin, peripheral nerve, testis or uterus tissue, or peripheral blood mononuclear cells (PBMCs); (c) inhibits binding of CCL1 to CCR8 and inhibits CCR8/CCL1 signaling with an $IC_{50}$ of about 5 nM or lower; (d) when bound to CCR8 on the surface of a cell mediates depletion of the cell with an $EC_{50}$ of about 10 pM or lower or an $EC_{50}$ of about 60 pM or lower; (e) when administered to a subject mediates depletion of tumor-infiltrating Tregs but substantially spares $CCR8^+$ T cells in the spleen, blood, skin or thymus; (f) when bound to CCR8 on the surface of a cell does not cause internalization of CCR8 either in the presence or absence of a cross-linking Ab; (g) inhibits growth of tumor cells in a subject when administered as monotherapy to the subject; and (h) inhibits growth of tumor cells in a subject when administered to the subject in combination with an additional therapeutic agent, such as an immune checkpoint inhibitor, for treating a cancer.

In particular, in certain preferred embodiments, the anti-CCR8 mAb or antigen-binding portion thereof exhibits at least the following properties: (a) specifically binds to CCR8 expressed on the surface of a cell with an $EC_{50}$ of about 1 nM or lower or an $EC_{50}$ of about 2 nM or lower; (b) inhibits binding of CCL1 to CCR8 and inhibits CCR8/CCL1 signaling with an $IC_{50}$ of about 5 nM or lower; (c) when bound to CCR8 on the surface of a cell mediates depletion of the cell with an $EC_{50}$ of about 10 pM or lower or an $EC_{50}$ of about 60 pM or lower; (d) when administered to a subject mediates depletion of tumor-infiltrating Tregs but substantially spares $CCR8^+$ T cells in the spleen, blood, skin or thymus; (e) inhibits growth of tumor cells in a subject when administered as monotherapy to the subject; and (f) inhibits growth of tumor cells in a subject when administered to the subject in combination with an additional therapeutic agent, such as an immune checkpoint inhibitor, for treating a cancer.

In other embodiments, the anti-CCR8 mAb or antigen-binding portion thereof exhibits at least the following properties: (a) specifically binds to CCR8 expressed on the surface of a cell with an $EC_{50}$ of about 1 nM or lower or an $EC_{50}$ of about 2 nM or lower; (b) when bound to CCR8 on the surface of a cell mediates depletion of the cell with an $EC_{50}$ of about 10 pM or lower or an $EC_{50}$ of about 60 pM or lower; (c) when administered to a subject mediates depletion of tumor-infiltrating Tregs but substantially spares $CCR8^+$ T cells in the spleen, blood, skin or thymus; and (d) inhibits growth of tumor cells in a subject when administered to the subject in combination with an additional therapeutic agent, such as an immune checkpoint inhibitor, for treating a cancer.

These properties have been examined in detail for certain Abs of the invention including, for example, those designated herein as 14S15 and 4A19. MAb 4A19 is a nf humanized Ab whereas mAb 14S15 is a nf chimeric Ab comprising a mouse Fab fragment grafted onto a human Fc region, and several of the assays described herein were performed with mAbs including 14S15 and 4A19. The 14S15 mAb was subsequently humanized to generate the Ab designated 14S15h by modifying the framework sequences to correspond to the closest human germline sequences (see Example 10). The final iteration of the humanized mAb, produced after affinity maturation of the heavy chain variable domain, exhibited a binding affinity for hCCR8 comparable to, and in fact slightly higher, than that of the original mouse or chimeric versions of this Ab ($K_D$ of 0.64 nM for 14S15h Fab fragment vs. 1.4 nM for the starting mouse mAb). Thus, 14S15h is expected to exhibit the same or very similar functional properties as those demonstrated with the chimeric 14S15 mAb. The functional properties noted above, alone or in combination, may therefore be present in combination with the structural features of mAbs 14S15, 14S15h and 4A19.

For example, in certain embodiments of the invention, an Ab or antigen-binding portion thereof may comprise one or more of the above properties (e.g. at least 2, 3, 4, 5 or 6 of the above properties) and comprise the CDR1, CDR2 and CDR3 domains in each of a $V_H$ comprising consecutively linked amino acids having the sequence set forth as SEQ ID NO: 4 and a $V_L$ comprising consecutively linked amino acids having the sequence set forth as SEQ ID NO: 16. As another example, such an Ab or antigen-binding portion thereof may comprise the following CDR domains as defined by the Kabat method: a $V_H$ CDR1 comprising consecutively linked amino acids having the sequence set forth as SEQ ID NO: 33; a $V_H$ CDR2 comprising consecutively linked amino acids having the sequence set forth as SEQ ID NO: 34; a $V_H$ CDR3 comprising consecutively linked amino acids having the sequence set forth as SEQ ID NO: 35; a $V_L$ CDR1 comprising consecutively linked amino acids having the sequence set forth as SEQ ID NO: 36; a $V_L$ CDR2 comprising consecutively linked amino acids having the sequence set forth as SEQ ID NO: 37; and a $V_L$ CDR3 comprising consecutively linked amino acids having the sequence set forth as SEQ ID NO: 38. As a further example, such an Ab or antigen-binding portion thereof may comprise a $V_H$ comprising consecutively linked amino acids having the sequence set forth as SEQ ID NO: 4 and a $V_L$ comprising consecutively linked amino acids having the sequence set forth as SEQ ID NO: 16. As another example, such an Ab may comprise a heavy chain comprising consecutively linked amino acids having the sequence set forth as SEQ ID NO: 100 and a light chain comprising consecutively linked amino acids having the sequence set forth as SEQ ID NO: 112. Optionally, the Ab has reduced fucosylation of its heavy chain, or has a hypofucosylated or nonfucosylated heavy chain constant region as described elsewhere herein.

For example, in certain other embodiments of the invention, an Ab or antigen-binding portion thereof may comprise one or more of the above properties (e.g. at least 2, 3, 4, 5 or 6 of the above properties) and comprise the CDR1, CDR2 and CDR3 domains in each of a $V_H$ comprising consecutively linked amino acids having the sequence set forth as SEQ ID NO: 115 and a $V_L$ comprising consecutively linked amino acids having the sequence set forth as SEQ ID NO: 116. As another example, such an Ab or antigen-binding portion thereof may comprise the following CDR domains as defined by the Kabat method: a $V_H$ CDR1 comprising consecutively linked amino acids having the sequence set forth as SEQ ID NO: 103; a $V_H$ CDR2 comprising consecutively linked amino acids having the sequence set forth as SEQ ID NO: 104; a $V_H$ CDR3 comprising consecutively linked amino acids having the sequence set forth as SEQ ID NO: 105; a $V_L$ CDR1 comprising consecutively linked amino acids having the sequence set forth as SEQ ID NO: 106; a $V_L$ CDR2 comprising consecutively linked amino acids having the sequence set forth as SEQ ID NO: 107; and a $V_L$ CDR3 comprising consecutively linked amino acids having the sequence set forth as SEQ ID NO: 108. As a further example, such an Ab or antigen-binding portion thereof may comprise a $V_H$ comprising consecutively linked amino acids having the sequence set forth as SEQ ID NO: 115 and a $V_L$ comprising consecutively linked amino acids having the sequence set forth as SEQ ID NO: 116. As another example, such an Ab may comprise a heavy chain comprising consecutively linked amino acids having the sequence set forth as SEQ ID NO: 117 and a light chain comprising consecutively linked amino acids having the sequence set forth as SEQ ID NO: 118. Optionally, the Ab has reduced fucosylation of its heavy chain, or has a hypofucosylated or nonfucosylated heavy chain constant region as described elsewhere herein.

For example, in certain other embodiments of the invention, an Ab or antigen-binding portion thereof may comprise one or more of the above properties (e.g. at least 2, 3, 4, 5 or 6 of the above properties) and comprise the CDR1, CDR2 and CDR3 domains in each of a $V_H$ comprising consecutively linked amino acids having the sequence set forth as SEQ ID NO: 6 and a $V_L$ comprising consecutively linked amino acids having the sequence set forth as SEQ ID NO: 18. As another example, such an Ab or antigen-binding portion thereof may comprise the following CDR domains as defined by the Kabat method: a $V_H$ CDR1 comprising consecutively linked amino acids having the sequence set forth as SEQ ID NO: 45; a $V_H$ CDR2 comprising consecutively linked amino acids having the sequence set forth as SEQ ID NO: 46; a $V_H$ CDR3 comprising consecutively linked amino acids having the sequence set forth as SEQ ID NO: 47; a $V_L$ CDR1 comprising consecutively linked amino acids having the sequence set forth as SEQ ID NO: 48; a $V_L$ CDR2 comprising consecutively linked amino acids having the sequence set forth as SEQ ID NO: 49; and a $V_L$ CDR3 comprising consecutively linked amino acids having the sequence set forth as SEQ ID NO: 50. As a further example, such an Ab or antigen-binding portion thereof may comprise a $V_H$ comprising consecutively linked amino acids having the sequence set forth as SEQ ID NO: 6 and a $V_L$ comprising consecutively linked amino acids having the sequence set forth as SEQ ID NO: 18. As another example, such an Ab may comprise a heavy chain comprising consecutively linked amino acids having the sequence set forth as SEQ ID NO: 102 and a light chain comprising consecutively linked amino acids having the sequence set forth as SEQ ID NO: 114. Optionally, the Ab has reduced fucosylation of its heavy chain, or has a hypofucosylated or nonfucosylated heavy chain constant region as described elsewhere herein.

The disclosure further provides an isolated Ab, preferably a mAb, or an antigen-binding portion thereof, which specifically binds to hCCR8 expressed on the surface of a cell and comprises the CDR1, CDR2 and CDR3 domains in each of the following pairs of heavy and light chain variable regions:

(a) a $V_H$ comprising consecutively linked amino acids having the sequence set forth as SEQ ID NO: 3 and a $V_L$ comprising consecutively linked amino acids having the sequence set forth as SEQ ID NO: 15;

(b) a $V_H$ comprising consecutively linked amino acids having the sequence set forth as SEQ ID NO: 4 and a $V_L$ comprising consecutively linked amino acids having the sequence set forth as SEQ ID NO: 16;

(c) a $V_H$ comprising consecutively linked amino acids having the sequence set forth as SEQ ID NO: 5 and a $V_L$ comprising consecutively linked amino acids having the sequence set forth as SEQ ID NO: 17;

(d) a $V_H$ comprising consecutively linked amino acids having the sequence set forth as SEQ ID NO: 6 and a $V_L$ comprising consecutively linked amino acids having the sequence set forth as SEQ ID NO: 18;

(e) a $V_H$ comprising consecutively linked amino acids having the sequence set forth as SEQ ID NO: 7 and a $V_L$ comprising consecutively linked amino acids having the sequence set forth as SEQ ID NO: 19;

(f) a $V_H$ comprising consecutively linked amino acids having the sequence set forth as SEQ ID NO: 8 and a $V_L$ comprising consecutively linked amino acids having the sequence set forth as SEQ ID NO: 20;

(g) a $V_H$ comprising consecutively linked amino acids having the sequence set forth as SEQ ID NO: 9 and a $V_L$ comprising consecutively linked amino acids having the sequence set forth as SEQ ID NO: 21;

(h) a $V_H$ comprising consecutively linked amino acids having the sequence set forth as SEQ ID NO: 10 and a $V_L$ comprising consecutively linked amino acids having the sequence set forth as SEQ ID NO: 22;

(i) a $V_H$ comprising consecutively linked amino acids having the sequence set forth as SEQ ID NO: 11 and a $V_L$ comprising consecutively linked amino acids having the sequence set forth as SEQ ID NO: 23;

(j) a $V_H$ comprising consecutively linked amino acids having the sequence set forth as SEQ ID NO: 12 and a $V_L$ comprising consecutively linked amino acids having the sequence set forth as SEQ ID NO: 24;

(k) a $V_H$ comprising consecutively linked amino acids having the sequence set forth as SEQ ID NO: 13 and a $V_L$ comprising consecutively linked amino acids having the sequence set forth as SEQ ID NO: 25;

(l) a $V_H$ comprising consecutively linked amino acids having the sequence set forth as SEQ ID NO: 14 and a $V_L$ comprising consecutively linked amino acids having the sequence set forth as SEQ ID NO: 26; or (m) a $V_H$ comprising consecutively linked amino acids having the sequence set forth as SEQ ID NO: 115 and a $V_L$ comprising consecutively linked amino acids having the sequence set forth as SEQ ID NO: 116.

The isolated Ab, preferably a mAb, or an antigen-binding portion thereof, which specifically binds to hCCR8 expressed on the surface of a cell and comprising the CDR1, CDR2 and CDR3 domains in each of the following pairs of heavy and light chain variable regions are particular examples:

(a) a $V_H$ comprising consecutively linked amino acids having the sequence set forth as SEQ ID NO: 4 and a $V_L$ comprising consecutively linked amino acids having the sequence set forth as SEQ ID NO: 16;

(b) a $V_H$ comprising consecutively linked amino acids having the sequence set forth as SEQ ID NO: 115 and a $V_L$ comprising consecutively linked amino acids having the sequence set forth as SEQ ID NO: 116; and (c) a $V_H$ comprising consecutively linked amino acids having the sequence set forth as SEQ ID NO: 6 and a $V_L$ comprising consecutively linked amino acids having the sequence set forth as SEQ ID NO: 18, An isolated Ab, preferably a mAb, or an antigen-binding portion thereof, which specifically binds to hCCR8 expressed on the surface of a cell and comprising the CDR1, CDR2 and CDR3 domains in the following pair of heavy and light chain variable regions is a particular example:

(a) a $V_H$ comprising consecutively linked amino acids having the sequence set forth as SEQ ID NO: 6 and a $V_L$ comprising consecutively linked amino acids having the sequence set forth as SEQ ID NO: 18.

Sequences of the CDRs may be defined by a variety of methods, including the Kabat, Chothia, AbM, contact and IMGT definitions. Unless explicitly indicated otherwise, CDRs in the present disclosure have been identified by the Kabat definitions.

The disclosure also provides an isolated nucleic acid encoding any of the anti-CCR8 mAbs or antigen-binding portions thereof described herein. The disclosure provides an expression vector comprising said isolated nucleic acid, and a host cell comprising said expression vector. This host cell may be used in a method for preparing an anti-CCR8 mAb or an antigen-binding portion thereof, which method comprises expressing the mAb or antigen-binding portion thereof in said host cell and isolating the mAb or antigen-binding portion thereof from the host cell.

In certain embodiments, the present disclosure provides a method for treating a subject afflicted with a cancer comprising administering to the subject a therapeutically effective amount of an anti-CCR8 mAb or an antigen-binding portion thereof described herein, e.g., that mediates depletion of CCR8-expressing cells, such that the subject is treated. In other embodiments, the disclosure provides a method for inhibiting growth of tumor cells in a subject, comprising administering to the subject a therapeutically effective amount of an anti-CCR8 mAb or an antigen-binding portion described herein, e.g., that mediates depletion of CCR8-expressing cells, such that growth of tumor cells in the subject is inhibited. In certain embodiments of these methods, the anti-CCR8 mAb, when bound to CCR8 on the surface of a cell, mediates depletion of the cell with an $EC_{50}$ of about 10 pM or lower. In certain other embodiments, the anti-CCR8 mAb, when bound to CCR8 on the surface of a cell, inhibits binding of CCL1 to CCR8 and inhibits CCR8/CCL1 signaling with an $IC_{50}$ of about 5 nM or lower. In additional embodiments, this disclosure provides an anti-CCR8 mAb or an antigen-binding portion thereof described herein, e.g. that mediates depletion of CCR8-expressing cells, for use in a method for treating a subject afflicted with a cancer or for use in a method for inhibiting growth of tumor cells in a subject, each method comprising administering to the subject a therapeutically effective amount of the anti-CCR8 mAb or antigen-binding portion thereof.

This disclosure further provides a method for treating a subject afflicted with a cancer comprising administering to the subject a combination of therapeutically effective amounts of (a) an anti-CCR8 Ab, e.g., a mAb or an antigen-binding portion thereof described herein, e.g., that mediates depletion of CCR8-expressing cells, and (b) an additional therapeutic agent for treating cancer, optionally wherein the additional therapeutic agent is a compound that reduces inhibition or increases stimulation of the immune system. In certain preferred embodiments, the additional therapeutic agent is an antagonistic Ab or antigen-binding portion thereof that binds specifically to PD-1, PD-L1, or CTLA-4. The method may also be a method for inhibiting growth of tumor cells in a subject.

Where such methods involve the use of a combination of therapeutic agents, they can be referred to in different manners. For example, where a method of treatment uses Agents (A) and (B), for instance to treat cancer, this can be referred to as: (i) Agent (A) and Agent (B) for use in a method of treating cancer; (ii) Agent (A) for use with Agent (B) in a method of treating cancer; or (iii) Agent (B) for use with Agent (A) in a method of treating cancer. Therefore, the above combination can be referred to as:

(i) (A) an anti-CCR8 mAb or an antigen-binding portion thereof, e.g., that mediates depletion of CCR8-expressing cells, and (B) an additional therapeutic agent for treating cancer, for use in a in a method for treating a subject afflicted with a cancer or for use in a method for inhibiting growth of tumor cells in a subject, the method comprising administering to the subject a combination of therapeutically effective amounts of (A) the anti-CCR8 mAb or antigen-binding portion thereof, e.g., that mediates depletion of CCR8-expressing cells, and (B) the additional therapeutic agent for treating cancer; or (ii) (A) an anti-CCR8 mAb or an antigen-binding portion thereof, e.g., that mediates depletion of CCR8-expressing cells, for use with (B) an additional therapeutic agent for treating cancer, in a method for treating a subject afflicted with a cancer or in a method for inhibiting growth of tumor cells in a subject, the method comprising administering to the subject a combination of therapeutically effective amounts of (A) the anti-CCR8 mAb or antigen-binding portion thereof, e.g., that mediates depletion of CCR8-expressing cells, and (B) the additional therapeutic agent for treating cancer; or (iii) (B) an additional therapeutic agent for treating cancer for use with (A) an anti-CCR8 mAb or an antigen-binding portion thereof, e.g., that mediates depletion of CCR8-expressing cells, in a method for treating a subject afflicted with a cancer or in a method for inhibiting growth of tumor cells in a subject, the method comprising administering to the subject a combination of therapeutically effective amounts of (B) the additional therapeutic agent for treating cancer, and (A) the anti-CCR8 mAb or antigen-binding portion thereof, e.g., that mediates depletion of CCR8-expressing cells.

The disclosure also provides a kit comprising: (a) one or more dosages ranging from about 0.01 to about 20 mg/kg body weight, or about 0.1 to about 2,000 mg fixed dose, of an isolated Ab, preferably a mAb, or an antigen-binding portion thereof, that binds specifically to CCR8 expressed on the surface of a cell and mediates depletion of the CCR8-expressing cell by ADCC; (b) optionally one or more dosages ranging from about 200 to about 1600 mg of a mAb or an antigen-binding portion thereof that binds specifically to PD-1, PD-L1 or CTLA-4; and (c) instructions for using the isolated Ab or portion thereof that binds specifically to CCR8, and optionally the mAb or portion thereof that binds specifically to PD-1, PD-L1 or CTLA-4, in the therapeutic methods disclosed herein.

Other features and advantages of the instant invention will be apparent from the following detailed description and examples which should not be construed as limiting. The contents of all cited references, including scientific articles, GenBank entries, patents and patent applications cited throughout this application are expressly incorporated herein by reference.

to thymus tissue. MAbs 18Y12 does not show any staining whereas positive staining was observed with mAb 4A19 in rare and scattered immune cells in the medulla of the thymus. MAb 16B13 shows intense and diffuse staining in the vast majority of immune cells in the thymus, with predominate cytoplasmic and/or peri-nuclear patterns.

Figure 14A:
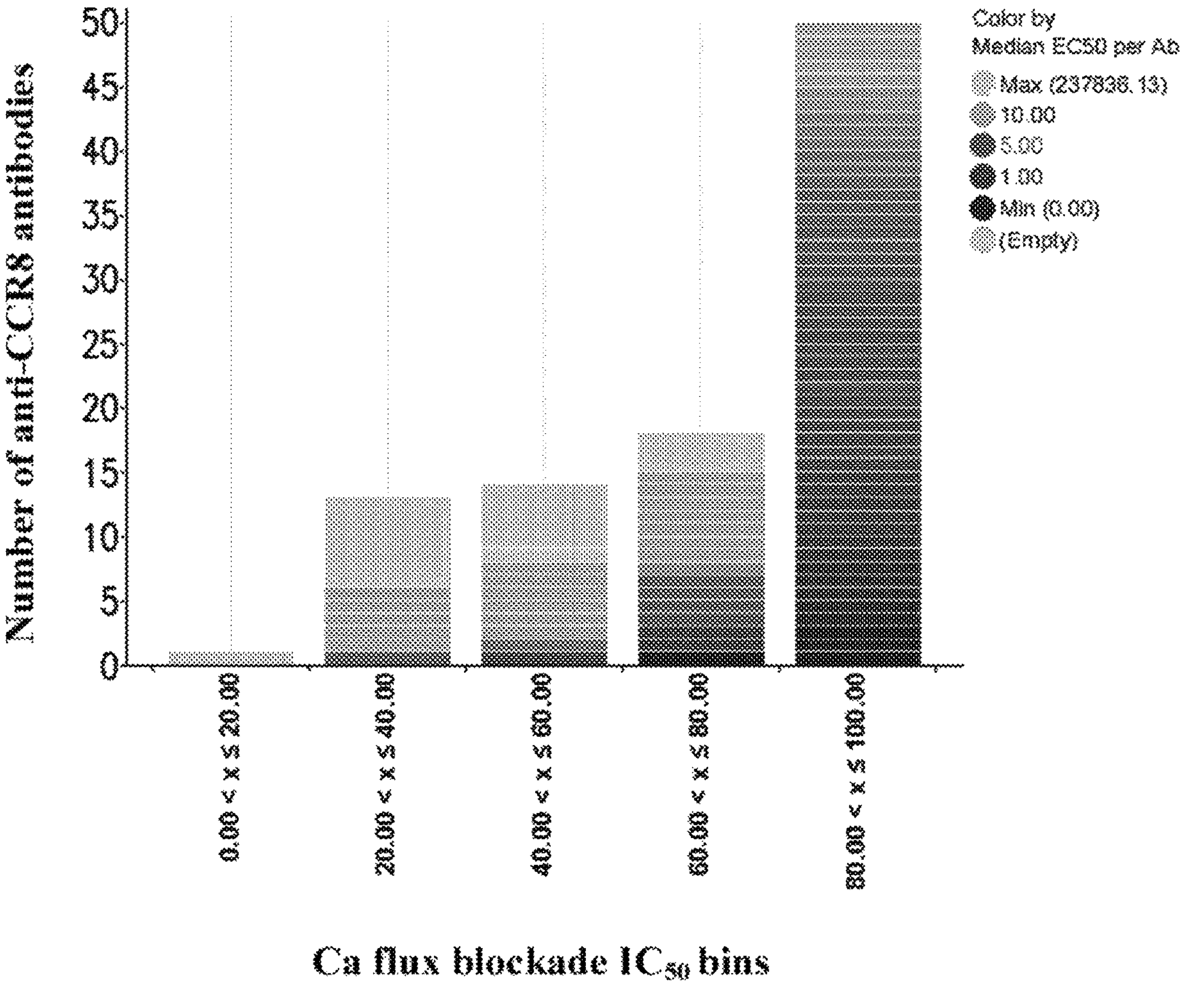
Figure 14B:
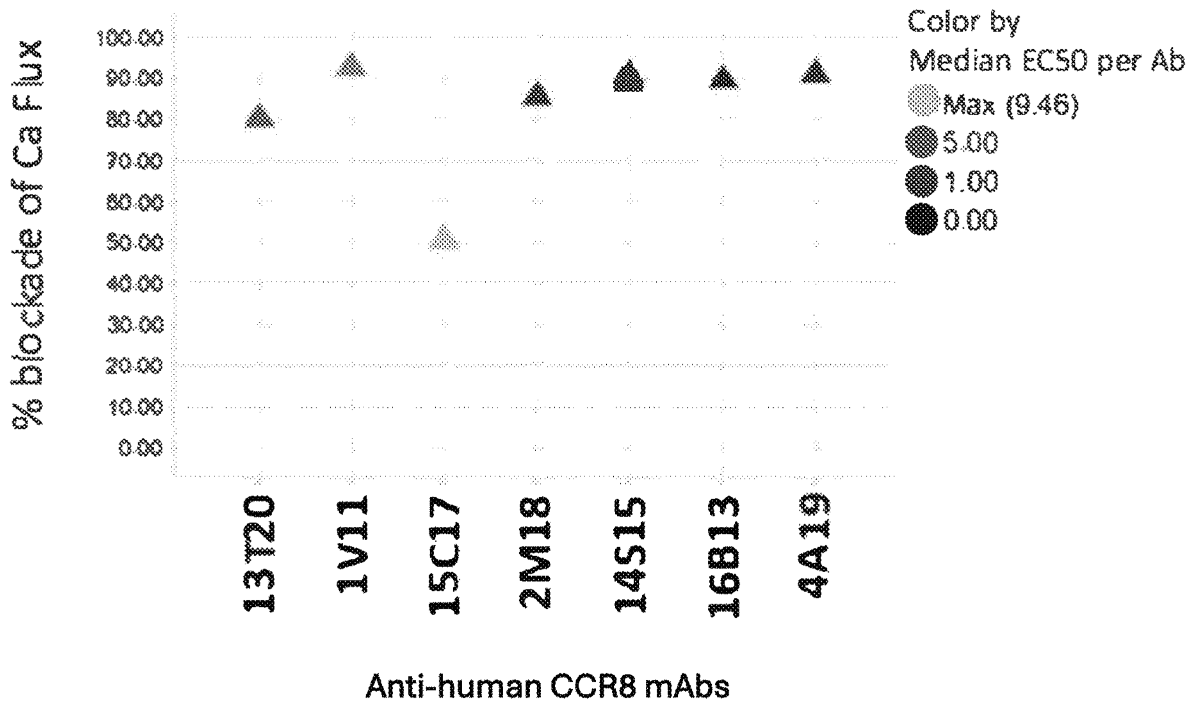
Figure 14C:
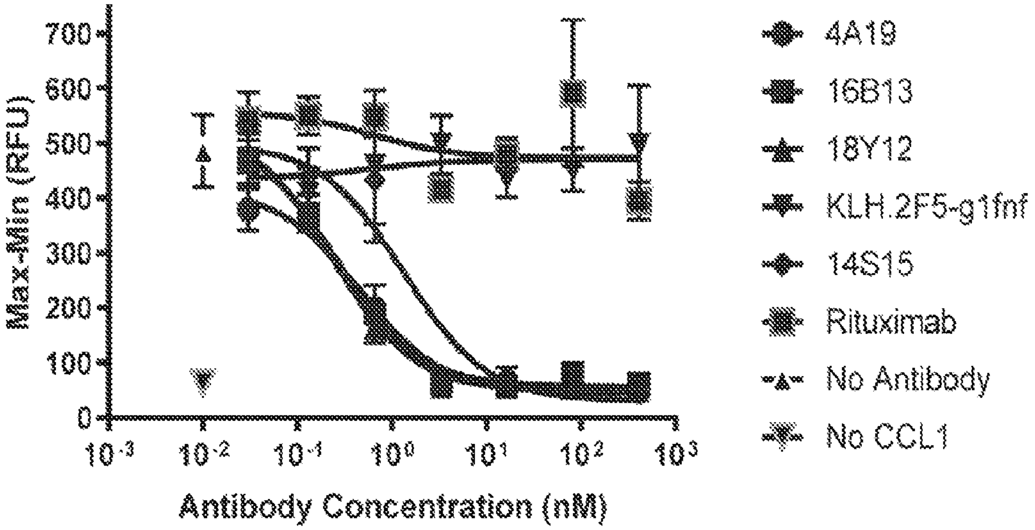

FIGS. 14A-14C show that anti-hCCR8 mAbs block the binding of human CCL1 (hCCL1) to hCCR8. A: Anti-hCCR8 mAbs exhibit varying capacities to block the binding of hCCL1 to hCCR8 on hCCR8-transfected CHO cells as assessed by inhibition of Ca flux. B: The percentage blockade of CCL1 signaling (CCL1-induced Ca flux) is shown for 7 selected anti-hCCR8 Abs. C: Ca flux-blocking $IC_{50}$ curves are shown for 4 selected anti-CCR8 mAbs.

Figure 15A:
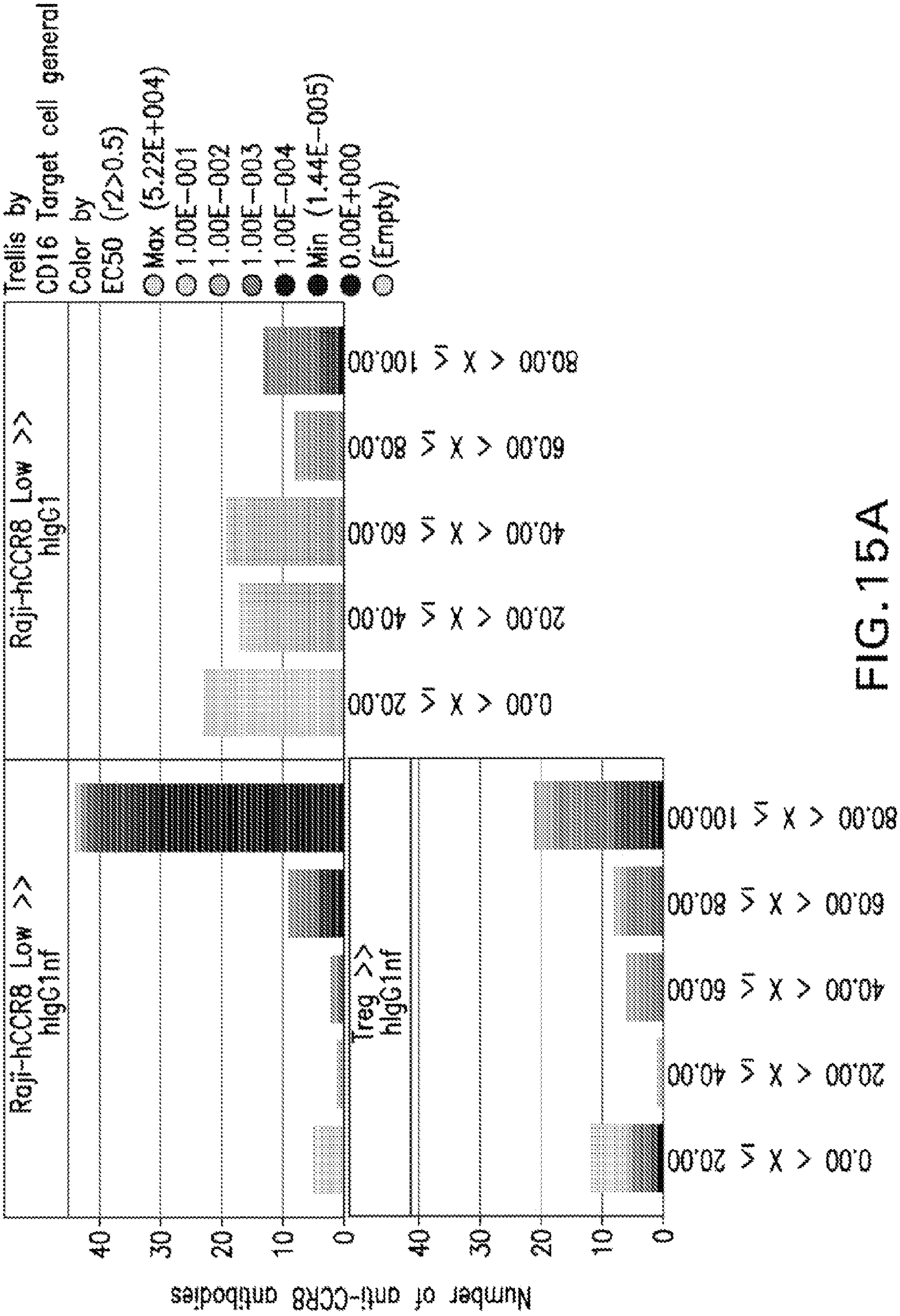
Figure 15B:
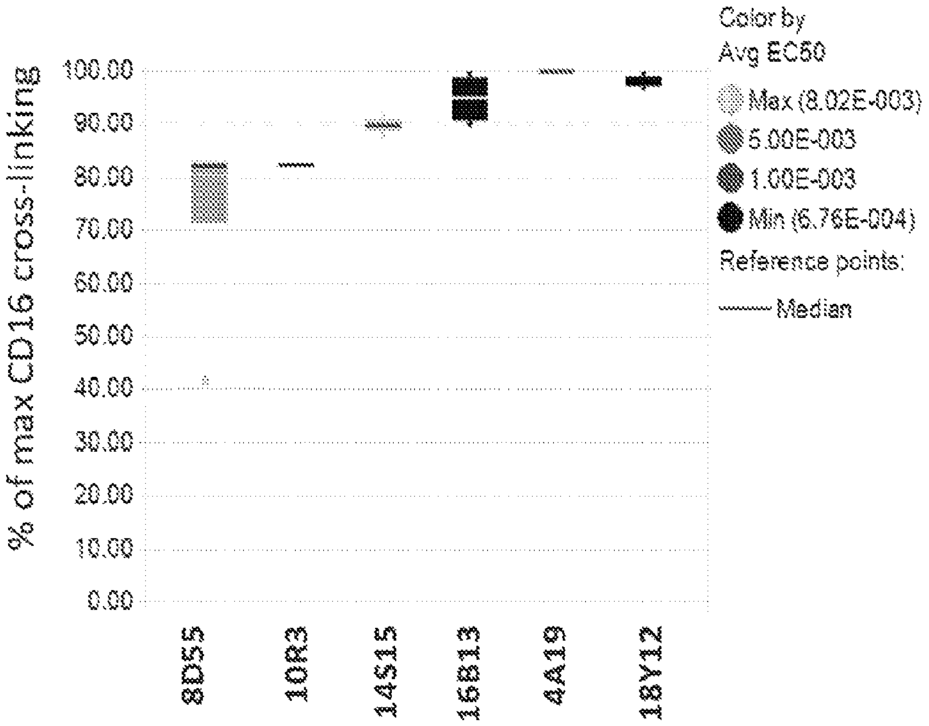

FIGS. 15A and 15B show that anti-hCCR8 mAbs mediate CD16 crosslinking of CD16 expression reporter cells, which reflects the ADCC potential of anti-CCR8 mAbs. Co-cultures of CD16-expressing luciferase reporter cells with CCR8-expressing Raji cells or activated Tregs were treated with anti-CCR8 Abs (with either nonfucosylated (nf) or wild-type hIgG1 backbones). A: A range of CD16 cross-linking capacities was observed. B: CD16 cross-linking using activated Treg as targets for a select set of anti-hCCR8 mAbs with the hIgG1-nf backbone is depicted.

Figure 16:
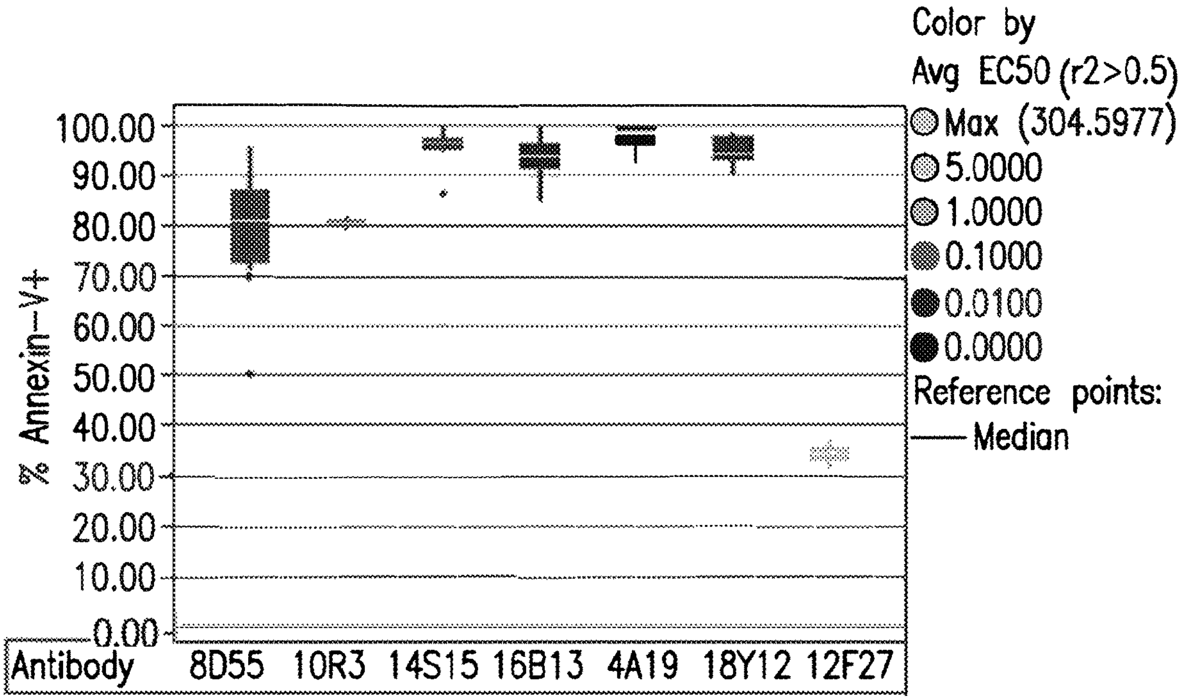

FIG. 16 shows that anti-CCR8 Abs mediate killing of activated Tregs by allogeneic NK cells. Activated Tregs were co-cultured with primed allogeneic NK cells and titrated anti-hCCR8 Abs. Cell death was measured by Annexin-V positivity on Tregs.

Figure 17A:
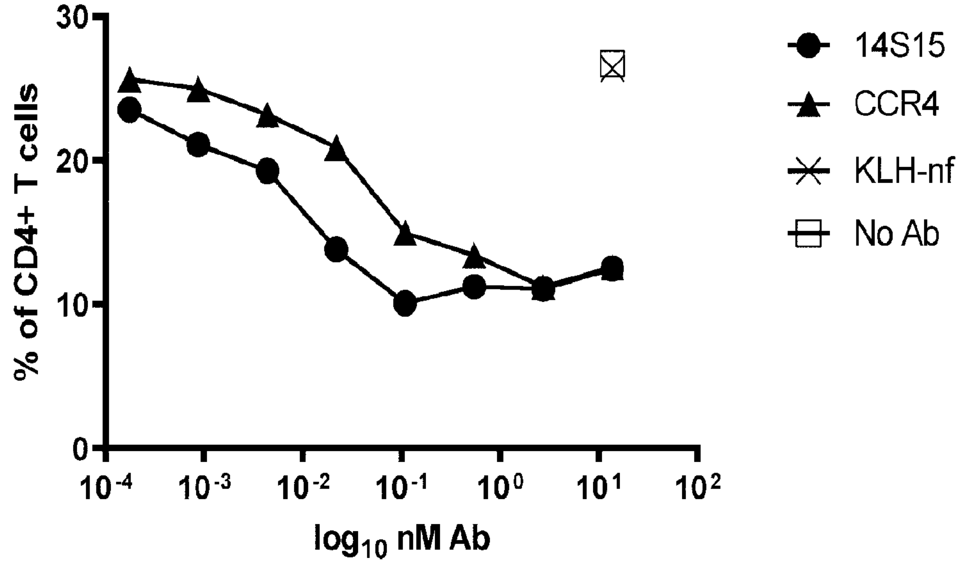
Figure 17B:
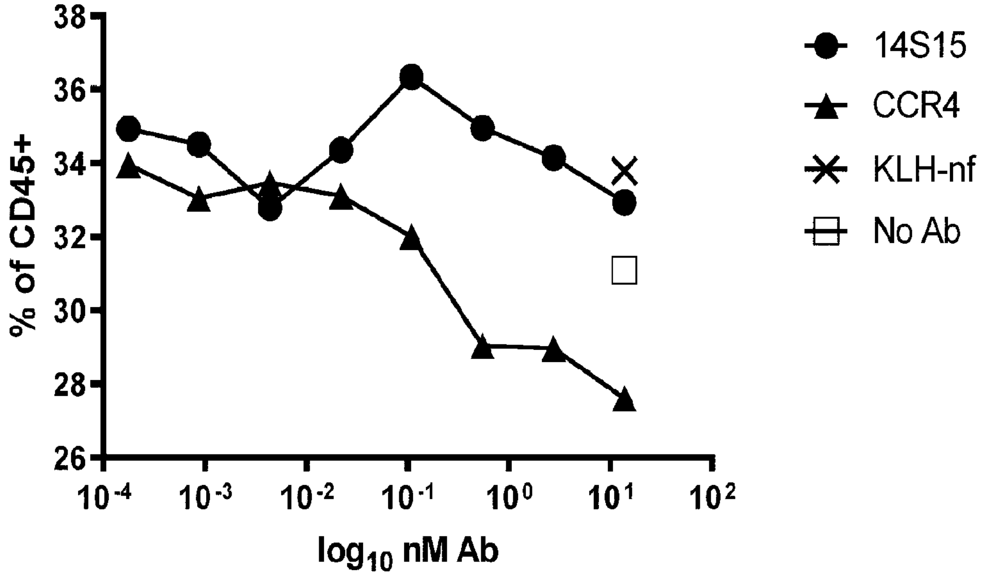

FIGS. 17A and 17B show that anti-CCR8 mAbs mediate killing of patient tumor Tregs by allogeneic NK cells in vitro. Enzymatically dissociated patient endometrial tumors were co-cultured with primed allogeneic NK cells for 24 hours at 37° C. The anti-CCR8 Ab, 14S15, specifically depleted patient tumor Tregs (FIG. 17A), but not conventional $CD4^+$ T cells (FIG. 17B). In contrast, an anti-CCR4 Ab (CCR4) mediated depletion of both Tregs and conventional $CD4^+$ T cells (FIGS. 17A and 17B).

FIGS. 18A-18I show that anti-hCCR8-hIgG1-nf Abs mediate $CCR8^+$ Treg depletion in ex vivo patient tumor slice culture system without the addition of allogeneic NK cells. A-C: Representative results for the depletion of peripheral blood Tregs (A), $CD4^+$ Tconv (B) and $CD8^+$ T cells (C) upon treatment with 14S15-IgG1-nf or anti-hCCR4-IgG1-nf in vitro. D-F: Representative plots from non-small cell lung carcinoma (NSCLC) tumor and allogeneic NK cell killing assays comparing 14S15-IgG1-nf (D), anti-hCCR4-IgG1-nf (E), and isotype (F) Abs. A-F: 14S15-IgG1-nf, closed circles; anti-hCCR4-IgG1-nf, squares; isotype IgG1-nf, open circles. G: Allogeneic NK and NSCLC tumor co-culture comparing 16B13-IgG1-nf to anti-hCCR8-inert and an isotype control Abs. G: isotype IgG1-nf, open circles; 14S15-IgG1-nf, closed circles; 14S15-IgG1-inert, triangles. H and I: Results from ex vivo primary intact tumor sections from renal cell carcinoma (H) and gastric cancer (I) cultured for 24 h in the presence of 16B13-IgG1-nf or IgG1-nf isotype control (3-5 technical replicates for each condition). H and I: isotype IgG1-nf, open circles; 14S15-IgG1-nf, closed circles. *$P<0.05$, ****$P<0.0001$. Ordinary one-way ANOVA with Tukey's multiple comparisons test (G). Mann-Whitney test (two-tailed) (G-I).

Figure 19:
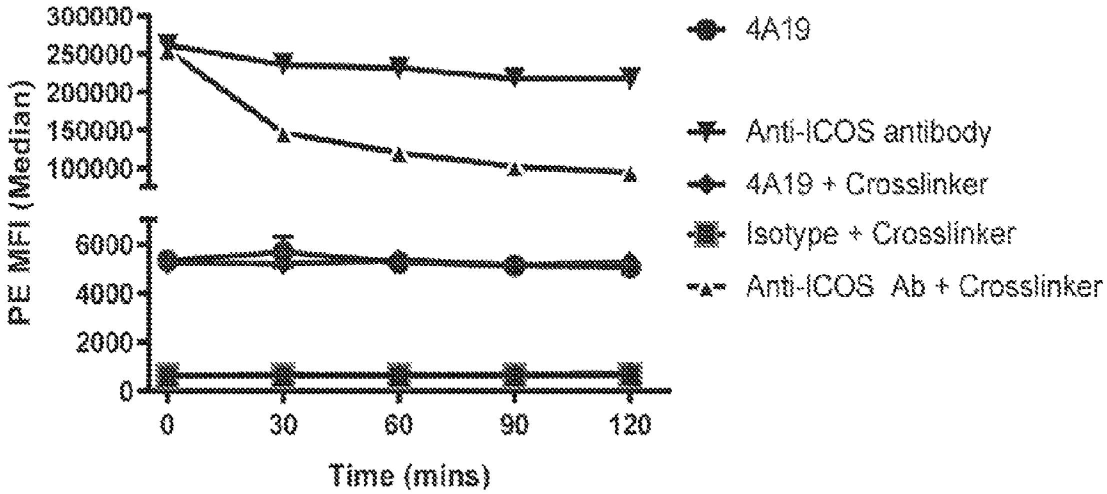

FIG. 19 shows that anti-CCR8 Abs, with or without cross-linking, do not induce CCR8 internalization on activated Tregs. Activated Tregs were incubated with the anti-CCR8 mAb 4A19, a positive control Ab (anti-ICOS), and an isotype control, with or without an anti-human Fc cross-linking Ab. CCR8 expression on the Treg surface was assessed at various times.

FIGS. 20A-20D show depletion of tumor Tregs by anti-CCR8 when digested patient tumors are co-cultured with allogeneic natural killer (NK) cells in vitro. A: MAb 4A19 (CCR8-nf) induced measurable depletion of patient tumor Tregs, more so than the depletion caused by a nonfucosylated anti-hCCR4 mAb (CCR4-nf). B: Conversely, the anti-CCR4-nf Ab, but not mAb 4A19, induced depletion of $CD4^+$ Teff cells. C: Neither anti-CCR8 nor anti-CCR4 depleted $CD8^+$ Teffs. D: In contrast to 4A19 (CCR8-nf), neither a control anti-keyhole limpet hemocyanin (KLH)-nf mAb with an irrelevant targeting arm (isotype) nor the 4A19 mAb with an inert backbone (CCR8-inert) depleted Tregs.

FIGS. 21A-21D show that anti-CCR8 inhibits growth of CT26 colon cancer in a mouse model. A: Treatment of CT26 colon cancer with anti-CCR8-mIgG2a, an anti-mCCR8 Ab having a mIgG2a isotype derived from BioLegend's rat anti-mCCR8 mAb, Clone SA214G2, significantly reduced tumor growth and increased the number of tumor-free mice. Individual tumor volumes are depicted. B: Changes in mean tumor volumes. C: Tumor Treg depletion was observed with the anti-CCR8 treatment, while the number of splenic Tregs was unaffected by anti-CCR8 treatment (D).

FIGS. 22A-22F show the effects of anti-CCR8 on T lymphocyte populations in mice having the CT26 colon adenocarcinoma as analyzed by flow cytometry. A: Percentage of CCR8-expressing $CD4^+FOXP3^+$ Tregs (Treg), $FOXP3^-CD4^+$ effector cells (CD4eff), and $CD8^+$ T (CD8T) cells in spleen, blood, tumor Tregs and skin. B: Percentage of CCR8-expressing Double Negative $CD4^-CD8^-$ (DN), Single Positive $CD4^+CD8^-$ (CD4 SP), Single Positive $CD4^-CD8^+$ (CD8 SP), and Double Positive $CD4^+CD8^+$ (DP) thymocytes. C: Percentage of $Foxp3^+$ Tregs in spleen, blood, tumor and skin following treatment with the anti-CCR8-mIgG2a mAb and an isotype control. D: Percentage of DP, CD8 SP, CD4 SP and DN thymocytes in the thymus following treatment with anti-CCR8-mIgG2a and an isotype control. E: Percentage of $CD4^+$ T cells in the skin following treatment with anti-CCR8-mIgG2a and an isotype control. F: Percentage of $CD8^+$ T cells in the skin following treatment with anti-CCR8-mIgG2a and an isotype control.

Figure 23A:
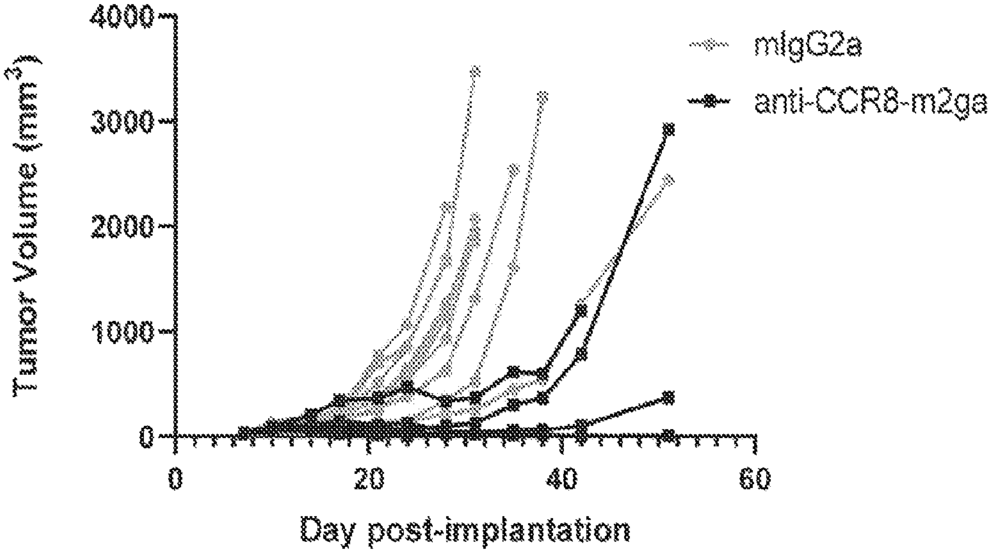
Figure 23B:
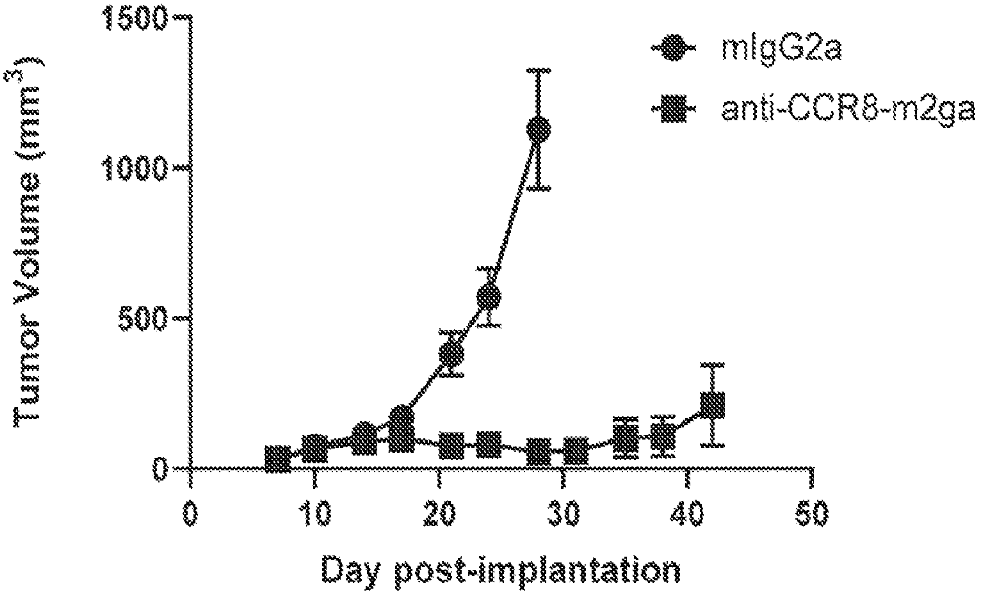

FIGS. 23A and 23B show that anti-CCR8 inhibits growth of MC38 colon cancer in a mouse model. A: Treatment of MC38 colon cancer with anti-CCR8-mIgG2a significantly reduced tumor growth and increased the number of tumor-free mice. B: Changes in mean tumor volumes.

FIGS. 24A-24D show that anti-mCCR8 Ab-induced Treg depletion leads to potent single agent efficacy and increased pharmacodynamic and pharmacokinetic responses in the MC38 colon cancer mouse model. A: Single dose of anti-mCCR8 mAb leads to a dose-dependent decrease in tumor volume, Treg (% $Foxp3^+CD4^+$) depletion (B), and an increase in the percentage of tumor-infiltrating $CD8^+$ T cells (C). Error bars indicate standard deviation of the mean. D: The anti-mCCR8 mAb demonstrates non-linear PK in the dosing range of 0.03 to 3 mg/kg.

Figure 25A:
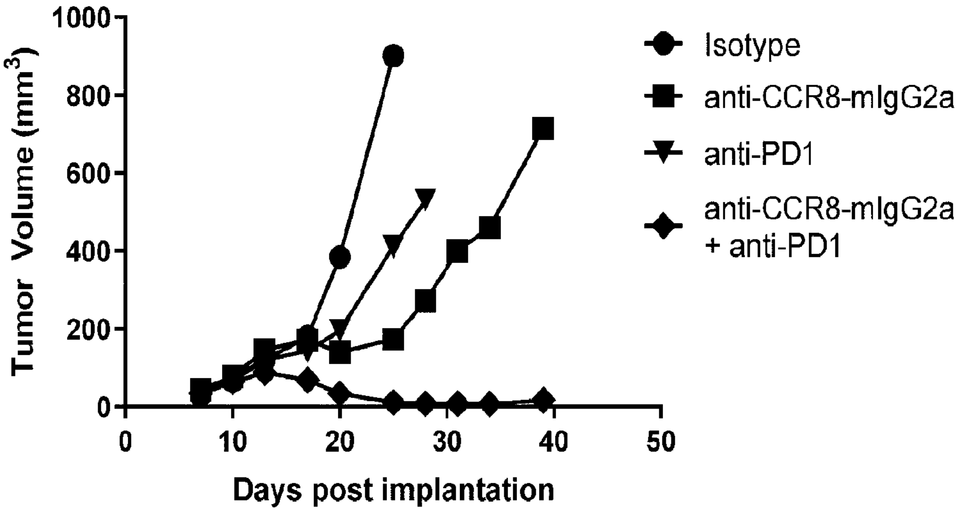
Figure 25B:
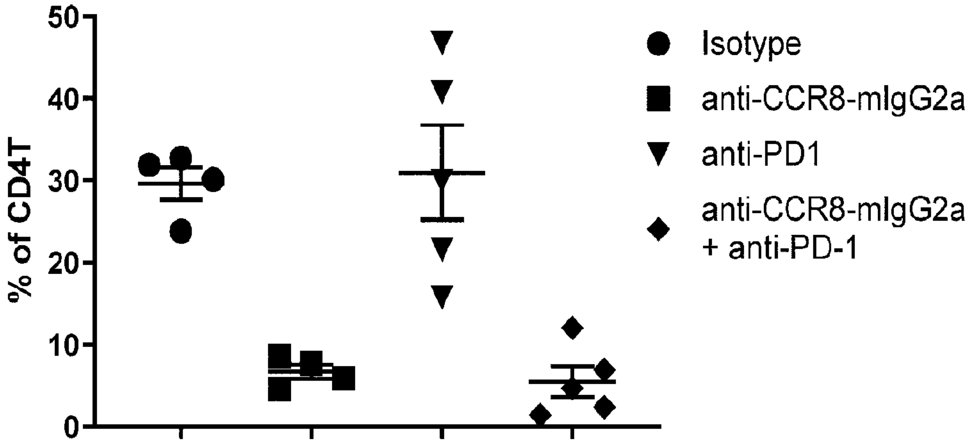
Figure 25C:
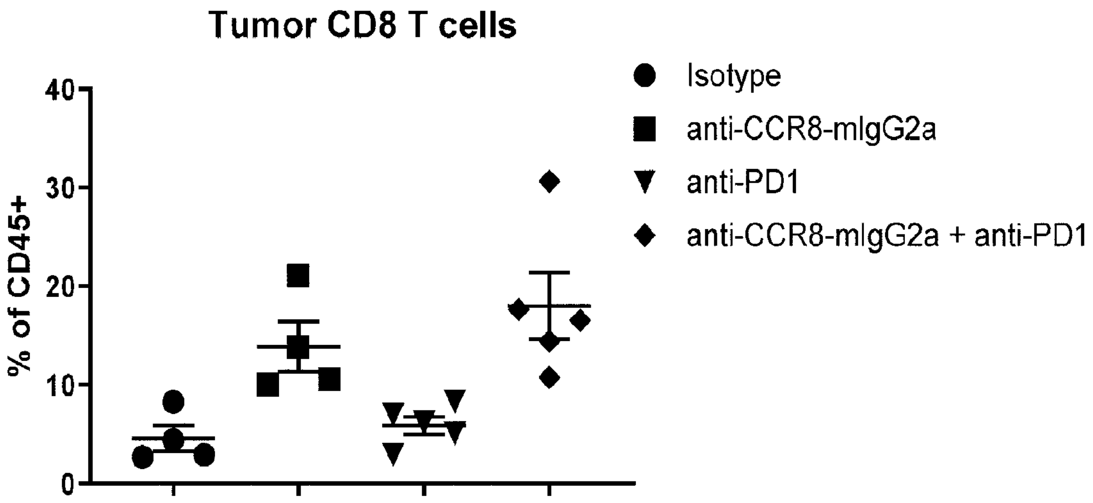

FIGS. 25A-25C show the effects on tumor growth of the combination of a mouse anti-mPD-1 Ab and a mouse anti-mCCR8 Ab compared to anti-PD-1 or anti-CCR8 Ab therapy alone, as measured by changes in the tumor volumes in a MB49 murine bladder cancer model. A: Anti-CCR8-mIgG2a and anti-PD-1 induce moderate and low levels, respectively, of tumor growth inhibition but in combination demonstrate synergistic efficacy in completely inhibiting tumor growth. B: Treatment with anti-CCR8-mIgG2a in the presence or absence of anti-PD-1 significantly decreased tumor Treg frequencies, but increased anti-tumor $CD8^+$ T cell frequencies (C).

Figure 26:
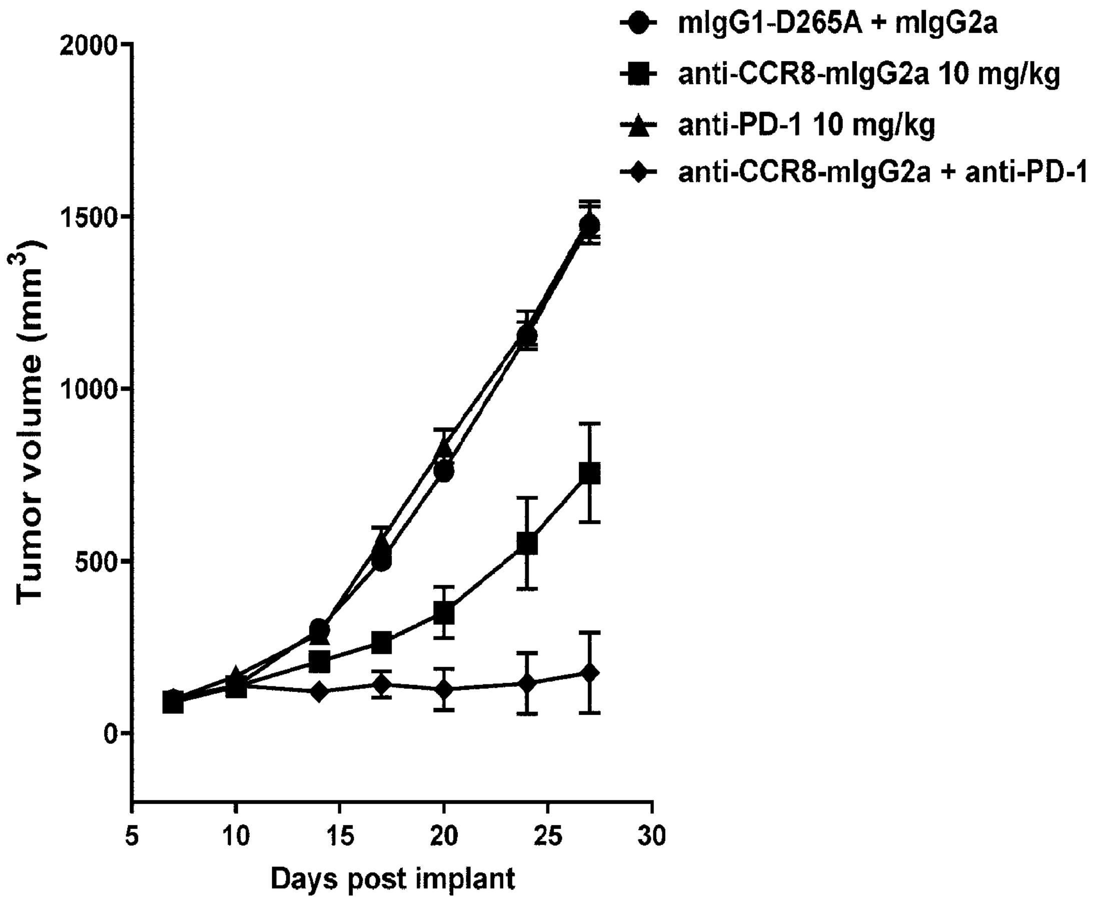

FIG. 26 shows the effects on tumor growth of the combination of a mouse anti-mPD-1 Ab and a mouse anti-mCCR8 Ab compared to anti-PD-1 or anti-CCR8 Ab therapy alone, as measured by changes in the tumor volumes in a 4T1 murine breast cancer model. Anti-PD-1 shows no activity in inhibiting tumor growth, with tumor growth closely mirroring that in the mice treated with a combination of negative control Abs, while anti-CCR8-mIgG2a induces a moderate level of tumor growth inhibition. Anti-CCR8 interacts synergistically with anti-PD-1 to almost completely inhibit tumor growth.

Figure 27A:
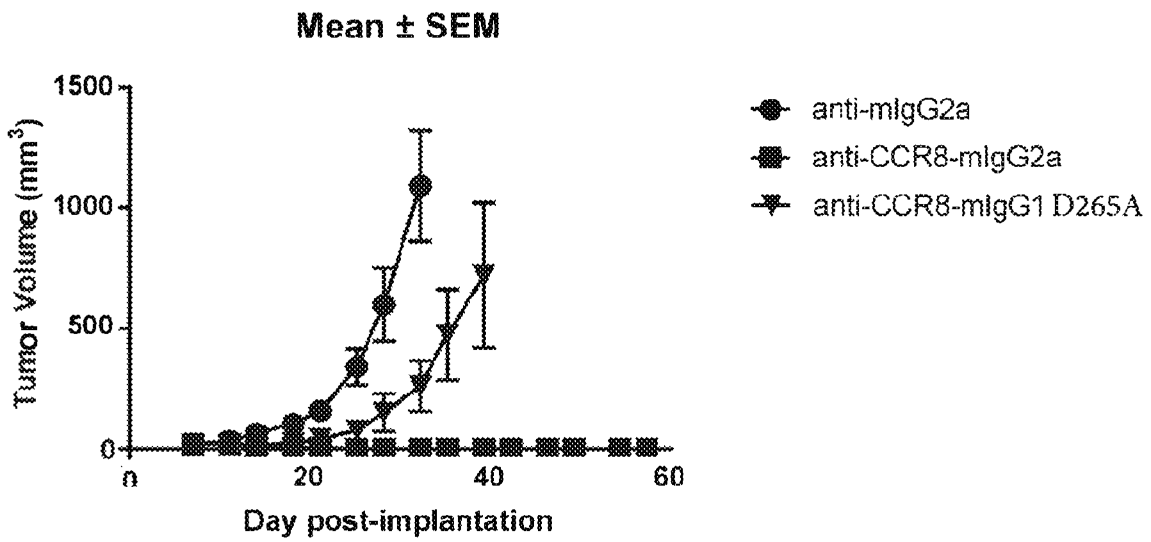
Figure 27B:
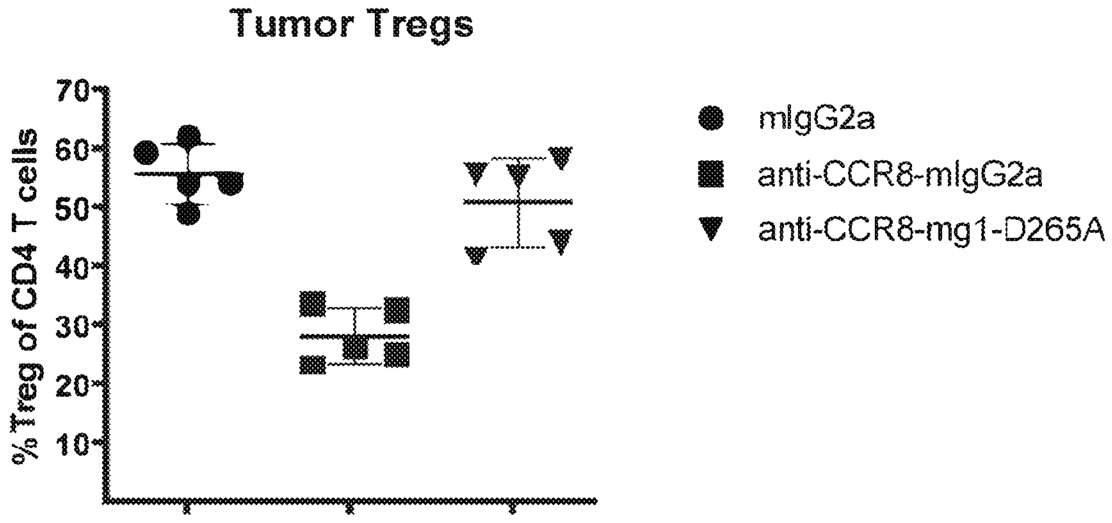

FIGS. 27A and 27B show that an anti-mCCR8 Ab comprising an inert Fc constant region exhibits anti-tumor activity in an SA1N fibrosarcoma mouse model. A: Anti-CCR8-mIgG2a treatment potently reduced tumor growth with all of the 9 mice being tumor-free by Day 25 post-implantation. Blockade of CCR8 with an Fc-inert Ab (Anti-CCR8-mIgG1-D265A) partially reduced tumor growth. B: Depletion of tumor Tregs by treatment with anti-CCR8 was achieved with anti-CCR8-mIgG2a treatment but not with the Fc-inert anti-CCR8-mIgG-1-D265A.

FIGS. 28A-28F show that Fc receptor engagement is required for anti-mCCR8 Ab activity in the MC38 tumor model. Mean (A) and individual growth curves of MC38 tumors implanted in C57BL/6 mice treated with anti-CCR8-mIgG2a (n=10) (B), anti-CCR8-mIgG1-D265A (n=10) (C) or IgG2a isotype control (n=10) (D) on Days 7, 10 and 14 post-tumor implantation at 200 μg/mouse/treatment. E: MC38 tumors were harvested on Day 15 post-implantation and Treg depletion was assessed by flow cytometry (n=5 per group) $P<0.01$. One-way ANOVA Kruskal-Wallis test with Dunn's multiple comparisons. F: Proportions of $Ccr8^{+/+}$ and $Ccr8^{-/-}$ donor-derived Tregs in MC38 tumors and peripheral tissues at 13 days post-MC38 tumor implantation. $P<0.01$. Two-way ANOVA followed by Bonferroni's multiple comparisons test.

FIGS. 29A-29I show that anti-CCR8-mIgG2a induces productive memory responses in a heterologous re-challenge model. Mice implanted with CT26 tumors were randomized once tumors reached 100-120 $mm^3$. A-C: Growth curves and Treg depletion in CT26 tumors treated with (A) anti-CCR8-mIgG2a (n=8), (B) anti-CTLA4-mIgG2a (n=8) or (C) mIgG2a isotype control (n=8) on 1, 4, and 8 days after randomization at 0.2 mg/mouse/treatment. Six tumors from each group were analyzed by flow cytometry to assess Treg depletion (D) and frequency of AH1-$Tetramer^+$ $CD8^+$ T cells (E) on day 9 post randomization. F: Frequency of AH1-$Tetramer^+$ $CD8^+$ T cells in the blood 92 days after treatment. G: Frequency of AH1-$Tetramer^+$ $CD8^+$ effector memory T cells (TEM) in the blood 5 days after challenge with LM-AH1A5. H and I: Intracellular cytokine staining for (H) $IFN\gamma^+$ and (I) polyfunctional $IFN\gamma^+TNF\alpha^+$ $CD8^+$ T cells in the spleen after stimulation with AH1A5 peptide for 5 h. ns, not significant; *$P<0.05$, **$P<0.01$. One-way ANOVA Kruskal-Wallis test with Dunn's multiple comparison's (D-I).

Figure 30A:
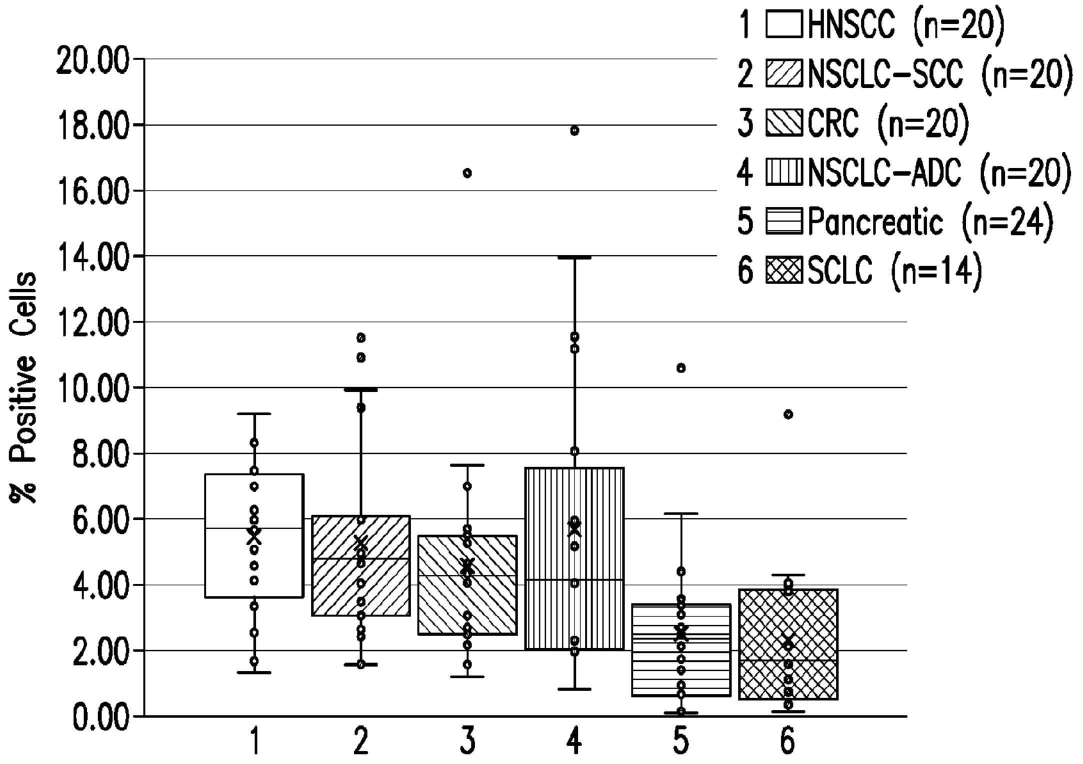
Figure 30B:
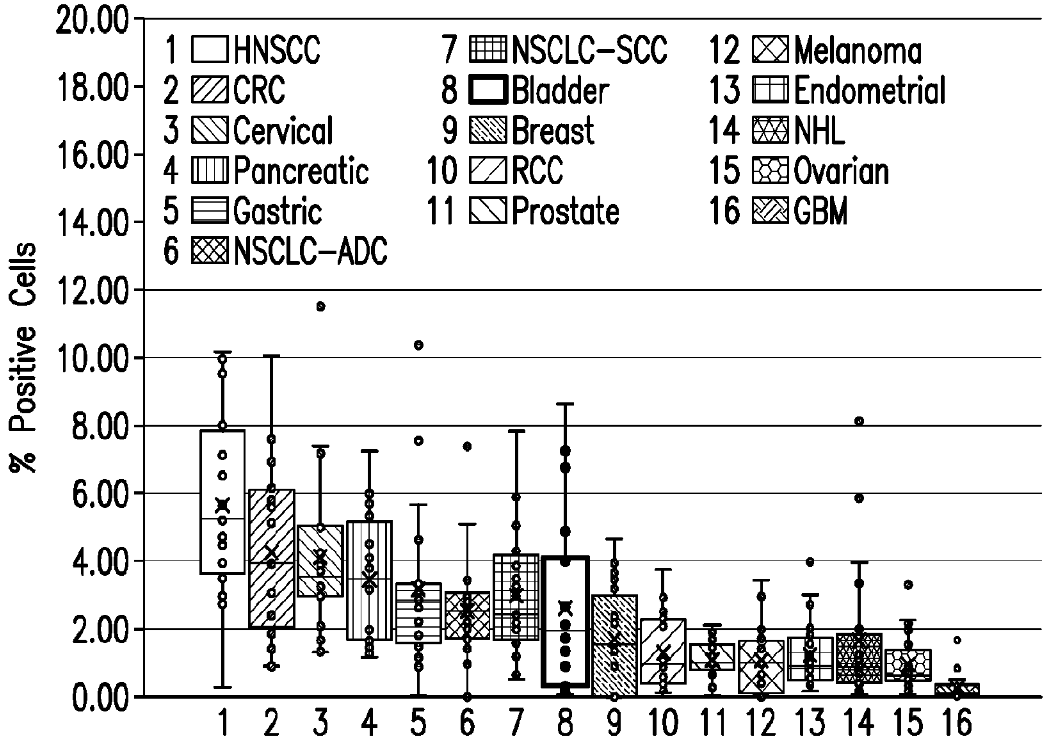

FIGS. 30A and 30B show the variable expression of CCR8 in multiple human cancers. Immunohistochemistry (IHC) was conducted in 17 cancer types/subtypes from two sets of samples (full-size tissue sections and MTB sets). A: Full-size tissue sections showing whole-slide image analysis of $CCR8^+$ cells in formalin-fixed paraffin-embedded (FFPE) slides of 6 tumor types/subtypes with 14-24 samples per tumor type. B: Multi-tumor blocks (MTB) set showing 16 tumor types/subtypes with 20 cases/tumor types. Each MTB contained 5 cases of a single indication per FFPE block and 1 hyperplastic tonsil sample as positive control.

DETAILED DESCRIPTION OF THE INVENTION

The present invention relates to mAbs that bind specifically and with high affinity to CCR8 expressed on a cell surface, and to methods for treating cancers in a subject comprising administering to the subject an anti-CCR8 Ab as monotherapy or in combination with an anticancer agent such as an immune checkpoint inhibitor, a chemotherapeutic agent and/or radiation therapy. The effects of CCR8-mediated Treg depletion alone and in combination with PD-1 blockade in potently inhibiting tumor growth are demonstrated herein in multiple, diverse preclinical mouse tumor models.

Terms

In order that the present disclosure may be more readily understood, certain terms are first defined. As used in this application, except as otherwise expressly provided herein, each of the following terms shall have the meaning set forth below. Additional definitions are set forth throughout the application.

"Administering", "administer" or "administration" refers to the physical introduction of a composition comprising a therapeutic agent to a subject, using any of the various methods and delivery systems known to those skilled in the art. A preferred route for administration of therapeutic Abs such as anti-CCR8 and anti-PD-1 Abs is intravenous (IV) administration. Other routes of administration include subcutaneous (SC), intraperitoneal (IP), intramuscular (IM), spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an Ab of the invention can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

An "antibody" (Ab) shall include, without limitation, a glycoprotein immunoglobulin (Ig) which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region of an IgG Ab comprises three constant domains, $C_{H1}$, $C_{H2}$ and $C_{H3}$. Each light chain comprises a light chain variable region (abbreviated herein as $V_L$) and a light chain constant region. The light chain constant region of an IgG Ab comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from aminoterminus to carboxy-terminus in the following order: FR1-CDR1-FR2-CDR2-FR3-CDR3-FR4. The variable regions of the heavy and light chains contain a binding domain that interacts with an antigen. A variety of methods have been used to delineate the CDR domains within an Ab, including the Kabat, Chothia, AbM, contact, and IMGT definitions. The constant regions of the Abs may mediate the binding of the Ig to host tissues or factors, including various cells of the immune system (e.g., effector cells) and the first component (C1q) of the classical complement system.

As used herein, and in accordance with conventional usage, an Ab that is described as comprising "a" heavy chain and/or "a" light chain refers to an Ab that comprise "at least one" of the recited heavy and/or light chains, and thus will encompass Abs having two or more heavy and/or light chains. Specifically, Abs so described will encompass conventional Abs having two substantially identical heavy chains and two substantially identical light chains. Ab chains may be substantially identical but not entirely identical if they differ due to post-translational modifications, including, for example, C-terminal cleavage of lysine residues, and alternative glycosylation patterns.

An Ig may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM, IgG1, or IgG4) that is encoded by the heavy chain constant region genes. The term "antibody" includes, by way of example, both naturally occurring and non-naturally occurring Abs, monoclonal and polyclonal Abs, chimeric and humanized Abs, human or nonhuman Abs, wholly synthetic Abs, and single chain Abs. A nonhuman Ab may be humanized partially or fully by recombinant methods to reduce its immunogenicity in man. Where not expressly stated, and unless the context indicates otherwise, the term "antibody" also includes an antigen-binding fragment or an antigen-binding portion of any of the aforementioned Ig's, and includes a monovalent and a divalent fragment or portion, and a single chain Ab.

An "isolated" Ab refers to an Ab that is substantially free of other Abs having different antigenic specificities (e.g., an isolated Ab that binds specifically to CCR8 is substantially free of Abs that bind specifically to antigens other than CCR8, such as Abs that bind to CCR4). An isolated Ab that binds specifically to human CCR8 (hCCR8) may, however, have cross-reactivity to other antigens, such as CCR8 polypeptides from different species such as mouse and cynomolgus monkey. Moreover, in certain contexts, an isolated Ab may also mean an Ab that is purified so as to be substantially free of other cellular material and/or chemicals. By comparison, an "isolated" nucleic acid refers to a nucleic acid composition of matter that is markedly different, i.e., has a distinctive chemical identity, nature and utility, from nucleic acids as they exist in nature. For example, an isolated DNA, unlike native DNA, is a free-standing portion of a native DNA and not an integral part of a larger structural complex, the chromosome, found in nature. Further, an isolated DNA, unlike native DNA, can be used as a PCR primer or a hybridization probe for, among other things, measuring gene expression and detecting biomarker genes or mutations for diagnosing disease or predicting the efficacy of a therapeutic. In addition, in certain contexts, an isolated nucleic acid may mean a nucleic acid that is purified so as to be substantially free of other cellular components or other contaminants, e.g., other cellular nucleic acids or proteins, using standard techniques well known in the art.

The term "monoclonal" Ab (mAb) refers to a non-naturally occurring preparation of Ab molecules of single molecular composition, i.e., Ab molecules whose primary sequences are essentially identical and which exhibit a single binding specificity and affinity for a particular epitope. A mAb is an example of an isolated Ab. MAbs may be produced by hybridoma, recombinant, transgenic or other techniques known to those skilled in the art.

A "chimeric" Ab refers to an Ab in which the variable regions are derived from one species and the constant regions are derived from another species, such as an Ab in which the variable regions are derived from a mouse Ab and the constant regions are derived from a human Ab.

A "human" mAb (HuMAb) refers to a mAb having variable regions in which both the framework and CDR regions are derived from human germline immunoglobulin sequences. Furthermore, if the Ab contains a constant region, the constant region also is derived from human germline immunoglobulin sequences. The human Abs of the invention may include amino acid residues not encoded by human germline immunoglobulin sequences (e.g., mutations introduced by random or site-specific mutagenesis in vitro or by somatic mutation in vivo). However, the term "human" Ab, as used herein, is not intended to include Abs in which CDR sequences derived from the germline of another mammalian species, such as a mouse, have been grafted onto human framework sequences. The terms "human" Abs and "fully human" Abs are used synonymously.

A "humanized" mAb refers to a mAb in which some, most or all of the amino acids outside the CDR domains of a non-human mAb are replaced with corresponding amino acids derived from human immunoglobulins. In one embodiment of a humanized form of an Ab, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the Ab to bind to a particular antigen. A "humanized" Ab retains an antigenic specificity similar to that of the original Ab.

An "anti-antigen" Ab refers to an Ab that binds specifically to an antigen. For example, an anti-CCR8 Ab is an Ab that binds specifically to CCR8, whereas an anti-PD-1 Ab is an Ab that binds specifically to PD-1. As used herein, an "anti-PD-1/anti-PD-L1" Ab is an Ab that is used to disrupt the PD-1/PD-L1 signaling pathway, which may be an anti-PD-1 Ab or an anti-PD-L1 Ab.

An "antigen-binding portion" or "antigen-binding fragment" of an Ab refers to one or more fragments of an Ab, e.g., a mAb, that retain the ability to bind specifically to the antigen bound by the whole Ab.

"Antibody-dependent cell-mediated cytotoxicity" ("ADCC") refers to an in vitro or in vivo cell-mediated cytotoxic activity in which nonspecific effector cells that express Fc receptors (FcRs) on the effector cell surface (e.g., natural killer (NK) cells, macrophages, neutrophils and eosinophils) recognize the Fc region of the Abs bound to surface antigens on a target cell and actively lyses the target cell. In principle, any effector cell with an activating FcR can be triggered to mediate ADCC. Therapeutic Abs of the present invention for use in human subjects are preferably anti-hCCR8 Abs that have been specifically modified to mediate enhanced ADCC activity against cells expressing CCR8. ADCC activity of an Ab can be measured as described, for example, in any of Examples 17-20.

"Enhanced ADCC" or "enhanced ADCC activity" of a modified Ab of the present invention refer to ADCC activity levels greater than ADCC induced by an unmodified Ab. A modified anti-CCR8 IgG1 Ab of the present invention exhibiting enhanced ADCC, for example, is a modified form of the Ab that induces greater ADCC than the Ab with its native IgG1 constant domain. A nonfucosylated (nf) mAb is an example of a modified Ab that induces enhances ADCC via improved binding of IgG to activating FcγRIIIA In certain embodiments, the level of enhancement in ADCC activity is at least a 2-fold, preferably at least a 10-fold, more preferably at least a 100-fold reduction in the $EC_{50}$ e.g., as measured by a reduction in the $EC_{50}$ for cell lysis in a NK cell lysis assay, for example, the NK cell lysis assay described in Example 17.

A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream.

"C-C Motif Chemokine Receptor 8" ("CCR8"; also known in the art as, for example, CY6, TER1, CCR-8, CKRL1, CDw198, CMKBR8, GPRCY6, CMKBRL2, or CC-CKR-8) is a seven-transmembrane GPCR; this GPCR has been shown to be expressed primarily on intratumoral $FOXP3^{hi}$ Tregs. The term "CCR8" as used herein includes human CCR8 (hCCR8), variants, isoforms, species homologs of hCCR8 such as mouse CCR8 (mCCR8), and analogs having at least one common epitope with hCCR8. The complete hCCR8 and mCCR8 amino acid sequences can be found under GENBANK® Accession Nos. AAI07160.1 and NP_031746.1, respectively.

A "cell surface receptor" refers to molecules or complexes of molecules expressed on the surface of a cell that are capable of receiving a signal and transmitting the signal across the plasma membrane of the cell.

"Effector function" refers to the interaction of an Ab Fc region with an FcR or ligand, or a biochemical event that results therefrom. Exemplary "effector functions" include Clq binding, complement dependent cytotoxicity (CDC), FcR binding, FcγR-mediated effector functions such as ADCC and Ab dependent cell-mediated phagocytosis (ADCP), and down-regulation of a cell surface receptor (e.g., the B cell receptor; BCR). Such effector functions generally require the Fc region to be combined with a binding domain (e.g., an Ab variable domain).

An "Fc receptor" or "FcR" is a receptor that binds to the Fc region of an immunoglobulin. FcRs that bind to an IgG Ab comprise receptors of the FcγR family, including allelic variants and alternatively spliced forms of these receptors. The FcγR family consists of three activating receptors (FcγRI, FcγRIII, and FcγRIV in mice; FcγRIA, FcγRIIA, and FcγRIIIA in humans) and one inhibitory receptor (FcγRIIB) Various properties of human FcγRs are summarized in Table 1. The majority of innate effector cell types co-express one or more activating FcγR and the inhibitory FcγRIIB, whereas NK cells selectively express one activating Fc receptor (FcγRIII in mice and FcγRIIIA in humans) but not the inhibitory FcγRIIB in mice and humans.

TABLE 1

Properties of Human FcγRs

| Fcγ | Allelic variants | Affinity for human IgG | Isotype preference | Cellular distribution |
|---|---|---|---|---|
| FcγRI | None described | High ($K_D$ ~10 nM) | IgG1 = 3 > 4 >> 2 | Monocytes, macrophages, activated neutrophils, dendritic cells? |
| FcγRIIA | H131 | Low to medium | IgG1 > 3 > 2 > 4 | Neutrophils, monocytes, macrophages, eosinophils, |
| | R131 | Low | IgG1 > 3 > 4 > 2 | dendritic cells, platelets |
| FcγRIIIA | V158 | Medium | IgG1 = 3 >> 4 > 2 | NK cells, monocytes, |
| | F158 | Low | IgG1 = 3 >> 4 > 2 | macrophages, mast cells, eosinophils, dendritic cells? |
| FcγRIIB | I232 | Low | IgG1 = 3 = 4 > 2 | B cells, monocytes, |
| | T232 | Low | IgG1 = 3 = 4 > 2 | macrophages, dendritic cells, mast cells |

An "Fc region" (fragment crystallizable region), "Fc domain" or "Fc" refers to the C-terminal region of the heavy chain of an Ab that mediates the binding of the Ig to host tissues or factors, including binding to FcRs located on various cells of the immune system (e.g., effector cells) or to the first component (C1q) of the classical complement system. Thus, the Fc region is a polypeptide comprising the constant region of an Ab excluding the first constant region Ig domain. In IgG, IgA and IgD Ab isotypes, the Fc region is composed of two identical protein fragments, derived from the second ($C_{H2}$) and third ($C_{H3}$) constant domains of the Ab's two heavy chains; IgM and IgE Fc regions contain three heavy chain constant domains ($C_H$ domains 2-4) in each polypeptide chain. For IgG, the Fc region comprises Ig domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 to the C-terminus of the heavy chain, wherein the numbering is according to the EU index as in Kabat. The $C_{H2}$ domain of a human IgG Fc region extends from about amino acid 231 to about amino acid 340, whereas the $C_{H3}$ domain is positioned on C-terminal side of a $C_{H2}$ domain in an Fc region, i.e., it extends from about amino acid 341 to about amino acid 447 of an IgG. As used herein, the Fc region may be a native sequence Fc or a variant Fc.

"Fucosylation" and "nonfucosylation," as used herein, refer to the presence and absence, respectively, of a core fucose residue on the N-linked glycan at position N297 of an Ab. Unless otherwise indicated, or is clear from the context, amino acid residue numbering in the Fc region of an Ab is according to the EU numbering convention (the EU index as in Kabat et al., 1991).

An "immune response" refers to a biological response within a vertebrate against foreign agents, which response protects the organism against these agents and diseases caused by them. The immune response is mediated by the action of a cell of the immune system (for example, a T lymphocyte, B lymphocyte, NK cell, macrophage, eosinophil, mast cell, dendritic cell or neutrophil) and soluble macromolecules produced by any of these cells or the liver (including Abs, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response.

The term "monotherapy" refers to a single type of treatment such as, for example, the administration to a patient of a single drug, or the use of radiation therapy or surgery alone, to treat a disease or condition. The administration of a drug by itself does not constitute monotherapy if in the same course of treatment it is preceded or followed by another type of treatment for the disease or condition, such as the administration of an additional drug.

In contrast, "combination therapy" refers to a treatment modality that combines at least two types of therapy such as, for example, the administration to a patient of two or more drugs, or the administration of a drug plus radiation therapy or surgery, to treat a disease or condition. These two or more treatments need not be delivered concurrently to the patient but are part of the same course of treatment. In certain embodiments, the different therapies are administered simultaneously. In other embodiments, the administration of one therapy overlaps with the administration of at least one other therapy. In further embodiments, the different therapies are administered sequentially.

"Potentiating an immune response" means increasing the effectiveness or potency of an immune response, which could be an existing or an induced immune response, in a subject. This increase in effectiveness and potency may be achieved, for example, by reducing or overcoming mechanisms that suppress an endogenous host immune response, by stimulating mechanisms that enhance the endogenous host immune response, or by enhancing the immune response elicited by an immunotherapeutic agent.

"Programmed Death-1" (PD-1) refers to an immunoinhibitory receptor belonging to the CD28 family that is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 amino acid sequence can be found under GENBANK® Accession No. U64863.

"Programmed Death Ligand-1" (PD-L1) is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GENBANK® Accession No. Q9NZQ7.

A "subject" includes any human or nonhuman animal. The term "nonhuman animal" includes, but is not limited to, vertebrates such as nonhuman primates, sheep, dogs, and rodents such as mice, rats and guinea pigs. In preferred embodiments, the subject is a human. The terms "subject" and "patient" are used interchangeably herein.

A "therapeutically effective amount" or "therapeutically effective dosage" of a drug or therapeutic agent is any amount of the drug or agent that, when used alone or in combination with another therapeutic agent, protects a subject against the onset of a disease or promotes disease regression evidenced by a decrease in severity of disease symptoms, an increase in frequency and duration of disease symptom-free periods, a prevention or reduction of impairment or disability due to the disease affliction, or otherwise an amelioration of disease symptoms in the subject. In addition, the terms "effective" and "effectiveness" with regard to a treatment includes both pharmacological effectiveness and physiological safety. Pharmacological effectiveness refers to the ability of the drug to promote disease regression, e.g., cancer regression, in the patient. Physiological safety refers to an acceptable level of toxicity, or other adverse physiological effects at the cellular, organ and/or organism level (adverse effects) resulting from administration of the drug. The efficacy of a therapeutic agent can be evaluated using a variety of methods known to the skilled practitioner, such as in human subjects during clinical trials, in animal model systems predictive of efficacy in humans, or by assaying the activity of the agent in in vitro assays.

By way of example for the treatment of tumors, a therapeutically effective amount of an anti-cancer agent preferably inhibits cell growth or tumor growth by at least about 20%, preferably by at least about 40%, more preferably by at least about 60%, even more preferably by at least about 80%, and still more preferably by about 100% relative to untreated subjects. The ability of an agent or treatment to inhibit tumor growth can be evaluated in an animal model system such as any of the CT26 colon adenocarcinoma, MC38 colon adenocarcinoma, SA1N fibrosarcoma, 4T1 mammary carcinoma, and MB49 bladder carcinoma mouse tumor models, which is predictive of efficacy in human tumors. Alternatively, tumor growth inhibition can be measured by evaluating the ability of the agent or treatment to inhibit cell growth in vitro using assays known to the skilled practitioner. In preferred embodiments of the invention, tumor regression may be observed and continue for a period of at least about 30 days in a human subject, more preferably at least about 60 days, or even more preferably at least about 6 months.

A therapeutically effective amount of a drug includes a "prophylactically effective amount," which is any amount of the drug that, when administered alone or in combination with an another therapeutic agent to a subject at risk of developing a disease (e.g., a subject having a pre-malignant condition who is at risk of developing a cancer) or of suffering a recurrence of the disease, inhibits the development or recurrence of the disease (e.g., a cancer). In preferred embodiments, the prophylactically effective amount prevents the development or recurrence of the disease entirely. "Inhibiting" the development or recurrence of a disease means either lessening the likelihood of the disease's development or recurrence, or preventing the development or recurrence of the disease entirely.

"Treatment" or "therapy" of a subject refers to any type of intervention or process performed on, including the administration of an active agent to, the subject with the objective of reversing, alleviating, ameliorating, inhibiting, slowing down or preventing the onset, progression, development, severity or recurrence of a symptom, complication or condition, or biochemical indicia associated with a disease.

As used herein, the indefinite articles "a" or "an" should be understood to refer to "one or more" of any recited or enumerated component.

The term "about", when applied to numeric value, a refers to a value that is reasonably close to the stated value and within an acceptable error range as determined by one of ordinary skill in the art, which will depend in part on how the value is measured or determined, i.e., the limitations of the measurement system. For example, "about" can mean a range of plus or minus 50% of a stated reference value, preferably a range of plus or minus 25%, or more preferably a range of plus or minus 10%. When particular values are provided in the application, the meaning of "about", unless otherwise stated, should be understood to be within an acceptable error range for that particular value according to the practice in the art.

The term "substantially the same" or "essentially the same" refers to a sufficiently high degree of similarity between two or more numeric values, compositions or characteristics that one of skill in the art would consider the difference between these values, compositions or characteristics to be of little or no biological and/or statistical significance within the context of the property being measured. The difference between numeric values being measured may, for example, be less than about 50%, preferably less than about 25%, and more preferably less than about 10%.

As described herein, any concentration range, percentage range, ratio range or integer range is to be understood to include the value of any integer within the recited range and, when appropriate, fractions thereof (such as one tenth and one hundredth of an integer), unless otherwise indicated.

Various aspects of the invention are described in further detail in the following subsections.

Figure 1A:
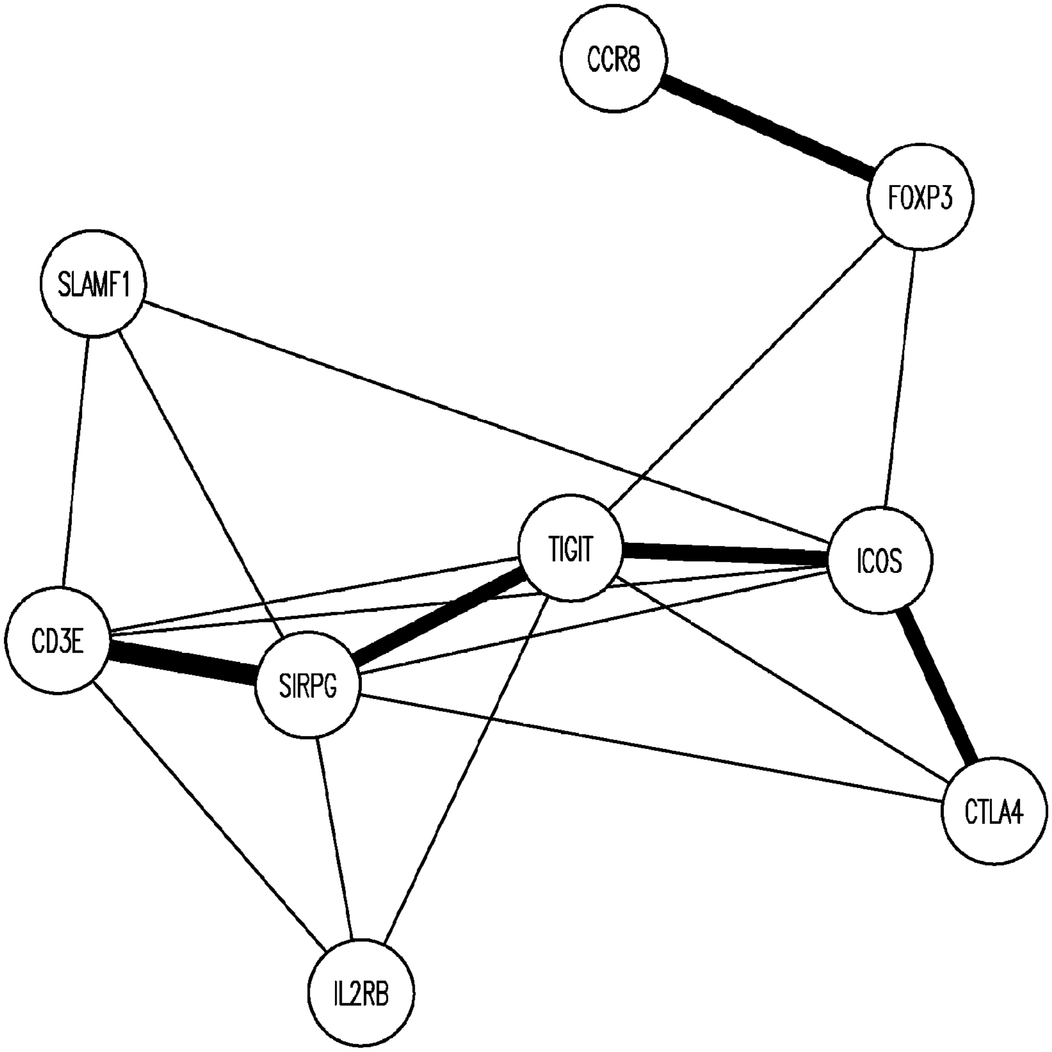
FIGS. 1A-1C show analyses of human CCR8 and FOXP3 gene-gene correlations in The Cancer Genome Atlas (TCGA). A: Mutual rank-based network of gene-gene correlation across all non-heme TCGA tumor RNA-seq identifies CCR8 as a Treg-selective marker. B: Analysis of hepatocellular carcinoma (HCC) single cell RNA-seq demonstrates that CCR8 is selectively expressed on $FOXP3^{high}$ lymphocytes in HCC tumor samples. C: Spearman correlation analysis performed in $FOXP3^{+}$ T lymphocytes shows that CCR8 expression is associated with higher levels of FOXP3 expression.
Figure 1B:
Figure 1C:
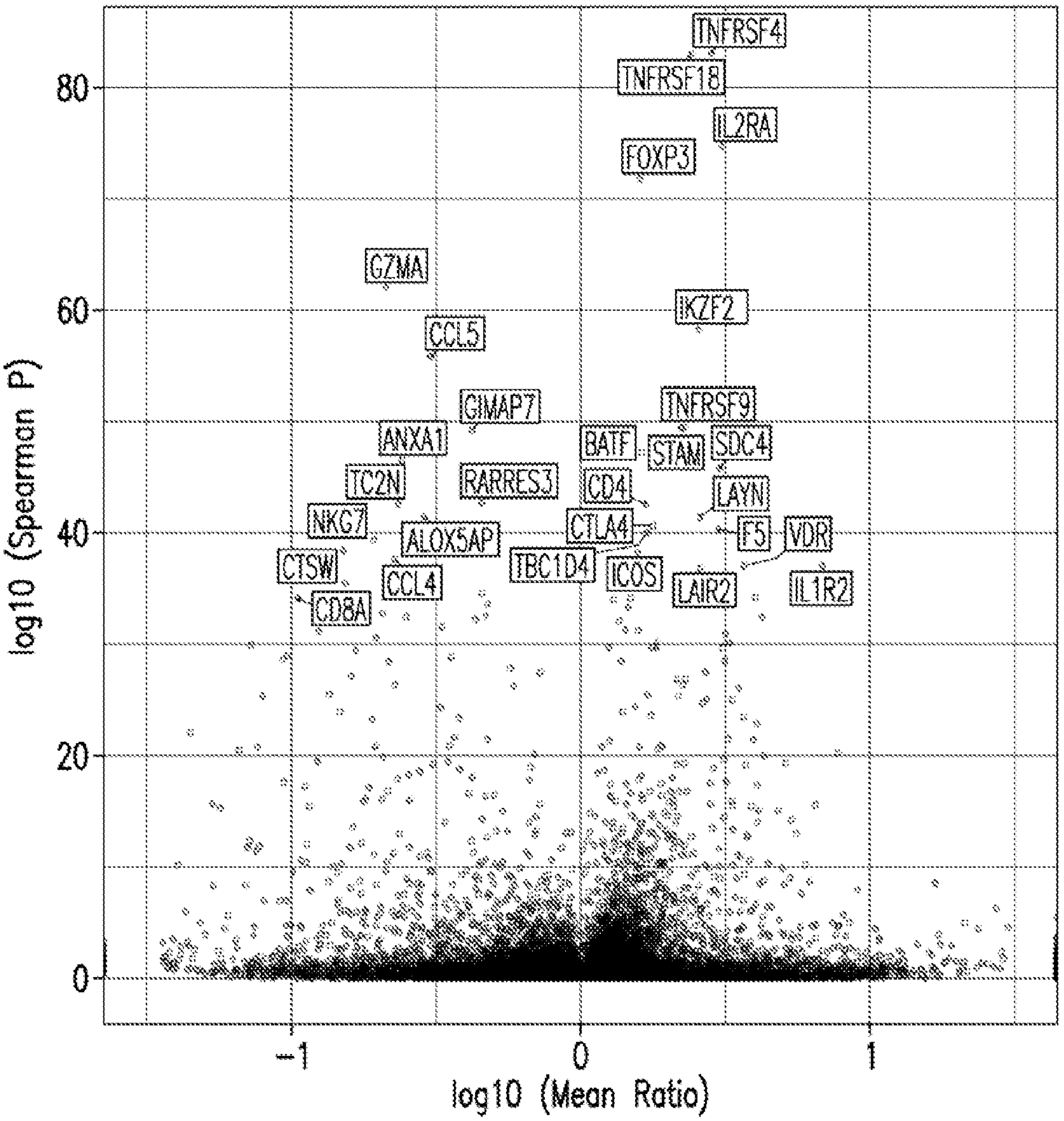

Expression of CCR8 Specifically in Highly Immunosuppressive Tumor-Infiltrating Tregs A variety of experiments reported herein demonstrate that CCR8 is expressed specifically by Tregs in human tumors, and unlike CCR4, a Treg depletion target currently undergoing clinical trials, CCR8 is selectively expressed on suppressive tumor Tregs and minimally on proinflammatory Teffs. Analysis of human CCR8 and FOXP3 gene-gene correlations in The Cancer Genome Atlas (TCGA; National Cancer Institute, 2021) (Example 1) showed that CCR8 expression has the highest correlation with FOXP3 (master transcriptional regulator of Tregs) in most cancer types (FIG. 1A). CCR8 is expressed on tumor FOXP3$^{hi}$ Tregs, but rarely observed on Tregs and Teffs in the peripheral blood. CCR8 is also selectively expressed on FOXP3$^{hi}$ lymphocytes in HCC tumor samples but not in FOXP3$^{mid}$ and FOXP3$^{neg}$ CD8 and CD4 Teffs in patient tumors (FIG. 1B). CCR8 expression is associated with higher levels of FOXP3 expression and canonical markers of Tregs (IL2RA, IKZF2, BATF) whereas lower expression of CCR8 is associated with cytotoxic T cell markers (GZMA, CD8A; FIG. 1C).

Figure 2A:
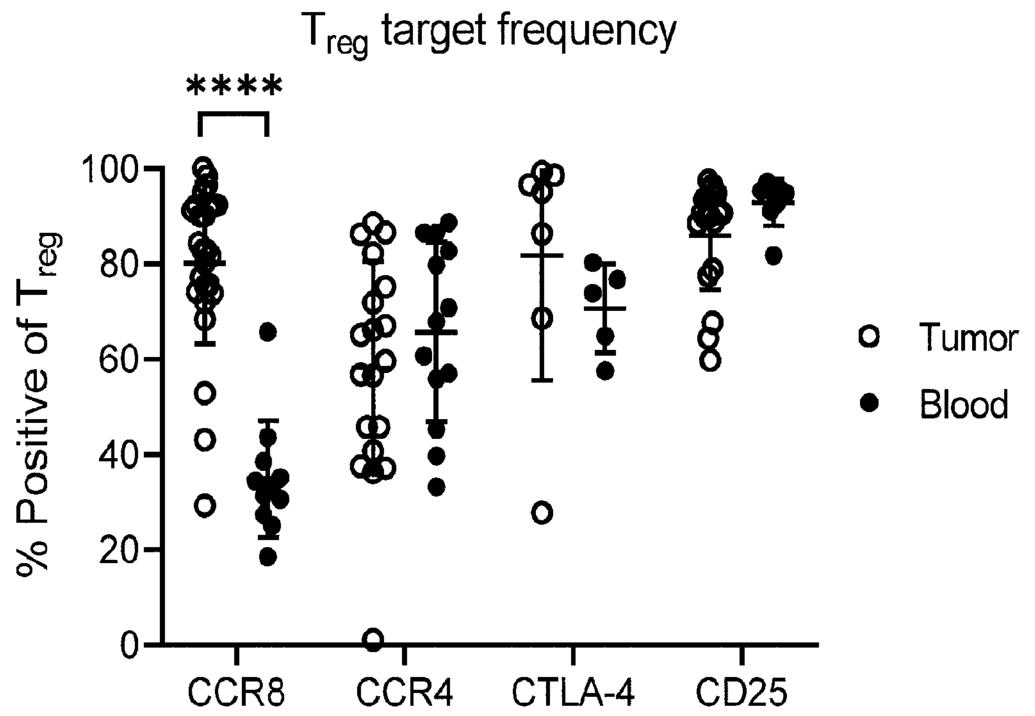
FIGS. 2A-2F show that CCR8 expression, compared to other Treg-targeted molecules, is enriched on tumor Tregs. A: Flow cytometry analysis of CCR8, CCR4, CTLA-4 and CD25 positive frequencies in Tregs from tumor and blood of cancer patients (colorectal, kidney, lung, and melanoma) (n=8-18). B: Relative expression levels (MFI) of Treg targets on $CD4^{+}FOXP3^{+}$ Tregs from the blood (n=6-10) and tumors (n=7-20) of cancer patients. C-E: Treg target frequencies on $CD4^{+}$ Tconv from tumors (C) and blood (D), and $CD8^{+}$ T cells from tumors (E) (n=7-17) and peripheral blood samples (F) (n=5-13) of cancer patients. Not all markers were analyzed for all patients, and not all patients have matching blood samples. *P<0.05, P<0.01, *P<0.001, ****P<0.0001. A-B: Two-way ANOVA followed by Bonferroni's multiple comparisons test; C-F: One-way ANOVA Kruskal-Wallis test followed by Dunn's multiple comparisons.
Figure 2B:
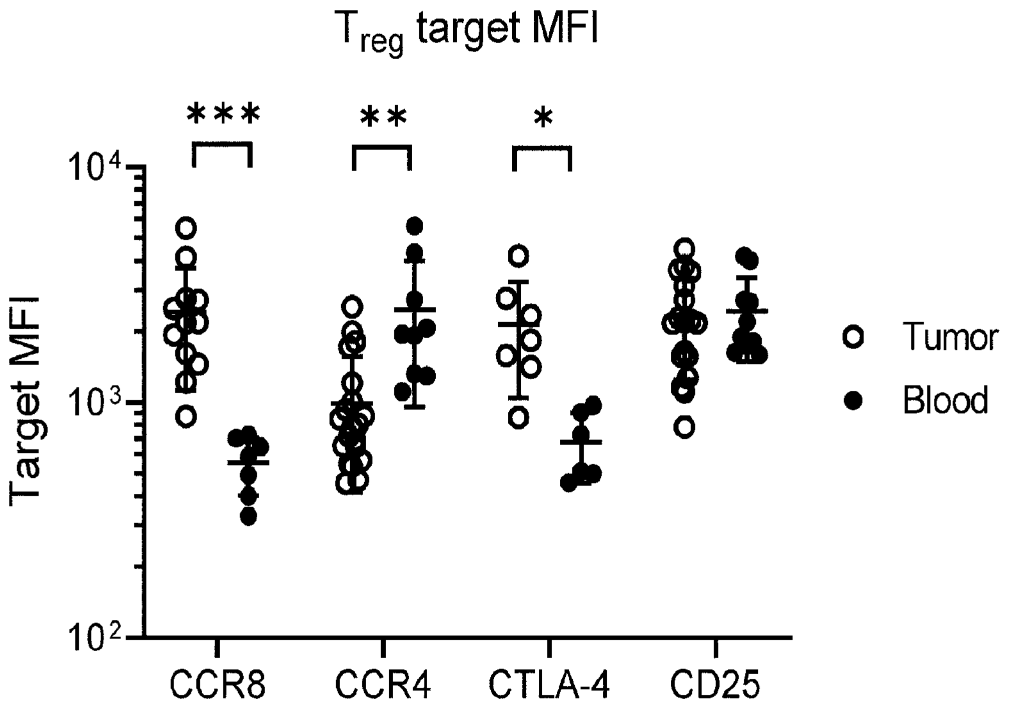

Comparing the expression profiles of different Treg-associated molecules (Example 3), CCR8 was shown to be more highly expressed on tumor-associated FOXP3$^+$ Tregs than on Treg from patient-matched blood, whereas there was little difference in expression of CCR4, CTLA-4, and CD25 on Tregs from tumor and blood (FIG. 2A). The high per-cell abundance of CCR8 on FOXP3$^+$ tumor Tregs compared to peripheral blood Tregs (FIG. 2B), coupled with the low frequency of expression of CCR8 on CD4+ Tconv (FIGS. 2C and D) and CD8$^+$ T cells (FIGS. 2E and F) in both tumor and peripheral blood suggest that CCR8 represents a highly selective therapeutic marker for targeting tumor Tregs with a a low risk of compromising anti-tumor Teff cell populations.

Figure 3A:
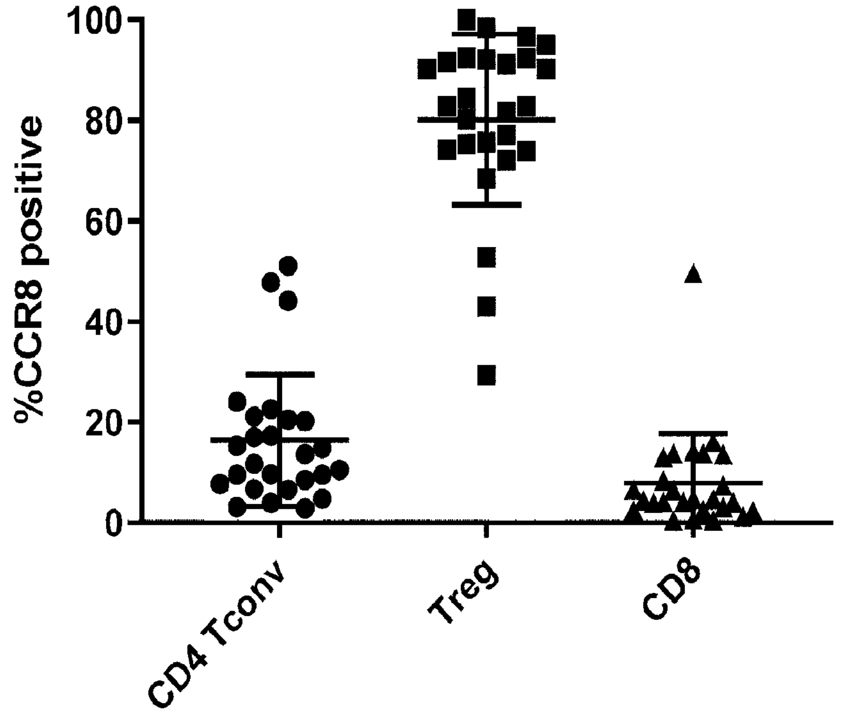
FIGS. 3A-3C show flow cytometry analyses which demonstrate that CCR8 is highly expressed on tumor-infiltrating Tregs. The level of expression of CCR8 was measured in different T cell populations. A: Percentage of tumor-infiltration T lymphocyte subsets expressing CCR8. A significantly higher frequency of tumor-infiltrating Tregs expresses CCR8 compared to conventional $CD4^{+}FOXP3^{-}$ (CD4 Tconv) T cells and $CD8^{+}$ T cells (CD8). B: Mean fluorescence intensity (MFI) of a PE-conjugated anti-CCR8 Ab bound to tumor-infiltrating T lymphocyte subsets. Tumor Tregs also express higher levels of CCR8 on a per cell basis as compared to CD4 Tconv and CD8 cells. C: Comparison of Treg CCR8 expression levels on $CCR8^{+}$ Tregs in the blood and tumor tissue of cancer patients. There is a low level of expression of CCR8 on Tregs in the peripheral blood compared to a significantly higher level on tumor-infiltrating Tregs.
Figure 3B:
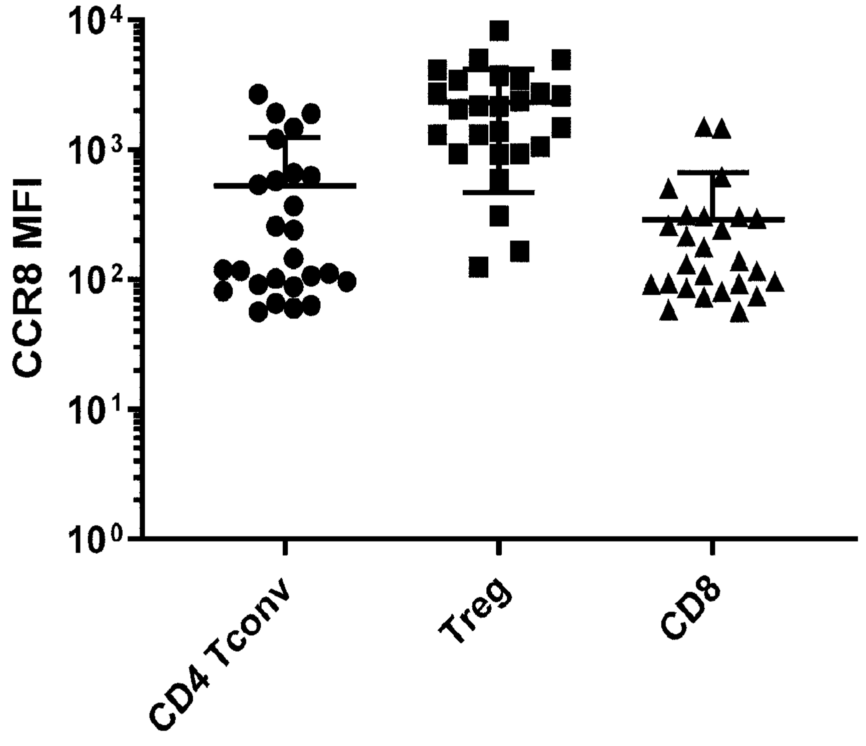
Figure 3C:
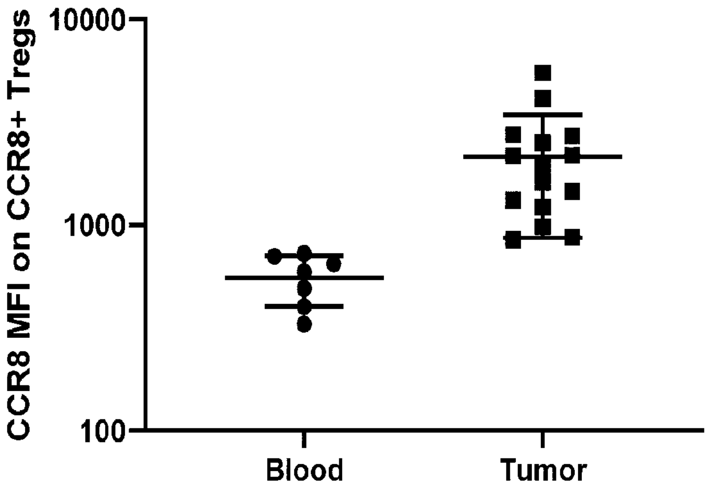

Flow cytometric analysis of the level of expression of CCR8 in different subsets of T lymphocytes associated with human tumors (Example 4) showed that CCR8 is expressed by a high proportion of tumor-resident Tregs (median 82%) as defined by FOXP3 (FIG. 3A). In contrast, a much lower proportion of tumor-infiltrating CD4$^+$T cells and CD8$^+$ T cells express CCR8 (medians 12.65% and 4.55%, respectively; FIG. 3B). Whereas a small proportion of CD4 Tconv cells express CCR8, the expression level of CCR8 on a per cell basis is significantly higher on Tregs than on CD4 Tconv cells (median MFI 2106 vs. 132, $P<0.0001$), while CD8$^+$ T cells express negligible levels of CCR8 (FIG. 3B). Tregs in the peripheral blood was also shown to express CCR8 but at a significantly lower level than on tumor-infiltrating Tregs (FIG. 3C).

Figure 4A:
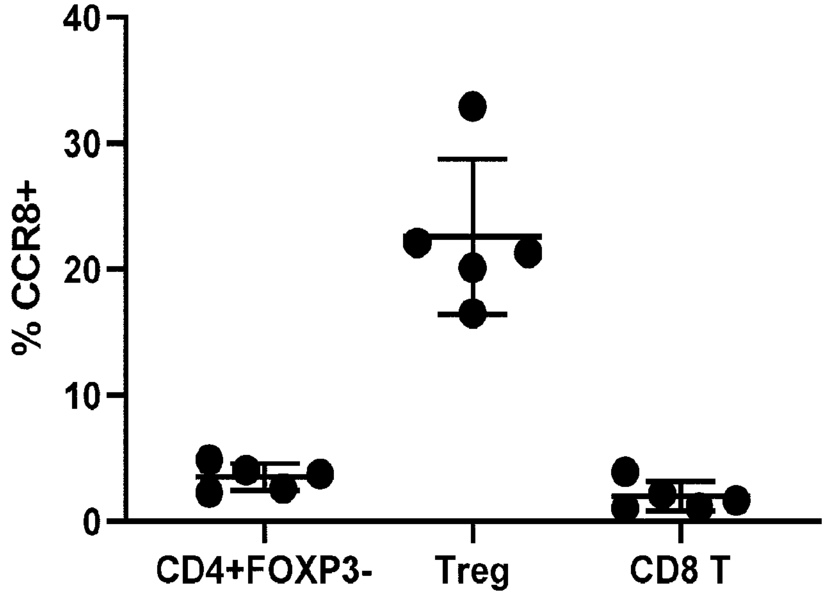
FIGS. 4A-4D show that CCR8 is differentially expressed on different Treg subpopulations. A: Percentage of cells within different T cell populations in PBMCs from healthy subjects expressing CCR8. CCR8 is predominantly expressed on peripheral Tregs. B: Percentage of cells within different Treg subpopulations in healthy subjects expressing CCR8. Within the Treg population, CCR8 is expressed more highly in the effector memory population (EM) and to a lesser degree in central memory cells (CM), with very little CCR8 expressed in naïve Tregs. C: Percentage of cells within conventional CD4 Tconv cells expressing CCR8. There is little CCR8 expression in any subpopulation of these CD4 Tconv cells. D: Mean fluorescence intensity (MFI) of anti-CCR8 Ab bound to $CCR8^{+}$ Tregs from peripheral blood or tumor-infiltrating Tregs from cancer patients. In cancer patients, there is higher CCR8 expression on a per cell basis on tumor-infiltrating Tregs than on Tregs from peripheral blood.
Figure 4B:
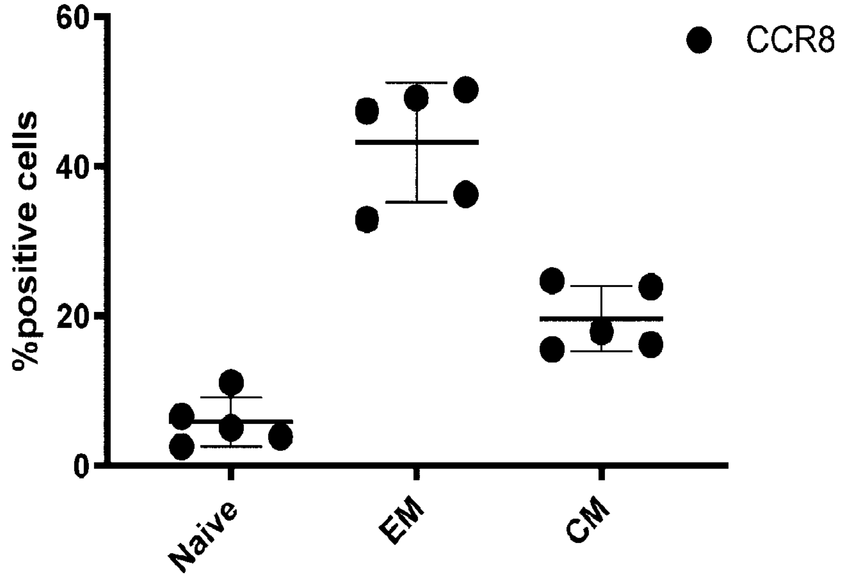
Figure 4C:
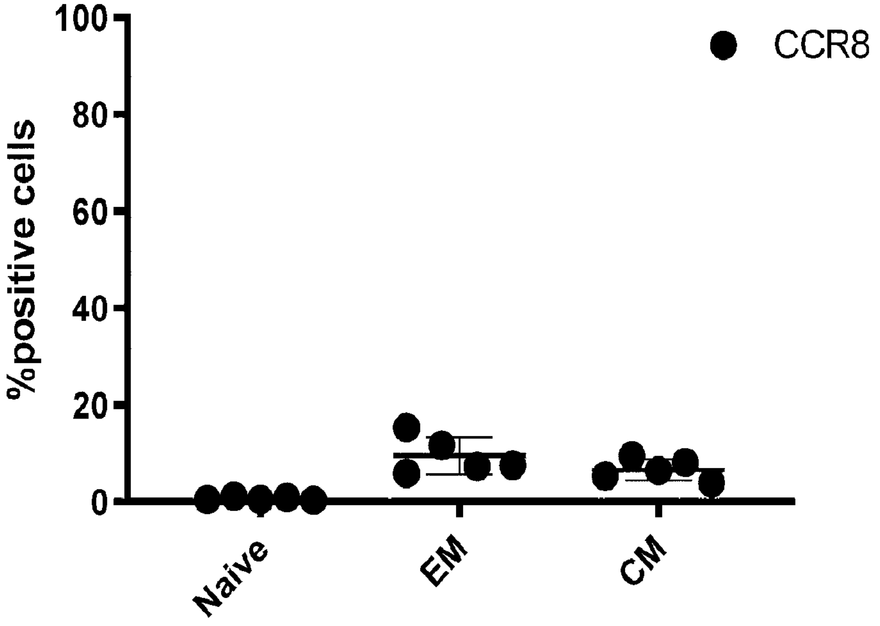
Figure 4D:
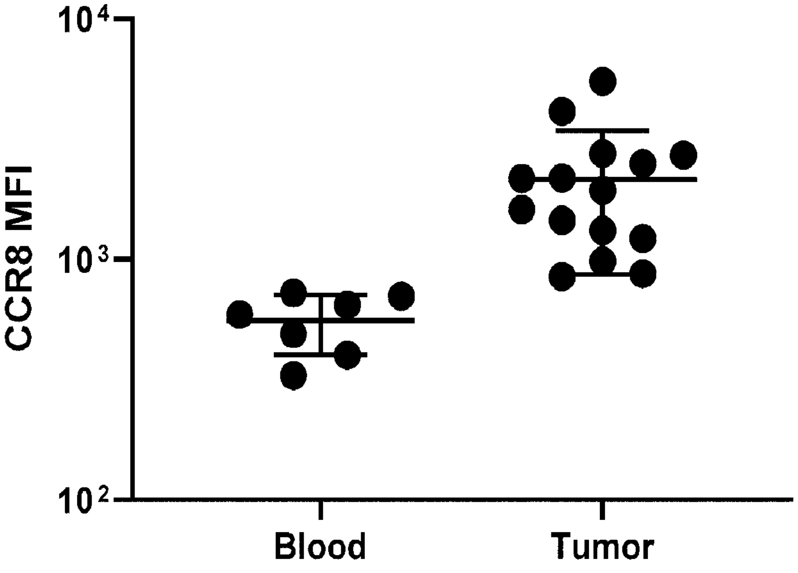

The differential expression of CCR8 on different human Treg subpopulations was also analyzed by flow cytometry (Example 5). In PBMCs from healthy subjects, CCR8 was found to be predominantly expressed on peripheral blood Tregs, but only on a small fraction (median 21%) of these peripheral Tregs (FIG. 4A) compared to the expression on about a median 82% of tumor-infiltrating Tregs (cf. FIG. 3A). Thus, anti-CCR8 Ab-mediated cell depletion would likely not significantly affect the peripheral Treg compartment due to the low proportion of CCR8$^+$ Tregs in the peripheral Treg population. This implies a lower risk of autoimmune toxicity associated with depleting tumor-associated Tregs by targeting CCR8 compared to indiscriminate depletion of non-tumor associated Tregs. Within the Treg population, CCR8 is expressed more highly in the effector memory population and to a lesser degree in central memory cells, with very little CCR8 expressed on naïve Tregs (FIG. 4B) or conventional CD4$^+$ T cells (FIG. 4C). In cancer patients, there is higher CCR8 expression on a per cell basis on tumor-infiltrating Tregs than on Tregs from peripheral blood as measured by the MFI of a bound anti-CCR8 Ab (FIG. 4D).

Figure 5:
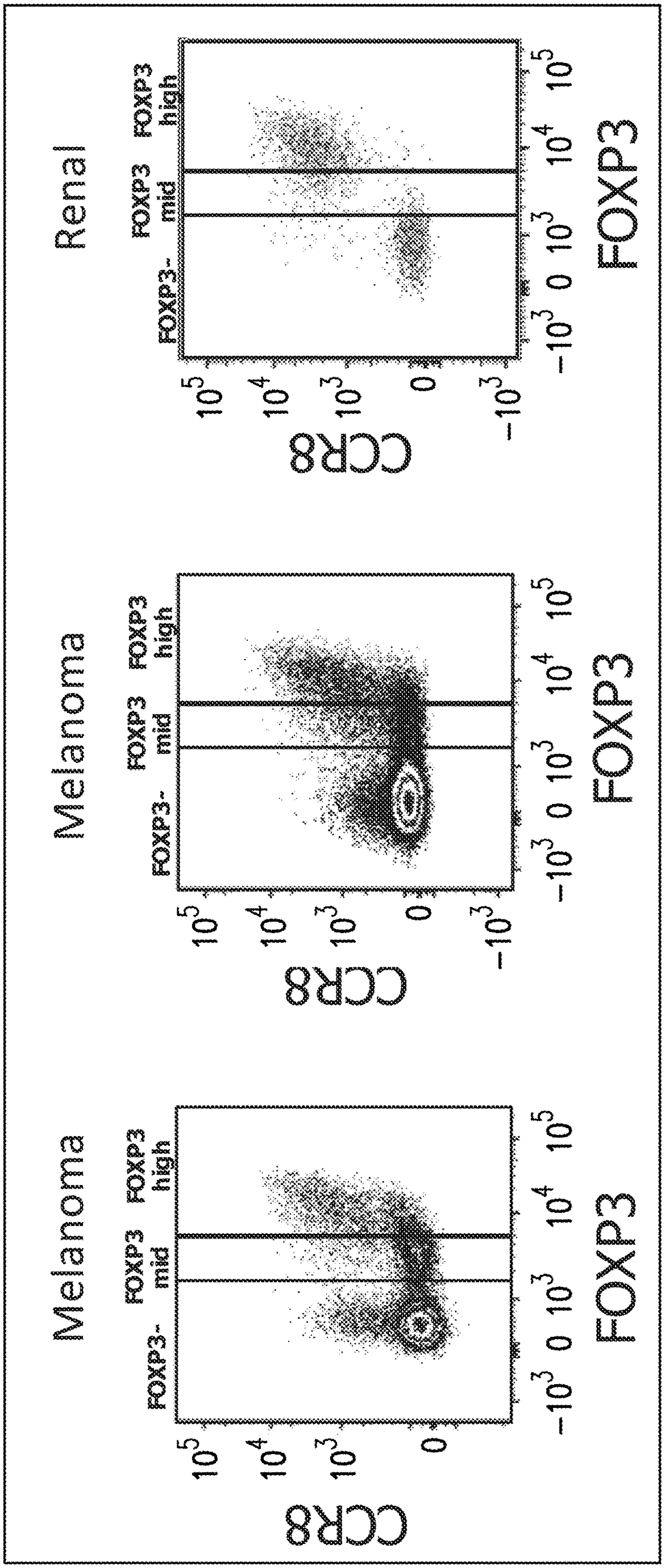
FIG. 5 shows that CCR8 is expressed on the most immunosuppressive $CD4^{+}FOXP3^{high}$ Treg population. Tumors from 2 melanoma patients and 1 renal cell carcinoma (RCC) patient were dissociated and stained for FOXP3 and CCR8 expression. CCR8 is mainly expressed by the $CD4^{+}FOXP3^{high}$ population, which represents the most activated Tregs.

In comparison to other Treg-targeting of agents in the clinic (CCR4-mogamulizumab and CTLA-4-Ipi-nf), CCR8 is specifically expressed on the most activated and immunosuppressive subset of FOXP3$^{hi}$ tumor Tregs associated with poor survival (Plitas et al., 2016; Wang et al., 2019), effectively excluding Teffs expressing granzyme and other effector cytokines. Two melanoma tumors and a RCC tumor were dissociated and stained for FOXP3 and CCR8 expression (Example 6). FIG. 5 shows that CCR8 is expressed on the most immunosuppressive CD4$^+$ FOXP3$^{high}$ Treg population, which represents the most activated Tregs. In the melanoma samples where there is a clear FOXP3$^{mid}$ population, most of the CCR8 expression is found in the FOXP3$^{high}$ T cells with the level of CCR8 expression significantly lower in the FOXP3$^{mid}$ and FOXP3$^{neg}$ tumor T cells that are mainly effector cells expressing granzyme and other effector cytokines. In the RCC sample where most of the patient FOXP3$^+$ T cells exhibit high levels of FOXP3, CCR8 expression overlaps with FOXP3 expression.

FOXP3$^{high}$ $CD4^+$ T cells have been shown to be true Tregs, in contrast to FOXP3mid $CD4^+$ T cells, which can be activated conventional T cells or resting Tregs.

Figure 8A:
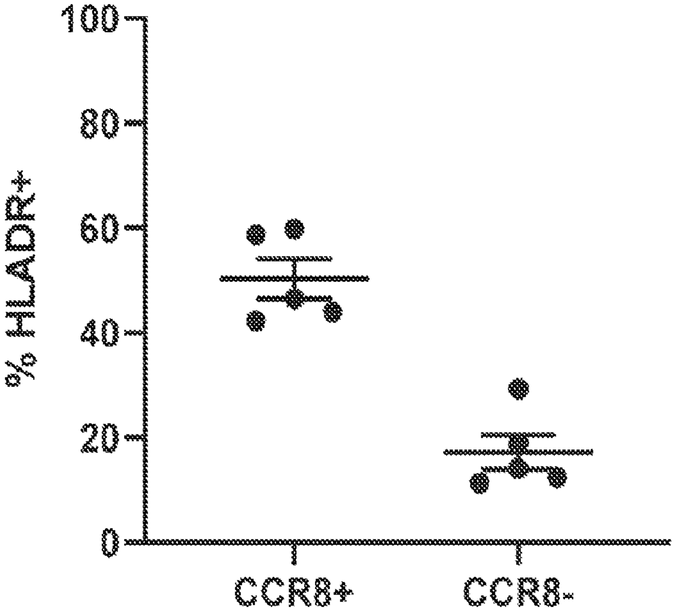
FIGS. 8A and 8B show the percentages of $CCR8^{+}$ and $CCR8^{-}$ T cells that express the activation marker HLA-DR (8A), and the percentages of $CCR4^{+}$ and $CCR4^{-}$ T cells that express this marker (8B).
Figure 8B:
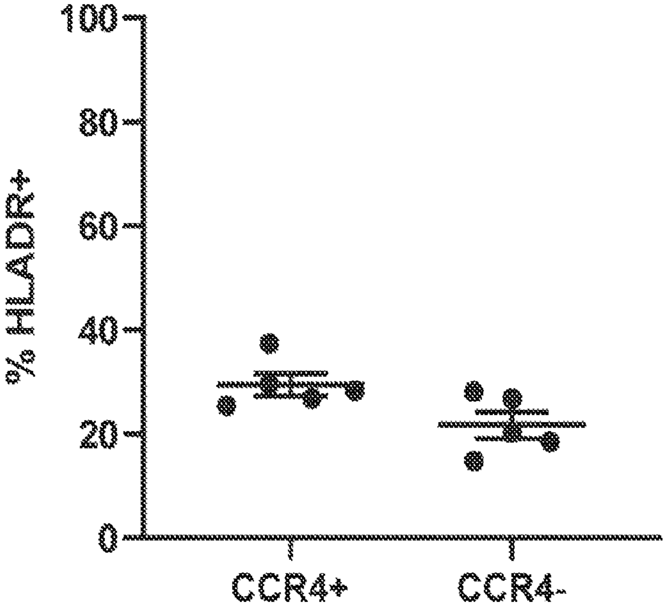
Figure 9A:
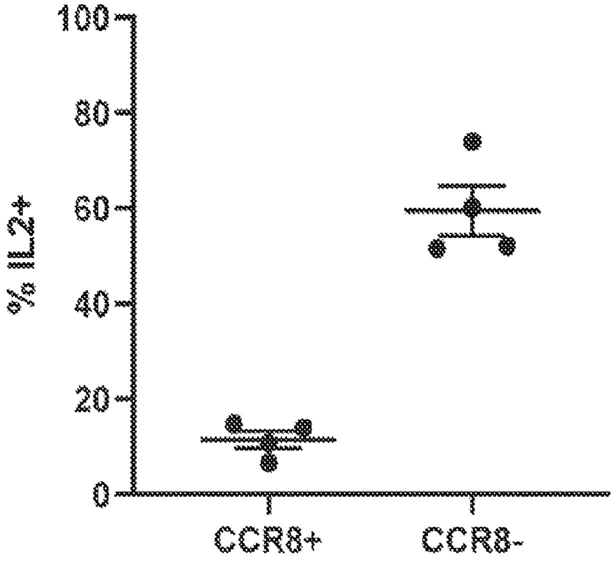
FIGS. 9A-9C show the percentages of stimulated $CCR8^{+}$ and $CCR8^{-}$ T cells that express IFNγ, IL-2, and granzyme B. A: Percentages of stimulated $CCR8^{+}$ and $CCR8^{-}$ cells that express IFNγ; B: Percentages of stimulated $CCR8^{+}$ and $CCR8^{-}$ cells that express IL-2; C: Percentages of stimulated $CCR8^{+}$ and $CCR8^{-}$ cells that express granzyme B.
Figure 9B:
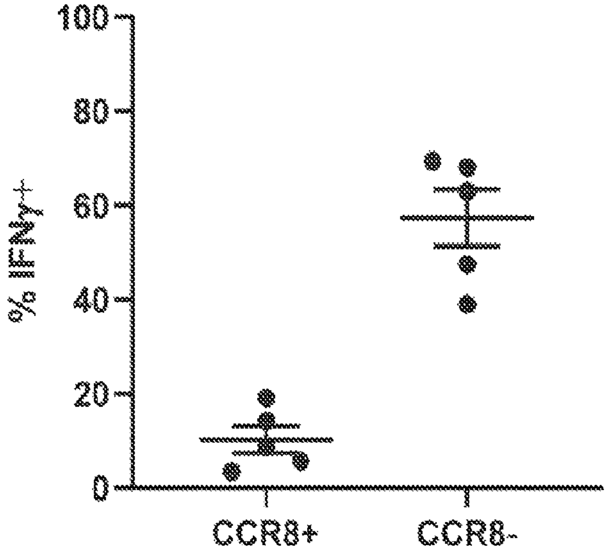
Figure 9C:
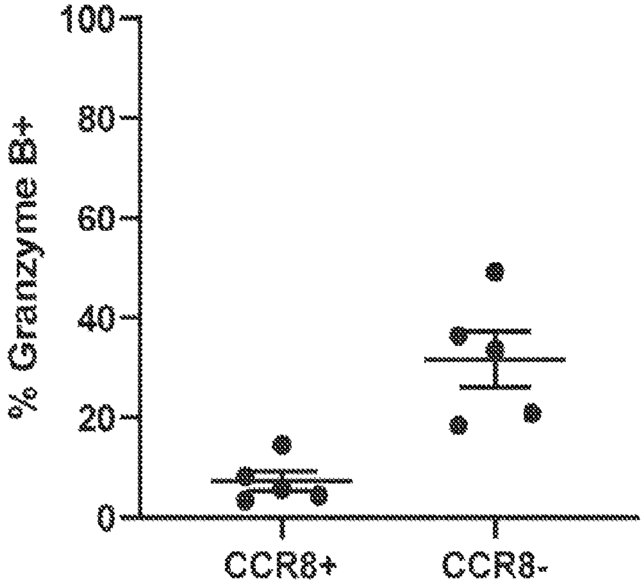
Figure 10A:
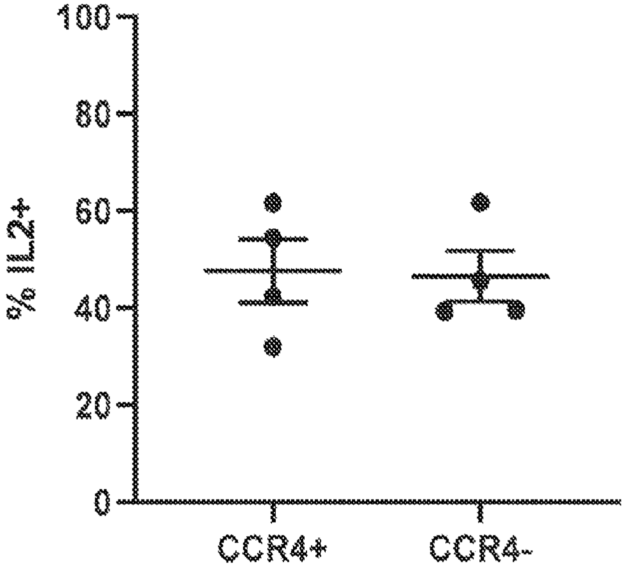
FIGS. 10A-10C show the percentages of stimulated $CCR4^{+}$ and $CCR4^{-}$ T cells that express IFNγ, IL-2, and granzyme B. A: Percentages of stimulated $CCR4^{+}$ and $CCR4^{-}$ cells that express IFNγ; B: Percentages of stimulated $CCR4^{+}$ and $CCR4^{-}$ cells that express IL-2; C: Percentages of stimulated $CCR4^{+}$ and $CCR4^{-}$ cells that express granzyme B.

The expression of functionally relevant molecules in $CCR8^+$ versus $CCR8^-$ tumor-infiltrating T cell populations was examined (Example 7). $CCR8^+$ cells from patient tumor samples were shown to co-express several proteins with potential immunosuppressive functions such as CD25, IL1R2, and CD39 (FIGS. 6A-D) whereas a comparable enrichment was not seen in $CCR4^+$ T cells (FIGS. 7A-D). Using HLA-DR as an activation marker, CCR8 expression also correlates with a higher level of HLA-DR expression (FIG. 8A) and thus identifies activated Tregs whereas CCR4 expression does not (FIG. 8B). Therefore, depletion of $CCR8^+$ cells would remove activated immunosuppressive Tregs expressing CD25, CD39 and IL1R2 whereas Tregs expressing these molecules would not be removed by CCR4-targeted depletion. Further, stimulation of dissociated patient tumor cells ex vivo with phorbol 12-myristate 13-acetate (PMA) and ionomycin induced minimal IL-2, IFNγ, and granzyme B production in the $CCR8^+$ fraction of $CD4^+$ T cells (FIGS. 9A-C). In contrast, $CCR4^+CD4^+$ T cells were major producers of IFNγ and IL-2 (FIGS. 10A and B), suggesting that targeted depletion of $CCR4^+$, but not $CCR8^+$ cells, may be detrimental to anti-tumor immunity.

The data revealed in Examples 1-7 and summarized above show that not all $CD4^+FOXP3^+$ T cells in the tumor express CCR8, and the $CCR8^+$ fraction appears to represent the more immunosuppressive subset of $FOXP3^+$ cells. Thus, CCR8 expression marks a subset of highly suppressive Treg that are enriched in the tumor and may hinder anti-tumor immunity. The high specificity of CCR8 expression to tumor-specific Tregs and, in particular, the most activated and immunosuppressive $CD4^+$ FOXP3$^{high}$ intratumoral Tregs, makes CCR8 an optimal target for mediating depletion of these highly immunosuppressive Tregs through ADCC using an anti-CCR8 Ab.

Accordingly, anti-hCCR8 mAbs were generated in experiments described herein (Example 8) and screened to identify Abs that exhibit multiple properties desirable in a therapeutic Ab for treating cancer (Examples 9-31). It is demonstrated herein that a surrogate mouse anti-mCCR8-mIgG2a Ab potently inhibited tumor growth in multiple mouse tumor models, and nonfucosylated (nf) anti-hCCR8 Abs depleted human tumor Tregs in ex vivo patient tumor samples and in vitro while sparing proinflammatory $CD4^+$ and $CD8^+$ Teff cells that drive anti-tumor immune responses (Examples 20 and 22). Depletion of tumor-associated Tregs reduces their immunosuppressive effect and thereby enhances the overall immune response in fighting cancer. Moreover, because CCR8 is rarely expressed on Tregs and Teffs in peripheral blood or in other tissues, targeting Tregs poses minimal toxicity risks. In comparison, anti-hCCR4-IgG1-nf treatment in vitro led to depletion of both Treg and $CD4^+$ Tconv cells in the periphery and in the tumor microenvironment (Examples 20 and 22). This is consistent with evidence that mogamulizumab (anti-CCR4) depletes Teff populations in peripheral blood in the clinic (Kurose et al., 2015).

Generation of Anti-hCCR8 MAbs

Chemokine receptors, including CCR8, have traditionally been "very difficult antigens to develop Ab against" because of their low profiles on the cell surface and relative inaccessibility to Ab binding (WO 2007/044756). Also, Abs generated against peptides corresponding to extracellular domains of chemokine receptors often fail to recognize the intact receptor on the cell, probably because of differences in secondary structure. Due to these difficulties, efforts to generate Abs against chemokine receptors have had a low success rate (WO 2007/044756). CCR8 is a particularly difficult GPCR, which has been described as an "extremely challenging" target against which to generate Abs (Harbour BioMed, 2020).

Initial efforts to generate anti-hCCR8 Abs by immunizing mice with hCCR8-expressing cells were unsuccessful. However, anti-hCCR8 mAbs were generated in the present study (Example 8) after trying immunization of different rodents with a variety of hCCR8 antigens and various combinations of these antigens.

Immunization of Rodents

Humanized or human anti-CCR8 mAbs were generated by immunizing different rodents, including regular C57B1/6 mice, different strains of transgenic mice that express a human Ig repertoire, a specifically generated $CCR8^{-/-}$ knockout mouse strain, rats and hamsters, with immunogens comprising a variety of hCCR8 antigens including Chinese hamster ovary (CHO), mouse BAF3 and human HEK 293F cells overexpressing hCCR8, or purified plasma membranes from these cells. These immunogens were boosted with chemically synthesized peptides from the hCCR8 N-terminus (residues 1-35 of hCCR8) that importantly contained singly or doubly sulfated tyrosine residues at positions 15 and/or 17, conjugated to either bovine serum albumin (BSA) or keyhole limpet hemocyanin (KLH). Certain of the mAbs generated in non-transgenic mice were subsequently modified to humanized or chimeric derivatives.

Proteins often display post-translational modifications, some of which, e.g., glycosylation, have been very well studied and documented. In comparison, the sulfation of certain extracellular tyrosine residues has been little studied and, to date, there are only 32 confirmed molecules that have been documented to contain sulfated tyrosines (Mehta et al., 2020). Even though additional proteins with sulfated tyrosines are yet to be discovered, sulfated tyrosines are estimated to be fairly rare (Moore, 2003). As a chemical moiety, they are very different from all other amino acids and therefore represent an excellent focal point to generate Abs with very high specificity and low off-target binding. Chemokine receptors that include CCR8 constitute one of the few protein classes that have been well documented to have sulfated tyrosines on their N-terminus (Ludeman and Stone, 2014). For several of these receptors, tyrosine sulfation has been found to be crucial for ligand, i.e., chemokine, engagement (Zhu et al., 2011). Thus, it is likely that an Ab that engages the tyrosine sulfates will disrupt binding between chemokine and chemokine receptor and thereby prevent chemokine receptor activation. As discussed elsewhere herein, Abs of the invention that bind to an epitope comprising at least one amino acid within a peptide having the sequence $V_{12}T_{13}D_{14}Y_{15}Y_{16}Y_{17}P_{18}D_{19}I_{20}F_{21}S_{22}$ (SEQ ID NO: 109), e.g. comprising 2, 3, 4, 5, 6, 7, 8, 9, 10 or all the amino acids within a peptide having the sequence $V_{12}T_{13}D_{14}Y_{15}Y_{16}Y_{17}P_{18}D_{19}I_{20}F_{21}S_{22}$ (SEQ ID NO: 109) and, in particular, wherein amino acids Y15 and Y17 are sulfated, are of particular interest and Example 11 shows that mAb 4A19 binds to the doubly sulfated CCR8 N-terminus with a $K_D$ of about 1.6 nM (see Table 5).

Reduced Fucosylation, Nonfucosylation and Hypofucosylation of Anti-CCR8 mAbs

The interaction of Abs with FcγRs can be enhanced by modifying the glycan moiety attached to each Fc fragment at the N297 residue (EU numbering). In particular, the absence of core fucose residues strongly enhances ADCC via improved binding of IgG to activating FcγRIIIA without altering antigen binding or complement-dependent cytotoxicity (CDC; Natsume et al., 2009). Binding of an of Ab to CCR8 on human Tregs facilitates engagement of the FcγR on NK cells and myelomonocytic Teffs. This FcγR engagement drives NK cell activation leading to enhanced Treg killing by ADCC. There is convincing evidence that afucosylated tumor-specific Abs translate into enhanced therapeutic activity in mouse models in vivo (Nimmerjahn and Ravetch, 2005; Mössner et al., 2010).

Modification of Ab glycosylation can be accomplished by, for example, expressing the Ab in a host cell with altered glycosylation machinery. Certain of the anti-hCCR8 mAbs disclosed herein possess reduced or eliminated fucosylation and exhibit enhanced ADCC, which is particularly useful in the methods of the present invention. The anti-hCCR8 mAbs disclosed herein may therefore be generated in a form in which they possess reduced or eliminated fucosylation, e.g., by expressing the anti-hCCR8 mAbs in cells with altered glycosylation machinery, and as a result exhibit enhanced ADCC, which is particularly useful in the methods of the present invention. Cells with altered glycosylation machinery have been described in the art and can be used as host cells in which to express recombinant Abs of this disclosure to thereby produce an Ab, e.g., a mAb, with altered glycosylation. For example, the cell lines Ms704, Ms705, and Ms709 lack the fucosyltransferase enzyme, FUT8 (α-(1,6) fucosyltransferase; see U.S. Publication No. 2004/0110704; Yamane-Ohnuki et al., 2004), such that Abs expressed in these cell lines lack fucose in their carbohydrates. EP 1176195 also describes a cell line with a functionally disrupted FUT8 gene as well as cell lines that have little or no activity for adding fucose to the N-acetylglucosamine that binds to the Fc region of the Ab, for example, the rat myeloma cell line YB2/0 (ATCC CRL 1662). Many other methods for producing Abs with Ab with reduced fucosylation have been described in the art. Hypofucosylated or nf chimeric, humanized or human anti-hCCR8 Abs disclosed herein were produced by expression in Expi293 $Fut8^{-/-}$ knock-out cells (Thermo Fisher Scientific, San Diego, CA) lacking the FUT8 enzyme essential to fucosylation.

Because nf Abs exhibit greatly enhanced ADCC compared with fucosylated Abs, Ab preparations need not be completely free of fucosylated heavy chains to be useful in the methods of the present invention. Residual levels of fucosylated heavy chains will not significantly interfere with the ADCC activity of a preparation of substantially nf heavy chains. Abs produced in conventional CHO cells, which are fully competent to add core fucose to N-glycans, may nevertheless comprise from a few percent up to 15% nf Abs. Nf Abs may exhibit about 10-fold higher affinity for CD16, and up to 30- to 100-fold enhancement of ADCC activity, so even a small increase in the proportion of nf Abs may drastically increase the ADCC activity of a preparation. Any preparation comprising more nf Abs than would be produced in normal CHO cells, e.g., wild-type CHO cells having unaltered glycosylation machinery, in culture may exhibit some level of enhanced ADCC. Such Ab preparations are referred to herein as preparations having reduced fucosylation. Depending on the original level of nonfucosylation obtained from normal CHO cells, e.g., wild-type CHO cells, reduced fucosylation preparations may comprise as little as 50%, 30%, 20%, 10% and even 5% nf Abs. Reduced fucosylation may be functionally defined as preparations exhibiting about a 2-fold or greater enhancement of ADCC compared with Abs prepared in normal CHO cells, and not with reference to any fixed percentage of nf species.

However, as used herein unless otherwise indicated, the level of nonfucosylation is structurally defined. Specifically, "nonfucosylated" (nf) or "afucosylated" (terms used synonymously) Ab preparations are Ab preparations comprising greater than 95% of Ab heavy chains, including 100%; "hypofucosylated" refers to Ab preparations in which 80 to 95% of heavy chains lack fucose; and "hypofucosylated or nonfucosylated" refers to Ab preparations in which 80% or more of heavy chains lack fucose.

The level of fucosylation in an Ab preparation may be determined by a method known in the art, including but not limited to gel electrophoresis, liquid chromatography (LC), and mass spectrometry (MS). Unless otherwise indicated, for the purposes of the present invention, the level of fucosylation in an Ab preparation is determined by hydrophilic interaction chromatography (or hydrophilic interaction liquid chromatography, HILIC). To determine the level of fucosylation of an Ab preparation, samples are denatured treated with PNGase F to cleave N-linked glycans, which are then analyzed for fucose content. LC/MS of full-length Ab chains is an alternative method to detect the level of fucosylation of an Ab preparation, but mass spectroscopy is inherently less quantitative.

Therapeutic Anti-hCCR8 mAbs Must Have a High Potential for ADCC

Because of the great difficulty we encountered in generating anti-CCR8 Abs in preliminary immunization experiments, immunizations were ultimately done with a wide variety of antigens as described above and in Example 8. Hybridomas generated were screened as described in Example 9 to confirm Ab binding to CCR8 and to a CCR8 N-terminal peptide. Selected mouse Abs were humanized as described in Example 10.

Also provided is a method of generating an Ab against CCR8, said method comprising immunizing a rodent at least once with one or more hCCR8 antigens in an immunization schedule which comprises one or more immunizations, wherein the immunization schedule includes in at least one of the immunizations administering a hCCR8 antigen which is a KLH-conjugated, hCCR8 peptide including residues Y15 and Y17 of hCCR8 and wherein residues Y15 and Y17 are sulphotyrosine residues. Preferably, residues both Y15 and Y17 are sulphotyrosine residues.

Optionally, the hCCR8 peptide comprises or consists of at least the N-terminal-most 25, 30, or 35 amino acids of hCCR8. Optionally, the hCCR8 peptide consists of the N-terminal-most 35 amino acids of hCCR8.

Optionally, the rodent is a mouse, rat or hamster. Preferably, the rodent is a mouse.

Optionally, the rodent is immunized with a cell expressing hCCR8 or preferably a plasma membrane-enriched fraction isolated from a cell expressing CCR8 in at least one of the immunizations, alone or in combination with the KLH-conjugated, hCCR8 peptide. Optionally the immunization schedule includes immunizing the rodent with HEK 293F cells expressing hCCR8 and with a KLH-conjugated, N-terminal hCCR8 peptide. Optionally the immunization schedule includes immunizing the rodent with plasma membrane enriched fractions of BAF3 cells expressing hCCR8 and with a KLH-conjugated, hCCR8 peptide.

In certain aspects, the present disclosure relates to an isolated Ab, preferably a mAb, or an antigen-binding portion thereof, that specifically binds to CCR8 expressed on the surface of a cell and mediates depletion of the CCR8-expressing cell by ADCC. In certain embodiments, the CCR8 to which the mAb or antigen-binding portion thereof binds is hCCR8, the sequence of which is set forth as SEQ ID NO: 1. In other embodiments, the CCR8 is mCCR8, the sequence of which is set forth as SEQ ID NO: 120.

Human IgG1 and IgG3 Ab isotypes are able to mediate ADCC through binding to activating Fcγ receptors, particularly the CD16 (FcγRIIIa) receptor expressed by human NK cells and monocytes (see Table 1). Many therapeutic Abs that have been commercialized have the human IgG1 isotype, which can induce strong ADCC and CDC when compared with other human Ab isotypes. Additionally, therapeutic IgG1 Abs have long-term stability in blood mediated via binding to the neonatal Fc receptor (FcRn). The activity of several therapeutic Abs, including anti-CD20 rituximab (RITUXAN®) (Dall'Ozzo et al., 2004), anti-Her2 trastuzumab (HERCEPTIN®) (Gennari et al., 2004), anti-tumor necrosis factor-α (anti-TNF-α) infliximab (REMICADE®) (Louis et al., 2004), and anti-RhD (Miescher et al., 2004) is mediated, at least in part, by ADCC.

In certain embodiments of the disclosed invention, the anti-CCR8 mAb or antigen-binding portion thereof comprises a heavy chain constant region which is of a human IgG1 or IgG3 isotype. In preferred embodiments, the anti-CCR8 mAb or antigen-binding portion thereof is of a human IgG1.

This invention also provides a modified anti-hCCR8 mAb, or an antigen-binding portion thereof, which comprises a modified heavy chain constant region that binds with higher affinity to a FcγR and mediates enhanced ADCC compared to the corresponding unmodified mAb or antigen-binding portion thereof. In certain embodiments, the modified anti-hCCR8 mAb or antigen-binding portion thereof mediates at least: (a) about 2 times enhanced ADCC activity; (a) about 5 times enhanced ADCC activity; (c) about 10 times enhanced ADCC activity; (d) about 30 times enhanced ADCC activity, or (e) about 100 times enhanced ADCC activity, e.g., as measured by a reduction in the $EC_{50}$ for cell lysis in a NK cell lysis assay, for example, the NK cell lysis assay that is described in Example 17. In certain embodiments, the modified anti-hCCR8 mAb or antigen-binding portion thereof comprises a modified IgG1 heavy chain constant region which exhibits reduced fucosylation.

In further embodiments, the modified anti-hCCR8 mAb or antigen-binding portion thereof comprises a modified IgG1 heavy chain constant region which is hypofucosylated or nonfucosylated. In certain other embodiments, the modified mAb or antigen-binding portion thereof comprises a modified IgG1 heavy chain constant region which contains a mutation, or a multiplicity of mutations, that mediate enhanced ADCC. In further embodiments, the mutation or multiplicity of mutations is chosen from G236A; S239D; F243L; E333A; G236A/I332E; S239D/I332E; S267E/H268F; S267E/S324T; H268F/S324T; G236A/S239D/I332E; S239D/A330L/I332E; S267E/H268F/S324T; and G236A/S239D/A330L/I332E. In certain embodiment, the modified anti-hCCR8 mAb or antigen-binding portion thereof comprises a modified IgG1 heavy chain constant region which is hypofucosylated or nonfucosylated, and further contains a mutation, or a multiplicity of mutations, such as are listed above, that mediate enhanced ADCC.

Functional Screening for Anti-hCCR8 MAbs that Mediate ADCC

Human, humanized and chimeric anti-hCCR8 mAb clones were functionally screened to identify Abs that exhibit properties desirable in a therapeutic Ab, including Abs that bind to hCCR8 with high affinity (Example 11), bind specifically to CCR8-expressing human cells (Example 14), block binding of the CCL1 ligand to CCR8 (Example 15), mediate ADCC of CCR8-expressing cells, including Tregs, when bound to CCR8 on the surface of such cells (Examples 17, 19 and 20), not cause internalization of cell CCR8 (Example 21), promote depletion of human tumor-associated Tregs in vitro (Example 22) and in ex vivo human tumor slice samples (Example 20), mediate depletion of tumor Tregs specifically while sparing $CCR8^+$ T cells in normal tissues (Example 24), and reduce tumor growth in preclinical mouse tumor models when administered to the mice as monotherapy or in combination with a checkpoint inhibitor (Examples 23-29).

Clones were selected for further characterization after being initially shown to bind to CCR8 on human cells with sub-nanomolar $EC_{50}$ values, and to bind specifically to CCR8-expressing cells with no cross-reactivity to diverse human tissues that do not express CCR8. The DNA encoding the variable regions in these Abs was sequenced by next generation sequencing and clones were selected for diversity based on sequence homology and limited potential sequence liabilities, e.g., asparagine deamidation, methionine oxidation and glycosylation sites. Based on their potency in mediating ADCC of CCR8-expressing cells, binding kinetics, and sequence family diversity, certain selected clones mAbs were further tested for functions deemed to be desirable in a therapeutic Ab, including the ability to inhibit tumor growth in mouse tumor models and were subjected to sequence optimization to mitigate sequence liabilities, optimize binding affinities and revert to germline amino acids. Select mAbs were also analyzed for their biophysical properties through a variety of means such as analytical size exclusion chromatography, capillary isoelectric focusing, hydrophobicity assessments, thermal stability, and aggregation potential, to identify clones suitable for further development.

Characterization of Binding Affinity of Anti-CCR8 mAbs to CCR8

Certain of the anti-CCR8 mAbs of this invention bind to hCCR8 with high affinity. Abs typically bind specifically to their cognate antigen with high affinity, reflected by a dissociation constant ($K_D$) of 1 μM to 10 pM or lower. Any $K_D$ greater than about 100 μM is generally considered to indicate nonspecific binding. As used herein, an IgG Ab that "binds specifically" to an antigen refers to an Ab that binds to the antigen and substantially identical antigens with high affinity, which means having a $K_D$ of about 100 nM or lower, preferably about 10 nM or lower, more preferably about 5 nM or lower, and even more preferably between about 5 nM and 0.1 nM or lower, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen.

The term "$K_D$," as used herein, is intended to refer to the dissociation constant for a particular Ab-antigen interaction, which is obtained from the ratio of $k_{off}$ to $k_{on}$ (i.e., $k_{off}/k_{on}$) and is expressed as a molar concentration (e.g., nM). The term "$k_{on}$" refers to the association rate or "on rate" for the association of an Ab and its antigen interaction, whereas the term "$k_{off}$" refers to the dissociation rate for the Ab-antigen complex. $K_D$ values for Abs can be determined using methods well established in the art, such as surface plasmon resonance (SPR), kinetic exclusion assay (KinExA®; Sapidyne Instruments, Boise, ID), or bio-layer interferometry (BLI; ForteBio, Fremont, CA). $K_D$ values determined by different methods for a single Ab can vary considerably, for example, up to a 1,000-fold. Thus, in comparing the $K_D$ values for different Abs, it is important that these $K_D$ values be determined using the same method. Where not explicitly stated, and unless the context indicates otherwise, $K_D$ values for Ab binding disclosed herein were determined by SPR using a BIACORE® biosensor system (GE Healthcare, Chicago, IL).

Figure 11A:
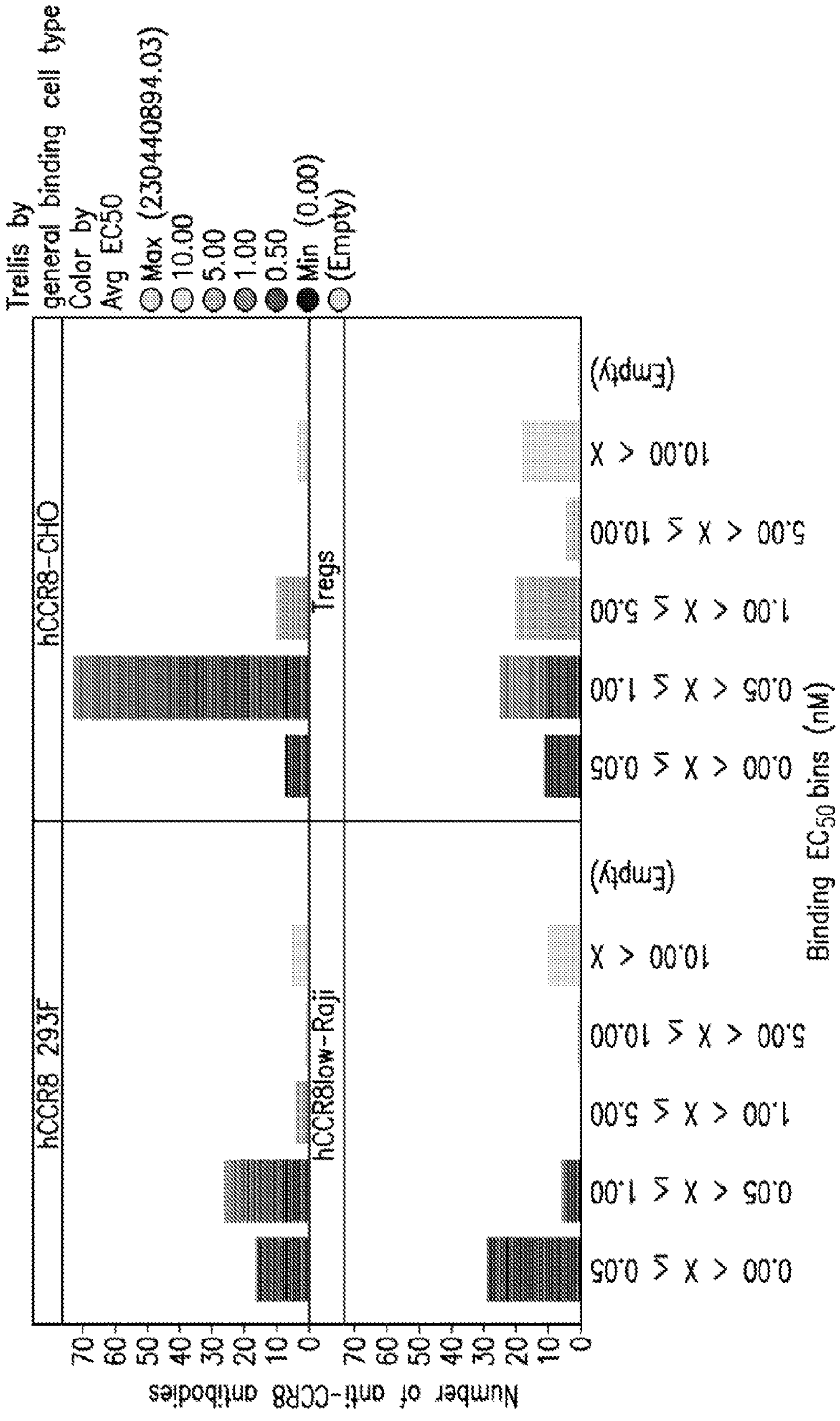
FIGS. 11A and 11B show the binding of different anti-hCCR8 mAbs to hCCR8-expressing cell lines or to activated human Tregs. A: Anti-hCCR8 Abs were generated exhibiting varying ranges of binding affinities ($EC_{50}$ bins in nM) to hCCR8-transfected cell lines (293F, CHO, Raji) and activated human Tregs. B: $EC_{50}$ values (nM) of a selected subset of anti-CCR8 mAbs binding to activated Tregs are shown.

Binding affinities for an Ab binding to a target such as hCCR8 can also be determined by measuring the $EC_{50}$ for binding to CCR8-expressing cell lines, which is the concentration of the Ab that achieves half of the maximal binding. Studies of mAbs binding to CHO, 293F, Raji cell lines expressing CCR8 exhibited $EC_{50}$ of under 1 nM (FIG. 11A). When bound against activated Tregs, these Abs exhibited a wider range of binding affinities, with less than half of the Abs exhibiting binding with $EC_{50}$'s less than 1 nM (FIG. 11A). The select set of mAbs shown in FIG. 11B exhibit $EC_{50}$'s ranging from picomolar to nanomolar.

Accordingly, in certain embodiments of the disclosed invention, the anti-CCR8 mAb or antigen-binding portion thereof specifically binds to human CCR8-expressing CHO cells with an $EC_{50}$ of: about 10 nM or lower; preferably about 5 nM or lower; preferably about 2 nM or lower; more preferably about 1.7 nM or lower; more preferably about 1 nM or lower; more preferably about 0.5 nM or lower; and even more preferably about 0.1 nM or lower. In certain preferred embodiments, the anti-hCCR8 mAb or antigen-binding portion thereof binds to hCCR8-expressing CHO cells with an $EC_{50}$ of about 0.1 nM. In certain other preferred embodiments, the anti-hCCR8 mAb or antigen-binding portion thereof binds to hCCR8-expressing CHO cells with an $EC_{50}$ of about 1.7 nM. In certain embodiments, the mAb binds with an $E_{50}$ of between about 0.1 nM and about 10 nM. In certain other embodiments, the $E_{50}$ is between about 0.1 nM and about 2 nM. In certain other embodiments, the $E_{50}$ is between about 0.5 nM and about 5 nM. In certain preferred embodiments, the $E_{50}$ is between about 1 nM and about 2 nM. In other embodiments, the mAb or antigen-binding portion thereof binds to human hCCR8 with an $E_{50}$ of between about 0.5 nM and about 1 nM. In certain preferred embodiments, the $E_{50}$ value is measured by the binding assay described in Example 11.

In certain other embodiments of the present invention, the anti-hCCR8 mAb or antigen-binding portion thereof specifically binds to activated human Tregs with an $E_{50}$ of: about 50 nM or lower, about 14 nM or lower, about 10 nM or lower; preferably about 5 nM or lower; more preferably about 2 nM or lower; more preferably about 0.5 nM or lower; more preferably about 0.3 nM or lower; even more preferably about 0.1 nM or lower; and yet more preferably about 0.03 nM or lower. In certain preferred embodiments, the anti-hCCR8 mAb or antigen-binding portion thereof binds to hCCR8-expressing CHO cells with an $E_{50}$ of about 1.7 nM. In certain embodiments, the mAb binds with an $E_{50}$ of between about 0.03 nM and about 10 nM. In certain preferred embodiments, the $E_{50}$ is between about 0.1 nM and about 5 nM. In more preferred embodiments, the mAb or antigen-binding portion thereof binds to human hCCR8 with an $E_{50}$ of between about 0.2 nM and about 2 nM. In certain preferred embodiments, the $E_{50}$ value is measured by the binding assay described in Example 11.

Figure 12A:
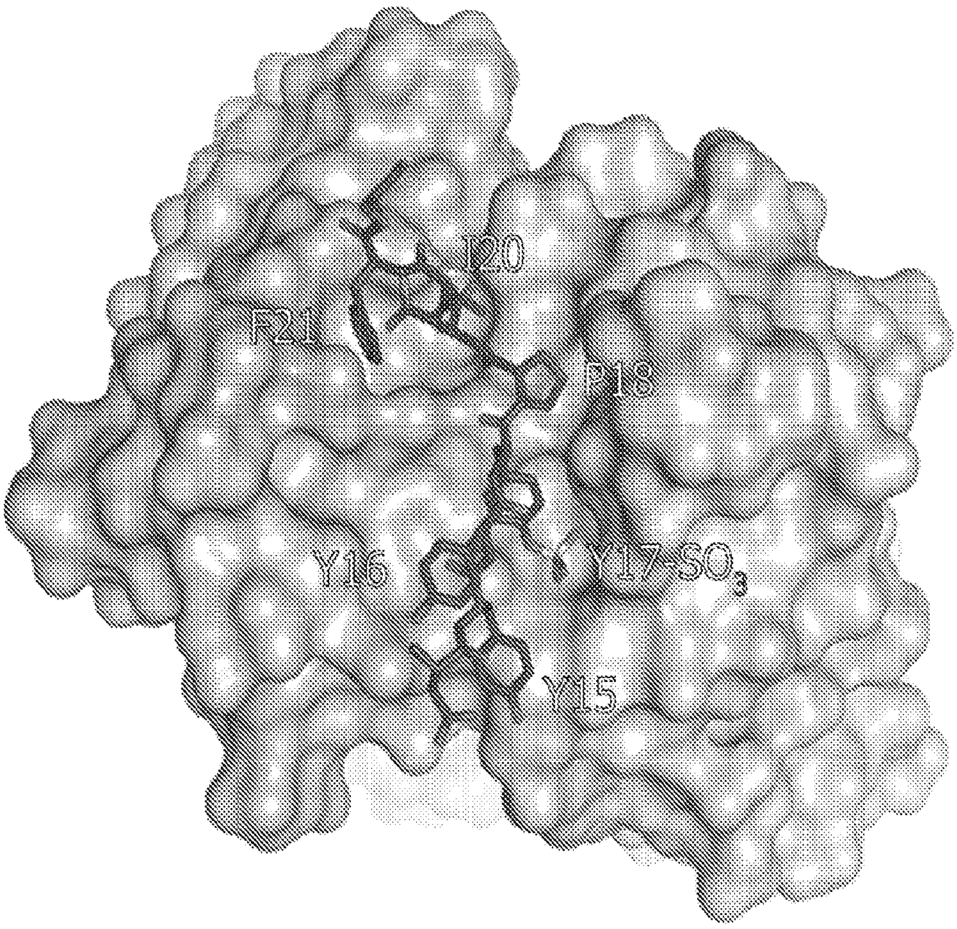
FIGS. 12A and 12B show the crystal structure of the 4A19 Fab fragment bound to the hCCR8 N-terminal peptide. A: 4A19 Fab fragment bound to the singly sulfated (at tyr-17) hCCR8 N-terminal peptide at 2.03 Å resolution. The epitope bound by the 4A19 mAb comprises residues 15-21 with the sulfated tyrosine-17 residue at the center of the epitope; B: 4A19 Fab fragment bound to the doubly sulfated (at tyr-15 and tyr-17) hCCR8 N-terminal peptide at 1.80 Å resolution. The epitope bound by the 4A19 mAb comprises residues 12-22.

The Fab fragment of a selected anti-hCCR8 mAb, 4A19, was shown by X-ray crystallography to bind to an epitope comprising residues 15-21 in the N-terminal peptide of hCCR8 (Example 11), with the sulfated tyrosine-17 residue at the center of the epitope (FIG. 12A). Accordingly, in certain embodiments, the anti-hCCR8 mAb or antigen-binding portion thereof described herein binds to a N-terminal epitope of human CCR8 as determined by X-ray crystallography, wherein the epitope comprises at least one amino acid within a peptide having the sequence $Y_{15}Y_{16}Y_{17}P_{18}D_{19}I_{20}F_{21}$ (SEQ ID NO: 2). In certain preferred embodiments, the epitope peptide comprises a sulfated tyrosine-17 residue. In certain embodiments, the epitope comprises 2, 3, 4, 5, 6, or all the amino acids within a peptide having the sequence of SEQ ID NO: 2.

Figure 12B:
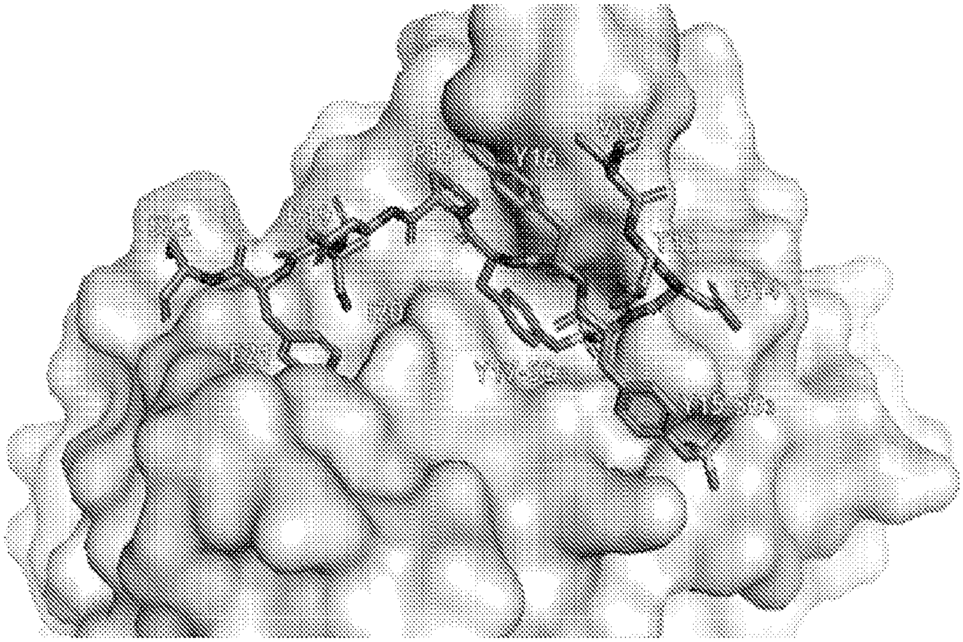

Binding of the doubly sulfated peptide (Y15 and Y17 sulfated) to the 4A19 Fab fragment confirmed the identity and orientation of the center of the epitope. It additionally allowed the delineation of a more extended linear epitope comprising the N-terminal residues 12-22 (VTDYYYPDIFS; SEQ ID NO: 109) of hCCR8 (FIG. 12B). The extension of the epitope from the one revealed by the monosulfated peptide is likely a consequence of the sulfo-Y15 ordering a larger segment of the hCCR8 N-terminal peptide, allowing visualization of its interactions with the 4A19 Ab. The epitope sequence observed in the structure with the doubly sulfated peptide may constitute the entire epitope bound by mAb 4A19 since this Ab was generated using an immunization strategy that involved multiple immunizations with a hCCR8 N-terminal peptide to enhance the immune response to the hCCR8 N-terminus. If other amino acid residues in the N-terminal peptide formed part of the epitope, this would likely be seen in the crystal structure but it is not (FIG. 12B).

Accordingly, in certain preferred embodiments, the epitope peptide bound by 4A19 comprises sulfated tyrosine-15 and tyrosine-17 residues. In certain embodiments, amino acids Y15 and/or Y17 of this peptide are sulfated. In certain preferred embodiments, both amino acids Y15 and Y17 of this peptide are sulfated.

This disclosure provides an Ab, e.g., a mAb, or an antigen-binding portion thereof, which is capable of mediating ADCC and which specifically binds to an epitope on hCCR8, the sequence of which is set forth as SEQ ID NO: 1, wherein the epitope is located in the N-terminal domain of hCCR8 within a peptide spanning approximately amino acid residues 15 to 21 ($Y_{15}Y_{16}Y_{17}P_{18}D_{19}I_{20}F_{21}$; SEQ ID NO: 2) as determined by X-ray crystallography. In certain embodiment, the epitope comprises at least one amino acid within a peptide having the sequence $Y_{15}Y_{16}Y_{17}P_{18}D_{19}I_{20}F_{21}$ (SEQ ID NO: 2). In other embodiments, the epitope comprises 2, 3, 4, 5, 6, or all the amino acids within a peptide having the sequence $Y_{15}Y_{16}Y_{17}P_{18}D_{19}I_{20}F_{21}$ (SEQ ID NO: 2). In certain preferable embodiments, the epitope comprises all 7 of the amino acids having the sequence of SEQ ID NO: 2.

This disclosure also provides an Ab, e.g., a mAb, or an antigen-binding portion thereof, which is capable of mediating ADCC and which specifically binds to an epitope on hCCR8, the sequence of which is set forth as SEQ ID NO: 1, wherein the epitope is located in the N-terminal domain of hCCR8 within a peptide spanning approximately amino acid residues 12 to 22 ($V_{12}T_{13}D_{14}Y_{15}Y_{16}Y_{17}P_{18}D_{19}I_{20}F_{21}S_{22}$; SEQ ID NO: 109) as determined by X-ray crystallography. In certain embodiment, the epitope comprises at least one amino acid within a peptide having the sequence $V_{12}T_{13}D_{14}Y_{15}Y_{16}Y_{17}P_{18}D_{19}I_{20}F_{21}S_{22}$ (SEQ ID NO: 109). In other embodiments, the epitope comprises 2, 3, 4, 5, 6, 7, 8, 9, 10 or all the amino acids within a peptide having the sequence $V_{12}T_{13}D_{14}Y_{15}Y_{16}Y_{17}P_{18}D_{19}I_{20}F_{21}S_{22}$ (SEQ ID NO: 109). In certain preferable embodiments, the epitope comprises all 11 of the amino acids having the sequence of SEQ ID NO: 109. In certain other embodiments, the epitope consists of a peptide having the sequence of SEQ ID NO: 109.

In certain aspects of this invention, the anti-CCR8 mAb or antigen-binding portion thereof binds to the N-terminal peptide of hCCR8 comprising sulfated tyr-15 and tyr-17 residues (e.g., a peptide of N-terminal CCR8 residues 1-35 sulfated at positions tyr-15 and tyr-17 (CCR8-2sulfo)) with a $K_D$ of: about 100 nM or lower; preferably about 50 nM or lower; preferably about 10 nM or lower; more preferably about 5 nM or lower; more preferably about 1.6 nM or lower; more preferably about 1.0 nM or lower; and even more preferably about 0.5 nM or lower; and yet more preferably about 0.1 nM or lower. In certain preferred embodiments, the anti-hCCR8 mAb or antigen-binding portion thereof binds to the N-terminal epitope peptide, e.g., a peptide of N-terminal CCR8 residues 1-35 sulfated at positions Tyr15 and Tyr17 (CCR8-2sulfo)) with a $K_D$ of about 1.6 nM. In certain embodiments, the mAb binds with a $K_D$ of between about 100 nM and about 0.1 nM. In certain preferred embodiments, the $K_D$ is between about 50 nM and about 0.5 nM. In more preferred embodiments, the mAb or antigen-binding portion thereof binds with a $K_D$ of between about 10 nM and about 1 nM. In yet more preferred embodiments, the mAb or antigen-binding portion thereof binds with a $K_D$ of between about 2 nM and about 1 nM. In certain preferred embodiments, the $K_D$ value is measured by the SPR method described in Example 11.

Sulfation of tyrosine (tyr-15 and tyr-17) in the N-terminus of hCCR8 is required for binding of the 4A19 Ab (see Example 11). If only one tyrosine residue, tyr-15, is sulfoylated, the 4A19 Fab fragment binds less tightly to the N-terminal peptide, evidenced by a $K_D$ of more than 10-fold higher and about 1,000-fold higher than the doubly sulfated peptide, while there is approximately a 10-fold decrease in affinity if only tyr-17 is sulfated (Table 5). Accordingly, this invention provides an anti-hCCR8 mAb or an antigen-binding portion thereof which binds to a N-terminal peptide of hCCR8 comprising a single sulfated residue, tyr-17 (CCR8-sulfoY17), of: about 100 nM or lower; preferably about 50 nM or lower; preferably about 25 nM or lower; more preferably about 10 nM or lower; and even more preferably about 1.0 nM or lower. In certain preferred embodiments, the anti-hCCR8 mAb or antigen-binding portion thereof binds to the singly sulfoylated epitope peptide with a $K_D$ of about 20 nM. In certain embodiments, the mAb binds with a $K_D$ of between about 100 nM and about 1 nM. In certain preferred embodiments, the $K_D$ is between about 50 nM and about 10 nM. In more preferred embodiments, the mAb or antigen-binding portion thereof binds with a $K_D$ of between about 30 nM and about 20 nM. In certain preferred embodiments, the $K_D$ value is measured by the SPR method described in Example 11.

Tissue Cross-Reactivity of Anti-hCCR8 MAbs

Since a therapeutic anti-CCR8 mAb will be used to deplete target cells expressing CCR8, it is important that the mAb bind specifically to the intended target cells, i.e., tumor-infiltrating Tregs, and not to other essential cell types in the body whose depletion would induce toxic or undesirable side effects. Candidate mAbs were, therefore, tested for binding to a wide variety of normal human tissue types (Example 14). Anti-hCCR8 mAbs 18Y12 and 4A19 were shown to bind to rare and scattered immune cells primarily in the medulla of the thymus and dermis of the skin whereas no binding was observed in numerous other tissues examined. Another mAb, 16B13, was observed to bind nonspecifically to PBMCs and a variety of human tissues including immune cells in lymphoid organs and lymphoid-rich tissues, and to many tissues where immune cells were present. The staining exhibited a cytoplasmic pattern. Abs such as 16B13 that bind nonspecifically to targets other than CCR8 on the cell surface are not suitable for therapeutic use in targeting CCR8-expressing cells for depletion notwithstanding other desirable functional properties they may exhibit.

Accordingly, this disclosure provides an anti-CCR8 mAb or antigen-binding portion thereof which binds specifically to CCR8-expressing cells such as tumor Tregs and rare and scattered immune cells in the medulla of the thymus and dermis of the skin but does not bind to a wide variety of human tissues including cerebrum, cerebellum, heart, liver, lung, kidney, tonsil, spleen, thymus, colon, stomach, pancreas, adrenal, pituitary, skin, peripheral nerve, testis or uterus tissue, or PBMCs. For example, the anti-CCR8 mAb or antigen-binding portion thereof may bind specifically to tumor-infiltrating Tregs but not bind to PBMCs, e.g., not show cytoplasmic staining in fixed PBMCs. Non-binding of the Ab to the above recited list of cells and tissues may be established, for instance, by carrying out standard staining with the relevant Abs, e.g., by the methods described in Example 14, e.g., on fixed tissue samples.

Inhibition of CCR8/Ligand Signaling by Anti-CCR8 MAbs

Figure 28A:
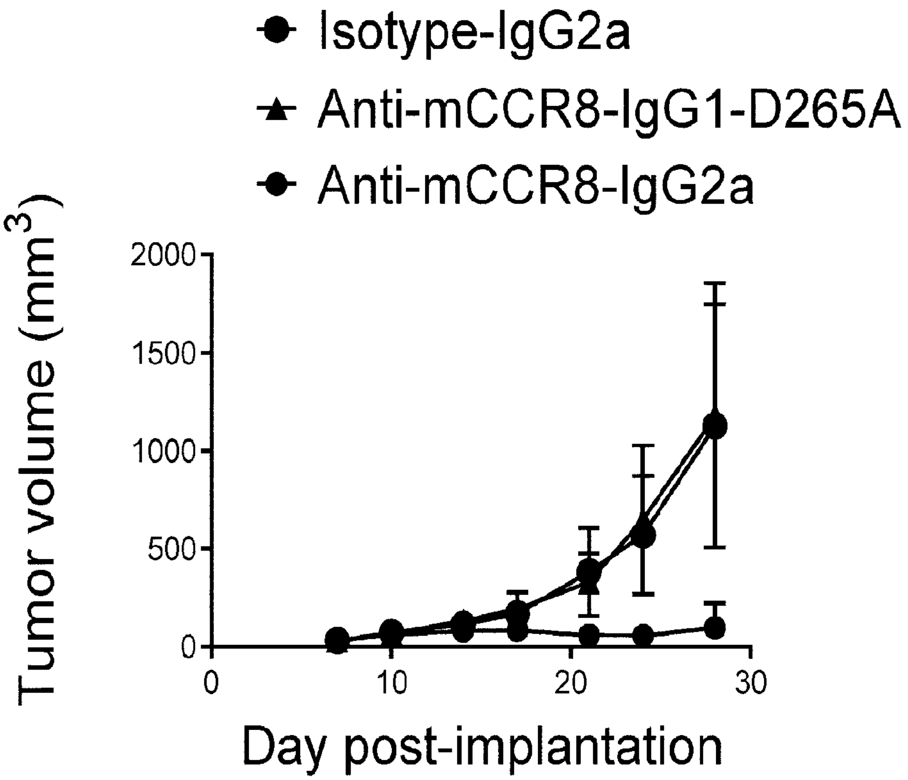
Figure 28B:
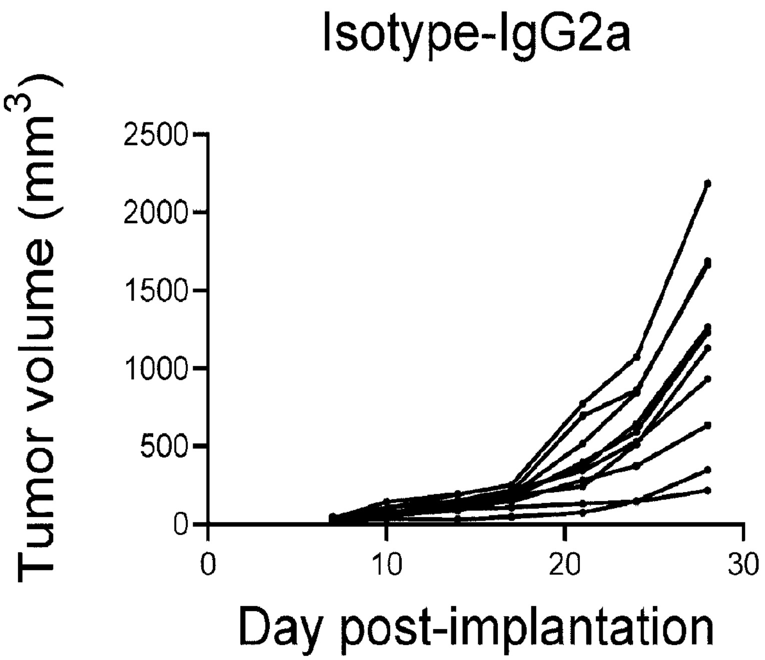
Figure 28C:
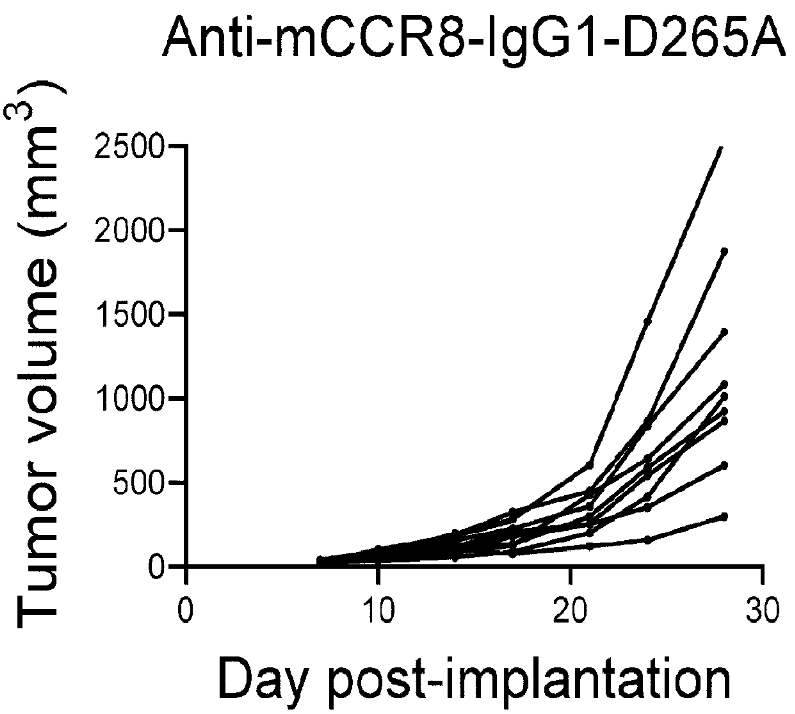
Figure 28D:
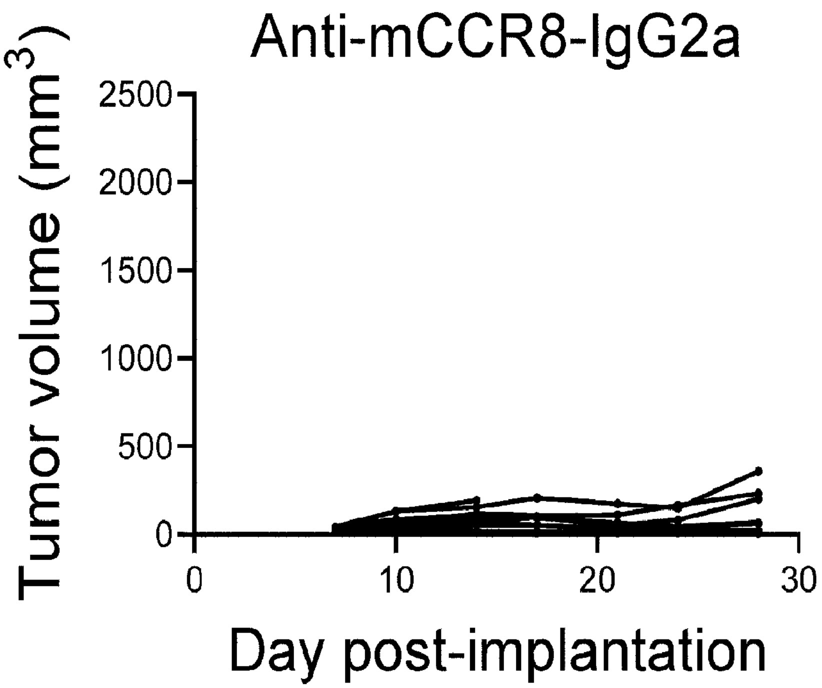

In Examples 15 and 16, blockade of hCCL1 and mCCL1 binding to hCCR8 and mCCR8, respectively, and blockade of CCR8/CCL1 signaling by anti-CCR8 mAbs was tested by conducting calcium (Ca) flux assays on CCR8-expressing CHO cell lines since CCL1 engagement of CCR8 on CHO cells induces Ca flux. CCL1 is the only ligand known to bind to CCR8. Studies have shown that CCL1 binding to CCR8 can enhance Treg suppression in in vitro assays as well as suppress autoimmune inflammatory responses in mouse models (Barsheshet et al., 2017). A blocking anti-CCR8 Ab in an SA1N fibrosarcoma model also demonstrated partial anti-tumor efficacy (FIG. 28A). Therefore, in certain embodiments of the present invention, an anti-CCR8 Ab or antigen-binding portion thereof of this invention inhibits binding of CCL1 to CCR8, for example hCCR8 or mCCR8, and inhibits CCR8/CCL1 signaling. In preferred embodiments, inhibition of Ca flux is measured as described in Examples 15 and 16 for hCCR8 and mCCR8, respectively.

In certain embodiments, the anti-hCCR8 mAb inhibits CCR8/CCL1 signaling with an $IC_{50}$ of about 10 nM or lower; about 5 nM or lower; preferably about 1 nM or lower; more preferably about 0.5 nM or lower; more preferably about 0.1 nM or lower; even more preferably about 0.01 nM or lower. In certain preferred embodiment, the anti-hCCR8 mAb inhibits CCR8/CCL1 signaling with an $IC_{50}$ of about 0.5 nM. In certain embodiments, the anti-hCCR8 Ab inhibits CCR8/CCL1 signaling with an $IC_{50}$ of between about 0.01 nM and about 10 nM. In certain other embodiments, the anti-hCCR8 Ab inhibits CCR8/CCL1 signaling with an $IC_{50}$ of between about 0.05 nM and about 5 nM. In certain preferred embodiments, the anti-hCCR8 Ab inhibits CCR8/CCL1 signaling with an $IC_{50}$ of between about 0.1 nM and about 1 nM. In more preferred embodiments, the anti-hCCR8 Ab inhibits CCR8/CCL1 signaling with an $IC_{50}$ of between about 0.2 nM and about 0.5 nM. These $IC_{50}$ values are based on the assay described in Example 15.

ADCC-Mediated Killing of CCR8-Expressing Cells by Anti-CCR8 MAbs

The capacity of the anti-hCCR8 and anti-mCCR8 mAbs to induce ADCC-mediated killing of CCR8-expressing cells was indirectly evaluated by measuring their ability to induce crosslinking of human or mouse reporter cells that express Fc receptors. In certain embodiments, a mAb or antigen-binding portion thereof of the invention mediates depletion of the CCR8-expressing cell with an $EC_{50}$, as measured by a CD16 cross-linking assay. In preferred embodiments, ADCC potential is measured by the cross-linking assays described in Examples 17 and 18 for hCCR8 and mCCR8, respectively.

In certain embodiments, the anti-hCCR8 mAb or antigen-binding portion thereof mediates depletion of a CCR8-expressing cell with an $EC_{50}$, as measured by a CD16 cross-linking assay, of about 100 pM or lower; preferably about 30 pM or lower; preferably about 10 pM or lower; preferably about 3 pM or lower; more preferably about 1 pM or lower; more preferably about 0.5 pM or lower; more preferably about 0.1 pM or lower; or even more preferably about 0.05 pM or lower. In certain preferred embodiment, the anti-hCCR8 mAb mediates depletion of the CCR8-expressing cell with an $EC_{50}$ of about 0.7 pM. In certain embodiments, the anti-hCCR8 Ab mediates depletion of the CCR8-expressing cell with an $EC_{50}$ of between about 0.05 pM and about 50 pM, preferably between about 0.1 pM and about 10 pM; more preferably between about 0.3 pM and about 7 pM; and even more preferably between about 0.6 pM and about 3 p M. These $EC_{50}$ values are based on the CD16 cross-linking assay described in Example 17.

The direct killing of activated Tregs and patient tumor Tregs was demonstrated in Examples 19 and 20. In certain embodiments, the anti-hCCR8 mAb or antigen-binding portion thereof mediates depletion of activated Tregs with an $EC_{50}$, as measured by an apoptosis assay, of about 500 pM or lower; preferably about 100 pM or lower; preferably about 30 pM or lower; more preferably about 15 pM or lower; even more preferably about 5 pM or lower; or yet more preferably about 1 pM or lower. In certain preferred embodiments, the anti-hCCR8 mAb mediates depletion of the CCR8-expressing cell with an $EC_{50}$ of about 13 pM. In certain embodiments, the anti-hCCR8 mAb mediates depletion of the CCR8-expressing cell with an $EC_{50}$ of between about 1 pM and about 500 pM, preferably between about 5 pM and about 100 pM; and more preferably between about 10 pM and about 50 pM. These $EC_{50}$ values are based on the apoptosis assay described in Example 19.

No Internalization of CCR8 by Anti-CCR8 mAbs

Abs specific for certain cell surface receptors induce internalization of the receptor through receptor-mediated endocytosis which may be essential for targeted delivery of certain drugs, toxins, or enzymes for therapeutic applications. As shown in FIG. 19, an anti-Inducible T cell Co-Stimulator (ICOS) mAb does not cause internalization of the ICOS receptor in the absence of a cross-linking Ab, but in the presence of the cross-linking Ab causes significant ICOS internalization. In contrast, an anti-CCR8 mAb causes no internalization of CCR8 either in the presence or absence of a cross-linking Ab. Internalization of CCR8 by an anti-CCR8 Ab would reduce its ability to mediate Treg depletion due to removal of the receptor from the Treg cell surface. Therefore, the lack of CCR8 internalization by anti-CCR8 Abs further validates the therapeutic potential of these Abs. CCR8 internalization may be measured by standard techniques used in the art, e.g., the experimental protocol in Example 21.

Accordingly, this invention provides an anti-CCR8 mAb or antigen-binding portion thereof that, when bound to CCR8 on the surface of a cell, does not cause internalization of CCR8 either in the presence or absence of a cross-linking Ab. In certain preferred embodiments, the cell expressing CCR8 on the cell surface is a Treg.

Depletion of Human Tumor Tregs In Vitro and in Ex-Vivo Patient Tumor Samples

Figure 20A:
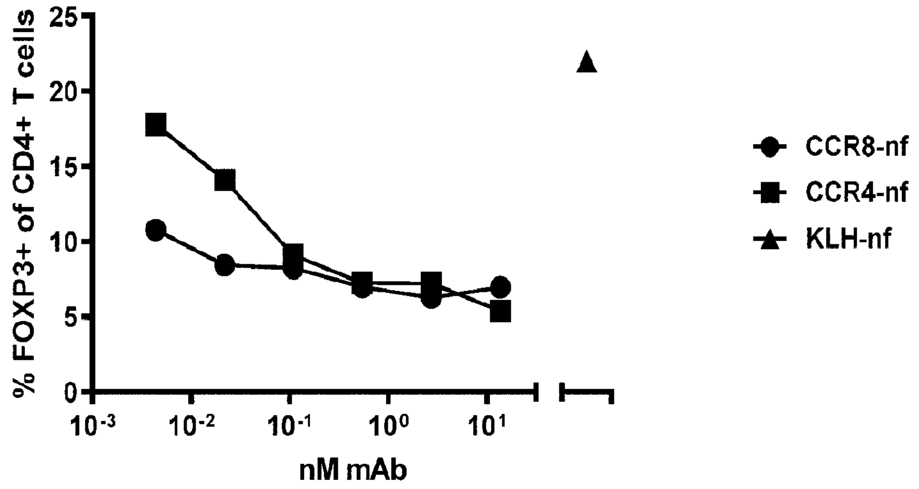
Figure 20B:
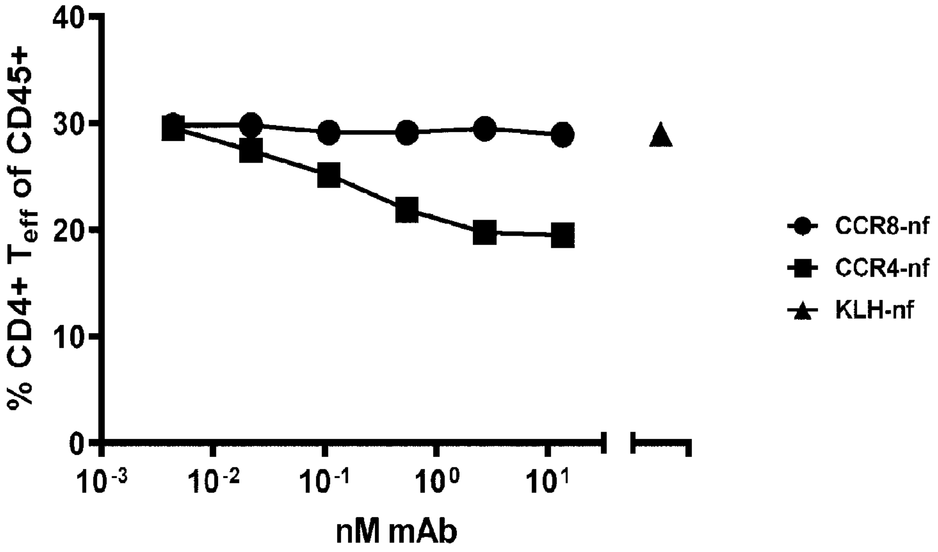
Figure 20C:
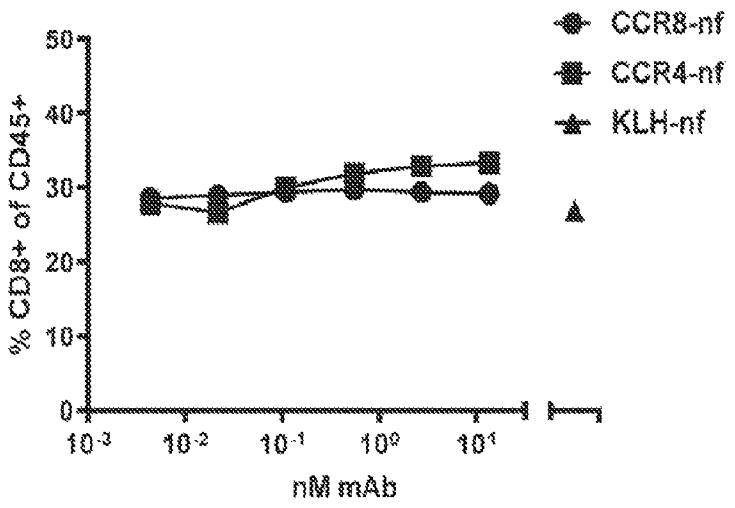

The capacity of the anti-hCCR8 mAbs to mediate the depletion of tumor Tregs was evaluated in an in vitro system in which digested patient tumors were co-cultured with allogeneic NK cells (Example 22). The anti-hCCR8 mAb, 4A19, was shown to induce depletion of tumor Tregs without reducing the population of Teffs. MAb 4A19 was more effective at Treg depletion than the anti-CCR4-nf mAb in this in vitro assay system (FIG. 20A) and did not induce depletion of $CD4^{+}$ effector T cells whereas the anti-CCR4-nf Ab measurably caused depletion of these cells (FIG. 20B). Neither anti-CCR8 nor anti-CCR4 depleted $CD8^{+}$ effector T cells (FIG. 20C).

The ability of the anti-hCCR8 mAbs to induce depletion of tumor Tregs was also evaluated in an ex vivo assay system using sliced patient tumors (Example 20). MAb 16B13-IgG1-nf was shown to mediate Treg depletion without the addition of allogeneic NK cells (FIGS. 18H and 18I).

In certain embodiments, an anti-CCR8 mAb or antigen-binding portion thereof of the invention induces depletion of tumor Tregs in vitro without reducing the population of $CD4^{+}$ or $CD8^{+}$ effector T cells. In preferred embodiments, depletion of tumor Tregs in vitro is measured using the assay described in Example 22.

In certain other embodiments, an anti-CCR8 mAb or antigen-binding portion thereof of the invention induces depletion of tumor Tregs in ex vivo patient tumor tissue samples. In certain preferred embodiments, depletion of tumor Tregs in the ex vivo patient tumor tissue samples is measured using the assay described in Example 20.

Anti-mCCR8-Mediated Depletion of Tumor Tregs Specifically, and Not CCR8 T Cells in Normal Tissues Samples In addition to tumor Tregs, CCR8 is also expressed on a small subset of thymic T cells, as well as skin resident T cells, which are a rare population found in the skin. In the CT26 mouse syngeneic tumor model, which exhibits a very similar CCR8 expression profile to humans, the anti-mCCR8 depleting mAb, anti-CCR8-mIgG2a, selectively depleted $CCR8^{+}$ Tregs in the tumor, but did not deplete $CCR8^{+}$ T cells in the skin, thymus, spleen, or blood (Example 24). The highly specific depleting activity of anti-CCR8-mIgG2a in the tumor but not in other CCR8-expressing organs may be due to the relatively low frequency of FcγRIV-expressing cells in proximity to Ab-bound target cells or to the lower CCR8 surface density on the $CCR8^{+}$ T cells in the skin, thymus, spleen and blood. This strongly supports the view that an anti-CCR8 Ab having optimized affinity for activating FcγRs, such as a human or humanized IgG1-nf anti-CCR8 mAb like 4A19 or 14S15, will enable potent tumor Treg depletion in human patients without inadvertent depletion of $CCR8^{+}$ T cells in the skin where CD16 expression is low.

In certain embodiments of the disclosed invention, an anti-hCCR8 mAb or antigen-binding portion thereof specifically induces depletion of tumor Tregs without depleting $CCR8^{+}$ T cells in the skin, thymus, spleen and blood. In certain preferred embodiments, depletion of tumor Tregs in vivo is measured using the assay described in Example 24.

Anti-CCR8 MAbs that Bind to the Same CCR8 Epitope as Does a Reference Ab

The present invention also provides an isolated Ab, preferably a mAb, or an antigen-binding portion thereof, which binds to the same epitope of hCCR8 as does a reference Ab, wherein the reference Ab comprises:

(a) a $V_H$ comprising consecutively linked amino acids having the sequence set forth as SEQ ID NO: 3 and a $V_L$ comprising consecutively linked amino acids having the sequence set forth as SEQ ID NO: 15;

(b) a $V_H$ comprising consecutively linked amino acids having the sequence set forth as SEQ ID NO: 4 and a $V_L$ comprising consecutively linked amino acids having the sequence set forth as SEQ ID NO: 16;

(c) a $V_H$ comprising consecutively linked amino acids having the sequence set forth as SEQ ID NO: 5 and a $V_L$ comprising consecutively linked amino acids having the sequence set forth as SEQ ID NO: 17;

(d) a $V_H$ comprising consecutively linked amino acids having the sequence set forth as SEQ ID NO: 6 and a $V_L$ comprising consecutively linked amino acids having the sequence set forth as SEQ ID NO: 18;

(e) a $V_H$ comprising consecutively linked amino acids having the sequence set forth as SEQ ID NO: 7 and a $V_L$ comprising consecutively linked amino acids having the sequence set forth as SEQ ID NO: 19;

(f) a $V_H$ comprising consecutively linked amino acids having the sequence set forth as SEQ ID NO: 8 and a $V_L$ comprising consecutively linked amino acids having the sequence set forth as SEQ ID NO: 20;

(g) a $V_H$ comprising consecutively linked amino acids having the sequence set forth as SEQ ID NO: 9 and a $V_L$ comprising consecutively linked amino acids having the sequence set forth as SEQ ID NO: 21;

(h) a $V_H$ comprising consecutively linked amino acids having the sequence set forth as SEQ ID NO: 10 and a $V_L$ comprising consecutively linked amino acids having the sequence set forth as SEQ ID NO: 22;

(i) a $V_H$ comprising consecutively linked amino acids having the sequence set forth as SEQ ID NO: 11 and a $V_L$ comprising consecutively linked amino acids having the sequence set forth as SEQ ID NO: 23;

(j) a $V_H$ comprising consecutively linked amino acids having the sequence set forth as SEQ ID NO: 12 and a $V_L$ comprising consecutively linked amino acids having the sequence set forth as SEQ ID NO: 24;

(k) a $V_H$ comprising consecutively linked amino acids having the sequence set forth as SEQ ID NO: 13 and a $V_L$ comprising consecutively linked amino acids having the sequence set forth as SEQ ID NO: 25;

(l) a $V_H$ comprising consecutively linked amino acids having the sequence set forth as SEQ ID NO: 14 and a $V_L$ comprising consecutively linked amino acids having the sequence set forth as SEQ ID NO: 26; or (m) a $V_H$ comprising consecutively linked amino acids having the sequence set forth as SEQ ID NO: 115 and a $V_L$ comprising consecutively linked amino acids having the sequence set forth as SEQ ID NO: 116.

In certain preferred embodiments an isolated Ab, preferably a mAb, or an antigen-binding portion thereof is provided, which binds to the same epitope of hCCR8 as does a reference Ab, wherein the reference Ab comprises:

(a) a $V_H$ comprising consecutively linked amino acids having the sequence set forth as SEQ ID NO: 4 and a $V_L$ comprising consecutively linked amino acids having the sequence set forth as SEQ ID NO: 16;

(b) a $V_H$ comprising consecutively linked amino acids having the sequence set forth as SEQ ID NO: 1144 and a $V_L$ comprising consecutively linked amino acids having the sequence set forth as SEQ ID NO: 116; or (c) a $V_H$ comprising consecutively linked amino acids having the sequence set forth as SEQ ID NO: 6 and a $V_L$ comprising consecutively linked amino acids having the sequence set forth as SEQ ID NO: 18.

In certain preferred embodiments, an isolated Ab, preferably a mAb, or an antigen-binding portion thereof is provided, which binds to the same epitope of hCCR8 as does a reference Ab, wherein the reference Ab comprises a $V_H$ comprising consecutively linked amino acids having the sequence set forth as SEQ ID NO: 6 and a $V_L$ comprising consecutively linked amino acids having the sequence set forth as SEQ ID NO: 18.

Anti-CCR8 MAbs that Cross-Compete with a Reference Ab for Binding to CCR8

Also encompassed within the scope of the disclosed invention is an isolated Ab, preferably a mAb, or an antigen-binding portion thereof, which specifically binds to hCCR8 expressed on the surface of a cell, and cross-competes with a reference Ab or a reference antigen-binding portion thereof for binding to hCCR8. The ability of a pair of Abs to "cross-compete" for binding to an antigen, e.g., CCR8, indicates that a first Ab binds to substantially the same epitope region of the antigen as, and sterically hinders the binding of, a second Ab to that particular epitope region and, conversely, the second Ab binds to substantially the same epitope region of the antigen as, and sterically hinders the binding of, the first Ab to that epitope region. Thus, the ability of a test Ab to competitively inhibit the binding of, for example, mAb 14S15 or 4A19 to hCCR8, demonstrates that the test Ab binds to substantially the same epitope region of hCCR8 as does mAb 14S15 or 4A19.

A first Ab is considered to bind to "substantially the same epitope" as does a second Ab if the first Ab reduces the binding of the second Ab to an antigen by at least about 40%. Preferably, the first Ab reduces the binding of the second Ab to the antigen by more than about 50% (e.g., at least about 60% or at least about 70%). In more preferred embodiments, the first Ab reduces the binding of the second Ab to the antigen by more than about 70% (e.g., at least about 80%, at least about 90%, or about 100%). The order of the first and second Abs can be reversed, i.e. the "second" Ab can be first bound to the surface and the "first" is thereafter brought into contact with the surface in the presence of the "second" Ab. The Abs are considered to "cross-compete" if a competitive reduction in binding to the antigen is observed irrespective of the order in which the Abs are added to the immobilized antigen.

Cross-competing Abs are expected to have functional properties very similar to the properties of the reference Abs by virtue of their binding to substantially the same epitope region of an antigen such as a CCR8 receptor. The higher the degree of cross-competition, the more similar will the functional properties be. For example, two cross-competing Abs are expected to have essentially the same functional properties if they each inhibit binding of the other to an epitope by at least about 80%. This similarity in function is expected to be even closer if the cross-competing Abs exhibit similar affinities for binding to the epitope as measured by the dissociation constant ($K_D$).

Cross-competing anti-antigen Abs can be readily identified based on their ability to detectably compete in standard antigen binding assays, including BIACORE® analysis, ELISA assays or flow cytometry, using either recombinant antigen molecules or cell-surface expressed antigen molecules. By way of example, a simple competition assay to identify whether a test Ab competes with mAb 4A19 for binding to hCCR8 may involve: (1) measuring the binding of 4A19, applied at saturating concentration, to a BIACORE® chip (or other suitable medium for SPR analysis) onto which hCCR8 is immobilized, and (2) measuring the binding of 4A19 to a hCCR8-coated BIACORE® chip (or other medium suitable) to which the test Ab has been previously bound. The binding of 4A19 to the hCCR8-1-coated surface in the presence and absence of the test Ab is compared. A significant (e.g., more than about 40%) reduction in binding of 4A19 in the presence of the test Ab indicates that both Abs recognize substantially the same epitope such that they compete for binding to the hCCR8 target. The percentage by which the binding of a first Ab to an antigen is inhibited by a second Ab can be calculated as: [1-(detected binding of first Ab in presence of second Ab)/(detected binding of first Ab in absence of second Ab)]×100. To determine whether the Abs cross-compete, the competitive binding assay is repeated except that the binding of the test Ab to the hCCR8-coated chip in the presence of 4A19 is measured.

Any of the anti-CCR8 Abs disclosed herein may serve as a reference Ab in cross-competition assays. In certain embodiments, the reference Ab comprises:

(a) a $V_H$ comprising consecutively linked amino acids having the sequence set forth as SEQ ID NO: 3 and a $V_L$ comprising consecutively linked amino acids having the sequence set forth as SEQ ID NO: 15;
(b) a $V_H$ comprising consecutively linked amino acids having the sequence set forth as SEQ ID NO: 4 and a $V_L$ comprising consecutively linked amino acids having the sequence set forth as SEQ ID NO: 16;
(c) a $V_H$ comprising consecutively linked amino acids having the sequence set forth as SEQ ID NO: 5 and a $V_L$ comprising consecutively linked amino acids having the sequence set forth as SEQ ID NO: 17;
(d) a $V_H$ comprising consecutively linked amino acids having the sequence set forth as SEQ ID NO: 6 and a $V_L$ comprising consecutively linked amino acids having the sequence set forth as SEQ ID NO: 18;
(e) a $V_H$ comprising consecutively linked amino acids having the sequence set forth as SEQ ID NO: 7 and a $V_L$ comprising consecutively linked amino acids having the sequence set forth as SEQ ID NO: 19;
(f) a $V_H$ comprising consecutively linked amino acids having the sequence set forth as SEQ ID NO: 8 and a $V_L$ comprising consecutively linked amino acids having the sequence set forth as SEQ ID NO: 20;
(g) a $V_H$ comprising consecutively linked amino acids having the sequence set forth as SEQ ID NO: 9 and a $V_L$ comprising consecutively linked amino acids having the sequence set forth as SEQ ID NO: 21;
(h) a $V_H$ comprising consecutively linked amino acids having the sequence set forth as SEQ ID NO: 10 and a $V_L$ comprising consecutively linked amino acids having the sequence set forth as SEQ ID NO: 22;
(i) a $V_H$ comprising consecutively linked amino acids having the sequence set forth as SEQ ID NO: 11 and a $V_L$ comprising consecutively linked amino acids having the sequence set forth as SEQ ID NO: 23;
(j) a $V_H$ comprising consecutively linked amino acids having the sequence set forth as SEQ ID NO: 12 and a $V_L$ comprising consecutively linked amino acids having the sequence set forth as SEQ ID NO: 24;
(k) a $V_H$ comprising consecutively linked amino acids having the sequence set forth as SEQ ID NO: 13 and a $V_L$ comprising consecutively linked amino acids having the sequence set forth as SEQ ID NO: 25;
(l) a $V_H$ comprising consecutively linked amino acids having the sequence set forth as SEQ ID NO: 14 and a $V_L$ comprising consecutively linked amino acids having the sequence set forth as SEQ ID NO: 26; or
(m) a $V_H$ comprising consecutively linked amino acids having the sequence set forth as SEQ ID NO: 115 and a $V_L$ comprising consecutively linked amino acids having the sequence set forth as SEQ ID NO: 116.

In certain preferred embodiments, the reference Ab comprises:

(a) a $V_H$ comprising consecutively linked amino acids having the sequence set forth as SEQ ID NO: 4 and a $V_L$ comprising consecutively linked amino acids having the sequence set forth as SEQ ID NO: 16;
(b) a $V_H$ comprising consecutively linked amino acids having the sequence set forth as SEQ ID NO: 1144 and a $V_L$ comprising consecutively linked amino acids having the sequence set forth as SEQ ID NO: 116; or
(c) a $V_H$ comprising consecutively linked amino acids having the sequence set forth as SEQ ID NO: 6 and a $V_L$ comprising consecutively linked amino acids having the sequence set forth as SEQ ID NO: 18.

In certain preferred embodiments the reference Ab comprises a $V_H$ comprising consecutively linked amino acids having the sequence set forth as SEQ ID NO: 6 and a $V_L$ comprising consecutively linked amino acids having the sequence set forth as SEQ ID NO: 18.

Structurally Defined Anti-CCR8 MAbs;

The present disclosure also provides an isolated Ab, preferably a mAb, or an antigen-binding portion thereof, which specifically binds to hCCR8 expressed on the surface of a cell, and comprises the CDR1, CDR2 and CDR3 domains in each of:

(a) a $V_H$ comprising consecutively linked amino acids having the sequence set forth as SEQ ID NO: 3 and a $V_L$ comprising consecutively linked amino acids having the sequence set forth as SEQ ID NO: 15;
(b) a $V_H$ comprising consecutively linked amino acids having the sequence set forth as SEQ ID NO: 4 and a $V_L$ comprising consecutively linked amino acids having the sequence set forth as SEQ ID NO: 16;
(c) a $V_H$ comprising consecutively linked amino acids having the sequence set forth as SEQ ID NO: 5 and a $V_L$ comprising consecutively linked amino acids having the sequence set forth as SEQ ID NO: 17;
(d) a $V_H$ comprising consecutively linked amino acids having the sequence set forth as SEQ ID NO: 6 and a $V_L$ comprising consecutively linked amino acids having the sequence set forth as SEQ ID NO: 18;
(e) a $V_H$ comprising consecutively linked amino acids having the sequence set forth as SEQ ID NO: 7 and a $V_L$ comprising consecutively linked amino acids having the sequence set forth as SEQ ID NO: 19;
(f) a $V_H$ comprising consecutively linked amino acids having the sequence set forth as SEQ ID NO: 8 and a $V_L$ comprising consecutively linked amino acids having the sequence set forth as SEQ ID NO: 20;
(g) a $V_H$ comprising consecutively linked amino acids having the sequence set forth as SEQ ID NO: 9 and a $V_L$ comprising consecutively linked amino acids having the sequence set forth as SEQ ID NO: 21;
(h) a $V_H$ comprising consecutively linked amino acids having the sequence set forth as SEQ ID NO: 10 and a $V_L$ comprising consecutively linked amino acids having the sequence set forth as SEQ ID NO: 22;
(i) a $V_H$ comprising consecutively linked amino acids having the sequence set forth as SEQ ID NO: 11 and a $V_L$ comprising consecutively linked amino acids having the sequence set forth as SEQ ID NO: 23;
(j) a $V_H$ comprising consecutively linked amino acids having the sequence set forth as SEQ ID NO: 12 and a $V_L$ comprising consecutively linked amino acids having the sequence set forth as SEQ ID NO: 24;

(k) a $V_H$ comprising consecutively linked amino acids having the sequence set forth as SEQ ID NO: 13 and a $V_L$ comprising consecutively linked amino acids having the sequence set forth as SEQ ID NO: 25;

(l) a $V_H$ comprising consecutively linked amino acids having the sequence set forth as SEQ ID NO: 14 and a $V_L$ comprising consecutively linked amino acids having the sequence set forth as SEQ ID NO: 26; or (m) a $V_H$ comprising consecutively linked amino acids having the sequence set forth as SEQ ID NO: 115 and a $V_L$ comprising consecutively linked amino acids having the sequence set forth as SEQ ID NO: 116.

Preferred is an isolated Ab, preferably a mAb, or an antigen-binding portion thereof, which specifically binds to hCCR8 expressed on the surface of a cell, and comprises the CDR1, CDR2 and CDR3 domains in each of:

(a) a $V_H$ comprising consecutively linked amino acids having the sequence set forth as SEQ ID NO: 4 and a $V_L$ comprising consecutively linked amino acids having the sequence set forth as SEQ ID NO: 16;

(b) a $V_H$ comprising consecutively linked amino acids having the sequence set forth as SEQ ID NO: 1144 and a $V_L$ comprising consecutively linked amino acids having the sequence set forth as SEQ ID NO: 116; or (c) a $V_H$ comprising consecutively linked amino acids having the sequence set forth as SEQ ID NO: 6 and a $V_L$ comprising consecutively linked amino acids having the sequence set forth as SEQ ID NO: 18.

Preferred is an isolated Ab, preferably a mAb, or an antigen-binding portion thereof, which specifically binds to hCCR8 expressed on the surface of a cell, and comprises the CDR1, CDR2 and CDR3 domains in each of a $V_H$ comprising consecutively linked amino acids having the sequence set forth as SEQ ID NO: 6 and a $V_L$ comprising consecutively linked amino acids having the sequence set forth as SEQ ID NO: 18.

Different methods have been developed to delineate the CDR domains within an Ab. The approach of Kabat and co-workers (Wu and Kabat, 1970; Kabat et al., 1983), was based on the assumption that CDRs include the most variable positions in Abs and therefore could be identified by aligning the fairly limited number of Ab sequences then available. Based on this alignment, Kabat et al. introduced a numbering scheme for the residues in the hypervariable regions and determined which positions mark the beginning and the end of each CDR (http://bioinf.org.uk/abs/simkab.html).

In addition to the widely used Kabat definition, others including the Chothia (Chothia et al., 1987; 1989; Al-Lazikani et al., 1997; http://bioinforg.uk/abs/chothia.html), AbNum (Abhinandan and Martin, 2008; see AbNum; available at http://www.bioinf.org.uk/abs/abnum/), AbM (http://www.bioinforg.uk/abs; Martin et al., 1989), contact (http://bioinf.org.uk/abs/; MacCallum et al., 1996) and IMGT (Lefranc et al., 2003; http://www.imgt.org) definitions that seek to address deficiencies of the Kabat definitions, have been employed. The Kabat definition is the most commonly used method to predict CDR domains, notwithstanding it was developed when no structural information on Abs was available.

Where not explicitly stated, and unless the context indicates otherwise, CDRs disclosed herein have been identified using the Kabat definition. The amino acid sequences for the 6 CDR domains as defined using the Kabat method, as well as the amino acid sequences for the $V_H$, $V_L$, heavy chain and light chain for mAbs 16B13, 14S15, 14S15h, 18Y12, 4A19, 2M18, 15C17, 13T20, 10R3, 8D55, 1V11, 11K16 and 12F27 are shown in Table 10.

The present invention provides isolated Abs, preferably mAbs, comprising the following CDR domains as defined by the Kabat method:

(a) a heavy chain variable region CDR1 comprising consecutively linked amino acids having the sequence set forth as SEQ ID NO: 27; a heavy chain variable region CDR2 comprising consecutively linked amino acids having the sequence set forth as SEQ ID NO: 28; a heavy chain variable region CDR3 comprising consecutively linked amino acids having the sequence set forth as SEQ ID NO: 29; a light chain variable region CDR1 comprising consecutively linked amino acids having the sequence set forth as SEQ ID NO: 30; a light chain variable region CDR2 comprising consecutively linked amino acids having the sequence set forth as SEQ ID NO: 31; and a light chain variable region CDR3 comprising consecutively linked amino acids having the sequence set forth as SEQ ID NO: 32;

(b) a heavy chain variable region CDR1 comprising consecutively linked amino acids having the sequence set forth as SEQ ID NO: 33; a heavy chain variable region CDR2 comprising consecutively linked amino acids having the sequence set forth as SEQ ID NO: 34; a heavy chain variable region CDR3 comprising consecutively linked amino acids having the sequence set forth as SEQ ID NO: 35; a light chain variable region CDR1 comprising consecutively linked amino acids having the sequence set forth as SEQ ID NO: 36; a light chain variable region CDR2 comprising consecutively linked amino acids having the sequence set forth as SEQ ID NO: 37; and a light chain variable region CDR3 comprising consecutively linked amino acids having the sequence set forth as SEQ ID NO: 38;

(c) a heavy chain variable region CDR1 comprising consecutively linked amino acids having the sequence set forth as SEQ ID NO: 39; a heavy chain variable region CDR2 comprising consecutively linked amino acids having the sequence set forth as SEQ ID NO: 40; a heavy chain variable region CDR3 comprising consecutively linked amino acids having the sequence set forth as SEQ ID NO: 41; a light chain variable region CDR1 comprising consecutively linked amino acids having the sequence set forth as SEQ ID NO: 42; a light chain variable region CDR2 comprising consecutively linked amino acids having the sequence set forth as SEQ ID NO: 43; and a light chain variable region CDR3 comprising consecutively linked amino acids having the sequence set forth as SEQ ID NO: 44;

(d) a heavy chain variable region CDR1 comprising consecutively linked amino acids having the sequence set forth as SEQ ID NO: 45; a heavy chain variable region CDR2 comprising consecutively linked amino acids having the sequence set forth as SEQ ID NO: 46; a heavy chain variable region CDR3 comprising consecutively linked amino acids having the sequence set forth as SEQ ID NO: 47; a light chain variable region CDR1 comprising consecutively linked amino acids having the sequence set forth as SEQ ID NO: 48; a light chain variable region CDR2 comprising consecutively linked amino acids having the sequence set forth as SEQ ID NO: 49; and a light chain variable region CDR3 comprising consecutively linked amino acids having the sequence set forth as SEQ ID NO: 50;

(e) a heavy chain variable region CDR1 comprising consecutively linked amino acids having the sequence set forth as SEQ ID NO: 51; a heavy chain variable region CDR2 comprising consecutively linked amino acids having the sequence set forth as SEQ ID NO: 52; a heavy chain variable region CDR3 comprising consecutively linked amino acids having the sequence set forth as SEQ ID NO: 53; a light chain variable region CDR1 comprising consecutively linked amino acids having the sequence set forth as SEQ ID NO: 54; a light chain variable region CDR2 comprising consecutively linked amino acids having the sequence set forth as SEQ ID NO: 55; and a light chain variable region CDR3 comprising consecutively linked amino acids having the sequence set forth as SEQ ID NO: 56;

(f) a heavy chain variable region CDR1 comprising consecutively linked amino acids having the sequence set forth as SEQ ID NO: 57; a heavy chain variable region CDR2 comprising consecutively linked amino acids having the sequence set forth as SEQ ID NO: 58; a heavy chain variable region CDR3 comprising consecutively linked amino acids having the sequence set forth as SEQ ID NO: 59; a light chain variable region CDR1 comprising consecutively linked amino acids having the sequence set forth as SEQ ID NO: 60; a light chain variable region CDR2 comprising consecutively linked amino acids having the sequence set forth as SEQ ID NO: 61; and a light chain variable region CDR3 comprising consecutively linked amino acids having the sequence set forth as SEQ ID NO: 62;

(g) heavy chain variable region CDR1 comprising consecutively linked amino acids having the sequence set forth as SEQ ID NO: 63; a heavy chain variable region CDR2 comprising consecutively linked amino acids having the sequence set forth as SEQ ID NO: 64; a heavy chain variable region CDR3 comprising consecutively linked amino acids having the sequence set forth as SEQ ID NO: 65; a light chain variable region CDR1 comprising consecutively linked amino acids having the sequence set forth as SEQ ID NO: 66; a light chain variable region CDR2 comprising consecutively linked amino acids having the sequence set forth as SEQ ID NO: 67; and a light chain variable region CDR3 comprising consecutively linked amino acids having the sequence set forth as SEQ ID NO: 68;

(h) a heavy chain variable region CDR1 comprising consecutively linked amino acids having the sequence set forth as SEQ ID NO: 69; a heavy chain variable region CDR2 comprising consecutively linked amino acids having the sequence set forth as SEQ ID NO: 70; a heavy chain variable region CDR3 comprising consecutively linked amino acids having the sequence set forth as SEQ ID NO: 71; a light chain variable region CDR1 comprising consecutively linked amino acids having the sequence set forth as SEQ ID NO: 72; a light chain variable region CDR2 comprising consecutively linked amino acids having the sequence set forth as SEQ ID NO: 73; and a light chain variable region CDR3 comprising consecutively linked amino acids having the sequence set forth as SEQ ID NO: 74;

(i) a heavy chain variable region CDR1 comprising consecutively linked amino acids having the sequence set forth as SEQ ID NO: 75; a heavy chain variable region CDR2 comprising consecutively linked amino acids having the sequence set forth as SEQ ID NO: 76; a heavy chain variable region CDR3 comprising consecutively linked amino acids having the sequence set forth as SEQ ID NO: 77; a light chain variable region CDR1 comprising consecutively linked amino acids having the sequence set forth as SEQ ID NO: 78; a light chain variable region CDR2 comprising consecutively linked amino acids having the sequence set forth as SEQ ID NO: 79; and a light chain variable region CDR3 comprising consecutively linked amino acids having the sequence set forth as SEQ ID NO: 80;

(j) a heavy chain variable region CDR1 comprising consecutively linked amino acids having the sequence set forth as SEQ ID NO: 81; a heavy chain variable region CDR2 comprising consecutively linked amino acids having the sequence set forth as SEQ ID NO: 82; a heavy chain variable region CDR3 comprising consecutively linked amino acids having the sequence set forth as SEQ ID NO: 83; a light chain variable region CDR1 comprising consecutively linked amino acids having the sequence set forth as SEQ ID NO: 84; a light chain variable region CDR2 comprising consecutively linked amino acids having the sequence set forth as SEQ ID NO: 85; and a light chain variable region CDR3 comprising consecutively linked amino acids having the sequence set forth as SEQ ID NO: 86;

(k) a heavy chain variable region CDR1 comprising consecutively linked amino acids having the sequence set forth as SEQ ID NO: 87; a heavy chain variable region CDR2 comprising consecutively linked amino acids having the sequence set forth as SEQ ID NO: 88; a heavy chain variable region CDR3 comprising consecutively linked amino acids having the sequence set forth as SEQ ID NO: 89; a light chain variable region CDR1 comprising consecutively linked amino acids having the sequence set forth as SEQ ID NO: 90; a light chain variable region CDR2 comprising consecutively linked amino acids having the sequence set forth as SEQ ID NO: 91; and a light chain variable region CDR3 comprising consecutively linked amino acids having the sequence set forth as SEQ ID NO: 92;

(l) a heavy chain variable region CDR1 comprising consecutively linked amino acids having the sequence set forth as SEQ ID NO: 93; a heavy chain variable region CDR2 comprising consecutively linked amino acids having the sequence set forth as SEQ ID NO: 94; a heavy chain variable region CDR3 comprising consecutively linked amino acids having the sequence set forth as SEQ ID NO: 95; a light chain variable region CDR1 comprising consecutively linked amino acids having the sequence set forth as SEQ ID NO: 96; a light chain variable region CDR2 comprising consecutively linked amino acids having the sequence set forth as SEQ ID NO: 97; and a light chain variable region CDR3 comprising consecutively linked amino acids having the sequence set forth as SEQ ID NO: 98; or (m) a heavy chain variable region CDR1 comprising consecutively linked amino acids having the sequence set forth as SEQ ID NO: 103; a heavy chain variable region CDR2 comprising consecutively linked amino acids having the sequence set forth as SEQ ID NO: 104; a heavy chain variable region CDR3 comprising consecutively linked amino acids having the sequence set forth as SEQ ID NO: 105; a light chain variable region CDR1 comprising consecutively linked amino acids having the sequence set forth as SEQ ID NO: 106; a light chain variable region CDR2 comprising consecutively linked amino acids having the sequence set forth as SEQ ID NO: 107; and a light chain variable region CDR3 comprising consecutively linked amino acids having the sequence set forth as SEQ ID NO: 108.

Preferred isolated Abs, preferably mAbs, comprise the following CDR domains as defined by the Kabat method:

(a) a heavy chain variable region CDR1 comprising consecutively linked amino acids having the sequence set forth as SEQ ID NO: 33; a heavy chain variable region CDR2 comprising consecutively linked amino acids having the sequence set forth as SEQ ID NO: 34; a heavy chain variable region CDR3 comprising consecutively linked amino acids having the sequence set forth as SEQ ID NO: 35; a light chain variable region CDR1 comprising consecutively linked amino acids having the sequence set forth as SEQ ID NO: 36; a light chain variable region CDR2 comprising consecutively linked amino acids having the sequence set forth as SEQ ID NO: 37; and a light chain variable region CDR3 comprising consecutively linked amino acids having the sequence set forth as SEQ ID NO: 38;

(b) a heavy chain variable region CDR1 comprising consecutively linked amino acids having the sequence set forth as SEQ ID NO: 103; a heavy chain variable region CDR2 comprising consecutively linked amino acids having the sequence set forth as SEQ ID NO: 104; a heavy chain variable region CDR3 comprising consecutively linked amino acids having the sequence set forth as SEQ ID NO: 105; a light chain variable region CDR1 comprising consecutively linked amino acids having the sequence set forth as SEQ ID NO: 106; a light chain variable region CDR2 comprising consecutively linked amino acids having the sequence set forth as SEQ ID NO: 107; and a light chain variable region CDR3 comprising consecutively linked amino acids having the sequence set forth as SEQ ID NO: 108; or (c) a heavy chain variable region CDR1 comprising consecutively linked amino acids having the sequence set forth as SEQ ID NO: 45; a heavy chain variable region CDR2 comprising consecutively linked amino acids having the sequence set forth as SEQ ID NO: 46; a heavy chain variable region CDR3 comprising consecutively linked amino acids having the sequence set forth as SEQ ID NO: 47; a light chain variable region CDR1 comprising consecutively linked amino acids having the sequence set forth as SEQ ID NO: 48; a light chain variable region CDR2 comprising consecutively linked amino acids having the sequence set forth as SEQ ID NO: 49; and a light chain variable region CDR3 comprising consecutively linked amino acids having the sequence set forth as SEQ ID NO: 50.

In certain preferred embodiments, the isolated Abs, preferably mAbs, comprise the following CDR domains as defined by the Kabat method: a heavy chain variable region CDR1 comprising consecutively linked amino acids having the sequence set forth as SEQ ID NO: 45; a heavy chain variable region CDR2 comprising consecutively linked amino acids having the sequence set forth as SEQ ID NO: 46; a heavy chain variable region CDR3 comprising consecutively linked amino acids having the sequence set forth as SEQ ID NO: 47; a light chain variable region CDR1 comprising consecutively linked amino acids having the sequence set forth as SEQ ID NO: 48; a light chain variable region CDR2 comprising consecutively linked amino acids having the sequence set forth as SEQ ID NO: 49; and a light chain variable region CDR3 comprising consecutively linked amino acids having the sequence set forth as SEQ ID NO: 50.

The disclosed invention also encompasses an isolated Ab, preferably a mAb, or an antigen-binding portion thereof, which specifically binds to hCCR8 expressed on the surface of a cell, wherein the isolated Ab or antigen-binding portion thereof comprises:

(a) a $V_H$ comprising consecutively linked amino acids having the sequence set forth as SEQ ID NO: 3 and a $V_L$ comprising consecutively linked amino acids having the sequence set forth as SEQ ID NO: 15;

(b) a $V_H$ comprising consecutively linked amino acids having the sequence set forth as SEQ ID NO: 4 and a $V_L$ comprising consecutively linked amino acids having the sequence set forth as SEQ ID NO: 16;

(c) a $V_H$ comprising consecutively linked amino acids having the sequence set forth as SEQ ID NO: 5 and a $V_L$ comprising consecutively linked amino acids having the sequence set forth as SEQ ID NO: 17;

(d) a $V_H$ comprising consecutively linked amino acids having the sequence set forth as SEQ ID NO: 6 and a $V_L$ comprising consecutively linked amino acids having the sequence set forth as SEQ ID NO: 18;

(e) a $V_H$ comprising consecutively linked amino acids having the sequence set forth as SEQ ID NO: 7 and a $V_L$ comprising consecutively linked amino acids having the sequence set forth as SEQ ID NO: 19;

(f) a $V_H$ comprising consecutively linked amino acids having the sequence set forth as SEQ ID NO: 8 and a $V_L$ comprising consecutively linked amino acids having the sequence set forth as SEQ ID NO: 20;

(g) a $V_H$ comprising consecutively linked amino acids having the sequence set forth as SEQ ID NO: 9 and a $V_L$ comprising consecutively linked amino acids having the sequence set forth as SEQ ID NO: 21;

(h) a $V_H$ comprising consecutively linked amino acids having the sequence set forth as SEQ ID NO: 10 and a $V_L$ comprising consecutively linked amino acids having the sequence set forth as SEQ ID NO: 22;

(i) a $V_H$ comprising consecutively linked amino acids having the sequence set forth as SEQ ID NO: 11 and a $V_L$ comprising consecutively linked amino acids having the sequence set forth as SEQ ID NO: 23;

(j) a $V_H$ comprising consecutively linked amino acids having the sequence set forth as SEQ ID NO: 12 and a $V_L$ comprising consecutively linked amino acids having the sequence set forth as SEQ ID NO: 24;

(k) a $V_H$ comprising consecutively linked amino acids having the sequence set forth as SEQ ID NO: 13 and a $V_L$ comprising consecutively linked amino acids having the sequence set forth as SEQ ID NO: 25;

(l) a $V_H$ comprising consecutively linked amino acids having the sequence set forth as SEQ ID NO: 14 and a $V_L$ comprising consecutively linked amino acids having the sequence set forth as SEQ ID NO: 26; or (m) a $V_H$ comprising consecutively linked amino acids having the sequence set forth as SEQ ID NO: 115 and a $V_L$ comprising consecutively linked amino acids having the sequence set forth as SEQ ID NO: 116.

A preferred isolated Ab, preferably a mAb, or an antigen-binding portion thereof, specifically binds to hCCR8 expressed on the surface of a cell and comprises:

(a) a $V_H$ comprising consecutively linked amino acids having the sequence set forth as SEQ ID NO: 4 and a $V_L$ comprising consecutively linked amino acids having the sequence set forth as SEQ ID NO: 16;

(b) a $V_H$ comprising consecutively linked amino acids having the sequence set forth as SEQ ID NO: 115 and a $V_L$ comprising consecutively linked amino acids having the sequence set forth as SEQ ID NO: 116; or (c) a $V_H$ comprising consecutively linked amino acids having the sequence set forth as SEQ ID NO: 6 and a $V_L$ comprising consecutively linked amino acids having the sequence set forth as SEQ ID NO: 18;

A preferred isolated Ab, preferably a mAb, or an antigen-binding portion thereof, specifically binds to hCCR8 expressed on the surface of a cell and comprises a $V_H$ comprising consecutively linked amino acids having the sequence set forth as SEQ ID NO: 6 and a $V_L$ comprising consecutively linked amino acids having the sequence set forth as SEQ ID NO: 18.

Anti-CCR8 Abs comprising $V_H$ and $V_L$ regions having amino acid sequences that are highly similar or homologous to the amino acid sequences of any of the above anti-CCR8 Abs and which retain the functional properties of these Abs are also suitable for use in the present methods. For example, suitable Abs include mAbs comprising a $V_H$ and/or $V_L$ region each comprising consecutively linked amino acids having a sequence that is at least 80% identical to the amino acid sequence set forth in SEQ ID Nos. 6 and/or 18, respectively. In further embodiments, for example, the $V_H$ and/or $V_L$ amino acid sequences exhibits at least 85%, 90%, 95%, or 99% identity to the sequences set forth in SEQ ID Nos. 6 and/or 18, respectively. As used herein, the percent sequence identity between two amino acid sequences is a function of the number of identical positions shared by the sequences relative to the length of the sequences compared (i.e., % identity=number of identical positions/total number of positions being compared×100), taking into account the number of any gaps, and the length of each such gap, introduced to maximize the degree of sequence identity between the two sequences. The comparison of sequences and determination of percent identity between two sequences can be accomplished using mathematical algorithms that are well known to those of ordinary skill in the art.

Where anti-CCR8 Abs comprising $V_H$ and $V_L$ regions having amino acid sequences that are highly similar or homologous to the amino acid sequences of any of the above anti-CCR8 Abs and which retain the functional properties of these Abs are disclosed, they may have 100% identity within at least 1, 2, 3, 4, 5, or all 6 CDRs and at least 85%, 90%, 95%, or 99% identity to the relevant full $V_H$ and/or $V_L$ sequence.

For example, an isolated Ab, preferably a mAb, or an antigen-binding portion thereof, which specifically binds to hCCR8 expressed on the surface of a cell, may comprise:

(a) a $V_H$ comprising consecutively linked amino acids having a sequence that is at least 85%, 90%, 95%, or 99% identical to the sequence set forth as SEQ ID NO: 4 and a $V_L$ comprising consecutively linked amino acids having a sequence that is at least 85%, 90%, 95%, or 99% identical to the sequence set forth as SEQ ID NO: 16, optionally wherein the $V_H$ comprises at least 1, 2 or all 3 of the CDRs as defined for SEQ ID NO:4 (SEQ ID Nos 33-35) and the $V_H$ comprises at least 1, 2, or all 3 of the CDRs as defined for SEQ ID NO:16 (SEQ ID Nos 36-38);

(b) a $V_H$ comprising consecutively linked amino acids having a sequence that is at least 85%, 90%, 95%, or 99% identical to the sequence set forth as SEQ ID NO: 115 and a $V_L$ comprising consecutively linked amino acids having a sequence that is at least 85%, 90%, 95%, or 99% identical to the sequence set forth as SEQ ID NO: 116, optionally wherein the $V_H$ comprises at least 1, 2 or all 3 of the CDRs as defined for SEQ ID NO: 115 (SEQ ID NOs. 103-105) and the $V_L$ comprises at least 1, 2, or all 3 of the CDRs as defined for SEQ ID NO: 116 (SEQ ID NOs. 106-108); or (c) a $V_H$ comprising consecutively linked amino acids having a sequence that is at least 85%, 90%, 95%, or 99% identical to the sequence set forth as SEQ ID NO: 6 and a $V_L$ comprising consecutively linked amino acids having a sequence that is at least 85%, 90%, 95%, or 99% identical to the sequence set forth as SEQ ID NO: 18, optionally wherein the $V_H$ comprises at least 1, 2 or all 3 of the CDRs as defined for SEQ ID NO: 6 (SEQ ID NOs. 45-47) and the $V_L$ comprises at least 1, 2 or all 3 of the CDRs as defined for SEQ ID NO:18 (SEQ ID NOs. 48-50).

Likewise, for any of the other isolated Abs referred to herein, the Ab may comprise a $V_H$ comprising consecutively linked amino acids having a sequence that is at least 85%, 90%, 95%, or 99% identical to the reference $V_H$ sequence, and a $V_L$ comprising consecutively linked amino acids having a sequence that is at least 85%, 90%, 95%, or 99% identical to the reference $V_H$ sequence, optionally wherein the $V_H$ comprises at least 1, 2 or all 3 of the CDRs as defined for the reference $V_H$ sequence, and the $V_L$ comprises at least 1, 2, or all 3 of the CDRs as defined for the reference $V_L$ sequence.

The present invention further encompasses an isolated Ab, preferably a mAb, or an antigen-binding portion thereof, which optionally specifically binds to hCCR8 expressed on the surface of a cell, wherein the isolated Ab or antigen-binding portion thereof comprises:

(a) a heavy chain comprising consecutively linked amino acids having the sequence set forth as SEQ ID NO: 99 and a light chain comprising consecutively linked amino acids having the sequence set forth as SEQ ID NO: 111;

(b) a heavy chain comprising consecutively linked amino acids having the sequence set forth as SEQ ID NO: 100 and a light chain comprising consecutively linked amino acids having the sequence set forth as SEQ ID NO: 112;

(c) a heavy chain comprising consecutively linked amino acids having the sequence set forth as SEQ ID NO: 101 and a light chain comprising consecutively linked amino acids having the sequence set forth as SEQ ID NO: 113;

(d) a heavy chain comprising consecutively linked amino acids having the sequence set forth as SEQ ID NO: 102 and a light chain comprising consecutively linked amino acids having the sequence set forth as SEQ ID NO: 114;

(e) a heavy chain comprising consecutively linked amino acids having the sequence set forth as SEQ ID NO: 117 and a light chain comprising consecutively linked amino acids having the sequence set forth as SEQ ID NO: 118; or (f) a heavy chain comprising consecutively linked amino acids having the sequence set forth as SEQ ID NO: 110 and a light chain comprising consecutively linked amino acids having the sequence set forth as SEQ ID NO: 119.

Preferred is an isolated Ab, preferably a mAb, or an antigen-binding portion thereof, which optionally specifically binds to hCCR8 expressed on the surface of a cell, wherein the isolated Ab or antigen-binding portion thereof comprises:

(a) a heavy chain comprising consecutively linked amino acids having the sequence set forth as SEQ ID NO: 100 and a light chain comprising consecutively linked amino acids having the sequence set forth as SEQ ID NO: 112;

(b) a heavy chain comprising consecutively linked amino acids having the sequence set forth as SEQ ID NO: 117 and a light chain comprising consecutively linked amino acids having the sequence set forth as SEQ ID NO: 118; or (c) a heavy chain comprising consecutively linked amino acids having the sequence set forth as SEQ ID NO: 102 and a light chain comprising consecutively linked amino acids having the sequence set forth as SEQ ID NO: 114.

Preferred is an isolated Ab, preferably a mAb, or an antigen-binding portion thereof, which optionally specifically binds to hCCR8 expressed on the surface of a cell, wherein the isolated Ab or antigen-binding portion thereof comprises:

(a) a heavy chain comprising consecutively linked amino acids having the sequence set forth as SEQ ID NO: 102 and a light chain comprising consecutively linked amino acids having the sequence set forth as SEQ ID NO: 114.

In certain embodiments, the isolated anti-CCR8 Ab or antigen-binding portion thereof of this invention is a human Ab or fragment thereof. In other embodiments, it is a humanized Ab or fragment thereof. In further embodiments, it is a chimeric Ab or fragment thereof. In other embodiments, the isolated anti-CCR8 Ab or antigen-binding portion thereof is a mouse Ab or fragment thereof. For administration to human subjects, the Abs are preferably chimeric Abs or, more preferably, humanized or human Abs. Such chimeric, humanized, human or mouse mAbs can be prepared and isolated by methods well known in the art.

Anti-CCR8 Abs disclosed herein also include antigen-binding fragments that are capable of mediating ADCC, in addition to full-length Abs.

Anti-CCR8 Immunoconjugates

In another aspect, the present invention relates to any one of the isolated anti-hCCR8 Abs disclosed herein, or an antigen-binding portion thereof, linked to a cytolytic agent, such as a cytotoxin or a radioactive isotope. Such conjugates are referred to herein as "immunoconjugates". Cytotoxins can be conjugated to Abs of the invention using linker technology available in the art. Methods for preparing radioimmunoconjugates are also established in the art.

Bispecific Molecules

In another aspect, the present invention relates to bispecific molecules comprising any one of the isolated anti-hCCR8 mAbs disclosed herein, or an antigen-binding portion thereof, linked to a binding domain that has a different binding specificity than the anti-hCCR8 mAb or antigen-binding portion thereof. The binding domain may be a functional molecule, e.g., another Ab, antigen-binding portion of an Ab, or a ligand for a receptor), such that the bispecific molecule generated binds to at least two different binding sites or target molecules.

Nucleic Acids Encoding Anti-hCCR8 MAbs and Use for Expressing Abs

Another aspect of the disclosure pertains to nucleic acids that encode any of the isolated anti-hCCR8 Abs of the invention. The disclosure provides an isolated nucleic acid encoding any of the anti-CCR8 mAbs or antigen-binding portions thereof described herein.

An "isolated" nucleic acid refers to a nucleic acid composition of matter that is markedly different, i.e., has a distinctive chemical identity, nature and utility, from nucleic acids as they exist in nature. For example, an isolated DNA, unlike native DNA, is a free-standing portion of a native DNA and not an integral part of a larger structural complex, the chromosome, found in nature. Further, an isolated DNA, unlike native DNA, can be used as a PCR primer or a hybridization probe for, among other things, measuring gene expression and detecting biomarker genes or mutations for diagnosing disease or predicting the efficacy of a therapeutic. An isolated nucleic acid may also be purified so as to be substantially free of other cellular components or other contaminants, e.g., other cellular nucleic acids or proteins, using standard techniques well known in the art.

Nucleic acids of the invention can be obtained using standard molecular biology techniques. For Abs expressed by hybridomas (e.g., hybridomas prepared from transgenic mice carrying human Ig genes as described in Example 8), cDNAs encoding the light and heavy chains or variable regions of the Ab made by the hybridoma can be obtained by standard PCR amplification techniques. Once DNA fragments encoding $V_H$ and $V_L$ segments are obtained, these DNA fragments can be further manipulated using standard recombinant DNA techniques, for example, to convert the variable region DNAs to full-length Ab chain genes, to Fab fragment genes, or to a scFv gene. For Abs obtained from an Ig gene library (e.g., using phage display techniques), nucleic acids encoding the Ab can be recovered from the library.

A nucleic acid of the invention can be, for example, RNA or DNA such as cDNA or genomic DNA. In preferred embodiments, the nucleic acid is a cDNA.

The disclosure also provides an expression vector comprising an isolated nucleic which encodes an anti-CCR8 mAb or antigen-binding portion thereof. The disclosure further provides a host cell comprising said expression vector. Eukaryotic cells, and most preferably mammalian host cells, are preferred as host cells for expressing Abs because such eukaryotic cells, and in particular mammalian cells, are more likely than prokaryotic cells to assemble and secrete a properly folded and immunologically active Ab. Preferred mammalian host cells for expressing the recombinant Abs of the invention include Chinese Hamster Ovary (CHO) cells (Kaufman and Sharp, 1982), NSO myeloma cells, COS cells and SP2 cells.

The host cell may be used in a method for preparing an anti-CCR8 mAb or an antigen-binding portion thereof, which method comprises expressing the mAb or antigen-binding portion thereof in the host cell and isolating the mAb or antigen-binding portion thereof from the host cell. The host cell may be used ex vivo or in vivo. The DNAs encoding the Ab heavy and light chains can be inserted into separate expression vectors or, more typically, are both inserted into the same vector. The $V_H$ and $V_L$ segments of an Ab can be used to create full-length Abs of any isotype by inserting DNAs encoding these variable regions into expression vectors already encoding heavy chain and light chain constant regions of the desired isotype such that the $V_H$ segment is operatively linked to the $C_H$ segment(s) within the vector and the $V_\kappa$ segment is operatively linked to the $C_L$ segment within the vector. Cell lines that lack the α-(1,6) fucosyltransferase (FUT8) enzyme can be used to produce mAbs that lack fucose in their carbohydrates (see, e.g., U.S. Publication No. 2004/0110704; Yamane-Ohnuki et al., 2004; EP 1176195).

Another aspect of this invention relates to a transgenic mouse comprising human Ig heavy and light chain transgenes, wherein the mouse expresses any of the anti-CCR8 HuMAbs disclosed herein. The invention also encompasses a hybridoma prepared from said mouse, wherein the hybridoma produces the HuMAb.

Therapeutic Anti-CCR8 Methods

Since the anti-hCCR8 Abs generated in the present study do not bind to mCCR8, a mouse anti-mCCR8 mAb was used as a surrogate for human or humanized nf IgG1 anti-hCCR8 mAbs to test the efficacy of anti-CCR8 as an anti-cancer drug in mouse tumor models. Selection of the appropriate Ab isotype can be used to enhance CCR8-mediated tumor Treg depletion by ADCC/ADCP in mice, which has been demonstrated to be primarily driven by interaction of the Ab with FcγRIV$^{+}$ cells (Nimmerjahn et al., 2010) that are abundant in murine tumors (Simpson et al., 2013). An anti-mCCR8 mAb having a mouse IgG2a isotype, designated anti-CCR8-mIgG2a, was used as a surrogate for the humanized or human anti-hCCR8 mAbs that would likely be used as a human therapeutic. Anti-CCR8-mIgG2a is derived from the commercial rat anti-mCCR8 mAb sold by BioLegend as Clone SA214G2, which was modified to change the rat IgG2b isotype to a mouse IgG2a isotype. Like the human anti-hCCR8 mAbs, A419 and 14S15, anti-CCR8-mIgG2a is an N-terminal binder and its mIgG2a backbone provides maximal FcγR binding for driving an ADCC response similar to the human nf format.

Anti-CCR8-mIgG2a was demonstrated to have high ADCC potential (Example 18), similar to the high ADCC potential of several of the anti-hCCR8 mAbs tested (Example 17), and to block binding of mCCL1 to mCCR8-expressing cells (Example 16) though with lower potency than several of the anti-hCCR8 mAbs tested block binding of hCCL1 to hCCR8-expressing cells (Example 15). The anti-hCCR8 mAbs also exhibit potent ADCC activity (Examples 19 and 20). Anti-CCR8-mIgG2a also binds to mCCR8-expresing cells with lower affinity than certain of the disclosed anti-hCCR8 mAbs (Example 13). This suggests that anti-CCR8-mIgG2a is a suitable surrogate for the anti-hCCR8 mAbs in direct studies on the inhibition of tumor growth in mouse models, though the anti-hCCR8 Abs may be even more potent in inhibiting tumor growth in human subjects given their higher-affinity binding to their cognate hCCR8 target, higher activity in blocking binding of the CCL1 ligand to CCR8, and higher ADCC potential.

A variety of syngeneic mouse tumor models were used to determine anti-tumor activity of the anti-CCR8-mIgG2a mouse surrogate mAb alone and in combination with anti-PD-1. Anti-CCR8-mIgG2a mAb-mediated Treg depletion and subsequent pro-inflammatory responses (increases in CD8, CD4, interferon-γ, GranzymeB, and Ki67) induced robust tumor growth inhibition, with a high percentage of complete tumor clearance, as a single agent in immunogenic mouse tumor models including the CT26 and MC38 colon adenocarcinoma models and SA1N fibrosarcoma model (see Examples 23-26 and 29), and in combination with anti-PD-1 in the immunotherapy-resistant models, MB49 and 4T1. In contrast, treatment with CCR8-mIgG1-D265A, a variant Ab comprising the Fc-inert mIgG1-D265A heavy chain (Baudino et al., 2008), had minimal effects on tumor regression (Examples 29 and 30). To determine whether there is a dose-dependent relationship between Treg depletion and tumor efficacy upon anti-CCR8 Ab treatment, a single dose monotherapy study was conducted in the MC38 model and a dose-dependent pharmacokinetic/pharmacodynamic/efficacy relationship was observed (Example 26). In addition, increased and titratable CCL1 ligand changes were observed in tumor supernatants upon depletion (data not shown), which might serve as a surrogate biomarker.

In the MB49 mouse bladder carcinoma, anti-CCR8-mIgG2a showed only partial anti-tumor activity though this was stronger than the activity of an anti-PD-1 mAb (Example 27). Similarly, in the 4T1 mouse breast cancer model, anti-CCR8-mIgG2a also showed only partial anti-tumor activity but this tumor was completely resistant to treatment with the anti-PD-1 mAb (Example 28). In both tumor models, anti-CCR8-mIgG2a potentiates the immune response induced by anti-PD-1, resulting in a striking increase in the potency of the anti-tumor response. The combination of the two Abs is synergistic in strongly inhibiting tumor growth in these recalcitrant tumor models. Abs are considered herein to interact synergistically if the anti-tumor efficacy of the combination of these Abs is greater than the sum of the anti-tumor efficacy exhibited by each Ab individually.

Tumor Treg-specific depletion in human tumor explant models was also demonstrated upon treatment with the 14S15, 16B13 and 4A19 mAbs (Example 20).

Treatment of Cancer with an Anti-CCR8 mAb as Monotherapy

The data provided herein demonstrate the generation of anti-hCCR8 mAbs that bind to hCCR8 on the surface of activated Tregs with high affinity ($E_{50}$=about 0.1-2 nM; Example 11), induce potent killing of Tregs via ADCC in an in vitro system where primary activated human Tregs are co-cultured with allogeneic activated NK cells ($EC_{50}$=about 10-60 pM; Example 19), and mediate the depletion specifically of CCR8$^{+}$ tumor-infiltrating Tregs in human tumor explant and mouse models (Examples 20, 22 and 24). These mAbs exhibit robust inhibition of tumor growth in diverse immunogenic and immunotherapy-resistant mouse tumor models (Examples 23, 25, 27-29), and the data strongly support clinical evaluation of CCR8 depletion, as monotherapy or in combination with immune checkpoint blockade, as a novel immunotherapy for cancer.

Accordingly, as supported by the data provided in the Examples, this disclosure provides a method for treating a subject afflicted with a cancer, comprising administering to the subject a therapeutically effective amount of any one of the Treg-depleting anti-CCR8 Abs, e.g., mAbs, immunoconjugates or bispecific molecules disclosed herein, or a pharmaceutical composition comprising any one of said Abs, e.g., anti-CCR8 mAbs, immunoconjugates or bispecific molecules, such that the subject is treated.

The disclosure also provides a method for inhibiting growth of tumor cells in a subject, comprising administering to the subject a therapeutically effective amount any one of the Treg-depleting anti-CCR8 Abs, e.g., mAbs, immunoconjugates or bispecific molecules disclosed herein, or a pharmaceutical composition comprising any one of said anti-CCR8 Abs, e.g., mAbs, immunoconjugates or bispecific molecules, such that growth of tumor cells in the subject is inhibited.

Treatment of Cancer with an Anti-CCR8 Ab in Combination with Another Anti-Cancer Agent This disclosure provides a method for treating a subject afflicted with a cancer, comprising administering to the subject a therapeutically effective amount of: (a) any one of the Treg-depleting anti-CCR8 Abs, immunoconjugates or bispecific molecules disclosed herein, or a pharmaceutical composition comprising any one of said anti-CCR8 Abs, immunoconjugates or bispecific molecules; and (b) an additional therapeutic agent for treating cancer, optionally wherein the additional therapeutic agent is a compound that reduces inhibition, or increases stimulation, of the immune system, such that the subject is treated.

The disclosure also a method for inhibiting growth of tumor cells in a subject, comprising administering to the subject a therapeutically effective amount of: (a) any one of the Treg-depleting anti-CCR8 Abs, immunoconjugates or bispecific molecules disclosed herein, or a pharmaceutical composition comprising any one of said anti-CCR8 Abs, immunoconjugates or bispecific molecules; and (b) an additional therapeutic agent for treating cancer. In certain preferred embodiments, the additional therapeutic agent is a compound that reduces inhibition, or increases stimulation, of the immune system, such that growth of tumor cells in the subject is inhibited.

In other preferred embodiments of any of the present methods, the subject is a human patient.

Treg-mediated immunosuppression is potentially a major obstacle to optimal anti-tumor immune responses in immuno-oncology. Many of the molecules targeted by cancer immunotherapies, such as PD-1, CTLA-4, LAG3, TIM3, and TIGIT, are upregulated on Tregs (Kumar et al., 2018). Consequently, these T cell-based immunotherapies have the potential to augment Treg responses as well. For example, PD-1 blockade may enhance Treg suppression and increase Treg proliferation (Kamada et al., 2019), and there is evidence of Treg expansion following anti-CTLA-4 therapies in the clinic (Kavanagh et al., 2008). Therefore, a Treg-depleting agent not only improves anti-tumor responses as monotherapy, but also enhances the activities of other immunotherapies as disclosed herein (see Examples 27 and 28). Thus, the disclosure provides a method for potentiating an anti-tumor immune response elicited by a therapeutic agent in a subject afflicted with a cancer, wherein the therapeutic agent is an immunotherapeutic agent such as cancer immunotherapies, such as an antibody binding specifically to PD-1, CTLA-4, LAG3, TIM3, or TIGIT.

In mouse tumor models, potent combinatorial anti-tumor activity was observed in mice treated with both anti-CCR8-mIgG2a and anti-PD-1 (Examples 27 and 28). Despite similar increases in $CD8^+$ T cell frequency in the anti-CCR8-monotherapy and the combination treatments, anti-PD-1 may be required for enhancing effector functionality. In addition, it has been demonstrated that anti-CCR8 treatment results in long-lasting, antigen specific $CD8^+$ T cell memory (Example 31). These findings have important clinical implications for the treatment of advanced cancers, which often develop resistance to anti-PD1/PD-L1 therapies (Jenkins et al., 2018) and present with high rates of recurrence (Mahvi et al., 2018). Overall, these studies highlight the specificity and targetability of CCR8 on tumor Treg, and support the evaluation of anti-CCR8 depleting Abs in the treatment of advanced solid tumors as monotherapy or in combination with another immunotherapy such as anti-PD-1, anti-PD-L1 or anti-CTLA-4.

In certain embodiments of the disclosed methods, the additional therapeutic agent is a compound that reduces inhibition of the immune system. For example, the additional therapeutic agent may be a small-molecule compound, a macrocyclic peptide, a fusion protein, or an Ab, e.g., a mAb. In further embodiments, the additional therapeutic agent is an antagonistic agent, such as an antagonistic mAb, that binds specifically to Programmed Death-1 (PD-1), Programmed Death Ligand-1 (PD-L1), Cytotoxic T-Lymphocyte Antigen-4 (CTLA-4), Lymphocyte Activation Gene-3 (LAG-3), B and T lymphocyte Attenuator (BTLA), T cell Immunoglobulin and Mucin domain-3 (TIM-3), Killer Immunoglobulin-like Receptor (KIR), Killer cell Lectin-like Receptor G1 (KLRG-1), Adenosine A2a Receptor (A2aR), T Cell Immunoreceptor with Ig and ITIM Domains (TIGIT), V-domain Ig Suppressor of T cell activation (VISTA), proto-oncogene tyrosine-protein kinase MER (MerTK), Natural Killer Cell Receptor 2B4 (CD244), or CD160.

In certain preferred embodiments, the additional therapeutic agent is an antagonistic Ab or antigen-binding portion thereof that binds specifically to PD-1. In further embodiments, the Ab that binds specifically to PD-1 is chosen from nivolumab, pembrolizumab, cemiplimab, spartalizumab, camrelizumab, sintilimab, tislelizumab, toripalimab, dostarlimab, retifanlimab, and pimivalimab, e.g. chosen from nivolumab, pembrolizumab, cemiplimab, spartalizumab, camrelizumab, sintilimab, tislelizumab, and, e.g. toripalimab, e.g. chosen from nivolumab and pembrolizumab.

In other preferred embodiments, the additional therapeutic agent is an antagonistic Ab or antigen-binding portion thereof that binds specifically to PD-L1. In further embodiments, the Ab that binds specifically to PD-L1 is chosen from atezolizumab, durvalumab, avelumab, envafolimab, BMS-936559, CK-301, CS-1001, SHR-1316, CBT-502, BGB-A333, and KN035, e.g. chosen from atezolizumab, durvalumab, avelumab, envafolimab, BMS-936559, CK-301, CS-1001, SHR-1316, CBT-502, BGB-A333, e.g. chosen from atezolizumab, durvalumab and avelumab.

In other preferred embodiments, the additional therapeutic agent is an antagonistic Ab or antigen-binding portion thereof that binds specifically to CTLA-4. In further embodiments, the Ab that binds specifically to CTLA-4 is ipilimumab or tremelimumab, e.g., chosen from ipilimumab.

The disclosure further provides a method for potentiating an anti-tumor immune response elicited by a therapeutic agent in a subject afflicted with a cancer, comprising administering to the subject a therapeutically effective amount of any one of the Treg-depleting anti-CCR8 Abs, immunoconjugates or bispecific molecules disclosed herein, or a pharmaceutical composition comprising any one of said anti-CCR8 Abs, immunoconjugates or bispecific molecules, such that the subject experiences a stronger immune response against the cancer compared to the immune response elicited by the therapeutic agent alone. In certain preferred embodiments of this method, the therapeutic agent is a checkpoint inhibitor, for example an anti-PD-1, anti-PD-L1 or anti-CTLA-4 mAb. In certain preferred embodiments of this method, the therapeutic agent is the anti-PD-1 Ab nivolumab. In other preferred embodiments, the therapeutic agent is the anti-PD-1 Ab pembrolizumab. In certain preferred embodiments, the therapeutic agent is the anti-PD-L1 Ab atezolizumab. In other preferred embodiments, the therapeutic agent is the anti-PD-L1 Ab durvalumab. In further preferred embodiments, the therapeutic agent is the anti-PD-L1 Ab avelumab. In certain preferred embodiments of this method, the therapeutic agent is the anti-CTLA-4 Ab ipilimumab. In certain other embodiments, the therapeutic agent is radiotherapy.

Cancers Treatable by Disclosed Methods

Immuno-oncology, which relies on using the practically infinite flexibility of the immune system to attack and destroy cancer cells, is applicable to treating a very broad range of cancers (see, e.g., Yao et al., 2013; Callahan et al., 2016; Pianko et al., 2017; Farkona et al., 2016; Kamta et al., 2017). For example, the anti-PD-1 Ab, nivolumab, has been shown to be effective in treating many different types of cancers (see, e.g., Brahmer et al., 2015; Guo et al., 2017; Pianko et al., 2017; WO 2013/173223), and is currently undergoing clinical trials in multiple solid and hematological cancers. Accordingly, the disclosed methods, employing CCR8-mediated depletion of tumor-infiltrating Tregs as monotherapy or in combination with another immunotherapy such as immune checkpoint inhibition, are applicable to treating a wide variety of both solid and liquid tumors.

Broad Spectrum of Cancers Amenable to Treatment

Because the Abs used in the cancer treatment methods disclosed herein do not directly target cancer cells but, instead, target and enhance the immune system by depleting immunosuppressant Tregs, optionally in combination with immune checkpoint inhibition, which facilitates the immune system in attacking and destroying cancer cells, these Abs are applicable to the treatment of a broad range of cancers. The efficacy of nivolumab in treating diverse cancers has already been demonstrated, evidenced by the approval of this drug to treat advanced melanoma, advanced non-small cell lung cancer, metastatic renal cell carcinoma, classical Hodgkin lymphoma, advanced squamous cell carcinoma of the head and neck, metastatic urothelial carcinoma, MSI-H or dMMR metastatic colorectal cancer, hepatocellular carcinoma, small cell lung cancer, and esophageal squamous cell carcinoma (Drugs.com—Opdivo Approval History: https://www.drugs.com/history/opdivo.html), with clinical trials in many other cancers ongoing. Similarly, anti-PD-L1 drugs such as atezolizumab (TECENTRIQ®), durvalumab (IMFINZI®) and avelumab (BAVENCIO®) have been gaining approvals in a variety of indications. Accordingly, a wide variety of different cancers are treatable using an anti-CCR8 Ab, and optionally the combination of anti-CCR8 and anti-PD-1/PD-L1 Abs. The high efficacy demonstrated for this combination of therapeutics allows a focus on cancers plagued by large unmet medical need.

In certain embodiments, the disclosed cancer therapy methods may be broadly used to treat a cancer which is a solid tumor. For example, in certain embodiments, the solid tumor is a cancer selected from squamous cell carcinoma, small cell lung cancer (SCLC), non-small cell lung cancer (NSCLC), squamous NSCLC, non-squamous NSCLC, head and neck cancer, breast cancer, cancer of the esophagus, gastric cancer, gastrointestinal cancer, cancer of the small intestine, liver cancer, hepatocellular carcinoma (HCC), pancreatic cancer (PAC), kidney cancer, renal cell carcinoma (RCC), bladder cancer, cancer of the urethra, cancer of the ureter, colorectal cancer (CRC), colon cancer, colon carcinoma, cancer of the anal region, endometrial cancer, prostate cancer, a fibrosarcoma, neuroblastoma, glioma, glioblastoma, germ cell tumor, pediatric sarcoma, sinonasal natural killer, melanoma, skin cancer, bone cancer, cervical cancer, uterine cancer, carcinoma of the endometrium, carcinoma of the fallopian tubes, ovarian cancer, carcinoma of the cervix, carcinoma of the vagina, carcinoma of the vulva, testicular cancer, cancer of the endocrine system, thyroid cancer, cancer of the parathyroid gland, cancer of the adrenal gland, sarcoma of soft tissue, cancer of the penis, carcinoma of the renal pelvis, neoplasm of the central nervous system (CNS), primary CNS lymphoma, tumor angiogenesis, spinal axis tumor, brain cancer, brain stem glioma, pituitary adenoma, Kaposi's sarcoma, epidermoid cancer, squamous cell cancer, solid tumors of childhood, environmentally-induced cancers, virus-related cancers, cancers of viral origin, advanced cancer, unresectable cancer, metastatic cancer, refractory cancer, recurrent cancer, and any combination thereof. In certain embodiments, the cancer is an advanced, unresectable, metastatic, refractory cancer, and/or recurrent cancer.

Based on the demonstration of effective treatment of different cancers with anti-CCR8 in mouse models (Examples 23-29), certain tumor types are expected to be particularly amenable to treatment with an anti-CCR8 Ab. Accordingly, in certain embodiments, the solid tumor is a cancer chosen from colon adenocarcinoma, bladder carcinoma, mammary carcinoma, and fibrosarcoma. The finding that anti-CCR8 is effective in shrinking tumors in mouse models in which anti-PD-1 shows little efficacy, such as the MB49 bladder (Example 27) and the 4T1 breast cancer model (Example 28) suggests that anti-CCR8 may be very broadly applicable, and more broadly effective than anti-PD-1, in treating cancers and the combination of anti-CCR8 with checkpoint blockade, e.g., anti-PD-1, anti-PD-L1 or anti-CTLA-4 may have even broader application to treating diverse cancers.

Single-cell RNA-seq analysis was performed on human tumors for differential gene expression analysis of $CCR8^+$ Tregs (Example 32). The relatively high expression of CCR8 and CD8A, and their high CCR8/CD8A ratio, identify head and neck squamous cell carcinoma (HNSC), lung adenocarcinoma (LUAD), stomach adenocarcinoma (STAD), lung squamous cell carcinoma (LUSC), pancreatic adenocarcinoma (PAAD), rectum adenocarcinoma (READ), esophageal carcinoma (ESCA), breast invasive carcinoma (BRCA), colon adenocarcinoma (COAD) and cervical squamous cell carcinoma and endocervical adenocarcinoma (CESC) as tumor types that are expected to be particularly amenable to treatment with an anti-CCR8 Ab. Accordingly, in certain embodiments, the solid tumor is a cancer chosen from HNSC, LUAD, STAD, LUSC, PAAD, READ, ESCA, BRCA, COAD, CESC, follicular lymphoma, acute lymphocytic leukemia and lymphoma as tumor types that are expected to be particularly amenable to treatment with an anti-CCR8 Ab.

CCR8 expression, evaluated in 17 tumor types or subtypes by IHC on formalin-fixed, paraffin-embedded (FFPE) tissue samples, was found to be abundant in head and neck squamous cell carcinoma (HNSCC; also referred to herein as squamous cell carcinoma of the head and neck [SCCHN]) and least abundant in glioblastoma multiforme (GBM; Example 33). On the basis that tumors that express high levels of CCR8 are more likely to respond to treatment with an anti-CCR8 Ab, these tumor profiling data support the prioritization of HNSCC, cervical, CRC, non-small cell lung cancer-squamous cell carcinoma (NSCLC-SCC), NSCLC-adenocarcinoma (NSCLC-ADC), pancreatic, gastric, bladder, and breast cancers for anti-CCR8 therapy. Accordingly, in certain embodiments, the solid tumor is a cancer chosen from HNSCC, cervical, CRC, NSCLC-SCC, NSCLC-ADC, pancreatic, gastric, bladder, and breast cancers.

In certain embodiments, the present therapy methods may be used to treat a cancer which is a hematological malignancy. Hematological malignancies include liquid tumors derived from either of the two major blood cell lineages, i.e., the myeloid cell line (which produces granulocytes, erythrocytes, thrombocytes, macrophages and mast cells) or the lymphoid cell line (which produces B, T, NK and plasma cells), including all types of leukemias, lymphomas, and myelomas. Hematological malignancies that may be treated using the present therapy methods include, for example, cancers selected from acute lymphoblastic leukemia (ALL), acute myelogenous leukemia (AML), chronic lymphocytic leukemia (CLL), chronic myelogenous leukemia (CIVIL), Hodgkin's lymphoma (HL), non-Hodgkin's lymphomas (NHLs), multiple myeloma, smoldering myeloma, monoclonal gammopathy of undetermined significance (MGUS), advanced, metastatic, refractory and/or recurrent hematological malignancies, and any combinations of said hematological malignancies.

TARGET (Therapeutically Applicable Research to Generate Effective Treatments, https://ocg.cancer.gov/programs/target) analysis also indicated that, among hematological malignancies examined, follicular lymphoma, acute lymphocytic leukemia and lymphoma were found to have the highest relative expression of CCR8 and should be prioritized for treatment with an anti-CCR8 mAb (Example 32). Thus, in certain embodiments of the present therapeutic methods, the hematological malignancy is follicular lymphoma or acute lymphocytic leukemia and lymphoma.

In certain other embodiments, the hematological malignancy is a cancer selected from acute, chronic, lymphocytic (lymphoblastic) and/or myelogenous leukemias, such as ALL, AML, CLL, and CML; lymphomas, such as HL, NHLs, of which about 85% are B cell lymphomas, including diffuse large B-cell lymphoma (DLBCL), follicular lymphoma (FL), chronic lymphocytic leukemia (CLL)/small lymphocytic lymphoma (SLL), mantle cell lymphoma, marginal zone B-cell lymphomas (mucosa-associated lymphoid tissue (MALT) lymphoma, nodal marginal zone B-cell lymphoma, and splenic marginal zone B-cell lymphoma), Burkitt lymphoma, lymphoplasmacytoid lymphoma (LPL; also known as Waldenstrom's macroglobulinemia (WM)), hairy cell lymphoma, and primary central nervous system (CNS) lymphoma, NHLs that are T cell lymphomas, including precursor T-lymphoblastic lymphoma/leukemia, T-lymphoblastic lymphoma/leukemia (T-Lbly/T-ALL), peripheral T-cell lymphomas such as cutaneous T-cell lymphoma (CTLC, i.e., mycosis fungoides, Sezary syndrome and others), adult T-cell lymphoma/leukemia, angioimmunoblastic T-cell lymphoma, extranodal natural killer/T-cell lymphoma nasal type, enteropathy-associated intestinal T-cell lymphoma (EATL), anaplastic large-cell lymphoma (ALCL), and peripheral T-cell lymphoma unspecified, acute myeloid lymphoma, lymphoplasmacytoid lymphoma, monocytoid B cell lymphoma, angiocentric lymphoma, intestinal T-cell lymphoma, primary mediastinal B-cell lymphoma, post-transplantation lymphoproliferative disorder, true histiocytic lymphoma, primary effusion lymphoma, diffuse histiocytic lymphoma (DHL), immunoblastic large cell lymphoma, and precursor B-lymphoblastic lymphoma; myelomas, such as multiple myeloma, smoldering myeloma (also called indolent myeloma), monoclonal gammopathy of undetermined significance (MGUS), solitary plasmocytoma, IgG myeloma, light chain myeloma, nonsecretory myeloma, and amyloidosis; and any combinations of said hematological malignancies.

In further embodiments, the hematological malignancy is selected from acute lymphoblastic leukemia (ALL), acute myelogenous leukemia (AML), chronic lymphocytic leukemia (CLL), chronic myelogenous leukemia (CIVIL), a T cell lymphoma, Hodgkin's lymphoma (HL), non-Hodgkin's lymphomas (NHLs), multiple myeloma, smoldering myeloma, monoclonal gammopathy of undetermined significance (MGUS), advanced, metastatic, refractory and/or recurrent hematological malignancies, and any combinations of said hematological malignancies.

The present methods are also applicable to treatment of advanced, metastatic, refractory and/or recurrent hematological malignancies.

For a clinical trial of anti-CCR8 in treating cancer (Example 34), certain solid tumors were selected based on the results of the different pre-clinical studies noted above: demonstrated efficacy of anti-CCR8 in mouse tumor models (Examples 23-29); RNA expression of CCR8 and CD8A in the 33 tumor types represented in the Cancer Genome Atlas (National Cancer Institute, 2021), identifying tumor types having relatively high expression of CCR8 and enrichment for CD8A expression (Example 32); and levels of CCR8 expression in 17 tumor types or subtypes as measured by IHC (Example 33). The selected tumor types are NSCLC, SCCHN, MSS-CRC, gastric/gastroesophageal (GE) junction adenocarcinoma, and cervical cancer (squamous cell carcinoma [SCC] or adenocarcinoma). Although limited data are available for advanced tumors, this selection is supported by high CCR8 expression levels or presence of Tregs correlating with worse prognosis in NSCLC, CRC, gastric, and cervical cancers (Shah et al., 2011; Yi et al., 2018; Zhao et al., 2016; Tao et al., 2012; Xu et al., 2020). Reports on the prognosis for SCCHN is mixed, perhaps in part because of the varying methods and molecular markers used to detect the presence of Tregs (Saleh et al., 2020). Accordingly, in certain embodiments of the disclosed methods of treating cancer, the solid tumor is a cancer chosen from NSCLC, SCCHN, MSS-CRC, gastric/GE junction cancer, and cervical cancer. In certain preferred embodiments, the solid tumor is NSCLC. In other preferred embodiments, the solid tumor is SCCHN. In other preferred embodiments, the solid tumor is MSS-CRC. In further preferred embodiments, the solid tumor is gastric/GE junction cancer. In yet other preferred embodiments, the solid tumor is cervical cancer.

Medical Uses of Anti-CCR8 and Anti-PD-1/Anti PD-L1 Abs

This disclosure also provides an isolated anti-CCR8 Ab, preferably a mAb or an antigen-binding portion thereof, for use in a method for treating a subject afflicted with a cancer. The disclosure further provides an isolated anti-CCR8 Ab, preferably a mAb or an antigen-binding portion thereof, and a checkpoint inhibitor such as an isolated anti-PD-1/anti-PD-L1 Ab, preferably a mAb or an antigen-binding portion thereof, for use in combination in a method for treating a subject afflicted with cancer comprising dual Treg depletion and blockade of the checkpoint pathway, e.g., the PD-1/PD-L1 signaling pathway. The anti-CCR8 Ab may be used as monotherapy or in combination with a checkpoint inhibitor, such as anti-PD-1/anti-PD-L1 Ab, for treatment of the full range of cancers disclosed herein.

One aspect of the disclosed invention entails the use of an isolated anti-CCR8 Ab or an antigen-binding portion thereof of the invention for the preparation of a medicament for treating a subject afflicted with a cancer. The anti-CCR8 Ab may be used alone or in combination with a checkpoint inhibitor such as an isolated anti-PD-1/anti-PD-L1 Ab or an antigen-binding portion thereof for the preparation of the medicament for treating the cancer patient. Uses of any such anti-CCR8 Ab and anti-PD-1/anti-PD-L1 Ab for the preparation of medicaments are broadly applicable to the full range of cancers disclosed herein.

This disclosure also provides an anti-CCR8 Ab or an antigen-binding portion thereof in combination with a checkpoint inhibitor such as an isolated anti-PD-1/anti-PD-L1 Ab or an antigen-binding portion thereof for use in methods of treating cancer corresponding to all the embodiments of the methods of treatment employing this combination of therapeutics described herein.

Anti-CCR8 Abs Suitable for Use in the Disclosed Therapeutic Methods

An anti-CCR8 Ab suitable for use in the disclosed methods is an isolated Ab, preferably a mAb or antigen-binding portion thereof, that binds specifically to CCR8 expressed on the surface of a cell with high specificity and affinity and mediates depletion of the CCR8-expressing cell by ADCC. Such an Ab exhibits one or more properties that are important for therapeutic efficacy. In particular, the isolated Ab or antigen-binding portion thereof exhibits at least one of the following properties:

(a) specifically binds to CCR8 expressed on the surface of a cell with an $E_{50}$ of about 20 nM or lower, preferably about 2 nM or lower, preferably about 1 nM or lower;

(b) binds specifically to rare and scattered immune cells in the medulla of the thymus and dermis of the skin but, for example, does not bind to human cerebrum, cerebellum, heart, liver, lung, kidney, tonsil, spleen, thymus, colon, stomach, pancreas, adrenal, pituitary, skin, peripheral nerve, testis or uterus tissue, or PBMCs. For example, the anti-CCR8 mAb or antigen-binding portion thereof may bind specifically to tumor-infiltrating Tregs but not bind to PBMCs, e.g., not show cytoplasmic staining in fixed PBMCs. Non-binding of the Ab to the above recited list of cells and tissues may be established, for instance, by carrying out standard staining with the relevant Abs, e.g. by the methods described in Example 14, e.g., on fixed tissue samples;

(c) inhibits binding of CCL1 to CCR8 and inhibits CCR8/CCL1 signaling with an $IC_{50}$ of about 5 nM or lower;

(d) when bound to CCR8 on the surface of a cell mediates depletion of the cell with an $E_{50}$ of about 100 pM or lower, preferably about 60 pM or lower, preferably about 40 pM or lower, more preferably about 13 pM or lower, more preferably 10 pM or lower;

(e) when bound to CCR8 on the surface of a cell does not cause internalization of CCR8 either in the presence or absence of a cross-linking Ab;

(f) inhibits growth of tumor cells in a subject when administered as monotherapy to the subject; and (g) inhibits growth of tumor cells in a subject when administered to the subject in combination with an additional therapeutic agent for treating a cancer, optionally wherein the additional therapeutic agent is an immune checkpoint inhibitor, optionally wherein the checkpoint inhibitor is an anti-PD-1, anti-PD-L1 or anti-CTLA-4 Ab.

In certain embodiments, the isolated Ab or antigen-binding portion thereof exhibits at least 2 or 3, preferably 4, 5 or 6 of the aforementioned properties. In more preferred embodiments, the isolated Ab or antigen-binding portion thereof exhibits all of the aforementioned properties. For example, in certain preferred embodiments, the isolated Ab or antigen-binding portion thereof:

(a) specifically binds to CCR8 expressed on the surface of a cell with an $E_{50}$ of about 20 nM or lower, preferably about 2 nM or lower, preferably about 1 nM or lower;

(b) when bound to CCR8 on the surface of a cell mediates depletion of the cell with an $E_{50}$ of about 100 pM or lower, about 60 pM or lower, preferably about 40 pM or lower, more preferably about 13 pM or lower, more preferably 10 pM or lower;

(c) inhibits growth of tumor cells in a subject when administered as monotherapy to the subject; and (d) inhibits growth of tumor cells in a subject when administered to the subject in combination with an additional therapeutic agent for treating a cancer, optionally wherein the additional therapeutic agent is a checkpoint inhibitor.

In other preferred embodiments, the isolated Ab or antigen-binding portion thereof:

(a) specifically binds to CCR8 expressed on the surface of a cell with an $E_{50}$ of about 2 nM or lower;

(b) when bound to CCR8 on the surface of a cell mediates depletion of the cell with an $E_{50}$ of about 40 pM or lower; and (c) inhibits growth of tumor cells in a subject when administered to the subject in combination with an additional therapeutic agent for treating a cancer, optionally wherein the additional therapeutic agent is an anti-PD-1, anti-PD-L1, or anti-CTLA-4 Ab.

In certain embodiments, the isolated Ab, e.g., a mAb, or antigen-binding portion thereof exhibiting one or more, up to all, of the aforementioned functional properties further binds to an epitope located in the N-terminal domain of hCCR8 with a $K_D$ of about 10 nM or lower, wherein the epitope comprises a peptide having the sequence $Y_{15}Y_{16}Y_{17}P_{18}D_{19}I_{20}F_{21}$ (SEQ ID NO: 2) and sulfated tyr-15 and/or tyr-17 residues. In certain other embodiments, the isolated Ab, e.g., a mAb, or antigen-binding portion thereof exhibiting one or more, up to all, of the aforementioned functional properties further binds to an epitope located in the N-terminal domain of human CCR8 with a $K_D$ of about 10 nM or lower, wherein the epitope comprises a peptide having the sequence $V_{12}T_{13}D_{14}Y_{15}Y_{16}Y_{17}P_{18}D_{19}I_{20}F_{21}S_{22}$ (SEQ ID NO: 109) and sulfated tyr-15 and tyr-17 residues.

In certain embodiments the isolated Ab, preferably a mAb, or antigen-binding portion thereof may have the above properties and/or comprise the CDR1, CDR2 and CDR3 domains in each of a $V_H$ comprising consecutively linked amino acids having the sequence set forth as SEQ ID NO: 4 and a $V_L$ comprising consecutively linked amino acids having the sequence set forth as SEQ ID NO: 16. For example, such an Ab or antigen-binding portion thereof may comprise the following CDRs as defined by the Kabat method: a heavy chain variable region CDR1 comprising consecutively linked amino acids having the sequence set forth as SEQ ID NO: 33; a heavy chain variable region CDR2 comprising consecutively linked amino acids having the sequence set forth as SEQ ID NO: 34; a heavy chain variable region CDR3 comprising consecutively linked amino acids having the sequence set forth as SEQ ID NO: 35; a light chain variable region CDR1 comprising consecutively linked amino acids having the sequence set forth as SEQ ID NO: 36; a light chain variable region CDR2 comprising consecutively linked amino acids having the sequence set forth as SEQ ID NO: 37; and a light chain variable region CDR3 comprising consecutively linked amino acids having the sequence set forth as SEQ ID NO: 38. As another example, such an Ab or antigen-binding portion thereof may comprise a $V_H$ comprising consecutively linked amino acids having the sequence set forth as SEQ ID NO: 4 and a $V_L$ comprising consecutively linked amino acids having the sequence set forth as SEQ ID NO: 16. As a further example, such an Ab may comprise a heavy chain comprising consecutively linked amino acids having the sequence set forth as SEQ ID NO: 100 and a light chain comprising consecutively linked amino acids having the sequence set forth as SEQ ID NO: 112. Optionally, the Ab has reduced fucosylation of its heavy chain, or a hypofucosylated or nonfucosylated heavy chain constant region as described elsewhere herein.

In certain embodiments the isolated Ab, preferably a mAb, or antigen-binding portion thereof may have the above properties and/or comprise the CDR1, CDR2 and CDR3 domains in each of a $V_H$ comprising consecutively linked amino acids having the sequence set forth as SEQ ID NO: 115 and a $V_L$ comprising consecutively linked amino acids having the sequence set forth as SEQ ID NO: 116. For example, such an Ab or antigen-binding portion thereof may comprise the following CDRs as defined by the Kabat method: a heavy chain variable region CDR1 comprising consecutively linked amino acids having the sequence set forth as SEQ ID NO: 103; a heavy chain variable region CDR2 comprising consecutively linked amino acids having the sequence set forth as SEQ ID NO: 104; a heavy chain variable region CDR3 comprising consecutively linked amino acids having the sequence set forth as SEQ ID NO: 105; a light chain variable region CDR1 comprising consecutively linked amino acids having the sequence set forth as SEQ ID NO: 106; a light chain variable region CDR2 comprising consecutively linked amino acids having the sequence set forth as SEQ ID NO: 107; and a light chain variable region CDR3 comprising consecutively linked amino acids having the sequence set forth as SEQ ID NO: 108. As another example, such an Ab or antigen-binding portion thereof may comprise a $V_H$ comprising consecutively linked amino acids having the sequence set forth as SEQ ID NO: 115 and a $V_L$ comprising consecutively linked amino acids having the sequence set forth as SEQ ID NO: 116. As a further example, such an Ab may comprise a heavy chain comprising consecutively linked amino acids having the sequence set forth as SEQ ID NO: 117 and a light chain comprising consecutively linked amino acids having the sequence set forth as SEQ ID NO: 118. Optionally, the Ab has reduced fucosylation of its heavy chain, or a hypofucosylated or nonfucosylated heavy chain constant region as described elsewhere herein.

In certain embodiments the isolated Ab, preferably a mAb, or antigen-binding portion thereof may have the above properties and/or comprise the CDR1, CDR2 and CDR3 domains in each of a $V_H$ comprising consecutively linked amino acids having the sequence set forth as SEQ ID NO: 6 and a $V_L$ comprising consecutively linked amino acids having the sequence set forth as SEQ ID NO: 18. For example, such an Ab or antigen-binding portion thereof may comprise a heavy chain variable region CDR1 comprising consecutively linked amino acids having the sequence set forth as SEQ ID NO: 45; a heavy chain variable region CDR2 comprising consecutively linked amino acids having the sequence set forth as SEQ ID NO: 46; a heavy chain variable region CDR3 comprising consecutively linked amino acids having the sequence set forth as SEQ ID NO: 47; a light chain variable region CDR1 comprising consecutively linked amino acids having the sequence set forth as SEQ ID NO: 48; a light chain variable region CDR2 comprising consecutively linked amino acids having the sequence set forth as SEQ ID NO: 49; and a light chain variable region CDR3 comprising consecutively linked amino acids having the sequence set forth as SEQ ID NO: 50. In another example, such an Ab or antigen-binding portion thereof may comprise a $V_H$ comprising consecutively linked amino acids having the sequence set forth as SEQ ID NO: 6 and a $V_L$ comprising consecutively linked amino acids having the sequence set forth as SEQ ID NO: 18. In a further example, such an Ab may comprise a heavy chain comprising consecutively linked amino acids having the sequence set forth as SEQ ID NO: 102 and a light chain comprising consecutively linked amino acids having the sequence set forth as SEQ ID NO: 114. Optionally, the Ab has reduced fucosylation of its heavy chain, or a hypofucosylated or nonfucosylated heavy chain constant region as described elsewhere herein.

Combination Therapy

Human $CCR8^+$ Tregs also co-express PD-1 at high levels (data not shown). Treatment with an anti-PD-1 mAb may activate $PD\text{-}1^+$ Tregs, potentially explaining hyperprogression or primary resistance in nivolumab-treated patients with gastric cancer (Kamada et al., 2019). Therefore, Treg depletion likely improves overall response rates to anti-PD-1 therapy. This combination is also directed supported by preclinical mouse studies where the synergistic effects of anti-CCR8 with anti-PD-1 were observed in MB49 and 4T-1 tumor models (Examples 27 and 28).

Although the efficacy of combination therapy with an anti-CCR8 Ab and a checkpoint inhibitor have been demonstrated herein using an anti-PD-1 Ab, several other costimulatory and inhibitory receptors and ligands that regulate T cell responses have been identified. Examples of stimulatory receptors include Inducible T cell Co-Stimulator (ICOS), CD137 (4-1BB), CD134 (0X40), CD27, Glucocorticoid-Induced TNFR-Related protein (GITR), and Herpes-Virus Entry Mediator (HVEM), whereas examples of inhibitory receptors in addition to PD-1/PD-L1 include Cytotoxic T-Lymphocyte-Associated protein 4 (CTLA-4), B and T Lymphocyte Attenuator (BTLA), T cell Immunoglobulin and Mucin domain-3 (TIM-3), Lymphocyte Activation Gene-3 (LAG-3), Killer Immunoglobulin-like Receptor (KIR), adenosine A2a receptor (A2aR), Killer cell Lectin-like Receptor G1 (KLRG-1), Natural Killer Cell Receptor 2B4 (CD244), CD160, T cell Immunoreceptor with Ig and ITIM domains (TIGIT), and the receptor for V-domain Ig Suppressor of T cell Activation (VISTA), (Mellman et al., 2011; Pardoll, 2012; Baitsch et al., 2012). These receptors and their ligands provide targets for therapeutics designed to stimulate, or prevent the suppression, of an immune response so as to thereby attack tumor cells (Weber, 2010; Mellman et al., 2011; Pardoll, 2012). Stimulatory receptors or receptor ligands are targeted by agonist agents, whereas inhibitory receptors or receptor ligands are targeted by blocking agents. Because many of the immune checkpoints are initiated by ligand-receptor interactions, they can be readily blocked by Abs or modulated by recombinant forms of ligands or receptors. One or more of the costimulatory and inhibitory receptors and ligands that regulate T cell responses, other than PD-1/PD-L1, may provide targets for synergizing with the anti-CCR8 Abs disclosed herein for inhibiting tumor growth. For example, in certain embodiments, the anti-CCR8 Ab is combined with an anti-CTLA-4 Ab. In other embodiments, the anti-CCR8 Ab is combined with an anti-LAG-3 Ab.

Radiotherapy leads to an increase in Treg infiltration post treatment in murine models (Muroyama et al., 2017) and in humans (unpublished data). Increased Treg infiltration may lead to undesirable suppression of anti-tumor immunity, and CCR8-mediated depletion may potentiate the efficacy of radiation therapy.

The present disclosure provides anti-CCR8 mAbs that are effective in potentiating an immune response by enhancing the anti-tumor efficacy of treatments such as checkpoint inhibition or radiotherapy and which exhibit at least one, several or all of the following desirable characteristics: (a) specifically binding to hCCR8 expressed on the surface of a cell with an $E_{50}$ of about 1 nM or lower; (b) binding specifically to rare and scattered immune cells in the medulla of the thymus and dermis of the skin but, for example, not binding to human cerebrum, cerebellum, heart, liver, lung, kidney, tonsil, spleen, thymus, colon, stomach, pancreas, adrenal, pituitary, skin, peripheral nerve, testis or uterus tissue, or PBMCs. For example, the anti-CCR8 mAb or antigen-binding portion thereof may bind specifically to tumor-infiltrating Tregs but not bind to PBMCs, e.g., not show cytoplasmic staining in fixed PBMCs. Non-binding of the Ab to the above-recited list of cells and tissues may be established, for instance, by carrying out standard staining with the relevant Abs, e.g. by the methods described in Example 14, e.g. on fixed tissue samples; (c) inhibiting binding of CCL1 to CCR8 and inhibiting CCR8/CCL1 signaling with an $IC_{50}$ of about 5 nM or lower; (d) when bound to CCR8 on the surface of a cell mediates depletion of the cell with an $E_{50}$ of about 50 pM or lower; (e) when bound to CCR8 on the surface of a cell not causing internalization of CCR8 either in the presence or absence of a cross-linking Ab; (f) inhibiting growth of tumor cells in a subject when administered as monotherapy to the subject; and (g) inhibiting growth of tumor cells in a subject when administered to the subject in combination with an additional therapeutic agent for treating a cancer, optionally wherein the additional therapeutic agent is an anti-PD-1, anti-PD-L1, or anti-CTLA-4 Ab.

Certain anti-CCR8 mAbs that may be used in the therapeutic methods, compositions or kits described herein include mAbs that bind specifically to hCCR8 on a cell surface with high affinity, mediate depletion of the cell with an $E_{50}$ of about 10 pM or lower, and exhibit at least two other, and preferably all, of the preceding properties. In certain embodiments the isolated Ab, preferably a mAb, or antigen-binding portion thereof may have at least one of the above properties and/or comprise the CDR1, CDR2 and CDR3 domains in each of a $V_H$ comprising consecutively linked amino acids having the sequence set forth as SEQ ID NO: 4 and a $V_L$ comprising consecutively linked amino acids having the sequence set forth as SEQ ID NO: 16. For example, such an Ab or antigen-binding portion thereof may comprise the following CDRs as defined by the Kabat method: a $V_H$ CDR1 comprising consecutively linked amino acids having the sequence set forth as SEQ ID NO: 33; a $V_H$ CDR2 comprising consecutively linked amino acids having the sequence set forth as SEQ ID NO: 34; a $V_H$ CDR3 comprising consecutively linked amino acids having the sequence set forth as SEQ ID NO: 35; a $V_L$ CDR1 comprising consecutively linked amino acids having the sequence set forth as SEQ ID NO: 36; a $V_L$ CDR2 comprising consecutively linked amino acids having the sequence set forth as SEQ ID NO: 37; and a $V_L$ CDR3 comprising consecutively linked amino acids having the sequence set forth as SEQ ID NO: 38. In another example, such an Ab or antigen-binding portion thereof may comprise a $V_H$ comprising consecutively linked amino acids having the sequence set forth as SEQ ID NO: 4 and a $V_L$ comprising consecutively linked amino acids having the sequence set forth as SEQ ID NO: 16. In a further example, such an Ab may comprise a heavy chain comprising consecutively linked amino acids having the sequence set forth as SEQ ID NO: 100 and a light chain comprising consecutively linked amino acids having the sequence set forth as SEQ ID NO: 112. Optionally, the Ab has reduced fucosylation of its heavy chain, or a hypofucosylated or nonfucosylated heavy chain constant region as described elsewhere herein.

In certain embodiments the isolated Ab, preferably a mAb, or antigen-binding portion thereof may have at least one of the above properties and/or comprise the CDR1, CDR2 and CDR3 domains in each of a $V_H$ comprising consecutively linked amino acids having the sequence set forth as SEQ ID NO: 115 and a $V_L$ comprising consecutively linked amino acids having the sequence set forth as SEQ ID NO: 116. For example, such an Ab or antigen-binding portion thereof may comprise the following CDRs as defined by the Kabat method: a $V_H$ CDR1 comprising consecutively linked amino acids having the sequence set forth as SEQ ID NO: 103; a $V_H$ CDR2 comprising consecutively linked amino acids having the sequence set forth as SEQ ID NO: 104; a h $V_H$ CDR3 comprising consecutively linked amino acids having the sequence set forth as SEQ ID NO: 105; a1 $V_L$ CDR1 comprising consecutively linked amino acids having the sequence set forth as SEQ ID NO: 106; a $V_L$ CDR2 comprising consecutively linked amino acids having the sequence set forth as SEQ ID NO: 107; and a $V_L$ CDR3 comprising consecutively linked amino acids having the sequence set forth as SEQ ID NO: 108. As another example, such an Ab or antigen-binding portion thereof may comprise a $V_H$ comprising consecutively linked amino acids having the sequence set forth as SEQ ID NO: 115 and a $V_L$ comprising consecutively linked amino acids having the sequence set forth as SEQ ID NO: 116. As a further example, such an Ab may comprise a heavy chain comprising consecutively linked amino acids having the sequence set forth as SEQ ID NO: 117 and a light chain comprising consecutively linked amino acids having the sequence set forth as SEQ ID NO: 118. Optionally, the Ab has reduced fucosylation of its heavy chain, or a hypofucosylated or nonfucosylated heavy chain constant region as described elsewhere herein.

In certain embodiments the isolated Ab, preferably a mAb, or antigen-binding portion thereof may have at least one of the above properties and/or comprise the CDR1, CDR2 and CDR3 domains in each of a $V_H$ comprising consecutively linked amino acids having the sequence set forth as SEQ ID NO: 6 and a $V_L$ comprising consecutively linked amino acids having the sequence set forth as SEQ ID NO: 18. For example, such an Ab or antigen-binding portion thereof may comprise the following CDRs as defined by the Kabat method: a $V_H$ CDR1 comprising consecutively linked amino acids having the sequence set forth as SEQ ID NO: 45; a $V_H$ CDR2 comprising consecutively linked amino acids having the sequence set forth as SEQ ID NO: 46; a $V_H$ CDR3 comprising consecutively linked amino acids having the sequence set forth as SEQ ID NO: 47; a $V_L$ CDR1 comprising consecutively linked amino acids having the sequence set forth as SEQ ID NO: 48; a $V_L$ CDR2 comprising consecutively linked amino acids having the sequence set forth as SEQ ID NO: 49; and a $V_L$ CDR3 comprising consecutively linked amino acids having the sequence set forth as SEQ ID NO: 50. In another example, such an Ab or antigen-binding portion thereof may comprise a $V_H$ comprising consecutively linked amino acids having the sequence set forth as SEQ ID NO: 6 and a $V_L$ comprising consecutively linked amino acids having the sequence set forth as SEQ ID NO: 18. In a further example, such an Ab or antigen-binding portion thereof may comprise a heavy chain comprising consecutively linked amino acids having the sequence set forth as SEQ ID NO: 102 and a light chain comprising consecutively linked amino acids having the sequence set forth as SEQ ID NO: 114. Optionally, the Ab has reduced fucosylation of its heavy chain, or a hypofucosylated or nonfucosylated heavy chain constant region as described elsewhere herein.

Anti-PD-1/Anti-PD-L1 Abs Suitable for Use in the Disclosed Therapeutic Methods

Anti-PD-1 Abs suitable for use in the methods for cancer treatment, compositions or kits disclosed herein include isolated Abs, preferably mAbs or antigen-binding portions thereof, that bind to PD-1 with high specificity and affinity, block the binding of PD-L1 and/or PD-L2 to PD-1, and inhibit the immunosuppressive effect of the PD-1 signaling pathway. Similarly, anti-PD-L1 Abs suitable for use in these methods are isolated Abs, preferably mAbs or antigen-binding portions thereof, that bind to PD-L1 with high specificity and affinity, block the binding of PD-L1 to PD-1 and CD80 (B7-1), and inhibit the immunosuppressive effect of the PD-1 signaling pathway. In any of the therapeutic methods disclosed herein, an anti-PD-1 or anti-PD-L1 Ab includes an antigen-binding portion or fragment that binds to the PD-1 receptor or PD-L1 ligand, respectively, and exhibits its functional properties similar to those of whole Abs in inhibiting receptor-ligand binding and reversing the inhibition of T cell activity, thereby upregulating an immune response.

Anti-PD-1 mAbs

MAbs that bind specifically to PD-1 with high affinity have been disclosed in U.S. Pat. No. 8,008,449. Other anti-PD-1 mAbs have been described in, for example, U.S. Pat. Nos. 7,488,802, 8,168,757, 8,354,509, and 9,205,148. The anti-PD-1 mAbs disclosed in U.S. Pat. No. 8,008,449 have been demonstrated to exhibit several or all of the following characteristics: (a) binding to human PD-1 with a $K_D$ of about 50 nM or lower, as determined by the SPR (BIACORE®) biosensor system; (b) not substantially binding to human CD28, CTLA-4 or ICOS; (c) increasing T-cell proliferation, interferon-γ production and IL-2 secretion in a Mixed Lymphocyte Reaction (MLR) assay; (d) binding to human PD-1 and cynomolgus monkey PD-1; (e) inhibiting the binding of PD-L1 and PD-L2 to PD-1; (f) releasing inhibition imposed by Treg cells on proliferation and interferon-γ production of $CD4^+CD25^-$ T cells; (g) stimulating antigen-specific memory responses; (h) stimulating Ab responses; and (i) inhibiting tumor cell growth in vivo. Anti-PD-1 Abs usable in the disclosed methods of treatment, compositions or kits include mAbs that bind specifically to human PD-1 with high affinity and exhibit at least five, and preferably all, of the preceding characteristics. For example, an anti-PD-1 Ab suitable for use in the therapeutic methods disclosed herein (a) binds to human PD-1 with a $K_D$ of about 10 nM to 0.1 nM, as determined by SPR (BIACORE®); (b) increases T-cell proliferation, interferon-γ production and IL-2 secretion in a MLR assay; (c) inhibits the binding of PD-L1 and PD-L2 to PD-1; (d) reverses inhibition imposed by Tregs on proliferation and interferon-γ production of $CD4^+CD25^-$ T cells; (e) stimulates antigen-specific memory responses; and (f) inhibits tumor cell growth in vivo.

Other anti-PD-1 mAbs have been described in, for example, U.S. Pat. Nos. 6,808,710, 7,488,802, 8,168,757 and 8,354,509, U.S. Publication No. 2016/0272708, and PCT Publication Nos. WO 2008/156712, WO 2012/145493, WO 2014/179664, WO 2014/194302, WO 2014/206107, WO 2015/035606, WO 2015/085847, WO 2015/112800, WO 2015/112900, WO 2016/106159, WO 2016/197367, WO 2017/020291, WO 2017/020858, WO 2017/024465, WO 2017/024515, WO 2017/025016, WO 2017/025051, WO 2017/040790, WO 2017/106061, WO 2017/123557, WO 2017/132827, WO 2017/133540, the disclosure of each of which is incorporated herein by reference in its entirety.

In certain embodiments, the anti-PD-1 mAb is selected from the group consisting of nivolumab (OPDIVO®; formerly designated 5C4, BMS-936558, MDX-1106, or ONO-4538), pembrolizumab (KEYTRUDA®; formerly designated lambrolizumab and MK-3475; see WO 2008/156712A1), PDR001 (see WO 2015/112900), MEDI-0680 (formerly designated AMP-514; see WO 2012/145493), REGN-2810 see WO 2015/112800), JS001 (see Liu and Wu, 2017), BGB-A317 (see WO 2015/035606 and US 2015/0079109), INCSHR1210 (SHR-1210; see WO 2015/085847; Liu and Wu, 2017), TSR-042 (ANB011; see WO 2014/179664), GLS-010 (WBP3055; see Liu and Wu, 2017), AM-0001 (see WO 2017/123557), STI-1110 (see WO 2014/194302), AGEN2034 (see WO 2017/040790), and MGD013 (see WO 2017/106061).

In certain preferred embodiments of any of the therapeutic methods described herein comprising administration of an anti-PD-1 Ab, the anti-PD-1 Ab is nivolumab, OPDIVO®), which has already been approved by the U.S. Food and Drug Administration (FDA) for treating multiple different cancers. Nivolumab is a fully human IgG4 (S228P) PD-1 immune checkpoint inhibitor Ab that selectively prevents interaction with PD-1 ligands (PD-L1 and PD-L2), thereby blocking the down-regulation of anti-tumor T-cell functions (described as mAb C5 in U.S. Pat. No. 8,008,449; Wang et al., 2014). In other preferred embodiments, the anti-PD-1 Ab is pembrolizumab (KEYTRUDA®; a humanized monoclonal IgG4 Ab directed against PD-1 and described as h409A11 in U.S. Pat. No. 8,354,509), which has also been approved for multiple cancer indications.

Anti-PD-1 Abs usable in the disclosed methods, compositions or kits also include isolated Abs, preferably mAbs, that bind specifically to human PD-1 (hPD-1) and cross-compete for binding to human PD-1 with any one of the anti-PD-1 Abs described herein, e.g.: nivolumab (5C4; see, e.g., U.S. Pat. No. 8,008,449; WO 2013/173223) and pembrolizumab. Abs that cross-compete with a reference Ab, e.g., nivolumab or pembrolizumab, for binding to an antigen, in this case human PD-1, can be readily identified in standard PD-1 binding assays such as BIACORE® analysis, ELISA assays or flow cytometry (see, e.g., WO 2013/173223). In certain embodiments, the anti-PD-1 Ab binds to the same epitope as any of the anti-PD-1 Abs described herein, e.g., nivolumab or pembrolizumab.

An anti-PD-1 Ab usable in the methods of the disclosed invention also includes an antigen-binding portion, including a Fab, $F(ab')_2$, Fd or Fv fragment, a sdAb, a scFv, di-scFv or bi-scFv, a diabody, a minibody or an isolated CDR (see Hollinger and Hudson, 2005; Olafsen and Wu, 2010, for further details).

In certain embodiments, the isolated anti-PD-1 Ab or antigen-binding portion thereof comprises a heavy chain constant region which is of a human IgG1, IgG2, IgG3 or IgG4 isotype. In certain preferred embodiments, the anti-PD-1 Ab or antigen-binding portion thereof comprises a heavy chain constant region which is of a human IgG4 isotype. In other embodiments, the anti-PD-1 Ab or antigen-binding portion thereof is of a human IgG1 isotype. In certain other embodiments, the IgG4 heavy chain constant region of the anti-PD-1 Ab or antigen-binding portion thereof contains an S228P mutation (numbered using the Kabat system; Kabat et al., 1983) which replaces a serine residue in the hinge region with the proline residue normally found at the corresponding position in IgG1 isotype Abs. This mutation, which is present in nivolumab, prevents Fab arm exchange with endogenous IgG4 Abs, while retaining the low affinity for activating Fc receptors associated with wild-type IgG4 Abs (Wang et al., 2014). In yet other embodiments, the Ab comprises a light chain constant region which is a human kappa or lambda constant region.

In other embodiments of the present methods, the anti-PD-1 Ab or antigen-binding portion thereof is a mAb or an antigen-binding portion thereof. For administration to human subjects, the anti-PD-1 Ab is preferably a chimeric Ab or, more preferably, a humanized or human Ab. Such chimeric, humanized or human mAbs can be prepared and isolated by methods well known in the art, e.g., as described in U.S. Pat. No. 8,008,449.

Anti-PD-L1 mAbs

Because anti-PD-1 and anti-PD-L1 target the same signaling pathway and have been shown in clinical trials to exhibit comparable levels of efficacy in a variety of cancers (see, e.g., Brahmer et al., 2012; WO 2013/173223), an anti-PD-L1 Ab may be substituted for the anti-PD-1 Ab in the combination therapy methods disclosed herein.

Anti-PD-L1 Abs suitable for use in the disclosed methods, compositions or kits are isolated Abs that bind to PD-L1 with high specificity and affinity, block binding of PD-L1 to PD-1 and to CD80, and inhibit the immunosuppressive effect of the PD-1 signaling pathway. MAbs that bind specifically to PD-L1 with high affinity have been disclosed in U.S. Pat. No. 7,943,743. Other anti-PD-L1 mAbs have been described in, for example, U.S. Pat. Nos. 8,217,149, 8,779,108, 9,175,082 and 9,624,298, and PCT Publication No. WO 2012/145493. The anti-PD-1 HuMAbs disclosed in U.S. Pat. No. 7,943,743 have been demonstrated to exhibit one or more of the following characteristics: (a) binding to human PD-1 with a $K_D$ of about 50 mM or lower, as determined by SPR (BIACORE®); (b) increasing T-cell proliferation, interferon-γ production and IL-2 secretion in a MLR assay; (c) stimulating Ab responses; (d) inhibiting the binding of PD-L1 to PD-1; and (e) reversing the suppressive effect of Tregs on T cell effector cells and/or dendritic cells. Anti-PD-L1 Abs for use in the therapeutic methods disclosed herein include isolated Abs, preferably mAbs, that bind specifically to human PD-L1 with high affinity and exhibit at least one, in some embodiments at least three, and preferably all, of the preceding characteristics. For example, an anti-PD-L1 Ab suitable for use in these methods (a) binds to human PD-1 with a $K_D$ of about 50 mM to 0.1 mM, as determined by surface plasmon resonance (BIACORE®); (b) increases T-cell proliferation, interferon-γ production and IL-2 secretion in a MLR assay; (c) inhibits the binding of PD-L1 to PD-1 and to CD80; and (d) reverses the suppressive effect of Tregs on T cell effector cells and/or dendritic cells.

A suitable anti-PD-L1 Ab for use in the present methods is BMS-936559 (formerly MDX-1105; designated 12A4 in U.S. Pat. No. 7,943,743). Other suitable anti-PD-L1 Abs include atezolizumab (TECENTRIQ®; previously known as RG7446 and MPDL3280A; designated YW243.55S70 in U.S. Pat. No. 8,217,149; see, also, Herbst et al., 2014), durvalumab (IMFINZI®; previously known as MEDI-4736; designated 2.14H9OPT in U.S. Pat. No. 8,779,108), avelumab (BAVENCIO®; previously known as MSB-0010718C; designated A09-246-2 in U.S. Pat. No. 9,624,298), STI-A1014 (designated H6 in U.S. Pat. No. 9,175,082), CX-072 (see WO 2016/149201), KN035 (see Zhang et al., 2017), LY3300054 (see, e.g., WO 2017/034916), and CK-301 (see Gorelik et al., 2017).

In certain preferred embodiments of any of the therapeutic methods described herein comprising administration of an anti-PD-L1 Ab, the anti-PD-L1 Ab is atezolizumab (TECENTRIQ®). In other preferred embodiments, the anti-PD-L1 Ab is durvalumab (IMFINZI®). In further preferred embodiments, the anti-PD-L1 Ab is avelumab (BAVENCIO®).

Anti-PD-L1 Abs suitable for use in the disclosed methods, compositions or kits also include isolated Abs that bind specifically to human PD-L1 and cross-compete for binding to human PD-L1 with a reference Ab which may be any one of the anti-PD-L1 Abs disclosed herein, e.g., BMS-936559 (12A4; see, e.g., U.S. Pat. No. 7,943,743; WO 2013/173223), atezolizumab, durvalumab, avelumab or STI-A1014. The ability of an Ab to cross-compete with a reference Ab for binding to human PD-L1 demonstrates that such Ab binds to the same epitope region of PD-L1 as the reference Ab and is expected to have very similar functional properties to that of the reference Ab by virtue of its binding to substantially the same epitope region of PD-L1. In some embodiments, the anti-PD-L1 Ab binds the same epitope as any of the anti-PD-L1 Abs described herein, e.g., atezolizumab, durvalumab, avelumab or STI-A1014. Cross-competing Abs can be readily identified based on their ability to cross-compete with a reference Ab such as atezolizumab or avelumab in standard PD-L1 binding assays such as BIACORE® analysis, ELISA assays or flow cytometry that are well known to persons skilled in the art (see, e.g., WO 2013/173223).

In certain preferred embodiments, the isolated anti-PD-L1 Abs for use in the present methods are mAbs. In other embodiments, especially for administration to human subjects, these Abs are preferably chimeric Abs, or more preferably humanized or human Abs. Chimeric, humanized and human Abs can be prepared and isolated by methods well known in the art, e.g., as described in U.S. Pat. No. 7,943,743.

In certain embodiments, the anti-PD-L1 Ab or antigen-binding portion thereof comprises a heavy chain constant region which is of a human IgG1, IgG2, IgG3 or IgG4 isotype. In certain other embodiments, the anti-PD-L1 Ab or antigen-binding portion thereof is of a human IgG1 of IgG4 isotype. In further embodiments, the sequence of the IgG4 heavy chain constant region of the anti-PD-L1 Ab or antigen-binding portion thereof contains an S228P mutation. In other embodiments, the Ab comprises a light chain constant region which is a human kappa or lambda constant region.

Anti-PD-L1 Abs of the invention also include antigen-binding portions of the above Abs, including Fab, $F(ab')_2$, Fd, Fv, and scFv, di-scFv or bi-scFv, and scFv-Fc fragments, nanobodies, diabodies, triabodies, tetrabodies, and isolated CDRs, that bind to PD-L1 and exhibits functional properties similar to those of whole Abs in inhibiting receptor binding and up-regulating the immune system.

Pharmaceutical Compositions and Dosage Regimens

MAbs disclosed herein and used in the any of the therapeutic methods described may be constituted in a composition, e.g., a pharmaceutical composition containing an Ab and a pharmaceutically acceptable carrier. This invention also provides compositions comprising any of the disclosed immunoconjugates or bispecific molecule and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. Preferably, the carrier for a composition containing an Ab is suitable for intravenous (IV), intramuscular, subcutaneous (SC), parenteral, spinal or epidermal administration (e.g., by injection or infusion).

An option for SC injection is based on Halozyme Therapeutics' ENHANZE® drug-delivery technology, involving a co-formulation of an Ab, e.g., a mAb, with recombinant human hyaluronidase enzyme (rHuPH20) that removes traditional limitations on the volume of biologics and drugs that can be delivered subcutaneously due to the extracellular matrix (U.S. Pat. No. 7,767,429). It may be possible to co-formulate two Abs used in combination therapy into a single composition for SC administration.

A pharmaceutical composition of the invention may include one or more pharmaceutically acceptable salts, antioxidants, aqueous and non-aqueous carriers, and/or adjuvants such as preservatives, wetting agents, emulsifying agents and dispersing agents.

Dosage regimens are adjusted to provide the optimum desired response, e.g., a maximal therapeutic response and/or minimal adverse effects. For administration of an anti-CCR8, anti-PD-1 or anti-PD-L1 Ab or an antigen-binding portion thereof, including for combination use, the dosage may range from about 0.01 to about 20 mg/kg, preferably from about 0.1 to about 10 mg/kg, of the subject's body weight. For example, dosages can be about 0.1, 0.3, 1, 2, 3, 5 or 10 mg/kg body weight, and more preferably, about 0.3, 1, 3, or 10 mg/kg body weight. Alternatively, a fixed or flat dose, e.g., about 0.1 to about 2,000 mg, preferably about 1 to about 1,000 mg such as about 0.3, 1, 3, 5, 10, 30, 60, 100, 150, 200, 240, 300, 400, 500, 600, 800 or 1,000 mg, of the Ab or antigen-binding portion thereof, instead of a dose based on body weight, may be administered. Flat (vs. weight-based) dosing is attractive due to the ease of preparation, a reduced risk of medication errors, and the observation that for most biologics the two dosing approaches perform similarly (Wang et al., 2009).

The dosing schedule is typically designed to achieve exposures that result in sustained receptor occupancy (RO) based on typical pharmacokinetic properties of an Ab. An exemplary treatment regime entails administration once per week, once every 2 weeks, once every 3 weeks, once every 4 weeks, once a month, once every 3-6 months or longer. In certain preferred embodiments, the anti-CCR8, anti-PD-1 or anti-PD-L1 Ab or antigen-binding portion thereof is administered to the subject once every 2 weeks. In other preferred embodiments, the Ab or antigen-binding portion thereof is administered once every 3 weeks or once every 4 weeks. The dosage and scheduling may change during a course of treatment. The first-in-human (FIH) starting flat dose of 0.3 mg (4 μg/kg) IV Q2W for 4A19 was derived using the totality of data generated from a mix of pharmacology- and toxicology-based approaches with the goal of ensuring adequate safety while minimizing the participants' exposure to potentially sub-efficacious doses and risk of cytokine release.

In the clinical trial described in Example 34, the totality of data generated from a mix of pharmacology- and toxicology-based approaches were employed to determine dosages used in the first-in-human (FIH) clinical study. In the dose escalation phase of the anti-CCR8 monotherapy arm, a flat dose of 0.3, 1, 3, 10, 30, 100, 300 or 800 mg of 4A19 is administered intravenously (IV) to the subject once every 2 weeks (Q2W). In the combination therapy arm, the same doses of 4A19 are administered in the dose escalation phase in combination with nivolumab administered IV at the FDA-approved flat dose of 480 mg once every 4 weeks (Q4W). For dose expansion, single-arm and randomized cohorts are opened to include different tumor types and dose levels from the escalation phase, with treatment as monotherapy or combination therapy continuing until progression, unacceptable toxicity, withdrawal of consent, completion of 26 cycles of study therapy (104 weeks), or the study ends, whichever occurs first.

Accordingly, in certain embodiments of the disclosed therapy methods, an anti-CCR8 Ab is administered to the subject as monotherapy, or in combination with an immune checkpoint inhibitor, e.g., an anti-PD-1 or anti-PD-L1 Ab, at a flat dose of about 0.3 to about 800 mg Q2W. More specifically, in certain embodiments, the anti-CCR8 Ab is administered at 0.3, 1, 3, 10, 30, 100, 300 or 800 mg Q2W. In certain preferred embodiments, the anti-CCR8 Ab is mAb 4A19. In other preferred embodiments, the anti-CCR8 Ab is mAb 1455 or 14S15h. In certain embodiments, the anti-CCR8 Ab is administered to the subject at a flat dose of 3 mg Q2W. In certain other embodiments, the anti-CCR8 Ab is administered at 10 mg Q2W. In other embodiments, the anti-CCR8 Ab is administered at a flat dose of 30 mg Q2W. In yet other embodiments, the anti-CR8 Ab is administered to the subject at a flat does of 100 mg Q2W.

For combination therapy, in certain embodiments, the immune checkpoint inhibitor is an anti-PD-1, anti-PD-L1, or anti-CTLA-4 Ab. In certain preferred embodiments, the anti-PD-1 Ab is nivolumab. In preferred embodiments, nivolumab is administered to the subject at the flat dose of 480 mg Q4W.

When used in combinations, a subtherapeutic dosage of one or both Abs, e.g., a dosage of an anti-CCR8, anti-PD-1 and/or anti-PD-L1 Ab or antigen-binding portion thereof may be used. As used herein, a "subtherapeutic" dose or dosage of a therapeutic agent, such as a therapeutic Ab, refers to a dose that is lower than the typical or approved monotherapy dose. For example, a dosage of nivolumab that is lower than the initially FDA-approved 3 mg/kg every 2 weeks, for instance, 1.0 mg/kg or less every 2, 3 or 4 weeks, is regarded as a subtherapeutic dosage. Nivolumab has subsequently been approved by the FDA at 240 mg every two weeks or 480 mg every 4 weeks. Thus, for example, a dosage of nivolumab that is lower than the approved 480 mg every 4 weeks, for instance, 120 mg or less every 2, 3 or 4 weeks, is regarded as a subtherapeutic dosage. RO data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%) (Brahmer et al., 2010). Thus, 0.3 mg/kg dosing may allow for sufficient exposure to lead to significant biologic activity.

In contrast, as used herein, a "sub-efficacious" dose or dosage of a therapeutic agent, such as a therapeutic Ab, refers to a dose that is lower than the dose required for significant biologic activity and, therefore, does not cause any meaningful therapeutic effect when administered as monotherapy or in combination therapy.

The synergistic interaction observed in mouse tumor models between the anti-CCR8 and anti-PD-1/anti-PD-L1 Abs or antigen-binding portions thereof may permit the administration of one or both of these therapeutics to a cancer patient at subtherapeutic dosages. In certain embodiments of the disclosed combination therapy methods, the anti-CCR8 Ab or antigen-binding portion thereof is administered at a subtherapeutic dose to a cancer patient. In other embodiments, the anti-PD-1/anti-PD-L1 Ab or antigen-binding portion thereof is administered to the patient at a subtherapeutic dose. In further embodiments, the anti-PD-1/anti-PD-L1 and anti-CCR8 Abs or antigen-binding portions thereof are each administered to the patient at a subtherapeutic dose.

The administration of such a subtherapeutic dose of one or both Abs may reduce adverse events compared to the use of higher doses of the individual Abs in monotherapy. Thus, the success of the disclosed methods of combination therapy may be measured not only in improved efficacy of the combination of Abs relative to monotherapy with these Abs, but also in increased safety, i.e., a reduced incidence of adverse events, from the use of lower dosages of the drugs in combination relative to the monotherapy doses.

In certain embodiments of any of the methods disclosed herein, the anti-CCR8, anti-PD-1 and/or anti-PD-L1 Abs are formulated for intravenous (IV) administration or for subcutaneous (SC) injection. In certain embodiments, the anti-CCR8 Ab or antigen-binding portion thereof and the anti-PD-1/anti-PD-L1 Ab or antigen-binding portion thereof are administered sequentially to the subject. "Sequential" administration means that one of the anti-CCR8 and anti-PD-1/anti-PD-L1 Abs is administered before the other. Either Ab may be administered first; i.e., in certain embodiments, the anti-PD-1/anti-PD-L1 Ab is administered before the anti-CCR8 Ab, whereas in other embodiments, the anti-CCR8 Ab is administered before the anti-PD-1/anti-PD-L1 Ab. In certain embodiments, each Ab is administered by IV infusion, for example, by infusion over a period of about 60 minutes. In other embodiments, at least one Ab is administered by SC injection.

In certain embodiments of sequential IV administration, for the convenience of the patient, the anti-CCR8 and anti-PD-1/anti-PD-L1 Abs or portions thereof are administered within 30 minutes of each other. Typically, when both the anti-CCR8 and anti-PD-1/anti-PD-L1 Abs are to be delivered by IV administration on the same day, separate infusion bags and filters are used for each infusion. The infusion of the first Ab is promptly followed by a saline flush to clear the line of the Ab before starting the infusion of the second Ab. In other embodiments, the two Abs are administered within 1, 2, 4, 8, 24 or 48 h of each other.

The delivery of at least one Ab by SC administration reduces health care practitioner time required for administration and shortens the time for drug administration. For example, the use of SC injection could cut the time needed for IV administration, typically about 30-60 min, to about 5 min. In certain embodiments of sequential SC administration, the anti-CCR8 and anti-PD-1/anti-PD-L1 Abs or portions thereof are administered within 10 min of each other.

Because checkpoint inhibitor Abs have been shown to produce very durable responses, in part due to the memory component of the immune system (see, e.g., WO 2013/173223; Lipson et al., 2013; Wolchok et al., 2013), the activity of an administered anti-PD-1/anti-PD-L1 Ab may be ongoing for several weeks, several months, or even several years. In certain embodiments, the present combination therapy methods involving sequential administration entail administration of an anti-CCR8 Ab to a patient who has been previously treated with an anti-PD-1/anti-PD-L1 Ab. In further embodiments, the anti-CCR8 Ab is administered to a patient who has been previously treated with, and progressed on, an anti-PD-1/anti-PD-L1 Ab. In other embodiments, the present combination therapy methods involving sequential administration entail administration of an anti-PD-1/anti-PD-L1 Ab to a patient who has been previously treated with an anti-CCR8 Ab, optionally a patient whose cancer has progressed after treatment with the anti-CCR8 Ab.

In certain other embodiments, the anti-PD-1/anti-PD-L1 and anti-CCR8 mAbs are administered concurrently, either admixed as a single composition in a pharmaceutically acceptable formulation for concurrent administration, or concurrently as separate compositions with each Ab in formulated in a pharmaceutically acceptable composition. In certain preferred embodiments, the anti-PD-1/anti-PD-L1 and anti-CCR8 mAbs are administered concurrently as separate compositions with each Ab in formulated in a pharmaceutically acceptable composition. In other embodiments, the anti-PD-1/anti-PD-L1 and anti-CCR8 mAbs are administered concurrently as a single composition in a pharmaceutically acceptable formulation.

This disclosure provides a hypofucosylated or nonfucosylated isolated Ab, preferably a mAb, which specifically binds to hCCR8 expressed on the surface of a cell, wherein the isolated Ab comprises a heavy chain comprising consecutively linked amino acids having the sequence set forth as SEQ ID NO: 102 and a light chain comprising consecutively linked amino acids having the sequence set forth as SEQ ID NO: 114, for use in a method of treating a subject afflicted with a cancer, wherein the cancer is chosen from NSCLC, SCCHN, MSS-CRC, gastric/GE junction cancer, and cervical cancer.

In certain embodiments, the disclosure also provides a hypofucosylated or nonfucosylated isolated Ab, preferably a mAb, which specifically binds to hCCR8 expressed on the surface of a cell, wherein the isolated Ab comprises a heavy chain comprising consecutively linked amino acids having the sequence set forth as SEQ ID NO: 102 and a light chain comprising consecutively linked amino acids having the sequence set forth as SEQ ID NO: 114, for use in a method of treating in combination with another therapeutic agent a subject afflicted with a cancer, wherein the cancer is chosen from NSCLC, SCCHN, MSS-CRC, gastric/GE junction cancer, and cervical cancer, and wherein the other therapeutic agent is an anti-PD-1, an anti-PD-L1, or an anti-CTLA-4 Ab.

In certain other embodiments, the disclosure further provides a hypofucosylated or nonfucosylated isolated Ab, preferably a mAb, which specifically binds to hCCR8 expressed on the surface of a cell, wherein the isolated Ab comprises a heavy chain comprising consecutively linked amino acids having the sequence set forth as SEQ ID NO: 102 and a light chain comprising consecutively linked amino acids having the sequence set forth as SEQ ID NO: 114, for use in a method of treating in combination with another therapeutic agent a subject afflicted with a cancer, wherein the cancer is chosen from NSCLC, SCCHN, MSS-CRC, gastric/GE junction cancer, and cervical cancer, wherein the other therapeutic agent is nivolumab, and wherein the anti-CCR8 Ab is administered to the subject at a dose of 1-30 mg once every 2 weeks and nivolumab is administered to the subject at a dose of 240 mg once every 2 weeks or 480 mg once every 4 weeks.

This disclosure also provides a method for treating a subject afflicted with a cancer comprising administering to the subject a therapeutically effective amount of a hypofucosylated or nonfucosylated anti-CCR8 mAb which comprises a heavy chain comprising consecutively linked amino acids having the sequence set forth as SEQ ID NO: 102 and a light chain comprising consecutively linked amino acids having the sequence set forth as SEQ ID NO: 114 such that the subject is treated, wherein the cancer is chosen from NSCLC, SCCHN, MSS-CRC, gastric/GE junction cancer, and cervical cancer.

In certain embodiments, the disclosure also provides a method for treating a subject afflicted with a cancer comprising administering to the subject therapeutically effective amounts of: (a) a hypofucosylated or nonfucosylated anti-CCR8 mAb which comprises a heavy chain comprising consecutively linked amino acids having the sequence set forth as SEQ ID NO: 102 and a light chain comprising consecutively linked amino acids having the sequence set forth as SEQ ID NO: 114; and (b) another therapeutic agent, such that the subject is treated, wherein the cancer is chosen from NSCLC, SCCHN, MSS-CRC, gastric/GE junction cancer, and cervical cancer, and wherein the other therapeutic agent is an anti-PD-1, an anti-PD-L1, or an anti-CTLA-4 Ab.

In certain other embodiments, the disclosure further provides a method for treating a subject afflicted with a cancer comprising administering to the subject therapeutically effective amounts of: (a) a hypofucosylated or nonfucosylated anti-CCR8 mAb which comprises a heavy chain comprising consecutively linked amino acids having the sequence set forth as SEQ ID NO: 102 and a light chain comprising consecutively linked amino acids having the sequence set forth as SEQ ID NO: 114; and (b) another therapeutic agent, such that the subject is treated, wherein the cancer is chosen from NSCLC, SCCHN, MSS-CRC, gastric/GE junction cancer, and cervical cancer, wherein the other therapeutic agent is nivolumab, and wherein the anti-CCR8 Ab is administered to the subject at a dose of 1-30 mg once every 2 weeks and nivolumab is administered to the subject at a dose of 240 mg once every 2 weeks or 480 mg once every 4 weeks.

The disclosure further provides a method for inhibiting growth of tumor cells in a subject comprising administering to the subject a therapeutically effective amount of a hypofucosylated or nonfucosylated anti-CCR8 mAb which comprises a heavy chain comprising consecutively linked amino acids having the sequence set forth as SEQ ID NO: 102 and a light chain comprising consecutively linked amino acids having the sequence set forth as SEQ ID NO: 114 such that growth of tumor cells in the subject is inhibited, wherein the cancer is chosen from NSCLC, SCCHN, MSS-CRC, gastric/GE junction cancer, and cervical cancer.

In certain embodiments, the disclosure also provides a method for inhibiting growth of tumor cells in a subject comprising administering to the subject therapeutically effective amounts of: (a) a hypofucosylated or nonfucosylated anti-CCR8 mAb which comprises a heavy chain comprising consecutively linked amino acids having the sequence set forth as SEQ ID NO: 102 and a light chain comprising consecutively linked amino acids having the sequence set forth as SEQ ID NO: 114; and (b) another therapeutic agent, such that growth of tumor cells in the subject is inhibited, wherein the cancer is chosen from NSCLC, SCCHN, MSS-CRC, gastric/GE junction cancer, and cervical cancer, and wherein the other therapeutic agent is an anti-PD-1, an anti-PD-L1, or an anti-CTLA-4 Ab.

In certain other embodiments, the disclosure further provides a method for inhibiting growth of tumor cells in a subject comprising administering to the subject therapeutically effective amounts of: (a) a hypofucosylated or nonfucosylated anti-CCR8 mAb which comprises a heavy chain comprising consecutively linked amino acids having the sequence set forth as SEQ ID NO: 102 and a light chain comprising consecutively linked amino acids having the sequence set forth as SEQ ID NO: 114; and (b) another therapeutic agent, such that growth of tumor cells in the subject is inhibited, wherein the cancer is chosen from NSCLC, SCCHN, MSS-CRC, gastric/GE junction cancer, and cervical cancer, wherein the other therapeutic agent is nivolumab, and wherein the anti-CCR8 Ab is administered to the subject at a dose of 1-30 mg once every 2 weeks and nivolumab is administered to the subject at a dose of 240 mg once every 2 weeks or 480 mg once every 4 weeks.

Kits

Also within the scope of the present invention are kits comprising an anti-CCR8 Ab. Kits typically include a label indicating the intended use of the contents of the kit and instructions for use. The term label includes any writing, or recorded material supplied on or with the kit, or which otherwise accompanies the kit. Accordingly, this disclosure provides a kit for treating a subject afflicted with a cancer, the kit comprising: (a) one or more dosages ranging from about 0.01 to about 20 mg/kg body weight, e.g., about 0.1 or 1 mg/kg, or about 0.1 to about 2,000 mg fixed dose, e.g., about 3, 10, 30 or 100 mg, of an Ab, e.g., a mAb or an antigen-binding portion thereof that binds specifically to CCR8 and mediates depletion of a CCR8-expressing cell by ADCC; (b) optionally one or more dosages ranging from about 0.1 to about 20 mg/kg body weight, e.g., about 2 to about 10 mg/kg, or about 200 to about 1600 mg fixed dose, e.g., about 240 or 480 mg, of an Ab, e.g., a mAb or an antigen-binding portion thereof that binds specifically to PD-1, PD-L1 or CTLA-4; and (c) instructions for using the Ab or portion thereof that binds specifically to CCR8, and optionally the Ab or portion thereof that binds specifically to PD-1, PD-L1 or CTLA-4, in any of the therapeutic methods disclosed herein.

The disclosure further provides a kit for treating a subject afflicted with a cancer, the kit comprising: (a) one or more dosages ranging from about 0.01 to about 20 mg/kg body weight, e.g., about 0.1 or 1 mg/kg, or about 0.1 to about 2,000 mg fixed dose, e.g., about 3, 10, 30 or 100 mg, of an Ab, e.g., a mAb or an antigen-binding portion thereof that binds specifically to CCR8 and mediates depletion of a CCR8-expressing cell by ADCC; (b) one or more dosages of about 0.1 to about 20 mg/kg body weight, e.g., about 2 or 3 mg/kg, or 200 to about 1600 mg fixed dose, e.g., about 240 or 480 mg, of an anti-PD-1/anti-PD-L1 mAb or an antigen-binding portion thereof; and (c) instructions for using the anti-CCR8 mAb and the anti-PD-1/anti-PD-L1 mAb, in any of the combination therapy methods disclosed herein.

In certain embodiments, the kit comprises one or more fixed dosages of the anti-CCR8 Ab ranging from about 0.1 to about 2,000 mg, preferably about 0.3 to about 1,000 mg such as about 0.3, 1, 3, 5, 10, 30, 60, 100, 150, 200, 240, 300, 400, 500, 600, 800 or 1,000 mg, of the Ab or antigen-binding portion thereof, instead of a dose based on body weight. In certain embodiments, the kit comprises 0.3, 1, 3, 10, 30, 100, 300 and 800 mg of the anti-CCR8 Ab for administration once every 2 weeks. In certain other embodiments, the kit comprises about 100 to about 600 mg of the anti-PD-1/PD-L1 Ab, e.g., 240 mg of nivolumab for administration once every 2 weeks or 480 mg of nivolumab for administration once every 4 weeks. In certain preferred embodiments, the anti-CCR8 Ab is mAb 4A19. In other preferred embodiments, the anti-CCR8 Ab is mAb 14515 or 14S15h. In certain preferred embodiments, the anti-PD-1 Ab is nivolumab. In other preferred embodiments, the anti-PD-1 Ab is pembrolizumab.

In certain embodiments, the Abs may be co-packaged in unit dosage form. In certain preferred embodiments for treating human patients, the kit comprises an anti-human PD-1 Ab disclosed herein, e.g., nivolumab or pembrolizumab.

The present invention is further illustrated by the following examples which should not be construed as further limiting. The contents of all references cited throughout this application are expressly incorporated herein by reference.

Example 1

Correlation of CCR8 Expression with FOXP3 Expression in Tumor Tregs

CCR8 is a Treg-Selective Marker

TCGA samples (Goldman et al., 2019; Wang and Liu, 2019; batch-corrected FPKM values from UCSC Xena PanCan Repository) from tumors of non-hematopoetic origin were divided into tumor categories (TCGA designations, tumor only) and RNA-seq data for each transcript was transformed into a standard distribution (mean=0, standard deviation=1) within tumor type, after which all tumor RNA data were combined. Mutual-Rank distance measurements (Siemers et al., 2017; Huttenhower et al., 2007) were performed from the Pearson correlation matrix of log-transformed transcripts.

Mutual rank-based network of gene-gene correlation across all non-heme tcga tumor RNA-seq, shown in FIG. 1A, identified CCR8 as a Treg-selective marker as transcript abundances for CCR8 exhibited both a strong and selective correlation to FOXP3 when compared with other gene neighbors in most cancer types from TCGA. It is notable that costimulatory/coinhibitory molecules (CTLA4, ICOS, TIGIT) occupy a part of the network intermediary to FOXP3 and canonical T cell markers (e.g., CD3E, IL2RB, SLAMF1). Line weights and distances indicate strength of mutual-rank associations.

CCR8 is Selectively Expressed on $FOXP3^{high}$ Lymphocytes in Hepatocellular Carcinoma Data were plotted logarithmically scaled as log 2 (counts+1) from Zheng et al. (2017), NCBI Gene Expression Omnibus: GSE98638, and plots created with the Fauxflow R/Shiny toolkit (https://github.com/NathanSiemers/FauxFlow). A small amount of Gaussian noise was added to each point to aid in visualization.

As shown in FIG. 1B, CCR8 is selectively expressed on $FOXP3^{high}$ lymphocytes in hepatocellular carcinoma tumor samples, and there is an absence of CCR8 expression in $FOXP3^{mid}$ CD8 and CD4 populations.

Association of CCR8 Expression with Expression of Other Genes

Spearman correlation analysis was performed in $FOXP3^+$ (expression>=1) T lymphocytes (expression>=1) between CCR8 expression>=1 vs. CCR8 expression<1, and unadjusted Spearman P values were plotted vs. the ratio of mean gene expression of associated markers.

FIG. 1C shows that transcripts associated with CCR8 positivity and negativity within $FOXP3^+$ cells in Zheng et al. (2017). CCR8 expression is associated with higher levels of FOXP3 expression and canonical markers of Tregs (IL2RA, IKZF2, BATF), whereas lower expression of CCR8 is associated with cytotoxic T cell markers (GZMA, CD8A).

Example 2

Tissue Processing

Human Tumor Dissociation

Tumor samples were minced with dissecting lab scissors and further mechanically dissociated with a Dounce homogenizer or enzymatically digested using a human tumor dissociation kit (Miltenyi Biotec, Bergisch Gladbach, Germany) in conjunction with a gentleMACS dissociator (Miltenyi Biotec) according to the manufacturer's instructions. Cell suspensions were filtered through a 70 μm cell strainer.

Human Treg Isolation and Stimulation

PBMCs were isolated from a leukopak (AllCells) using a Ficoll density gradient (GE Healthcare). $CD25^+$ cells were magnetically enriched using anti-CD25 MicroBeads II (Miltenyi Biotec). Enriched cells were stained for CD25 (4E3, Miltenyi Biotec), CD127 (A019D5, BioLegend), CD45RA (HI100, BioLegend), and CD4 (SK3, BD Biosciences). $CD4^+$ $CD127_{low}$ $CD25_{high}$ $CD45RA^+$ Tregs were sorted on a BD FACSAria II. Isolated naïve Tregs were expanded using Dynabeads Human T-Activator CD3/CD28 (Thermo Fisher Scientific) (3 beads to 1 Treg) in Roswell Park Memorial Institute (RPMI) cell culture medium (Corning, Corning, NY) with 10% fetal bovine serum (FBS; (GE Healthcare, Chicago, IL). After 3 days, IL-2 (PeproTech) was added at 300 U/ml. Tregs were expanded and cryopreserved. Thawed Tregs were restimulated using CD3/CD28 Dynabeads (1 bead to 1 Treg) in RPMI medium with 10% FBS and 100 U/ml of IL-2.

Human Skin Processing

Skin biopsies from normal female abdominal human skin, age 43, was digested overnight in a MACS C tube (Miltenyi Biotec) using a whole skin dissociation kit (Miltenyi Biotec) without enzyme P. Cell suspensions were washed, filtered, and stained.

Mouse Tissue Processing

Tumors were minced and then enzymatically digested for 30 min at 37° C. using 250 U/ml Collagenase IV (Worthington Biochemical, Lakewood, NJ) and DNase I (MilliporeSigma, Burlington, MA). Shaved skin was minced and then enzymatically digested for 60 min at 37° C. with 500 μg/ml Collagenase XI (MilliporeSigma), 500 μg/ml Hyaluronidase (MilliporeSigma), and 100 μg/ml DNase I. Spleen and thymus were dissociated mechanically using a gentleMACS dissociator (Miltenyi Biotec). Red blood cells (RBCs) in dissociated spleen and blood samples were lysed with ammonium-chloride-potassium solution (Thermo Fisher Scientific) for 5 min.

Study Approval

Human tumor, skin, spleen, patient blood, and healthy blood leukopack samples were collected through commercial providers (BioIVT, Westbury, N.ZY.; MT Group, Avaden, BioOptions, Discovery Life Sciences, Los Osos, CA; AllCells, Alameda, CA) or the Cooperative Human Tissue Network (CHTN). All samples were collected from donors giving written informed consent at IRB-approved study locations in the United States.

Blood from healthy donors was obtained from a blood donation program administered by the Bristol Myers Squibb (BMS) Occupational Health department in compliance with all relevant ethical regulations. All animal experiments complied with institutional guidelines and were approved by the IACUC at BMS under protocol 1612-01.

Example 3

CCR8 Marks Suppressive $FOXP3^+$Cells with Low Proinflammatory Potential in Human Tumors Expression profiles of several Treg-associated molecules were compared by flow cytometry.

Flow Cytometry

For flow cytometry, in general, cell suspensions were stained with amine reactive viability dyes. Human cells were then blocked with rat, mouse, and human AB serum (GEMCELL™; Gemini Bio, West Sacramento, CA), HUMAN TRUSTAIN FcX™ (BioLegend), and TRUE-STAIN MONOCYTE BLOCKER™ (BioLegend). Mouse cells were blocked with FcR blocking reagent (Miltenyi Biotec). Cells were surface stained, and intracellular staining was performed using the FOXP3 Transcription Factor Staining Buffer Set (Thermo Fisher Scientific) using manufacturer's protocols. For binding of unconjugated mAbs, an appropriate secondary Ab (Jackson ImmunoResearch Laboratories) was used. Samples were acquired using a BD LSRFortessa X-20 and analyzed using FlowJo (BD Biosciences). The complete list of flow cytometry Abs is provided in Table 2.

TABLE 2

| Abs used for flow cytometric analyses | | | | |
|---|---|---|---|---|
| Target | Species | Clone | Fluorophore | Manufacturer |
| CD45 | Human | HI10 | AF488 | Biolegend |
| CCR4 | Human | L291H4 | PE | Biolegend |
| CCR4 | Human | L291H4 | BV510 | Biolegend |
| CD16 | Human | 3G8 | AF647 | Biolegend |
| CD8a | Human | SK1 | PerCP-eFluor 710 | Thermo Fisher |
| CD56 | Human | CMSSB | PE-eFluor 610 | Thermo Fisher |
| FOXP3 | Human | 236A/E7 | PE-Cy7 | Thermo Fisher |
| CCR8 | Human | 433H | BV421 | BD Biosciences |
| CD15 | Human | W6D3 | BV510 | BD Biosciences |
| CD4 | Human | SK3 | BV650 | BD Biosciences |
| CD4 | Human | SK3 | BV605 | BD Biosciences |
| CTLA4 | Human | BNI3 | BV421 | BD Biosciences |
| HLA-DR | Human | G46-6 | BUV395 | BD Biosciences |
| PD-1 | Human | EH12.1 | BUV737 | BD Biosciences |
| CD3 | Human | UCHT1 | BUV805 | BD Biosciences |
| CD3 | Human | UCHT1 | APC | BD Biosciences |
| CD39 | Human | A1 | BV786 | Biolegend |
| Granzyme B | Human | QA16A02 | PE | Biolegend |
| IFNg | Human | 4S.B3 | PE-eFluor 610 | Thermo Fisher |
| IL-1R2 | Human | MA5-23626 | APC | Thermo Fisher |
| IL-2 | Human | MQ1-17H12 | BUV737 | BD Biosciences |
| CD19 | Human | SJ25C1 | BV510 | BD Biosciences |
| CD25 | Human | 2A3 | APC-R700 | BD Biosciences |
| CD3e | Mouse | 145-2C11 | BV421 | Biolegend |
| CCR8 | Mouse | SA214G2 | AF647 | Biolegend |
| CCR8 | Mouse | SA214G2 | PE | Biolegend |
| IFNg | Mouse | XMG1.2 | PE-Cy7 | Biolegend |
| TNFa | Mouse | MP6-XT22 | APC | Biolegend |
| FOXP3 | Mouse | FJK-16a | PE-eFluor 610 | Thermo Fisher |
| CD8a | Mouse | 53-6.7 | BUV805 | BD Biosciences |
| CD8b | Mouse | H35-17.2 | BV650 | BD Biosciences |
| CD4 | Mouse | RM4-4 | BV786 | BD Biosciences |
| CD4 | Mouse | RM4-5 | BV786 | BD Biosciences |
| CD45 | Mouse | 30-F11 | BUV395 | BD Biosciences |
| CD90.1 | Mouse | OX-7 | BB700 | BD Biosciences |
| CD90.2 | Mouse | 30-H12 | BV421 | Biolegend |
| CD45.2 | Mouse | 104 | APC | Biolegend |
| CD45.1 | Mouse | A20 | BUV395 | BD Biosciences |
| Fixable Viability Stain 575V | NA | NA | NA | BD Biosciences |

CCR8 is a Marker for Tumor-Associated Tregs

Figure 2C:
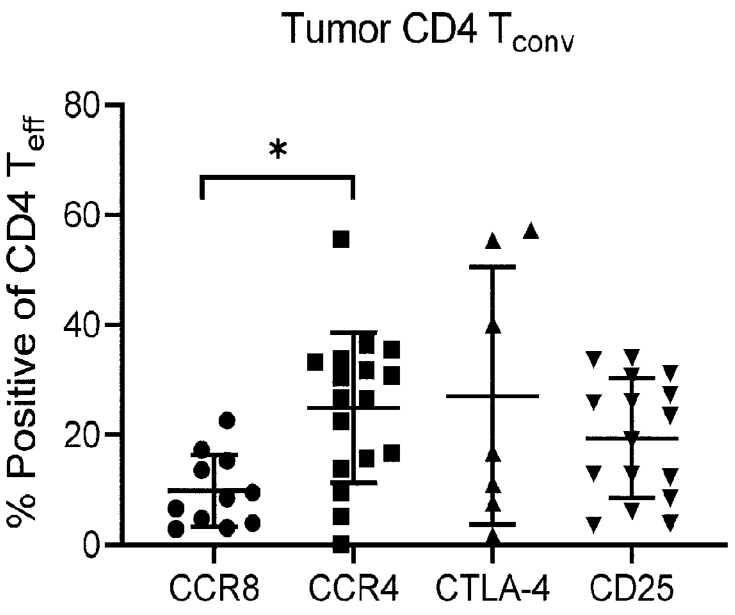
Figure 2D:
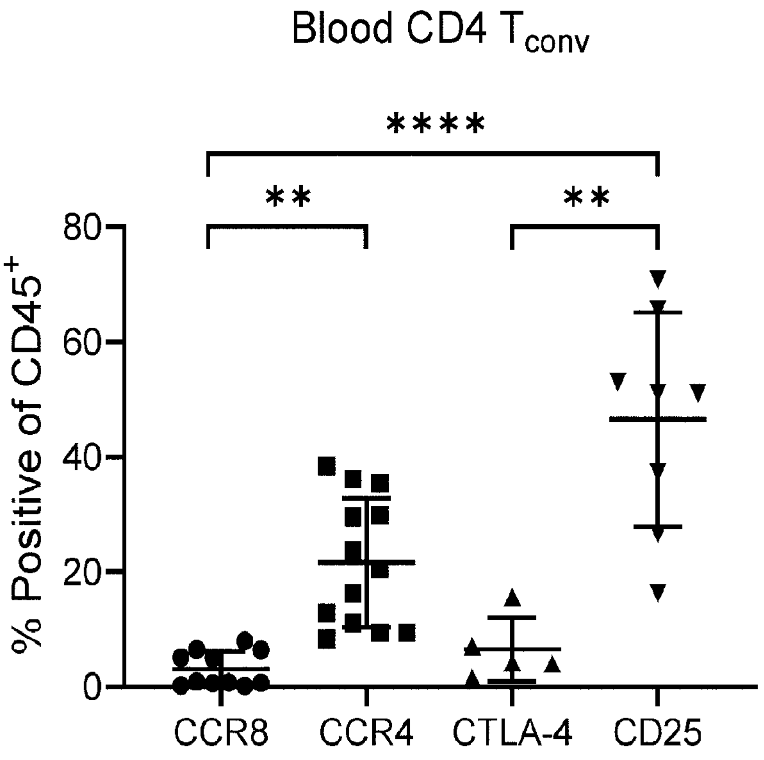
Figure 2E:
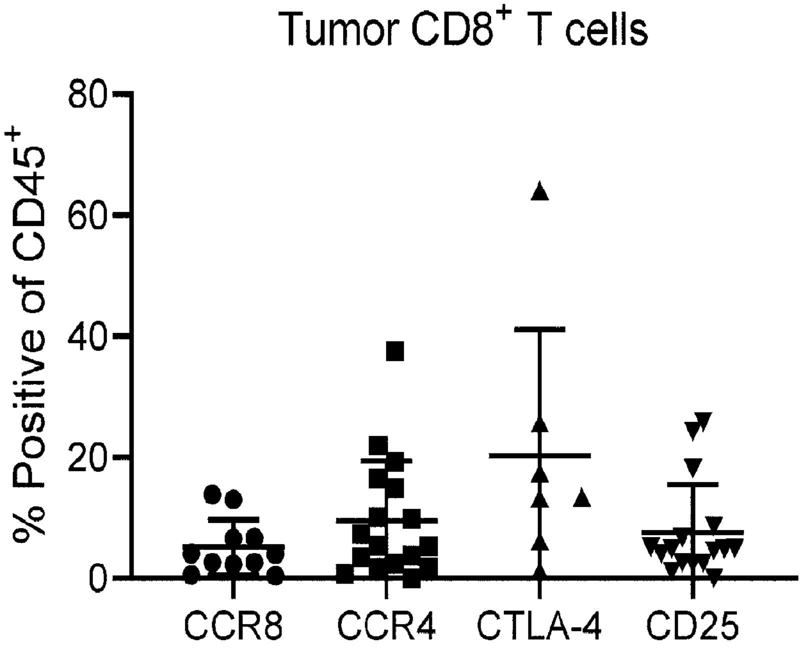
Figure 2F:
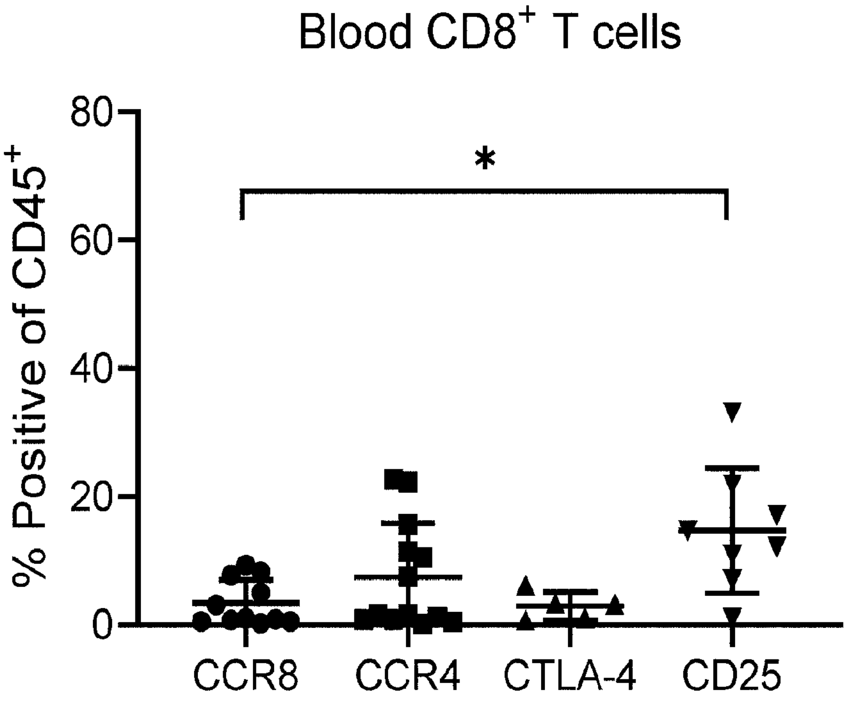

CCR8 was highly expressed on FOXP3$^+$ Tregs isolated from solid tumor surgical resections but expression was significantly lower on Tregs from patient-matched blood. In contrast, CCR4, CTLA-4, and CD25 were expressed at similar frequencies by Tregs from tumor and blood (FIG. 2A). The per-cell abundance of CCR8 on FOXP3$^+$ Tregs was higher on tumor Tregs compared to peripheral blood Tregs (FIG. 2B), whereas CCR4 expression was lower in tumor Tregs compared to peripheral blood Tregs. On CD4$^+$ FOXP3$^-$ conventional T cells (CD4$^+$ Tconv), CCR8 was less frequently expressed than CCR4 and CD25 in both tumor and peripheral blood (FIGS. 2C and D). Blood and tumor-infiltrating CD8$^+$ T cells showed marginal expression of all four molecules, with the exception of CD25 in the blood (FIGS. 2E and 2F). These data suggest that CCR8 is a highly selective marker for targeting tumor Tregs with a relatively low risk of compromising anti-tumor Teff cell populations.

Example 4

Expression of CCR8 on Different Subsets of T Lymphocytes

The level of expression of CCR8 of different subsets of T lymphocytes associated with human tumors was analyzed by flow cytometry. Excised human tumors (ampullary, colorectal (CRC), duodenal, head and neck, melanoma, NSCLC, ovarian, parotid, renal cell carcinoma (RCC), stomach, thyroid, tongue) were mechanically or enzymatically dissociated. To compare CCR8 expression levels in Tregs in the peripheral blood and tumor-infiltrating Tregs, resected tumors from CRC, RCC, melanoma, and NSCLC patients were used. After dissociation or digestion the cells were filtered and stained for viability before the labeling of surface markers, including with phycoerythrin (PE)-conjugated Abs that bind to CCR8 (anti-hCCR8 Ab Clone L263G8; BioLegend), CD3, CD4, and CD8). Upon the completion of surface staining, the cells were washed, then fixed and permeabilized for intracellular staining for FOXP3. After washing, the cell samples were processed on a flow cytometer and data analyzed using Flowjo software (FlowJo, Ashland, OR) to calculate the mean fluorescence intensity (MFI). Tregs are defined as CD3$^+$CD4$^+$FOXP3$^+$ T cells, while CD4 Tconv cells, or conventional CD4$^+$ T cells, are CD3$^+$CD4$^+$FOXP3$^-$ T cells.

As shown in FIG. 3A, CCR8 is expressed by a high proportion of tumor-resident Tregs (median 82%) as defined by FOXP3, a known Treg-associated transcription factor. In contrast, a significantly smaller fraction of conventional tumor-infiltrating CD4$^+$ T cells and CD8$^+$ T cells express CCR8 (medians 12.65% and 4.55%, respectively). Although a small proportion of CD4 Tconv cells express CCR8, the expression level of CCR8 on a per cell basis is significantly higher on Tregs than on CD4 Tconv cells (median MFI 2106 vs. 132, $P<0.0001$), while CD8$^+$ T cells express negligible levels of CCR8 (FIG. 3B). Tregs in the peripheral blood also express CCR8 but at much lower levels than seen on tumor-infiltrating Tregs (FIG. 3C). The high expression level of CCR8 specifically on Tregs makes CCR8 a suitable target for depleting the immunosuppressive cell population through ADCC using an anti-CCR8 Ab.

Example 5

Expression of CCR8 on Subpopulations of Peripheral Tregs

To investigate the level of expression of CCR8 by different subpopulations of peripheral Tregs, PBMCs were isolated using a density gradient from 5 healthy donors and stained for CCR8, CD3, CD4, CD8a, FOXP3 (intracellular), CCR8 and CD45RO. T cells were subdivided into CD4$^+$ FOXP3$^+$ T cells (Tregs), CD4$^+$FOXP3$^-$ T cells (CD4 Tconv), and CD8 T cell (CD3$^+$CD8a$^+$) subsets. These subsets were further divided into naïve (CD45RO$^-$CCR7$^+$), effector memory (EM; CD45RO$^+$CCR7$^-$), and central memory (CM, CD45RO$^+$CCR7$^+$) populations for examination of CCR8 expression. Cells were processed through a flow cytometer and analyzed using Flowjo software. PBMCs were also isolated from a subpopulation of cancer patients and stained for CCR8 expression as described in Example 4 for human tumor-infiltrating lymphocytes.

The results are shown in FIG. 4. FIG. 4A shows that CCR8 is expressed on a small fraction of peripheral blood Tregs from healthy subjects (median 21%) compared to the expression on a high percentage of tumor-infiltrating Tregs (median 82%; cf. FIG. 3A). Within the Treg population from healthy subjects, CCR8 is expressed more highly in the effector memory population (EM) and to a lesser degree in central memory cells (CM) (FIG. 4B), while very little CCR8 expression is observed on naïve Tregs (FIG. 4B) or CD4$^+$ conventional T cells (FIG. 4C). Within the CCR8$^+$ Treg population, tumor-associated CCR8$^+$ Tregs express more CCR8 on a per cell basis than peripheral $CCR8^+$ Tregs as measured by the MFI of the bound anti-CCR8 Ab (FIG. 4D).

Example 6

Expression of CCR8 on the Most Suppressive $FOXP3^{HIGH}$ Tregs

The expression of CCR8 on $FOXP3^-$ Tregs and Tregs expressing medium and high levels of expressing FOXP3 was investigated by flow cytometry. Excised human tumors from 2 melanoma and 1 RCC patients were mechanically dissociated using dissection scissors and a dounce. After dissociation, the cells were filtered and stained for viability before the labeling of surface markers with Abs that bind to CCR8, CD3, CD4, and CD8 as described in Example 4. Upon the completion of surface staining, the cells were washed, then fixed and permeabilized for intracellular staining for FOXP3. After washing, the samples were processed on a flow cytometer and data analyzed using Flowjo software. Cells were gated on the $CD3^+CD4^+$ population for analysis.

As shown in FIG. 5, CCR8 is mainly expressed by the $CD4^+FOXP3^{high}$ population, which represent the most activated Tregs. In samples where there is a clear $FOXP3^{mid}$ population as in the 2 melanoma patient tumor samples, most of the CCR8 expression is found in the $FOXP3^{high}$ T cells. The level of CCR8 expression is significantly lower in the $FOXP3^{mid}$ populations. In some instances, most of the patient $FOXP3^+$ T cells exhibit high levels FOXP3 (FIG. 5, RCC). In these cases, CCR8 expression overlaps with FOXP3 expression. $FOXP3^{high}CD4^+$ T cells have been shown to be true Tregs, in contrast to $FOXP3^{mid}$ $CD4^+$ T cells, which can be activated conventional T cells or resting Tregs.

Example 7

$CCR8^+$ Tregs Overexpress Immunosuppressive Molecules and Underexpress Proinflammatory Markers To investigate the expression of immunosuppressive and proinflammatory proteins by tumor-associated, CCR8- and CCR4-expressing T cells, resected lung tumors obtained from the clinician by overnight delivery were enzymatically digested using a kit (Miltenyi Biotec) into single-cell suspensions. Dissociated tumor cell suspensions were rested overnight in RPMI medium (Corning) containing 10% FBS. On the following day, cells were cultured for 4 h in the presence (for cell stimulation) or absence of phorbol myristate acetate (PMA) and ionomycin, with the addition of brefeldin A (BFA) and monensin (ThermoFisher, Waltham, MA) to block the transport of proteins at 37° C. After the 4 h culture, the cells were stained for surface and intracellular markers associated with Treg suppression and inflammation, and analyzed by flow cytometry.

Figure 6A:
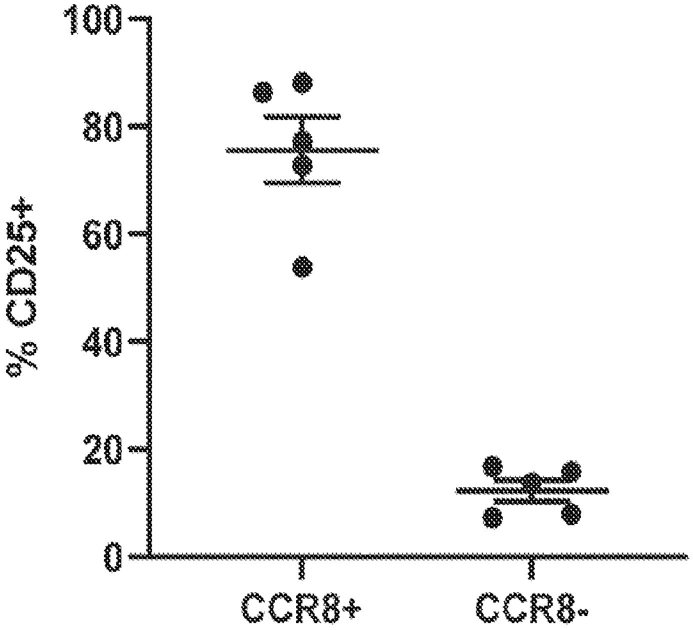
FIGS. 6A-6D show the percentages of $CCR8^{+}$ and $CCR8^{-}$ T cells that express CD25, CD39, and IL1R2. A: Percentages of $CCR8^{+}$ and $CCR8^{-}$ cells that express CD25; B: Percentages of $CCR8^{+}$ and $CCR8^{-}$ cells that express CD39; C: Percentages of $CCR8^{+}$ and $CCR8^{-}$ cells that express IL1R2; D: Percentages of stimulated $CCR8^{+}$ and $CCR8^{-}$ cells that express IL1R2.
Figure 6B:
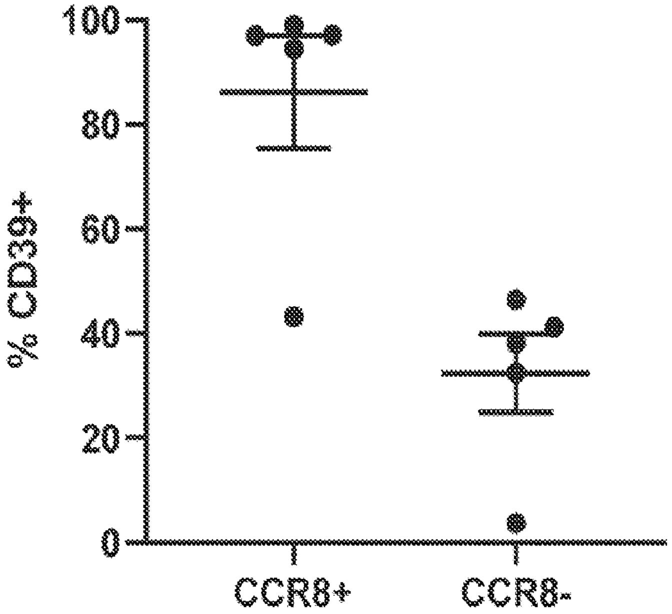
Figure 6C:
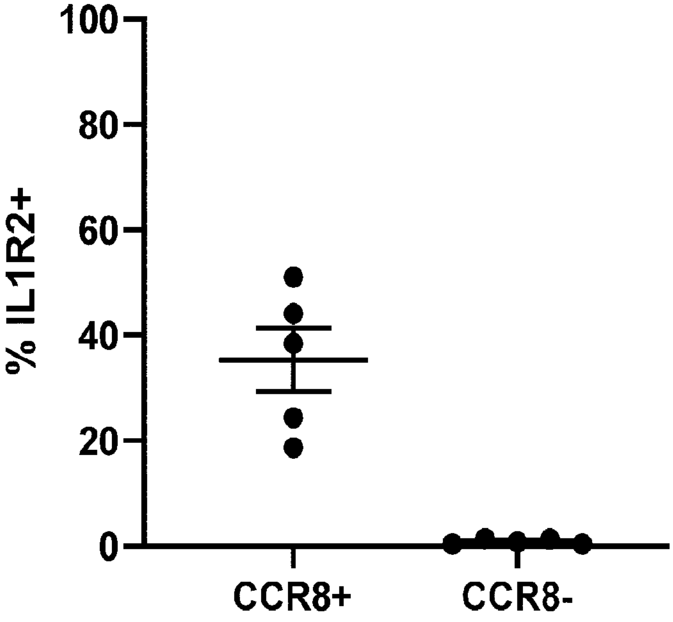
Figure 6D:
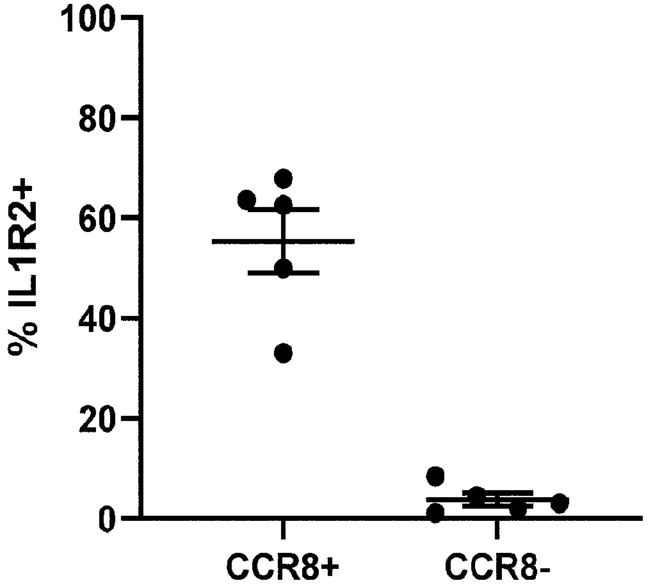
Figure 7A:
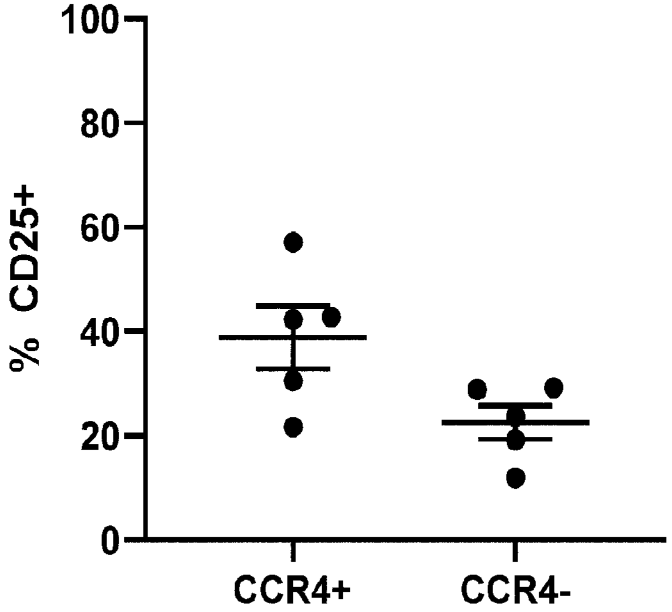
FIGS. 7A-7D show the percentages of $CCR4^{+}$ and $CCR4^{-}$ T cells that express CD25, CD39, and IL1R2. A: Percentages of $CCR4^{+}$ and $CCR4^{-}$ cells that express CD25; B: Percentages of $CCR4^{+}$ and $CCR4^{-}$ cells that express CD39; C: Percentages of $CCR4^{+}$ and $CCR4^{-}$ cells that express IL1R2; D: Percentages of stimulated $CCR4^{+}$ and $CCR4^{-}$ cells that express IL1R2.
Figure 7B:
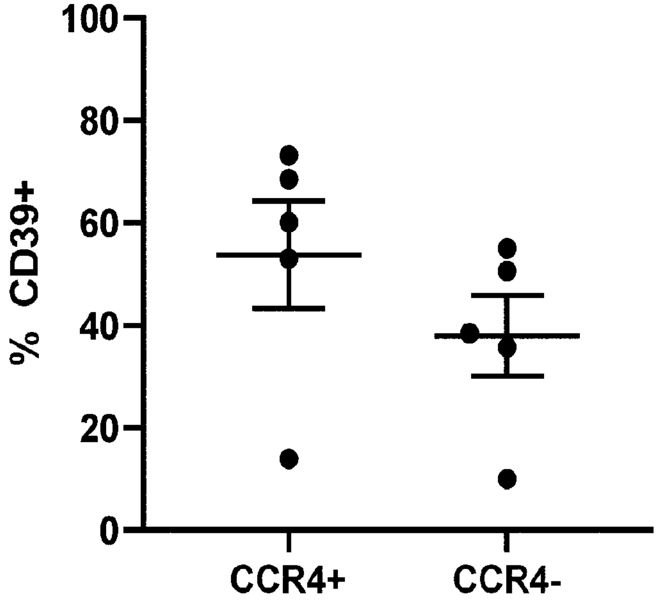
Figure 7C:
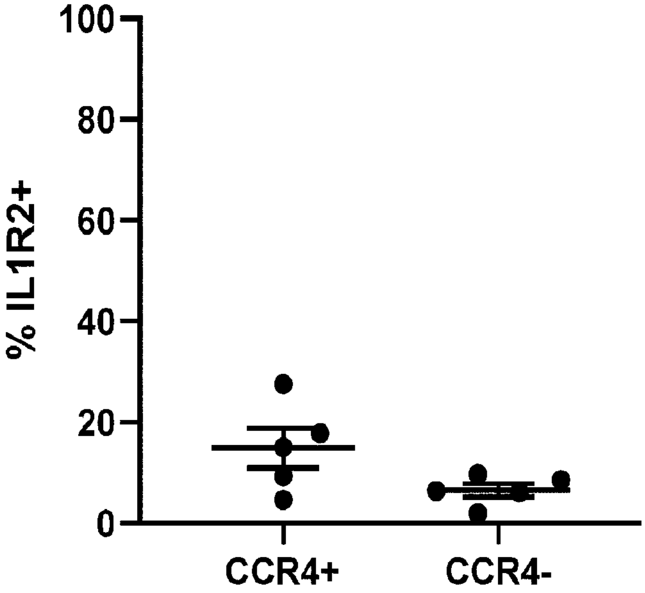
Figure 7D:
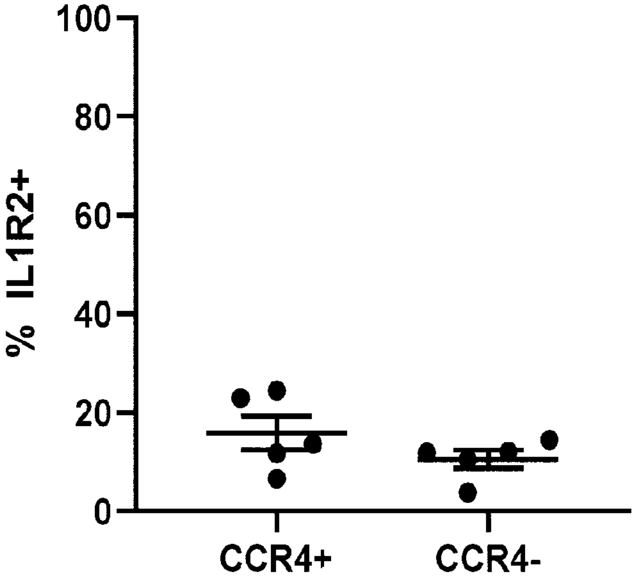

FIGS. 6A-D show that $CCR8^+$ Tregs in patient tumors are enriched for immune suppressive molecules, whereas a comparable enrichment is not seen in $CCR4^+$ T cells (FIGS. 7A-D). The majority (about 80%) of the $CD25^+$ cells are found in the $CCR8^+$ fraction whereas less than 20% of $CD25^+$ cells are found in the $CCR8^-$ fraction (FIG. 6A). Similarly, virtually all the $CD39^+$ cells are found in the $CCR8^+$ fraction whereas less than 40% of cells expressing this marker are $CCR8^-$ cells (FIG. 6B). About one third of cells expressing IL1R2 are $CCR8^+$ cells but no IL1R2-expressing cells are found in the $CCR8^-$ fraction (FIG. 6C), and the disparity between IL1R2 expression in $CCR8^+$ and $CCR8^-$ T cells is even greater when measured in stimulated T cells (FIG. 6D). Thus, in terms of immunosuppression, $CCR8^+$ T cells from patient tumor samples are enriched for several proteins with suppressive functions such as CD25, CD39, and IL1R2. CD39 is an ectonucleotidase that converts ATP to AMP and then to adenosine, which is suppressive to T cells (Cekic et al., 2011), whereas CD25 (the IL-2 receptor used by Tregs for the sequestration of IL-2) and IL1R2 (a decoy receptor for IL-1) potentially act as sinks for proinflammatory cytokines IL-2(Pandiyan et al., 2012) and IL-1D/E (Garlanda et al., 2013), respectively.

In contrast to T cells that are $CCR8^+$ or $CCR8^-$, there are smaller differentials in the levels of expression of CD25 (FIG. 7A), CD39 (FIG. 7B) and IL1R2 (FIGS. 7C and 7D) in $CCR4^+$ and $CCR4^-$ T cells. Therefore, targeted depletion of $CCR8^+$ cells would remove the immunosuppressive Tregs expressing CD25, CD39 and IL1R2 whereas CCR4-targeted depletion would leave behind Tregs expressing these molecules.

Using HLA-DR as an activation marker, CCR8 expression also correlates with a higher level of HLA-DR expression (FIG. 8A) and thus identifies activated Tregs whereas CCR4 expression does not (FIG. 8B).

Figure 10B:
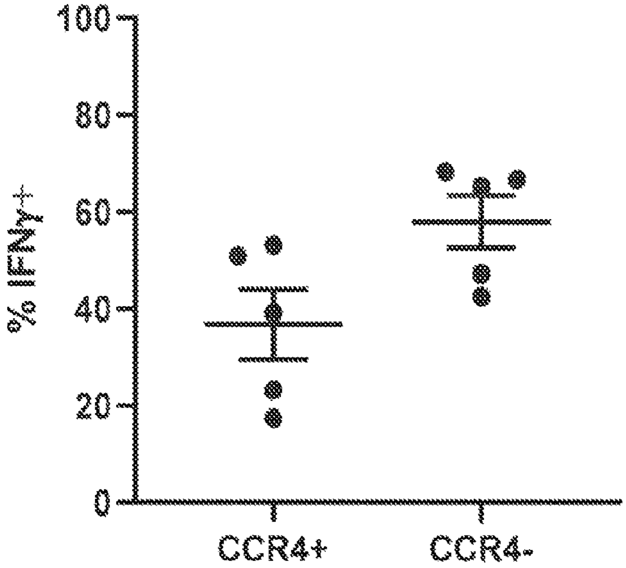
Figure 10C:
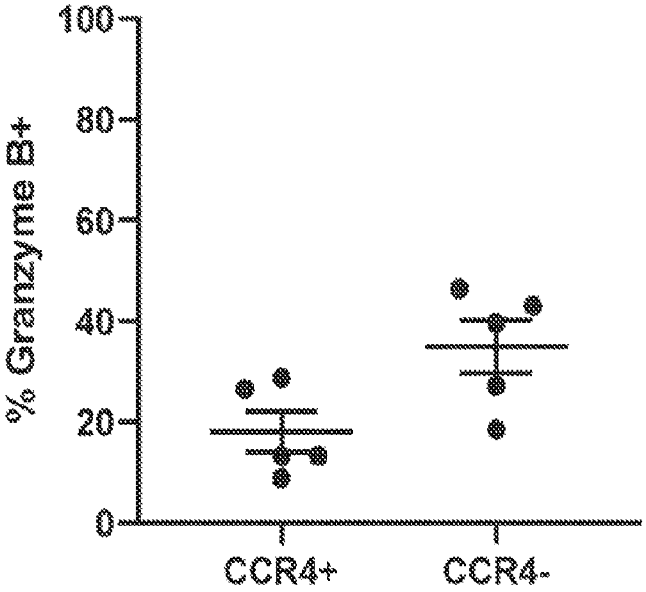

Stimulation of enzymatically dissociated patient tumor cultures ex vivo with PMA and ionomycin revealed that the $CCR8^-$ fraction of $CD4^+$ T cells contained the vast majority of IFNγ—(FIG. 9A), IL-2—(FIG. 9B), and granzyme B—(FIG. 9C) producing cells. In contrast, $CCR4^+CD4^+$ T cells were major producers of IFNγ (FIG. 10A) and IL-2 (FIG. 10B) in this assay, suggesting that targeted depletion of CCR4-expressing, but not CCR8-expressing, cells may be detrimental to anti-tumor immunity. $CCR4^+$ and $CCR4^-$ T cells produced comparable levels of granzyme B (FIG. 10C).

Example 8

Generation of MAbs Against CCR8

Anti-hCCR8 mAbs

Humanized, chimeric or human anti-CCR8 mAbs were generated by immunizing different rodents, including regular C57B1/6 mice, different strains of transgenic mice that express a human Ig repertoire, and also a specifically generated mouse strain harboring a CCR8 knockout, with a variety of human CCR8 (hCCR8) antigens. A selection of Abs generated in non-transgenic mice were subsequently converted to humanized or chimeric Abs.

Immunizations with CCR8 Antigens

To generate Abs against hCCR8, cohorts of 2-5 rodents were immunized with hCCR8 antigens, with each cohort being subjected to an immunization strategy comprising a unique combination of CCR8 antigen, dose, injection route, adjuvant, animal strain, animal age, and immunization timing. A total of 222 animals in 58 cohorts were immunized. Homozygous CCR8 knockout mice (derived from C57BL/6), 5 different strains of human Ig transgenic mice, wild-type mice (BALB/C, C57BL/6), and Armenian hamsters were immunized.

Immunizations were done with a wide variety of antigens comprising one or more of 17 antigen compositions containing full or partial hCCR8 protein sequences. Typically, mice were immunized via either footpad or base of tail up to 12 times with $2\text{-}5\times10^6$ CCR8 overexpressing cells (transfected or transduced HEK 293F, BA/F3, or CHO stable lines), plasma membrane-enriched fractions isolated from those cells via differential centrifugation, detergent-solubilized, lipid-stabilized CCR8 proteins (proteoliposome, bicelle, micelle) derived from 293 cells transiently overexpressing hCCR8, or cell lines with CCR8 transmembrane mutations for enhanced stability (Abilita Bio, San Diego, CA). Similar immunizations with cells and plasma membrane fractions were delivered via intraperitoneal and subcutaneous injections.

In many cases, 3-10 μg of a keyhole limpet hemocyanin (KLH)-conjugated, 35-residue peptide with two sulfotyrosine residues corresponding to the N-terminal sequence of hCCR8 was used as the antigen. In some instances, this N-terminal peptide was given on the 3rd, 5th, and 7th doses along with hCCR8 293F cells in a 10-immunization schedule, with the goal of enhancing and maturing the Ab response against the CCR8 N-terminus, as Ab binding to this peptide sequence was associated with efficacy in downstream assays. In other instances, this N-terminal peptide was given in combination with every cell or plasma membrane fraction immunization, or alone with no other antigens given.

In some cases, mice were immunized with CCR8-encoding DNA plasmids via tibialis anterior and quadriceps intramuscular injections, followed by the previously described cell or N-terminal peptide immunizations. Constrained peptides mimicking the second extracellular loop of CCR8, virus-like particles with CCR8, and other recombinantly engineered CCR8 materials (apolipoprotein, and cell lines with CCR8 transmembrane mutations for enhanced stability) were also used. Some cell- and plasma membrane-based antigens were hapten-labeled using picryclsulfonic acid (Sigma-Aldrich) to increase immunogenicity. In some cases, alternating hCCR8 and cynomolgus CCR8 (cCCR8) antigens were given during immunization. RIBI adjuvant (Sigma-Aldrich) containing monophosphoryl lipid A was typically delivered with immunizations, either mixed 1:1 with antigens, or delivered as an adjacent injection so as not to disrupt lipid bilayers and CCR8 protein conformation. Animals received immunizations over varying periods between 18 and 177 days.

To monitor immune responses, titrated serum from retroorbital or tail bleeds was screened by flow cytometry and ELISA as described below, typically after 4-6 weeks of immunizations. Serum was screened for Ab binding to multiple CCR8 overexpressing cell lines, corresponding negative control cell lines not overexpressing CCR8, and the sulfated N-terminal peptide of CCR8 conjugated to bovine serum albumin (BSA). CCR8-specific and CCR8 non-specific Ab responses were measured in each animal, and animals with sufficient titers of anti-CCR8 Ig were selected for final immunizations 6 and 3 days before sacrifice and tissue harvest to create hybridoma fusions. Superior CCR8-specific Ab titer was observed in CCR8 knockout mice compared to other mouse strains, and limited efforts at immunizing rats and hamsters also did not lead to any Abs. The sulfated N-terminal peptide of CCR8 conjugated to KLH carrier protein was one of the best immunogens, and worked alone or best in combination with plasma membrane fractions. Conversely, not all of the antigens worked; for example, use of apolipoprotein and membrane mutant cell lines as immunogens did not lead to any Abs.

Generation of Hybridomas Producing MAbs to CCR8

Lymphoid organs, including spleens and lymph nodes, were isolated from mice immunized as described above. Most typically, popliteal, inguinal, and iliac lymph nodes from mice immunized via footpad and base of tail with CCR8 immunogens were collected. Hybridomas were generated by fusions with immortalized mouse myeloma cells derived from the P3X63AgU.1 cell line (ATCC CRL-1597) by electric field-based electrofusion using a cell fusion electroporator (BTX, Holliston, MA). The resulting cells were plated in flat-bottom microtiter plates in Medium E (StemCell Technologies, Cambridge, MA) supplemented with aminopterin (Sigma-Aldrich, St. Louis, MO) for selection of hybridomas.

Anti-mCCR8 mAbs

The isotype of the commercially available rat IgG2b anti-mCCR8 mAb (Clone SA214G2; BioLegend) was changed to mIgG2a or mIgG1-D265A by cloning DNAs encoding the variable regions into two different pTT5 vectors (National Research Council of Canada) and expressed using the Expi293 expression system.

Example 9

Screening and Selection of Anti-Human CCR8 MAbs

Screening for MAbs that Selectively Bind to Human CCR8

In order to generate mAbs that bind to hCCR8, rodents, including human Ig transgenic mice, were immunized with a variety of hCCR8 antigens, and hybridomas were generated as described in Example 8. After 10-13 days of culture and growth media replacement, hybridoma culture supernatants were collected from individual wells and screened to identify wells with secreted CCR8-specific Abs. All supernatants were initially screened against at least two cell lines, one overexpressing hCCR8 and a corresponding control cell line not overexpressing CCR8. Ab binding on cells was measured through image-based fluorometric microvolume assay technology (FMAT) screening, high throughput 384-well flow cytometry using the Intellicyt iQue Screener (Sartorius, Albuquerque, N.Mex.), or an adherent cell-based enzyme-linked immunoassay (ELISA). Initial binding assays were sometimes performed in parallel to maximize identification of CCR8 Abs. Supernatants from approximately 157,250 culture wells in 66 hybridoma fusions were screened for hCCR8 Abs.

Hybridomas from positive wells were transferred to 24-well plates with new culture media, allowed to grow for 2-3 days, then screened again by flow cytometry to confirm Ab binding to CCR8. Briefly, 75-100 μl of hybridoma culture supernatant and CCR8-overexpressing cells (such as CHO or 293F) or control cells (such as GFP-CHO or parental 293F) were co-incubated for 30-60 min, washed, and incubated with anti-mouse IgG Fc or anti-human IgG Fc secondary Ab conjugated to AF647, APC, or PE (Jackson ImmunoResearch, West Grove, PA). After incubation and washing, fluorescence was measured by flow cytometry. Approximately 328 hybridoma clones were identified producing anti-hCCR8 Ab, i.e., these were FACS$^+$hybridoma supernatants obtained approximately 2 weeks after fusion and included low-affinity binders that showed binding in the initial screen for binding to CCR8-expressing cell lines but not to control cell lines. There was a high attrition rate in advancing Abs for a variety of reasons, e.g., clones were lost when an anti-CCR8-producng cell could not be isolated, certain clones did not perform well in CD16 crosslinking or Treg depletion assays, Ab yields in some clones were unacceptably low, and certain Abs contained sequence liabilities that could not be circumvented. Of the 328 FAC$^+$ clones, about 90 were not screened extensively, and of the remainder, about 55 advanced to the stage of being cloned into a human backbone for detailed testing. About 15% of these Abs, including mAbs 4A19, 14S15, 18Y12, 16B13, 10R3 and 8D55 were deemed to be good therapeutic candidates based on their performance in various functional assays (see, e.g., Examples 11, 14, 15, 17, 19-23, and 25-29). Accordingly, Abs described herein as Abs that mediate depletion of CCR8-expressing cells include mAbs 4A19, 14S15, 14S15h, 18Y12, 16B13, 10R3 and 8D55.

To broadly categorize the epitopes of confirmed anti-CCR8 specific Abs, culture supernatants were also screened by ELISA to measure binding to CCR8 N-terminal peptides. Briefly, BSA-conjugated peptide (2 μg/ml) representing the sulfated hCCR8 N-terminus was coated onto high-binding 96-well plates (Corning) overnight at 4° C. Plates were blocked with BSA and washed, then 100 μl of culture supernatant were added for 30-60 min on a plate shaker. After washing, an appropriate anti-Fc secondary Ab conjugated to horseradish peroxidase (HRP) was added, and the plates were developed with ABTS or HRP substrate (SurModics, Eden Prairie, MN) and absorbance measured at 405 or 650 nm on a Sunrise microplate reader (TECAN; Männedorf, Switzerland). Abs generated against hCCR8 predominantly, but not exclusively, bound by ELISA to the BSA-conjugated N-terminal peptide sequence with two sulfated tyrosine residues. Among these Abs, ELISA binding to alternate BSA-conjugated N-terminal peptides containing only one sulfated tyrosine was generally greatly reduced, and binding was generally lost when neither of the tyrosine residues were sulfated.

Anti-CCR8 Ab-secreting hybridomas were subcloned once or twice to ensure monoclonality. Briefly, approximately 700 viable hybridoma cells were plated in 5 ml of semi-solid methylcellulose medium (StemCell Technologies) with AF488-conjugated anti-human or anti-mouse IgG Ab (Jackson ImmunoResearch) used to detect hybridoma-secreted IgG. After 7 days, hybridoma colonies arising from single cells with desirable properties (distance from other colonies, IgG secretion levels, colony size, and colony circularity as measured by the ClonePix2 system (Molecular Devices, San Jose, CA) were picked to 96-well plate cultures and allowed to grow 2-4 days. Culture supernatant was screened by flow cytometry as previously described to confirm CCR8 Ab binding. Stable hybridoma subclones were cultured in vitro to generate Ab for affinity purification and further characterization. DNA sequences encoding the Ab heavy and light chains were obtained by standard sequencing techniques (Sanger sequencing and next generation sequencing). Predicted masses from Ab amino acid sequences were compared to known purified Ab masses obtained via mass spectroscopy to ensure sequencing accuracy.

Overall, in screening the Abs generated, binding to CCR8 as described above and, more importantly, CD16 crosslinking (Example 17), were the two main assays used in early screening to determine which Abs showed promise as therapeutic Abs to be characterized further. Binding titrations on Abs against hCCR8-overexpressing 293F cells (Example 11) generally distinguished the strong vs. weak binders, and weak binders typically performed poorly in functional assays, and therefore were generally not advanced to the next stage of screening. so they were not included in that next step in the funnel. Abs with good or moderate binding or activity in those assays were advanced into similar assays on primary Tregs, e.g., binding (Example 11), calcium flux (Example 15) and NK-mediated ADCC (Example 19), with the latter considered one of the most important for comparing Ab effectiveness and for selecting lead candidates. Because it was limited by primary cells, the cell line-based CD16 crosslinking assay was used as an ADCC surrogate assay, which generally correlated well with the results of Treg ADCC/depletion assays (Examples 19, 20 and 22).

In the primary Treg ADCC assays, the Y max (% Annexin V+ cells) considered at as important if not more important than the $EC_{50}$ value as certain Abs. Abs with the highest ADCC Ymax (while binding specifically) were considered superior to Abs with a comparable $EC_{50}$ but a lower Ymax.

Example 10

Humanization of Mouse Anti-CCR8 MAbs

Humanization of Mouse Anti-CCR8 MAb into 4A19 MAb

A mouse anti-hCCR8 mAb was engineered to humanize the framework to the closest human germline sequences which were hIgHV1-8*01 and hIGJ4 for the heavy chain, as well as IGKV2D-30 and hIGKJ2 for the light chain. Several potential sequence liabilities were removed. A single unpaired cysteine in the heavy chain CDR1 was mutated to serine (C35S). A potential isomerization site at an Asp-Gly sequence motif was removed by mutating the aspartate to glutamine (D52Q). Four other mutations at this site were attempted (D52E, D52S, D52V, D52A) and the best variant, D52Q, was chosen on the basis of the ability to bind with high affinity to a Raji cell line expressing CCR8. A potential glycosylation site in the framework of the heavy chain variable domain was removed by replacing an asparagine by aspartate (N72D). This mutation was chosen on the basis of aspartate occurring in the germline with a frequency of 27%. A valine in the CDR1 of the light chain was replaced by a phenylalanine (V27F) and resulted in a molecule with increased binding. The resulting mAb, 4A19, showed binding to Raji cells expressing CCR8 that was comparable to the parent 9D7 Ab (10 nM vs. 3 nM for 9D7 and 4A19, respectively).

TABLE 3

Functional Characterization Data for Representative Anti-hCCR8 MAbs

| mAb | Type of mAb | Immunogen |
|---|---|---|
| 4A19 | Nonfucosylated humanized IgG1 anti-hCCR8 | hCCR8 293F cells (+KLH hCCR8-N-Sulf peptide in 3 immunizations) |
| 14S15[a] | Nonfucosylated chimeric mouse-human[b] anti-hCCR8 | hCCR8-encoding DNA from In-Cell-Art (Nantes, France), which produced no detectable anti-CCR8 serum titer, then KLH hCCR8-N-Sulf Peptide |
| 18Y12 | Nonfucosylated chimeric mouse-human[b] anti-hCCR8 | KLH hCCR8-N-Sulf peptide |

TABLE 3-continued

| Functional Characterization Data for Representative Anti-hCCR8 MAbs | | |
|---|---|---|
| mAb | Type of mAb | Immunogen |
| 16B13 | Nonfucosylated IgG1 human | hCCR8 BAF3 plasma membranes + KLH hCCR8-N-Sulf peptide |
| 2M18 | human IgG1 anti-hCCR8 | hCCR8 BAF3 plasma membranes + KLH hCCR8-N-Sulf peptide |
| 15C17 | human IgG1 anti-hCCR8 | CCR8 293 plasma membranes + KLH/BSA N-sulf-hCCR8 Peptide |
| 13T20 | human IgG1 anti-hCCR8 | CCR8 293 plasma membranes + KLH/BSA N-sulf-hCCR8 Peptide |
| 10R3 | human IgG1 anti-hCCR8 | hCCR8 BAF3 plasma membranes + KLH hCCR8-N-Sulf Peptide |
| 8D55 | human IgG1 anti-hCCR8 | hCCR8 BAF3 plasma membranes + KLH hCCR8-N-Sulf Peptide |
| 1V11 | human IgG1 anti-hCCR8 | hCCR8 BAF3 plasma membranes + KLH hCCR8-N-Sulf Peptide |
| 11K16 | human IgG1 anti-hCCR8 | hCCR8 BAF3 plasma membranes + KLH hCCR8-N-Sulf Peptide |
| 12F27 | Nonfucosylated chimeric[c] (mFc/hFab) | hCCR8 293 plasma membranes + KLH hCCR8-N-Sulf Peptide |

[a]The mAb designated 14S15 herein refers to a chimeric derivative of a mouse anti-hCCR8 mAb in which the mouse Fc region was replaced by a nf IgG1 human Fc. A humanized, affinity matured, and sequence liability-fixed version of this mAb was generated as described below in this Example and is designated 14S15h.

[b]These mAbs are chimeric Abs comprising a mouse Fab grafted onto a human Fc.

[c]This mAb is a chimeric Ab in the opposite sense, in that it was generated in a transgenic mouse to comprise a mouse Fc and a fully human Fab. These mice were so designed to produce Abs comprising a mouse Fc to help with affinity maturation.

A representative number of anti-CCR8 mAbs generated are listed in Table 3, which indicates the type of mAb and the immunogen used to generate them. Human anti-hCCR8 Abs were produced recombinantly as hIgG1 isotypes using the Expi293 expression system (Thermo Fisher Scientific). Nf (hIgG1-nf) Abs were expressed in Expi293 $Fut8^{-/-}$ cells.

Several of the Abs in Table 3, namely mAbs 2M18, 15C17, 13T20, 1V11, 11K16 and 12F27 are Abs that performed poorly in screening assays, e.g., CD16 crosslinking and Treg ADCC assays (comparatively high $E_{50}$ values and comparatively low Ymax values) and were therefore deemed to be unpromising therapeutic candidates. However, they are included in Table 3 to emphasize the fact that the vast majority of CCR8-binding Abs generated, were not considered to be strong therapeutic candidates.

Humanization of Mouse Anti-CCR8 MAb into 14S15h MAb

Another mouse anti-CCR8 mAb was engineered to humanize the framework to the closest human germline sequences, which were hIgHV3-15 for the heavy chain and IGKV2-18 for the light chain. Humanization of the framework led to a decrease in binding of the human Fab as measured by SPR ($K_D$ of 4.2 nM compared to 1.4 nM for the starting mouse Ab, 9G10). Affinity maturation of the heavy chain variable domain was performed using 3 different NNK libraries and 4 cycles of panning with 200 nM, 50 nM, 10 nM and 1 nM biotinylated CCR8 N-terminal peptide from Anaspec (Freemont, CA) and increasing wash stringencies. A single substitution of N30G in the heavy chain CDR1 region, resulted in affinity maturation. Furthermore, a potential deamidation site at an Asn-Gly sequence motif was removed by mutating the asn to gln (N28Q, Kabat numbering). The resulting humanized, affinity-matured antibody and sequence liability-removed 14S15h had a fully restored and even increased affinity for the CCR8 N-terminal peptide ($K_D$ of 0.64 nM for 14S15h Fab fragment). Assays described herein involving the 14S15 mAb is the chimeric version of this mAb as indicated in Table 3.

Example 11

Anti-CCR8 mAbs that Bind with High Affinity to hCCR8-Expressing Cells $E_{50}$ Values for Binding of Anti-hCCR8 MAbs to Tregs Anti-hCCR8 mAbs were incubated with activated human Tregs or human CCR8-expressing cell lines (293F, CHO, Raji). Activated Tregs prepared from previously isolated and expanded Tregs were stimulated for 2 days with anti-CD3/CD28 activation beads (ThermoFisher) in the presence of 100 units/ml of recombinant human IL-2. The Abs were serially diluted from a starting concentration of 30 µg/ml. An appropriate PE-conjugated secondary Ab (Jackson ImmunoResearch) against the primary anti-CCR8 Ab was applied, incubated for 15 min at 4° C., and then washed off. Samples were processed on a flow cytometer and data was analyzed using Flowjo and shown in FIG. 11. $EC_{50}$ values for the binding of selected anti-CCR8 mAbs to activated Tregs, was calculated using GraphPad Prism (GraphPad Software, La Jolla, CA).

Figure 11B:
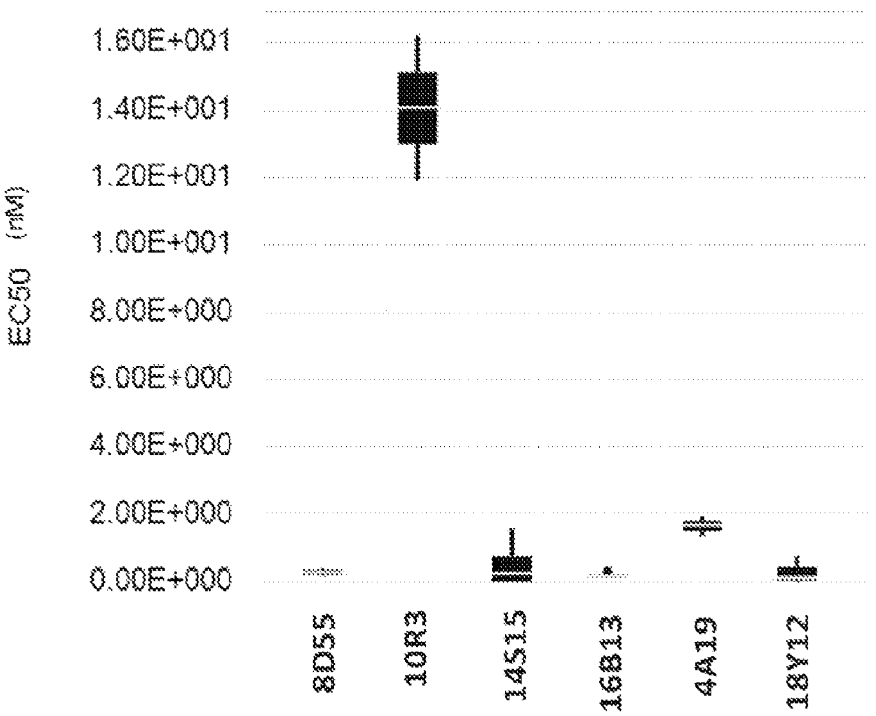

As shown in FIG. 11, a representative sample of the anti-CCR8 mAbs generated exhibit binding to various hCCR8-transfected cell lines and activated Tregs with a range of affinities. Abs were generally initially screened based on their binding affinities to CCR8-expressing cells lines (CHO, 293F, Raji), and it was found that most of the Abs screened exhibited half-maximal effective concentrations ($EC_{50}$) of under 1 nM (FIG. 11A). However, when these pre-screened Abs were tested for binding to activated Tregs, a wider range of binding affinities was observed, with fewer than half of the Abs exhibiting binding with $EC_{50}$'s below 1 nM (FIG. 11A). A select subset of Abs having $EC_{50}$ values ranging from picomolar to nanomolar is presented in FIG. 11B, and the respective $EC_{50}$ values are provided in Table 4.

TABLE 4

| Affinity ($EC_{50}$) of anti-CCR8 mAbs binding to activated Tregs | |
|---|---|
| Anti-CCR8 MAb | Median $EC_{50}$ (nM) |
| 8D55 | 0.284 |
| 10R3 | 14.1 |
| 14S15 | 0.252 |
| 16B13 | 0.149 |
| 4A19 | 1.65 |
| 18Y12 | 0.120 |

Since anti-hCCR8 mAbs including 18D55, 10R3, 14S15, 16B13, 4A19 and 18Y12 have been shown to have a high potential for eliciting ADCC (Example 17), or directly eliciting the efficient depletion (Examples 19, 20 and 22), of tumor-infiltrating Tregs it is clear that Abs which bind to CCR8 on activated Tregs with an affinity ($EC_{50}$) in the nM range (e.g., about 20 nM or lower, but the limit may be higher, e.g., in excess of 100 nM) can efficiently mediate Treg depletion. However, to be useful as a therapeutic that specifically targets tumor-infiltrating Tregs, the binding to CCR8 must be highly specific (cf. mAb 16B13 which binds with high affinity to CCR8 but also strongly binds to a target that is not CCR8 (Example 14)).

$K_D$ Values for Binding of Anti-CCR8 MAb, 4A19, to the CCR8 N-Terminus Peptide

The dissociation constant ($K_D$) for the binding of mAb 4A19 to an N-terminal peptide of human CCR8 was measured by surface plasmon resonance (SPR). SPR measurements were conducted on a Biacore T200 at 37° C. in HBST buffer (10 mM HEPES (pH 7.4), 150 mM NaCl, 0.05% with 1 g/l BSA). A CM4 chip with immobilized anti-human kappa capture pAb (Southern Biotech, Birmingham, AL), EDA (ethylene diamine)-blocked. CCR8 Abs (both Fabs and mAbs) were captured, and CCR8 N10 terminal peptides (200 nM, 40 nM, 8 nM or 1.6 nM) were injected as analytes for 2 min with a flow rate of 100 µl/min. All data were double-referenced and fitted to a 1:1 Langmuir binding model with mass transfer using Biacore T200 Evaluation Software 3.1. Peptides of CCR8 residues 1-35 were either non-sulfated (CCR8-nosulfo), sulfated at Tyr15 (CCR8-sulfoY15), at Tyr17 only (CCR8-sulfoY17), or at both positions Tyr15 and Tyr17 (CCR8-2sulfo), were produced by Anaspec (Fremont, CA).

TABLE 5

| Affinity ($K_D$) of anti-CCR8 mAb, 4A19, Fab fragment binding to CCR8 N-Terminus | | | | |
|---|---|---|---|---|
| MAb | Ligand | $k_a$ (1/Ms) | $K_d$ (1/s) | $K_D$ (M) |
| 4A19 | CCR8-2sulfo | $2.5 \times 10^7$ | $4.1 \times 10^{-2}$ | $1.6 \times 10^{-9}$ |
| 4A19 | CCR8-sulfoY17 | $4.3 \times 10^6$ | $8.4 \times 10^{-2}$ | $2.0 \times 10^{-8}$ |
| 4A19 | CCR8-sulfoY15 | Rough estimate: | | $\sim 1.3 \times 10^{-6}$ |
| 4A19 | CCR8-nosulfo | | No binding | |

The results summarized in Table 5 show that the 4A19 Fab fragment binds to the CCR8 N-terminus with a $K_D$ of 1.6 nM. Sulfoylated tyrosine is required for binding as the non-sulfoylated peptide does not show any binding to the 4A19 Fab fragment. The absence of the sulfoylation on Y15 leads (CCR8-sulfoY17) to an approximately 10-fold decrease in affinity compared to the doubly sulfoylated peptide, while the absence of sulfoylation on Y17 (CCR8-sulfoY15) leads to a decrease in 4A19 binding of approximately 1,000-fold (Table 5).

Example 12

Crystal Structure of 4A19 Bound to CCR8 N-Terminal Peptide

Binding of 4A19 Fab to Singly Sulfated Peptide

The Fab region (domains VH and CH1) of the 4A19 heavy chain was fused to a 8His tag and cloned into a pTT5 vector. A 4A19 Fab fragment comprising this modified 4A19 heavy chain and the 4A19 light chain was expressed in HEK cells. The supernatant was purified over a nickel affinity column, and the eluate was buffer-exchanged into phosphate-buffered saline (PBS) and sized over a size exclusion column (GE Superdex-200) with running buffer containing 10 mM Tris pH 7.4, 150 mM NaCl. The appropriate main peak was pooled and concentrated to 7-10 mg/ml. Residues 1-35 of human CCR8 with only Y17 sulfated was chemically synthesized by Bio-Synthesis (Lewisville, Tx.). Lyophilized peptide was dissolved in 10 mM Tris pH 7.4, 150 mM NaCl, and mixed in a 5:1 molar ratio with the 4A19 Fab fragment. Crystallization was carried out by mixing the protein solution with equal parts of 25% PEG3350 and cryoprotected using Al's oil. Crystals were diffracted to a resolution of 2.03 Å in space group C2. Collected data were indexed using XDS, scaled and truncated using ccp4i, and refined using refmac5.

FIG. 12A shows the crystal structure of the 4A19 Fab fragment (displayed in surface representation) bound to the CCR8 N-terminal peptide (shown in stick representation) at 2.03 Å resolution, revealing that the epitope bound by 4A19 comprises residues 15-21 of CCR8 with the sulfated tyrosine-17 at its center.

Binding of 4A19 Fab to Doubly Sulfated Peptide

The 4A19 Fab fragment was produced as described in the previous section. A peptide consisting of residues 1-35 of hCCR8 with both Y15 and Y17 sulfated was chemically synthesized by Anaspec. The Fab fragment was buffer exchanged into 50 mM NaCl, 10 mM Tris pH 8.0, and the doubly sulfated peptide was added to the Fab fragment at a 2-fold molar excess. Crystals were grown by sitting-drop vapor diffusion at 20° C. by mixing 200 nl of concentrated protein sample at 12.8 mg/ml with 200 nl of mother liquor (0.2 M ammonium acetate, 20% PEG 3350, pH 7.2). Crystals appeared within 7 days and x-ray diffraction data were collected to 1.80 Å resolution at beamline 17-ID (IMCA-CAT) at the Advanced Photon Source. Data were processed in space group P21 using XDS and the structure was determined by molecular replacement with Phaser and refined with Phenix.

FIG. 12B shows the crystal structure of the 4A19 Fab fragment (displayed in surface representation) bound to the CCR8 N-terminal peptide (shown in stick representation). The 4A19 Ab recognizes both tyr sulfate residues at positions Y15 and Y17. Molecular interactions for the CCR8 epitope were calculated using PISA software. The CCR8 residues V12, D14, Y(S03)15, Y16, Y(SO3)17, P18, I20, F21, and S22 show change in accessible surface area >3 Å2 when in complex with the 4A19 Fab fragment.

Example 13

Binding of Anti-mCCR8 MAb to mCCR8-Expressing Cells

Binding of Anti-CCR8-mIgG2a M4 b to mCCR8-Expressing CHO Cells

Anti-CCR8-mIgG2a (the mouse IgG2a isotype of a commercial rat anti-mCCR8 mAb [BioLegend Clone SA214G2], which is used herein as a surrogate for ADCC-eliciting anti-hCCR8 therapeutic Abs disclosed herein) was serially diluted from a starting concentration of 30 μg/ml and incubated with $5\times10^5$ mCCR8-expressing CHO cells. After incubation, the cells were washed and then stained with an anti-mouse IgG, PE-conjugated secondary Ab (Jackson ImmunoResearch) on ice for 30 min. Cells were washed and analyzed on a flow cytometer. The mean fluorescence intensity was calculated using Flowjo. The $EC_{50}$, calculated using GraphPad Prism, was determined to be 6.44 nM. This is significantly higher than the $EC_{50}$'s of many of the anti-hCCR8 Abs analyzed above which are about 0.05 nM, for binding to hCCR8-expressing CHO cells.

Binding of Anti-CCR8 MAb to Mouse Thymocytes and Primary Activated Mouse Splenic Tregs The binding of anti-CCR8-mIgG2a to mouse thymocytes and primary activated Tregs from mouse splenocytes was assayed by flow cytometry. Thymic T cells express CCR8 constitutively whereas CCR8 expression is induced on splenic Tregs. To induce CCR8 expression on mouse splenocytes, $CD4^+$ T cells were isolated and activated with anti-CD3/CD28 beads at a ratio of 3:1 and 2,000 U/ml of recombinant mouse recombinant IL-2 (rIL-2). Thymic $CD4^+$ T cells, isolated the same day, or $CD4^+$ splenic T cells, activated for 48 h, were mixed with titrations of anti-CCR8-mIgG2a or anti-KLH-mIgG2a control Ab. Binding of Abs to cell surface CCR8 was detected by fluorescently labeled anti-mouse IgG Ab. Relative cell binding was measured as frequency of total CD4 cells positive for fluorescently conjugated secondary Ab.

The anti-mCCR8 Ab was shown to bind to CCR8 on the surface of thymic $CD4^+$ cells ($EC_{50}$=4 nM) and activated mouse splenic $CD4^+$ cells ($EC_{50}$=6.16 nM).

Example 14

Tissue Cross-Reactivity of Different Anti-hCCR8 MAbs

Anti-hCCR8 mAbs, 18Y12, 16B13 and 4A19 were tested at 1 and 3 μg/ml for binding to CCR8-expressing cell lines, PBMCs, and diverse tissue types (n=1-2/each).

CCR8 Transfectants

All 3 Abs bound strongly to hCCR8-transfected CHO and 293F cell lines (data not shown). These transfected cell lines were used as positive controls in subsequent tissue staining experiments.

Normal Human PBMCs

Figure 13A:
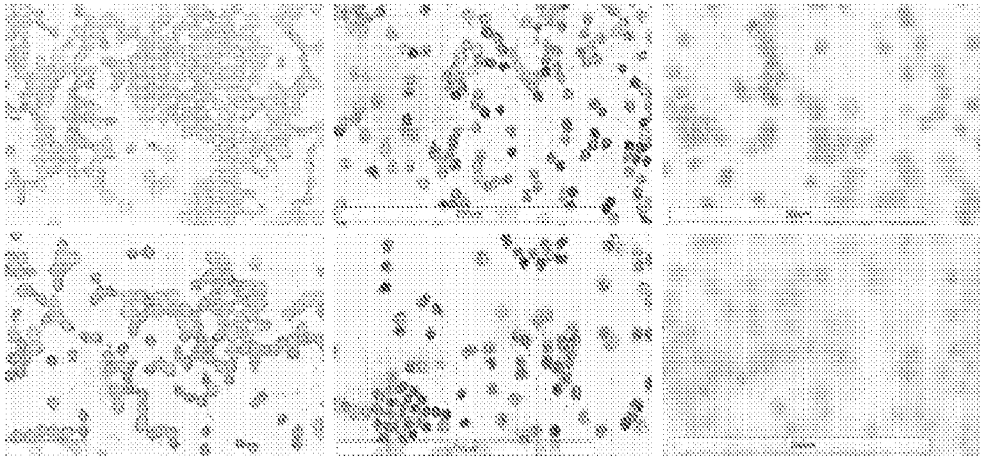
FIGS. 13A and 13B show tissue cross-reactivity of different anti-hCCR8 mAbs applied at 1 μg/ml (top panel) and 3 μg/ml (top panel) to normal human PBMCs and normal human thymus, respectively. A: Binding of mAbs 18Y12 (left panels), 16B13 (middle panels) and 4A19 (right panels) to PBMCs. MAbs 18Y12 and 4A19 do not bind to the PBMCs whereas 16B13 shows high-level binding to a target which in unlikely to be CCR8. B: Binding of mAbs 18Y12 (left panels), 16B13 (middle panels) and 4A19 (right panels)

As shown in FIG. 13A, mAbs 18Y12 and 4A19 did not bind to PBMCs. However, 16B13 showed strong binding to a target which was not CCR8. Although 16B13 shows attractive properties, e.g., in binding to activated Tregs with high affinity (Example 11), efficiently inhibiting calcium flux by CCR8-expressing cells (Example 15), and exhibiting high ADCC potential or activity (Examples 17 and 19), the non-specific binding to PBMCs observed with this mAb indicates its use in therapy would present problems with off-target depletion of cells, other than tumor-infiltrating Tregs, that do not express CCR8.

Diverse Human Tissue Types

MAbs 18Y12 and 4A19 was tested against a panel of 18 normal human tissue types including cerebrum, cerebellum, heart, liver, lung, kidney, tonsil, spleen, thymus, colon, stomach, pancreas, adrenal, pituitary, skin, peripheral nerve, testis, uterus, and PBMC smear (n=1-2/each) with hCCR8-expressing CHO and 293F cells were used as positive controls.

Figure 13B:
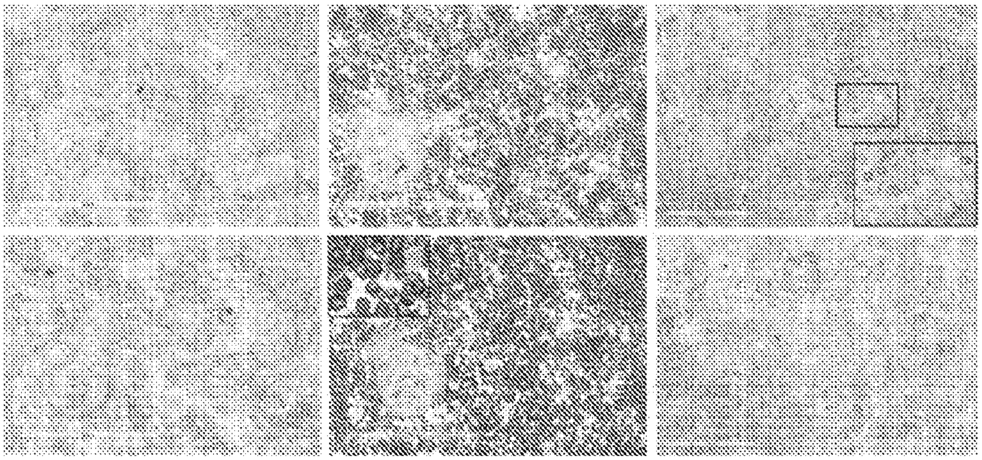

Positive staining was observed in rare and scattered immune cells primarily in the medulla of the thymus (FIG. 13B; 18Y12-left panels and 4A19-right panels) and dermis of the skin (data not shown), whereas no positive staining was observed in other tissues examined (data not shown). A similar expression profile was observed in mouse tumor models (data not shown).

MAb 16B13 was tested against a panel of 21 normal human tissue types including cerebrum, cerebellum, heart, liver, lung, kidney, tonsil, spleen, thymus, colon, stomach, pancreas, adrenal, thyroid, pituitary, skin, peripheral nerve, prostate, testis, uterus, and PBMC smear (n=1-2/each) with hCCR8-transfected CHO cells used as positive control.

The most profound staining was observed in immune cells primarily in lymphoid organs (thymus [FIG. 13B; middle panels], tonsil, spleen) and lymphoid-rich tissues (colon and small intestine; data not shown). The staining was strong and diffuse in the vast majority of immune cells, particularly in lymphocyte-rich regions (e.g., much stronger staining in the white pulp than red pulp in the spleen), with predominate cytoplasmic and/or peri-nuclear patterns. This staining was observed in many tissues where immune cells were present, including Kuepfer cells in the liver, alveolar macrophages in the lung, and mesangial-like cells in the glomeruli of the kidney.

In PBMC smears, no or minimum staining was observed in non-fixed (but air-dried) smears, while peri-nuclear and cytoplasmic staining was seen in acetone-fixed (i.e. permeabilized) slides, which further support the observation that the positive labeling is intracellular.

Strong and diffuse staining (primarily at the higher 3 μg/ml concentration) was also observed in smooth muscle cells in the muscularis in the guts (small intestine, colon, stomach), arrector pilli muscle in the skin, and the stroma of the prostate, as well as vasculatures in most tissues. The staining exhibited a cytoplasmic pattern.

Strong and diffuse peri-nuclear and/or cytoplasmic staining was revealed in neurons and glial cells in the cerebrum and cerebellum, as well as subset of cells in the neurohypophysis and spindle interstitial cells in the peripheral nerves.

Strong and diffuse cytoplasmic staining was also observed in subset of epithelial cells, including mesothelium in the heart, subset of distal or collecting tubule epithelium in the kidney, endocrine cells in the pituitary, airway epithelia in the lung, ductal epithelium in the pancreas, basal layer of seminiferous tubule epithelium in the testis, and gland epithelium in the endometrium of the uterus. The staining tended to be more profound at high concentration (3 μg/ml) in most cases.

Example 15

Anti-hCCR8 MAbs Block Binding of hCCL1 to hCCR8-Expressing Cells

Blockade of hCCL1 binding to hCCR8 by anti-hCCR8 mAbs was tested by conducting calcium (Ca) flux assays on hCCR8-expressing CHO cells (hCCR8-CHOs) since CCL1 engagement of CCR8 on CHO cells induces calcium flux. hCCR8-CHOs were seeded and incubated for 2 h at 37° C. in the presence of FLIPR Calcium 6 dye (Molecular Devices) and probenecid (Thermo Fisher Scientific). After incubation, different anti-CCR8 mAbs were added to the cells and left at room temperature for 15 min before the addition of 10 nM of recombinant human CCL1 (R&D Systems, Minneapolis, MN). The Ca flux fluorescent signal was measured by Max-Min using a FLIPR Tetra system (Molecular Devices). The half-maximal inhibitory concentration ($IC_{50}$) was calculated using GraphPad Prism.

TABLE 6

Blockade of calcium flux on CCR8-expressing cells by anti-CCR8 mAbs

| Anti-CCR8 MAb | $IC_{50}$ (nM) |
|---|---|
| 4A19 | 0.4645 |
| 16B13 | 0.2600 |
| 18Y12 | 0.2314 |
| 14S15 | 1.331 |
| KLH-g1fnf | N/A |
| Rituximab (anti-CD20) | N/A |

The capacity to block CCL1 binding to CCR8 can have an anti-suppressive effect on Tregs, and this function was used as a selection criterion in selecting anti-CCR8 therapeutic Ab candidates. About 52% (50 out of 96) anti-hCCR8 mAbs tested blocked CCL1 binding on hCCR8-CHO cells (FIG. 14A). A selected subset of these Abs blocked CCL1-induced Ca flux of CCR8-CHO cells from 51%-94% (FIG. 14B). $IC_{50}$ curves for the blockade of Ca flux on hCCR8-CHOs are shown for 4 select anti-CCR8 mAbs in FIG. 14C ($IC_{50}$ range 0.23 nM to 1.331 nM), and the $IC_{50}$ values for these mAbs are shown in Table 6.

Example 16

Anti-mCCR8 MAbs Block Binding of mCCL1 to mCCR8-Expressing Cells

Blockade of mCCL1 binding to mCCR8 by anti-CCR8-mIgG2a was tested by conducting Ca flux assays on mCCR8-expressing CHO cells (mCCR8-CHOs) as described in Example 15 except that mCCR8-CHOs were used instead of hCCR8-CHOs. The $IC_{50}$, calculated using GraphPad Prism, was determined to be 19.34 nM.

In order for anti-CCR8-mIgG2a serve as an appropriate mouse surrogate Ab for testing the therapeutic efficacy of anti-CCR8 Abs designed for human use, it is important that this mouse Ab exhibit similar functional characteristics to its hCCR8 Ab counterparts. Similar to anti-hCCR8 mAbs inhibiting hCCL1-induced Ca flux (FIG. 14, Table 6), anti-CCR8-mIgG2a was found to inhibit mCCL1-induced Ca flux in mCCR8-CHO cells, though less efficiently with an $IC_{50}$ value of 19.34 nM compared to $IC_{50}$ values of about 0.2 nM to 1.3 nM observed for the anti-hCCR8 Abs tested in Example 15.

Example 17

ADCC Potential of Anti-hCCR8 MAbs Measured by Capacity for CD16 Cross-Liunking The ADCC potential of anti-hCCR8 mAbs was measured by the capacity of these Abs to mediate crosslinking of CD16 expression reporter cells. Activated human Tregs or hCCR8-expressing Raji cells were co-cultured in a 1:5 ratio with CD16-expressing Jurkat NFAT luciferase reporter cells at 37° C. for 4 h in the presence of an anti-CCR8 Ab or a control Ab. BIO-GLO™ (Promega, Madison, WI) was added to the cells and incubated for 5 min at room temperate, and then the luminesce was read for measurement of luciferase activity. The half-maximal effective concentration ($EC_{50}$) was calculated using GraphPad Prism.

NK cells mediate ADCC through the engagement, or cross-linking, of Fc-γ receptor 3A (CD16). The capacity of anti-hCCR8 mAbs to mediate ADCC of target cells (hCCR8-expressing Raji cells or activated human Tregs) was measured by a CD16-expressing cell line as described above. Sixteen percent of anti-hCCR8 mAbs tested with the human IgG1 (hIgG1) backbone exhibited 80-100% of maximal CD16 engagement with CCR8-expressing Raji cells as targets (FIG. 15A). Selected mAbs were modified to the of hIgG1 format (hIgG1-nf) and screened in the same manner.

TABLE 7

Cross-linking of CD16 expression reporter cells by anti-CCR8 mAbs

| Anti-CCR8 MAb | $EC_{50}$ (pM) |
|---|---|
| 8D55 | 6.58 |
| 10R3 | 3.02 |
| 14S15 | 8.02 |
| 16B13 | 0.67 |
| 4A19 | 0.69 |
| 18Y12 | 0.698 |

A majority of these anti-CCR8 hIgG1-nf mAbs achieved 80-100% CD16 cross-linking (FIG. 15A). Twenty-seven percent of anti-CCR8 hIgG1-nf mAbs tested achieved maximal CD16 engagement with activated human Tregs as target cells (FIG. 15A). $EC_{50}$ values for the CD16 cross-linking capacities of a select set of anti-hCCR8 hIgG1-nf mAbs tested are shown in FIG. 15B and Table 7.

Example 18

ADCC Potential of Anti-mCCR8 MAbs Measured by Capacity for Cross-Linking of Mouse FcgIV4$^+$ Reporter Cells The capacity of anti-CCR8-mIgG2a to induce ADCC-mediated killing of CCR8-expressing cells was indirectly evaluated by measuring its ability to induce crosslinking of mouse FcgRIV$^+$ reporter cells (Promega). In this assay, FcgRIV$^+$ effector cells expressing firefly luciferase were co-cultured with primary activated Tregs from mouse splenocytes or mCCR8-expressing CHO cells at a 1:5 ratio. Cells were co-cultured at 37° C. for 4 h in the presence of a titration of anti-CCR8-mIgG2a, anti-CCR8-mIgG1-D265A having an inert backbone, or anti-KLH-mIgG2a control Abs. Target cell killing activity was measured as crosslinking and activation of FcgRIV$^+$ effector cells that shows an increase in bioluminescent signal (RLU) produced upon incubation of cells with the BIO-GLO™ (Promega) luciferin substrate.

Specific crosslinking of effector cells was observed ($EC_{50}$=6.34 nm), manifested by a high luciferase signal, at higher concentrations of anti-CCR8-mIgG2a. This showed that the Ab bound to target cells and engaged the FcgRIV in effector cells. The specificity of this interaction was assessed by using a non-target specific Ab (anti-KLH-mIgG2a) and a non-FcγRIV-engaging Ab (anti-CCR8-mIgG1-D265A), neither of which showed any luciferase signaling.

Example 19

Anti-CCR8 MAbs Promote NK Cel-Mediated Cytotoxicity of Tregs

Nonfucosylated anti-hCCR8 mAbs, which exhibit enhanced effector function, were tested for their ability to promote NK cell-mediated apoptosis of activated Treg cells, prepared as described in Example 2. Allogenic NK cells for use as effectors were isolated using Ficoll gradient separation of PBMCs from whole blood followed by magnetic bead negative selection (Miltenyi Biotec, Sunnyvale, CA) to remove non-NK cells. NK cells were isolated from fresh healthy donor PBMCs (Human NK Cell Isolation Kit, Miltenyi Biotec) and cultured for 24 h in Myelocult H5100 medium (StemCell Technologies) with 1 μM hydrocortisone (StemCell Technologies) and 500 U/ml of recombinant human IL-2 (PeproTech, Cranbury, NJ) to increase NK cell activation.

NK cells were fluorescently labeled with CellTrace Violet (Thermo Fisher Scientific) and combined with Treg cells at a ratio of 5:1 in RPMI medium with 10% ultra-low IgG FBS and 1 mM sodium pyruvate. Titrations of anti-hCCR8 Abs and isotype control Ab were added and incubated with the cells for 3 h at 37° C. Cells were stained with Annexin-V FITC-conjugated Ab and 7-AAD in buffer containing $Ca^{2+}$, and cell fluorescence was measured by flow cytometry using a BD Fortessa X-20 cytometer (BD Biosciences, San Jose, CA). The percentage of apoptotic Tregs among total Tregs (Annexin-V positive, CellTrace Violet negative) was determined through standard flow cytometry analysis.

ADCC of activated human Tregs by allogeneic NK cells in the presence of anti-hCCR8-hIgG1-nf mAbs was used to assess the capacity of anti-CCR8 Abs to mediate depletion of tumor-infiltrating Tregs. After screening of a larger pool of anti-hCCR8 Abs through CCR8 binding (Example 9), CCL1 blocking (Example 15) and CD16-crosslinking assays (Example 17), a subset of Abs were evaluated for their ability to mediate ADCC of activated Tregs through NK cells. The median percentages of cells subject to apoptosis induced by selected anti-hCCR8-hIgG1-nf Abs are depicted in FIG. 16, showing that these percentages range from around 34% to 99%. The $EC_{50}$ values for the killing of activated Tregs by allogeneic NK cells mediated by different anti-CCR8 Abs are shown in Table 8, with values ranging from about 13 pM to 304 nM.

TABLE 8

ADCC killing of activated Tregs mediated by anti-CCR8 mAbs

| Anti-CCR8 MAb | Median $EC_{50}$ (pM) |
|---|---|
| 8D55 | 38.6 |
| 10R3 | 56.6 |
| 14S15 | 39.7 |
| 16B13 | 13.4 |
| 4A19 | 13.1 |
| 18Y12 | 18.6 |
| 12F27 | $3.04 \times 10^5$ |

Example 20

Anti-CCR8 MAbs Promote Depletion of Tregs in Patient Tumors

Nonfucosylated anti-hCCR8 mAbs were tested for their ability to promote NK cell-mediated apoptosis of tumor Tregs from human patients. Briefly, dissociated patient endometrial tumors were purchased from Discovery Life Sciences. NK cells from a healthy donor were isolated and primed overnight for ADCC as described in Example 19 and fluorescently labeled (CellTrace Violet, ThermoFisher). These NK cells ($1.875\times10^5$ cells/well) were then incubated with endometrial tumor cells ($2.5\times10^5$ cells/well) for 24 h with titrations of anti-hCCR8 (14S15) and control Abs (the anti-CCR4 mAb, mogamulizumab, and anti-KLH-nf isotype) in RPMI medium with 10% ultra-low IgG FBS and 1 mM sodium pyruvate at 37° C. The resulting cells were stained for Tregs and other lymphocyte populations and processed through a flow cytometer. Treg and conventional T cell frequencies were analyzed using Flowjo software.

To determine whether anti-hCCR8 Abs can specifically mediate ADCC of patient tumor-infiltrating Tregs, allogeneic NK cells were co-cultured with digested endometrial tumor cells containing tumor-infiltrating Tregs. It has previously been shown that mogamulizumab, an anti-CCR4-hIgG1nf Ab, can mediate Treg killing in cancer patients. As shown in FIG. 17, both mogamulizumab and the anti-CCR8 mAb, 14S15, induce tumor Treg killing, with 14S15 being more potent (FIG. 17A). MAb 14S15 specifically depletes the endometrial tumor Tregs (FIG. 17A) but not conventional $CD4^+FOXP3^-$ T cells (FIG. 17B). In contrast, mogamulizumab also depletes $CD4^+FOXP3^-$ conventional T cells. 14S15 does not deplete any other lymphocyte subsets (data not shown).

In a further experiment, several Abs against hCCR8 with the following human heavy chain variants were generated: 1) hIgG1; 2) of IgG1 (IgG1-nf), which exhibit significantly higher FcγR binding affinity than IgG1 and can outcompete endogenous IgG for binding to CD16 for ADCC/ADCP (Iida, 2006); and 3) IgG1-L234A-L235E-G237A (hIgG1-inert), which minimally engages FcγRs (Hezareh et al., 2001). Anti-human CCR8 clones 16B13 and 14S15 as IgG1-nf Abs bound to in vitro activated human $FOXP3^+$ Tregs, blocked CCL1 binding, and cross-linked CD16 upon binding to CCR8 on activated Tregs (Examples 11, 15 and 17; Campbell et al., 2021, in which 16B13 is designated CCR8.1, and 14S15 is designated CCR8.2). Clone 16B13-IgG1 was also capable of cross-linking CD16 albeit at a lesser potency than its IgG1-nf counterpart (Campbell et al., 2021), whereas 16B13-IgG1-inert was entirely unable to mediate CD16 cross-linking (Campbell et al., 2021).

The capacity of anti-hCCR8-IgG1-nf Abs to deplete $FOXP3^+$ Tregs from peripheral blood and primary human tumor specimens was subsequently determined. PBMC depletion assays were performed by incubating $2.0\times10^5$ PBMCs in culture media and 100 U/ml IL-2 (Peprotech) in a U-bottom 96-well plate (Corning) for 48 h at 37° C. After two days, the relevant Abs were added and cells were further incubated for 96 h, followed by flow cytometric analysis.

Figure 18A:
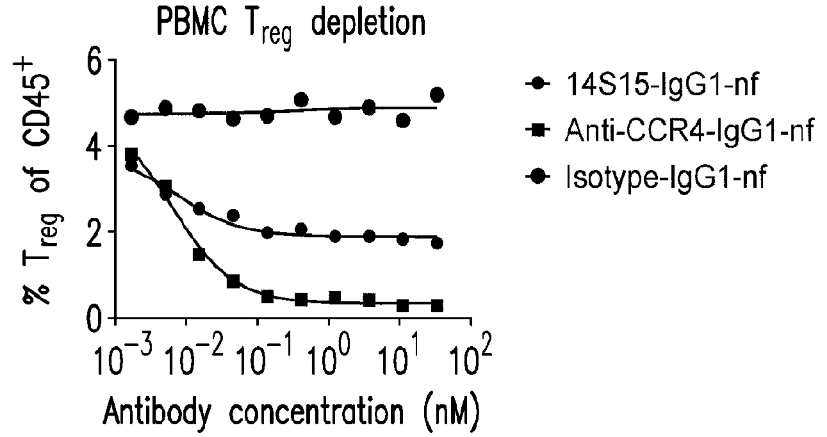
Figure 18B:
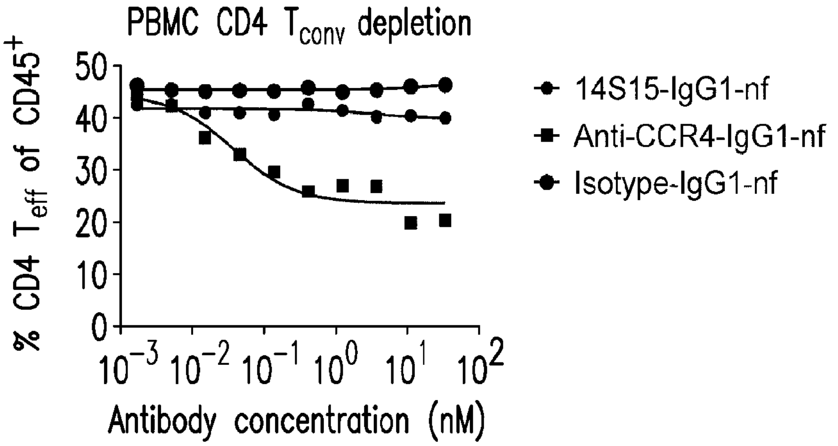
Figure 18C:
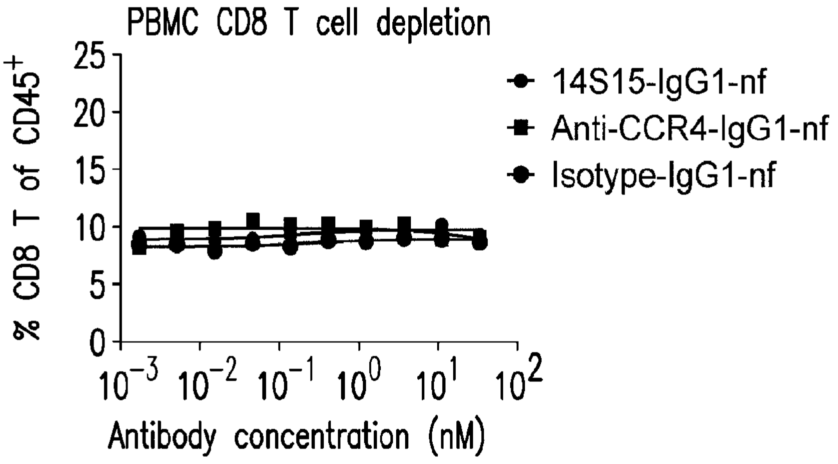

Although 14S15-IgG1-nf depleted a subset of peripheral blood Tregs (less than 50%) (FIG. 18A), a nf anti-human CCR4 Ab (anti-hCCR4-IgG1-nf, mogamulizumab biosimilar) removed more than 90% of these cells (FIG. 18A) as well as approximately half of peripheral $CD4^+$ Tconv (FIG. 18B). Neither Ab affected the $CD8^+$ T cell population (FIG. 18C). Thus, treatment of activated PBMCs with an anti-hCCR8-IgG1-nf Ab depletes a subset of peripheral blood Tregs, but importantly does not deplete Teff cells. In breast cancer patients, TCR sequencing revealed a significant clonal overlap between peripheral blood $CCR8^+$ Tregs and tumor Tregs (Wang et al., 2019), suggesting either that (1) Treg clones from the periphery migrate into the tumor and expand and enact Treg suppression, or (2) activated Treg from the tumor microenvironment expand into the periphery. Both scenarios could concurrently occur and lead to infiltration by circulating CCR8$^+$ Tregs into tumor metastatic sites to mediate immune suppression. Regardless of the mechanism, these results suggest that the wholesale depletion of CCR8$^+$ Tregs may serve as a method of systemically removing tumor specific Tregs in the periphery or in tumors.

Figure 18D:
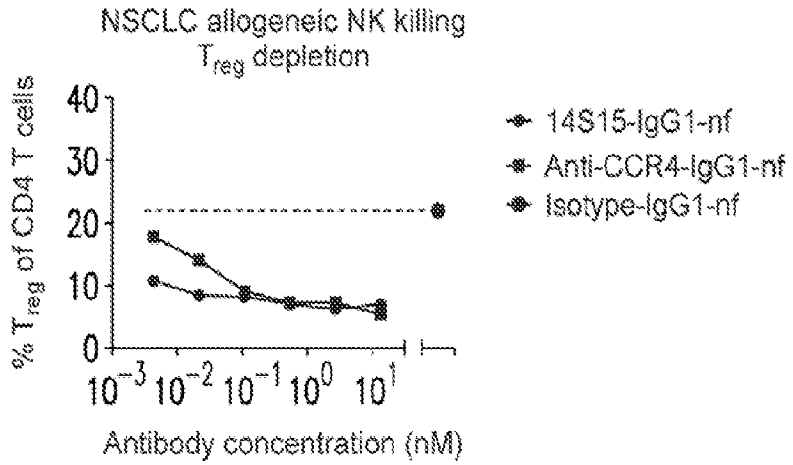
Figure 18E:
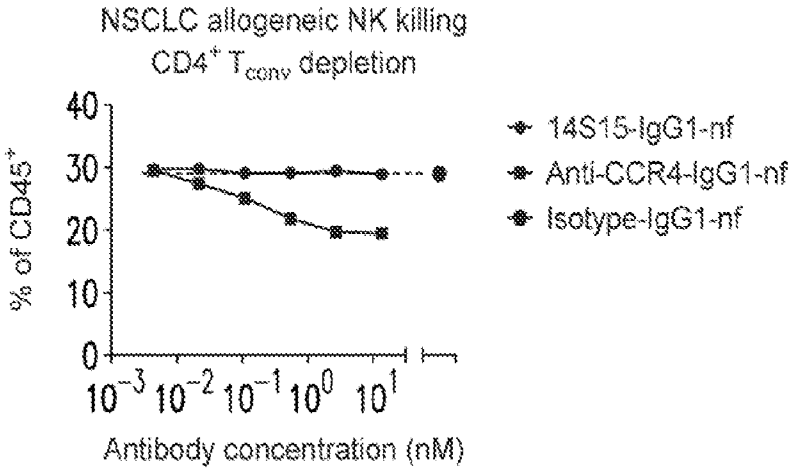
Figure 18F:
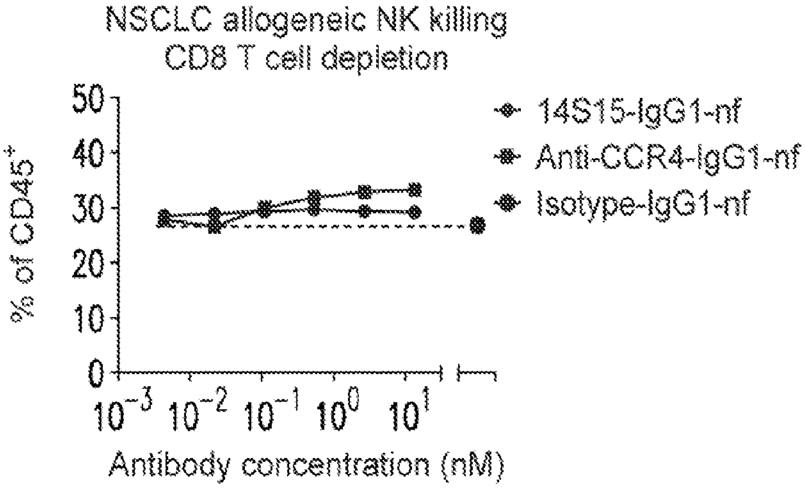
Figure 18G:
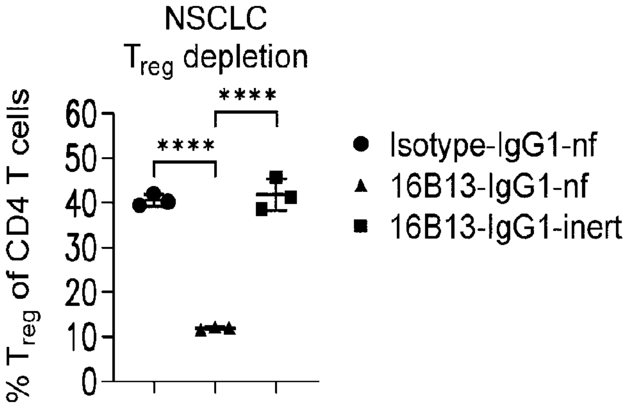
Figure 18H:
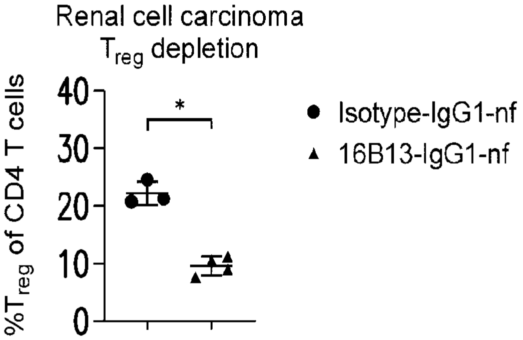
Figure 18I:
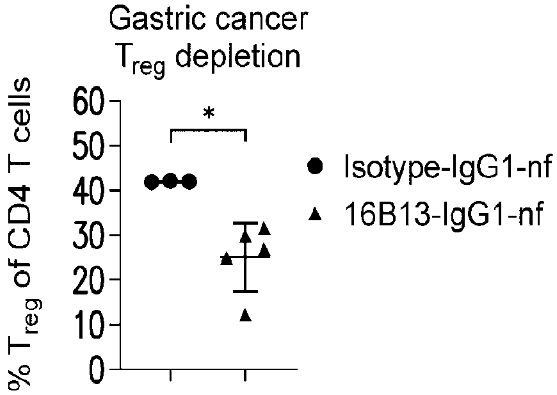

To test for anti-CCR8-mediated depletion in ex vivo tumor samples, cell suspensions of NSCLC surgical resections were cultured with activated allogeneic NK cells from healthy donor blood. Addition of 14S15-IgG1-nf resulted in a decrease in the frequency of FOXP3$^+$ Tregs (FIG. 18D) without any effect on overall CD4$^+$ Tconv (FIG. 18E) or CD8$^+$ T cell frequencies (FIG. 18F). In contrast, anti-hCCR4-IgG1-nf depleted about 30% of CD4$^+$ Tconv (FIG. 18E) in addition to depleting Tregs (FIG. 18D). No Treg depletion was observed after treatment with 16B13-IgG1-inert (FIG. 18G).

The ability of 16B13-IgG1-nf and 4A19 to deplete Tregs in ex vivo patient tumor samples in the absence of allogeneic NK cells was tested. For the 16B13 study, fresh clear cell renal cell carcinoma (RCC) and gastric tumor tissues were encased in agar and sequential 300-μM thick slices were created using a COMPRESSTOME® vibrating microtome (Precisionary Instruments; Greenville, NC) until all the tumor tissue was sliced. Tissue slices were cultured between two pieces of collagen hemostat (Becton Dickinson, Warwick, RI) in a 6-well tissue culture plates containing 5 ml of RPMI 1640 cell culture medium (Corning) with 10% FBS supplemented with 1 mM sodium pyruvate and 55 nM 2-mercaptoethanol (Thermo Fisher Scientific). Slice cultures were incubated at 37° C. on a plate shaker rotating at 80 rpm to facilitate media perfusion. After 24 h, slice culture wells were treated with 16B13-IgG1-nf or anti-KLH-nf hIgG1 isotype control. After 3 days of incubation with the mAbs, tumor tissue slices were enzymatically dissociated using a kit (Miltenyi Biotec) into single-cell suspensions and stained for flow cytometry analyses. The percentage of FOXP3$^+$ Tregs out of CD4$^+$ T cells was determined.

As shown in FIGS. 18H and 18I, treatment of renal cell and gastric tumors with 16B13-IgG1-nf exhibited an approximately 50% reduction in the frequency of Treg cells in the ex vivo patient tumor slice culture system without the addition of allogeneic NK cells, confirming that endogenous tumor-resident FcγR$^+$ cells are sufficient to mediate ADCC/ADCP against CCR8$^+$ target cells in situ.

For the 4A19 study, resected melanoma tumor was sliced and cultured for 3 days with 10 μg/ml of 4A19, mogamulizumab biosimilar, or anti-KLH-nf hIgG1 isotype control. After 3 days, the treated tumor slices were dissociated into single cell suspensions for flow cytometry analysis. Overall, the tumor slices treated with 4A19 showed reduced percentage of FOXP3$^+$ CD4 Tregs when compared to the mogamulizumab biosimilar- and isotype-treated slices.

Example 21

Anti-CCR8 MAbs Do Not Induce Cell Internalization of CCR8

To determine whether anti-CCR8 Abs induce internalization of the CCR8 receptor upon binding to CCR8 on the surface of a cell, Tregs were activated as described in Example 2. An anti-CCR8 mAb (4A19), a positive control Ab (anti-ICOS Ab), and an isotype control were each added at a concentration of 10 μg/ml to $4\times10^4$ activated Tregs and incubated at 37° C. for 5 time periods: 0, 30, 60, 90, and 120 min. In addition, a goat anti-human Fc-γ Ab was added to a subset of samples at 5 μg/ml to crosslink the primary Abs. After each time period, a sodium azide solution was added to the Tregs and the mixture placed on ice to prevent further receptor internalization. Finally, all of the samples were washed twice with a 0.05% sodium azide solution, then stained with an appropriate phycoerythrin (PE)-conjugated secondary Ab. Cells were fixed with 2% paraformaldehyde (PFA), then analyzed on a cytometer. The level of CCR8 expression on the cell surface was measured by the median fluorescence intensity as determined using Flowjo software.

As shown in FIG. 19, the anti-ICOS mAb in the absence of a cross-linking Ab caused minimal internalization of ICOS over the 120-min time period, but in the presence of the cross-linking Ab caused significant ICOS internalization. In contrast, the anti-CCR8 mAb, 4A19, caused no internalization of CCR8 either in the presence or absence of a cross-linking Ab. Treatment of activated Tregs by the isotype Ab with or without a cross-linking secondary Ab did not cause internalization of CCR8.

Example 22

Depletion of Human Tumor Tregs In Vitro

Donor natural killer (NK) cells were isolated and activated using Myelocult H5100 (StemCell), 1 μM hydrocortisone, and 500 U/ml of IL-2 (PeproTech) for 24 h. Frozen dissociated human lung adenocarcinoma tissue (Discovery Life Sciences) was thawed and co-cultured ex vivo in a 1:1 ratio with $2.5\times10^5$ allogeneic NK cells for 24 h in the presence of an anti-hCCR8 (mAb 4A19), anti-hCCR4 hIgG1-nf (a mogamulizumab biosimilar), or a control nf keyhole limpet hemocyanin (KLH-nf) mAb. The cells were stained and Treg depletion was measured by flow cytometry using Flowjo software to calculate cell populations.

As shown in FIG. 20, mAb 4A19 induced measurable depletion of tumor Tregs without impacting the frequency or number of Teffs. This was demonstrated in allogeneic NK killing assays with digested patient tumors and patient tumor slice explant systems. MAb 4A19 was more effective at Treg depletion than the anti-CCR4-nf Ab in vitro (FIG. 20A). Moreover, in contrast to the anti-CCR4-nf Ab, mAb 4A19 did not induce depletion of CD4$^+$ effector T cells (FIG. 20B). Neither anti-CCR8 nor anti-CCR4 depleted CD8$^+$ effector T cells (FIG. 20C).

Figure 20D:
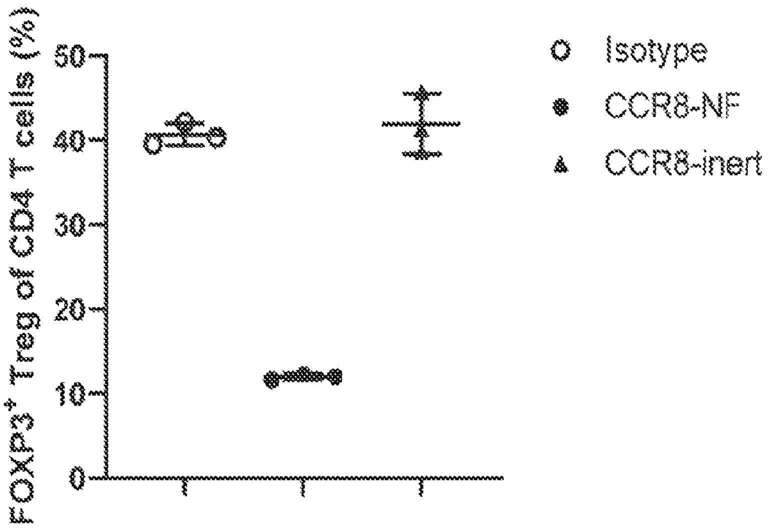

An Ab with an irrelevant targeting arm (anti-KLH-nf) or inert backbone (anti-CCR8-inert) did not deplete Tregs, suggesting that target-mediated FcγR coengagement through the nf backbone is required for Treg depletion (FIG. 20D).

Example 23

Anti-CCR8 MAbs Reduce Tumor Growth in CT26 Mouse Tumor Model

Diverse mouse tumor models, namely syngeneic CT26, MC38 and SA1N models, as well as tumor models MB49 and 4T1 that were resistant to anti-PD-1 treatment, were used to test the effects of anti-CCR8 mAbs. All Ab treatments were performed at 200 μg/mouse, and tumors were measured twice weekly for all studies.

The anti-tumor activity of an anti-mCCR8 mAb (anti-CCR8-mIgG2a) was assessed in the CT26 mouse colon adenocarcinoma model. Fifteen-week-old female BALB/cAnNHsd mice were each implanted subcutaneously (SC)

with $10^6$ CT26 tumor cells. Mice were randomized into treatment groups of 10 mice/group 7 days post-tumor implantation when tumors reached a median size of approximately 100 $mm^3$. Abs (anti-CCR8-mIgG2a or a control mIgG2a isotype Ab), formulated in PBS, were administered at 200 μg/mouse in a volume of 200 μl via IP injections at Days 7, 10, and 14 post-implantation. Tumor volumes, body weights and clinical observations were noted to establish efficacy and tolerability of test agents. Tumor caliper measurements were converted into tumor volumes using the formula: volume=½ (length×width×height). Tumor measurements were recorded twice per week for up to 35 days post-implantation. On study, mice received sterile rodent chow and water ad libitum and were housed in sterile filter-top cages with 12-h light/dark cycles. All mouse experiments were conducted in accordance with the guidelines of the Association for Assessment and Accreditation of Laboratory Animal Care International.

Figure 21A:
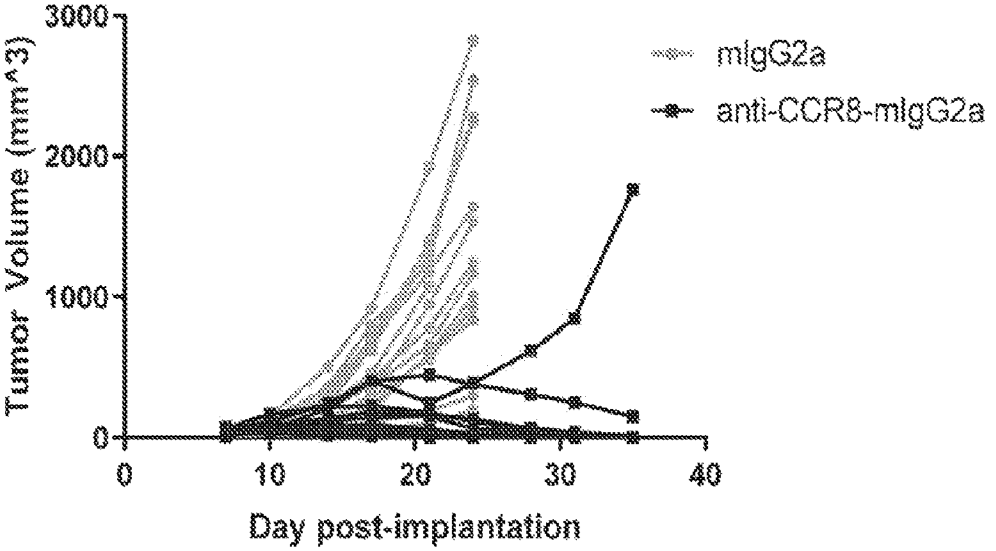
Figure 21B:
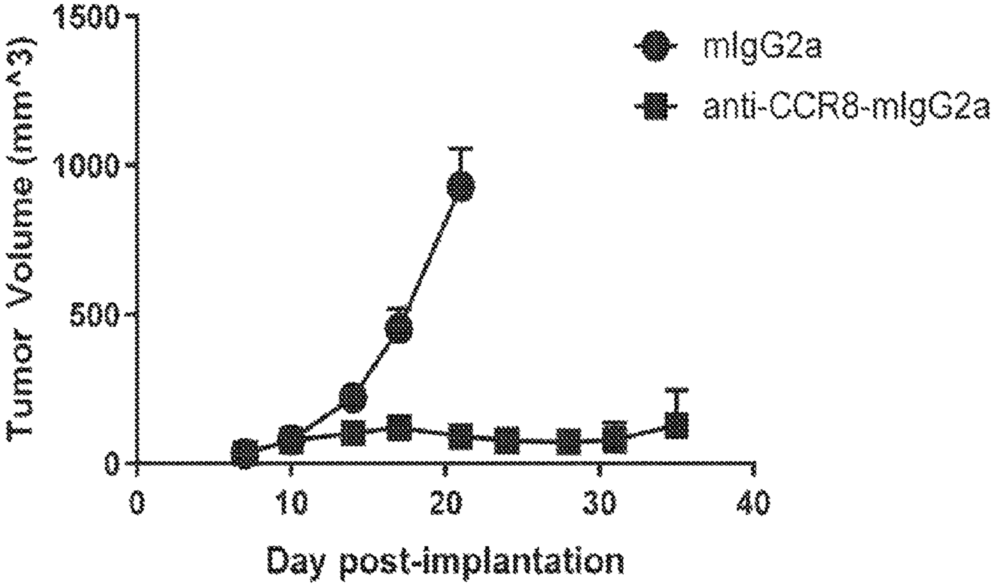

The data show that anti-CCR8-mIgG2a potently reduced the rate of tumor growth, with 8 out of the 10 mice being tumor-free by Day 28 post-implantation, whereas treatment with a control mIgG2a Ab did not inhibit tumor growth (FIG. 21A). For the experiments performed in mouse tumor models, tumor-free mice were monitored for tumor recurrences for ≥25 days following the last administration of Ab. Measurements for the control-treated mice stopped after about 35 days post-tumor implantation, after which the remaining mice were euthanized. The mean tumor volumes of the treated mice are shown in FIG. 21B, which confirms the strong inhibition of tumor growth by the anti-CCR8 mAb and uninhibited growth of tumors treated with the isotype control. These data show that the anti-CCR8 Ab is highly effective in inhibiting tumor growth in this CT26 mouse model and is associated with depletion of tumor-infiltrating Tregs.

For analysis of tumor-infiltrating lymphocytes, mice tumors were harvested 16 days post-implantation. Tumors were digested with collagenase, dissociated mechanically using an OctoMacs dissociator (Miltenyi Biotech), and filtered through sterile 100-μM strainers. Samples were blocked for Fc receptors by incubation with FcR Blocking Reagent (Miltenyi Biotech), followed by surface staining for lymphocyte populations, fixation, permeablization and intracellular staining for Foxp3. Cells were then washed and processed through a flow cytometer. Analysis was performed using FlowJo software and graphed using GraphPad Prism.

Figure 21C:
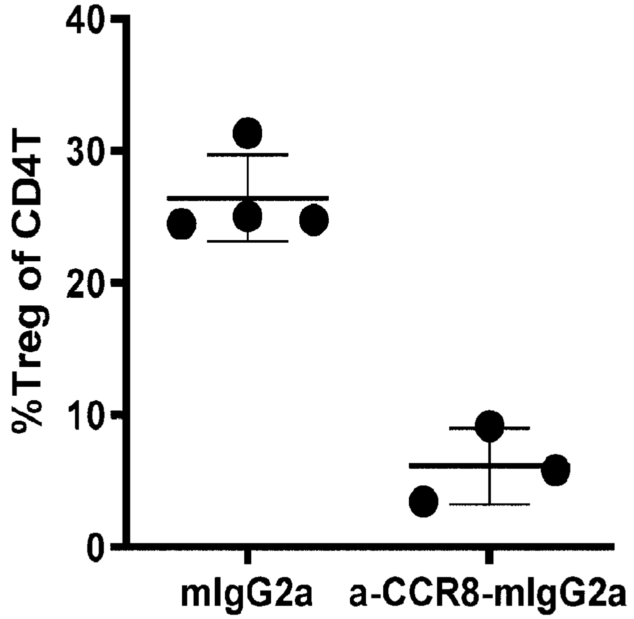
Figure 21D:
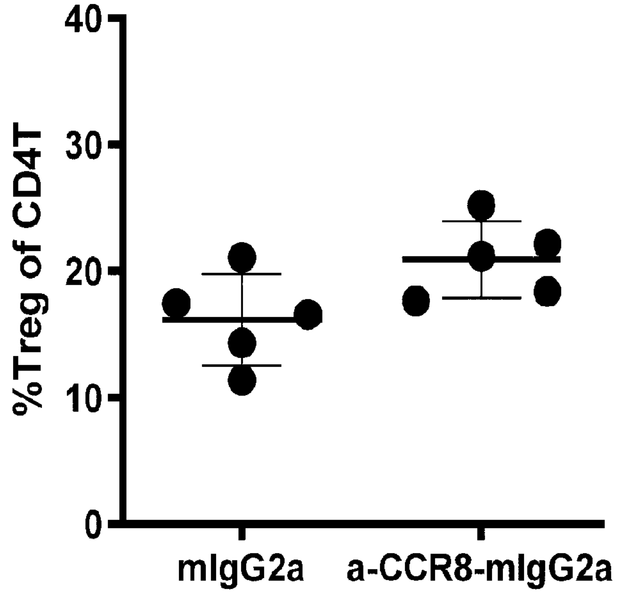

As shown in FIG. 21C, treatment of mice harboring CT26 tumors with anti-CCR8-mIgG2a drastically reduced the percentage of $Foxp3^+$ Tregs in the $CD4^+$ T cell population, compared to mice treated with the isotype control, whereas the Treg population in the spleen was unaffected by treatment with anti-CCR8-mIgG2a (FIG. 21D). These data indicate that CCR8 is expressed specifically on the surface of tumor-associated Tregs but not expressed on peripheral Tregs, and further, that binding of an Ab to CCR8 mediates depletion of tumor-associated Tregs by ADCC.

Example 24

Anti-mCCR8 Mediated Depletion of Only Tumor Tregs, Sparing $CCR8^+$ T Cells in Normal Tissues Murine tissue lymphocyte populations were evaluated in the CT26 mouse colon adenocarcinoma model. Female BALB/C mice were injected subcutaneously with $10^6$ CT26 tumor cells. Mice were randomized by tumor size into treatment groups after 12 days, when tumor volumes measured by calipers had reached about 100-150 $mm^3$. Mice were administered a 200-μg flat dose (approximately 10 mg/kg for mice weighing an average of 21.2 g) of either anti-CCR8-mIgG2a or a mIgG2a isotype control mAb 3 times on Days 12, 14, and 19 after implantation. On Day 20, 24 h after the third Ab dose, mice were sacrificed, blood samples collected, and tumor, skin, spleen, and thymus tissues were excised.

Tissues were processed into single-cell suspensions for flow cytometry. Tumors were minced and enzymatically digested, spleen and thymus tissue were mechanically dissociated, and RBCs in dissociated spleen and blood samples were depleted as described in Example 2. Cell suspensions from processed tissues were blocked for Fc receptors by incubation with FcR Blocking Reagent (Miltenyi Biotec), followed by surface staining for lymphocyte populations, fixation, permeablization and intracellular staining for Foxp3. Cells were then washed and processed through a flow cytometer. Analysis was performed using FlowJo software and results graphed using GraphPad Prism.

Figure 22A:
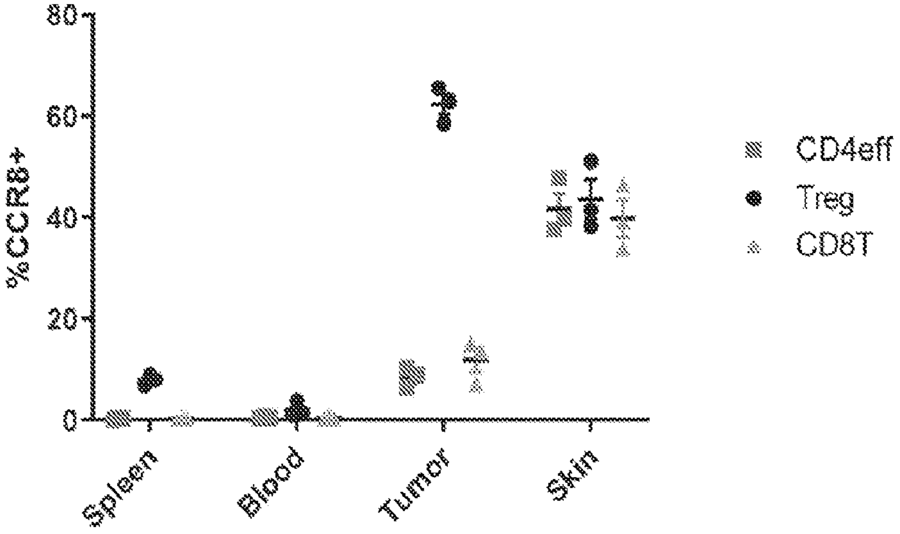
Figure 22B:
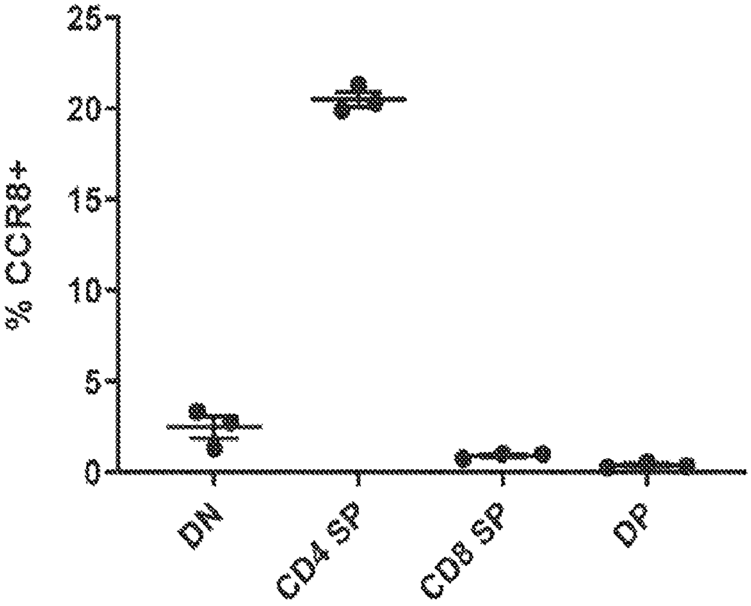
Figure 22C:
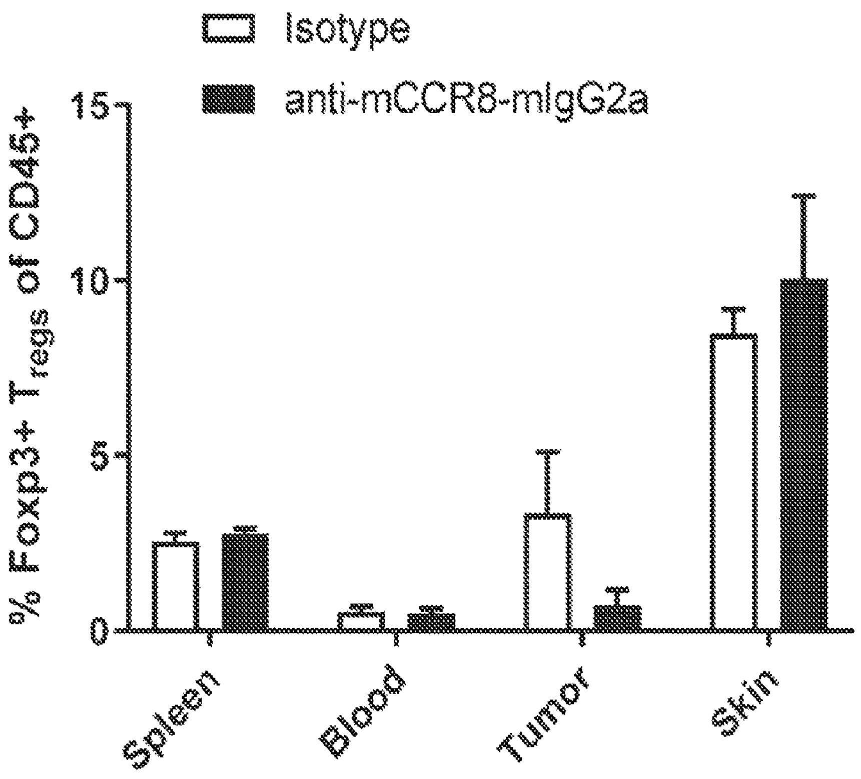
Figure 22D:
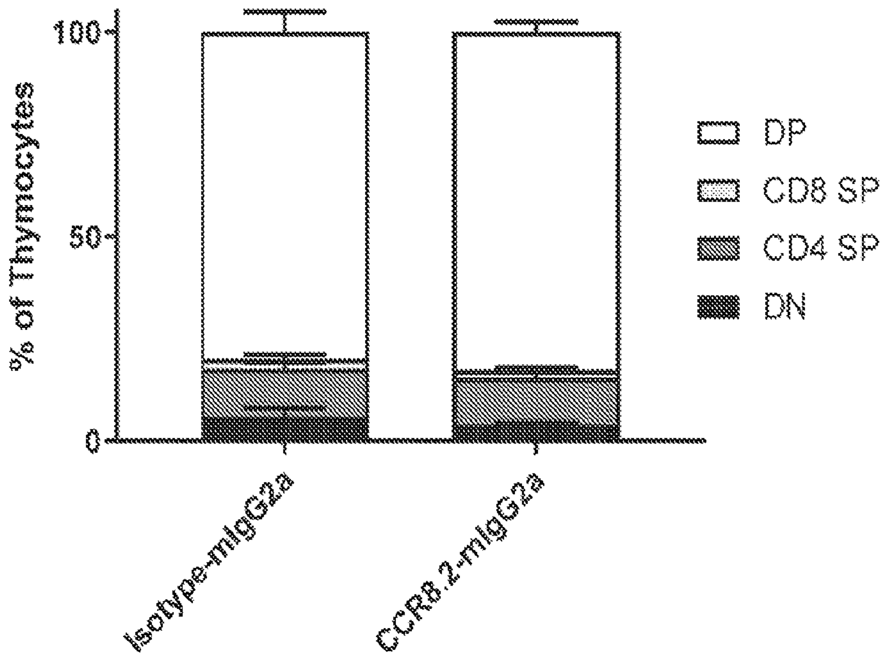
Figure 22E:
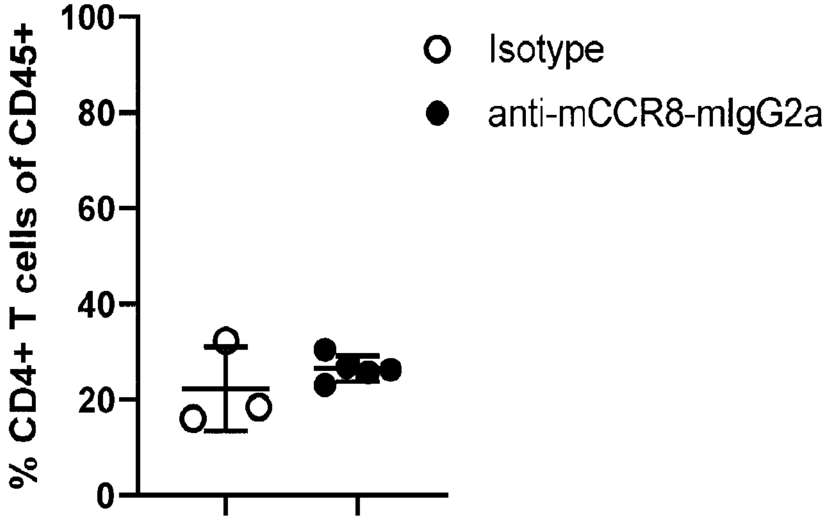
Figure 22F:
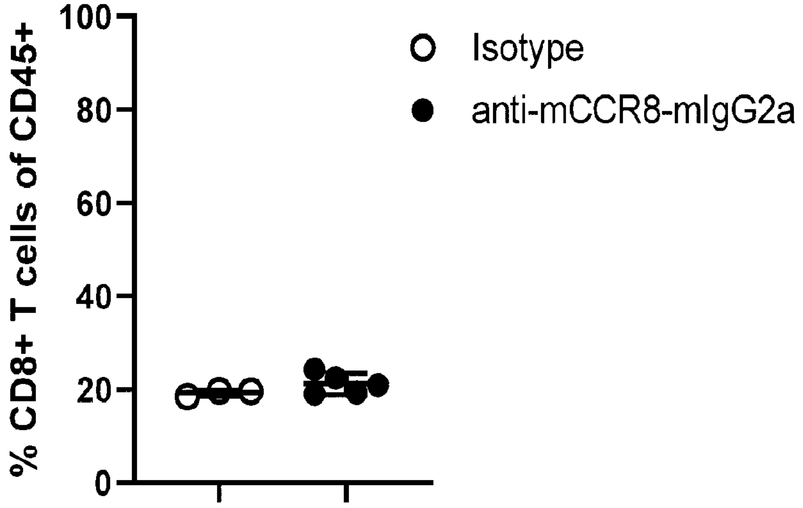

Among T cells infiltrating the mouse CT26 tumor, $CD4^+$ $FOXP3^+$ Tregs (Treg) were the most enriched for CCR8 expression compared to $FOXP3^-CD4^+$ effector (CD4eff) or $CD8^+$ T (CD8T) cells (FIG. 22A). CCR8 expression was also observed on a population of skin-resident T cells, with very little expression on T cells in the spleen or blood (FIG. 22A). In the thymus, CCR8 was expressed on a subset of $CD4^+CD8^-$ (single positive) thymocytes (FIG. 22B). Following treatment with anti-CCR8-mIgG2a, tumor infiltrating Tregs were depleted, whereas Tregs in the spleen, blood, and skin were not depleted (FIG. 22C). Thymocytes (FIG. 22D) as well as $CD4^+$ (FIG. 22E) and $CD8^+$ (FIG. 22F) T cells in the skin were also unaffected. Thus, in the mouse CT26 tumor model, treatment with an anti-mCCR8 depleting Ab selectively depleted $CCR8^+$ Tregs in the tumor, but not the relatively low number of $CCR8^+$ T cells in the skin, thymus, spleen, or blood.

Example 25

Anti-CCR8 MAbs Reduce Tumor Growth in MC38 Mouse Tumor Model

The anti-tumor activity of anti-CCR8-mIgG2a was measured in the MC38 mouse colon adenocarcinoma model. Fifteen-week-old female FOXP3_IRES-EGFP (C57BL/6) mice (Jackson Laboratory, Bar Harbor, ME) were each implanted SC with $10^6$ MC38 tumor cells and randomized into treatment groups of 10 mice/group 7 days post-tumor implantation. Abs (anti-CCR8-mIgG2a or a control mIgG2a Ab) were administered at 200 μg/mouse in a volume of 200 μl via IP injections at Days 7, 10, and 14 post-implantation. Tumor measurements were recorded twice per week for up to 51 days post-implantation, after which the mice were euthanized. Data analysis and graphing was performed using GraphPad Prism.

The data show that anti-CCR8-mIgG2a potently reduced the rate of tumor growth, with 7 out of the 10 mice having tumor volumes below 10 $mm^3$ by Day 51 post-implantation, compared to mean volumes of over 1,100 $mm^3$ for tumors showing uninhibited growth, whereas treatment with a control mIgG2a Ab did not inhibit tumor growth (FIG. 23A). The mean tumor volumes of the treated mice are shown in FIG. 23B, which confirms the strong inhibition of tumor growth by anti-CCR8-mIgG2a and uninhibited growth of tumors treated with the isotype control. These data show that the anti-CCR8 Ab is highly effective in inhibiting tumor growth in this MC38 mouse model.

Example 26

Pharmacodynamic and Pharmacokinetic Responses to Anto-CCR8 MAb Treatment in MC38 Mouse Tumor Model C57BL/6 mice were injected SC with $1.0\times10^6$ MC38 cells. Tumors were measured with calipers two-dimensionally, and tumor volume was calculated as $L\times(W^2/2)$, where L=length (the longer of the 2 measurements), and W=width. Mice were randomized into 6 groups of 25 mice each (21 mice for the isotype control) when they reached a mean tumor volume of about 77 $mm^3$, and dosed by IP injection with anti-CCR8-mIgG2a or a mIgG2a isotype control, diluted in PBS, on Day 10 post-implantation at the doses shown in Table 9. Animals were checked daily for postural, grooming, and respiratory changes, as well as lethargy. Tumors and group body weights were recorded at least twice a week until death, euthanasia or end of study period. Animals were euthanized if the tumor reached a volume greater than approximately 2,000 $mm^3$ or appeared ulcerated.

To investigate the effect of the anti-mCCR8 mAb on tumor-infiltrating lymphocytes, tumors (n=7 mice/treatment group) were harvested on Days 3, 5, and 10 post-treatment. Single cell suspensions from tumors were obtained by using gentleMACS C tubes. Cell suspensions were passed through a 70-μm filter then pelleted. After resuspension, cells were counted using Vi-cell counter (Beckman Coulter, Miami, FL). Cells were then plated in 96-well plates with $3.0\times10^6$ cells per well and stained for immune cell subsets and functional markers using the flow cytometry Abs. Ab fluorescence was detected by flow cytometry on the Fortessa X-20 cytometer (BD Biosciences), and the results were analyzed using FlowJo software.

To evaluate the pharmacokinetics (PK) of the anti-mCCR8 mAb, whole blood samples (n=4 mice/time point) were obtained by tail bleeds or terminal bleeds at 4, 24, 72, 120, 168 and 240 hours post-dose. Blood samples were coagulated and centrifuged at 4° C. (1,500 to 2,000×g) to obtain serum. Serum samples were stored at −80° C. until analysis. Mouse serum samples were analyzed using immune-capture LC-MS/MS for detection of the anti-mCCR8 mAb. Reference material was used to prepare calibrators and quality control samples. The range of the anti-mCCR8 mAb calibration curve was from 200 to 200,000 ng/ml in mouse serum. The upper and lower limits of quantification were 200,000 and 200 ng/ml, respectively (i.e., ULOQ 200,000 ng/ml, LLOQ 200 ng/ml). The PK parameters were obtained by non-compartmental analysis of serum concentration versus time data using Phoenix WinNonlin software (Certara, Menlo Park, CA). The area under the curve from time zero to the last sampling time [AUC (0-T)] and the area under the curve from time zero to infinity [AUC (INF)] were calculated using a combination of linear and log trapezoidal summations. The CLT Vss, and $T_{1/2}$ were estimated after IP administration. Specifically, CLT is the total clearance of drug and Vss is the volume of (drug) distribution at steady-state. Estimations of half-life ($T_{1/2}$) were made using a minimum of 3 terminal time points with quantifiable concentrations.

Figure 24A:
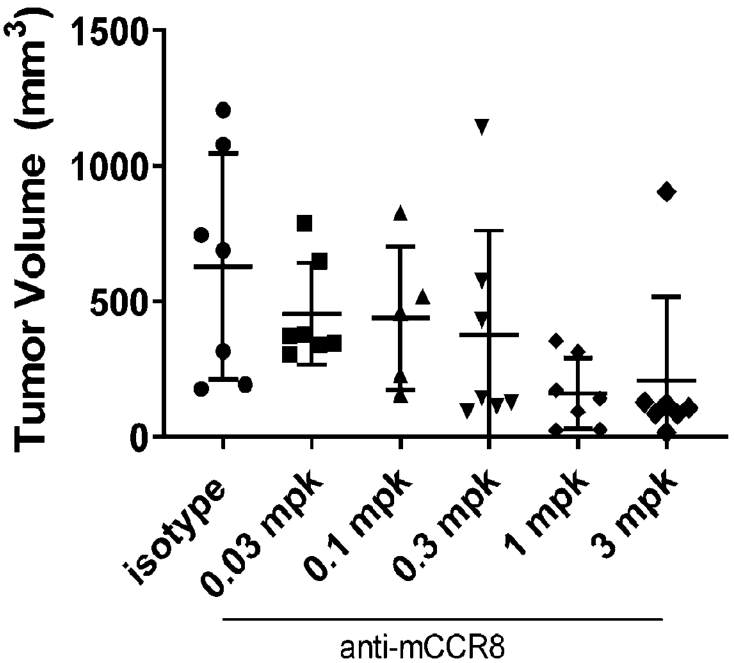
Figure 24B:
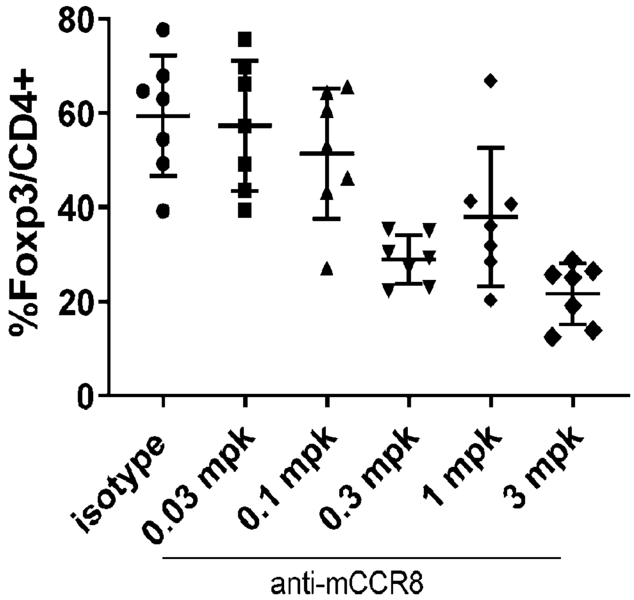

Consistent with the results in Example 25, treatment with a single dose of anti-mCCR8 mAb led to reduced tumor growth in the MC38 model. At Day 10 post-treatment, the mean tumor volumes were as shown in FIG. 24A and Table 9.

TABLE 9

ADCC killing of activated Tregs mediated by anti-CCR8 mAbs

| Group | Ab Treatment (Dose) | Tumor Vol. at Day 10 ($mm^3$) | % of Tregs | % of $CD8^+$ T cells |
|---|---|---|---|---|
| 1 | Control (10 mg/kg) | 629 | 59.5 ± 12.8 | 10.1 ± 2.0 |
| 2 | CCR8 (0.03 mg/kg) | 453 | 57.3 ± 13.8 | 17.8 ± 11.3 |
| 3 | CCR8 (0.1 mg/kg) | 438 | 51.4 ± 13.8 | 21.2 ± 8.4 |
| 4 | CCR8 (0.3 mg/kg) | 375 | 28.9 ± 5.2 | 29.0 ± 15.0 |
| 5 | CCR8 (1 mg/kg) | 161 | 38 ± 14.7 | 31.7 ± 15.5 |
| 6 | CCR8 (3 mg/kg) | 207 | 21.6 ± 6.5 | 32.0 ± 13.1 |

Immune-phenotyping studies in the MC38 model further showed that anti-mCCR8 induces Treg depletion in a dose-dependent manner. At Day 5 post-treatment, the mean (±SD) percentage of Tregs (% $Foxp3^+/CD4^+$ T cells) in the mice treated with anti-mCCR8 at the lower doses of 0.03 and 0.1 mg/kg remained comparable to that of the isotype control-treated group (see FIG. 24B; Table 9).

Figure 24C:
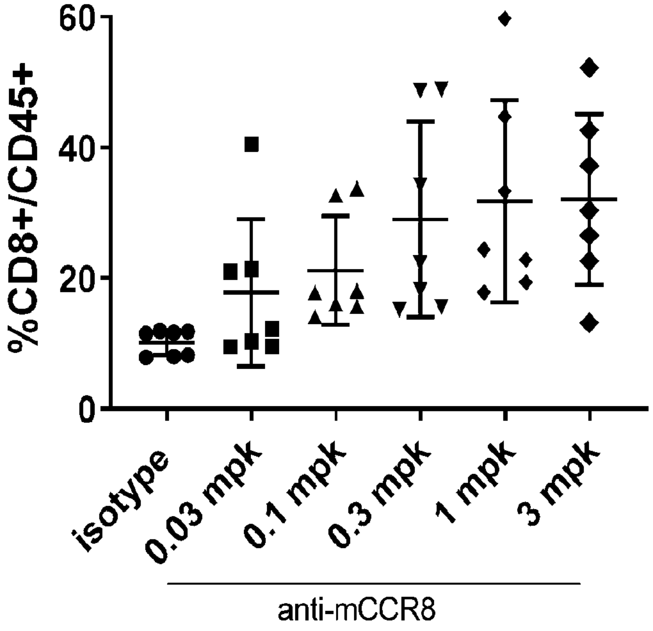

On Day 5 post treatment, the frequency (%) of tumor-infiltrating $CD8^+$ T cells increased in anti-mCCR8 mAb-treated groups compared to the isotype control-treated group as shown in FIG. 24C; Table 9.

Figure 24D:
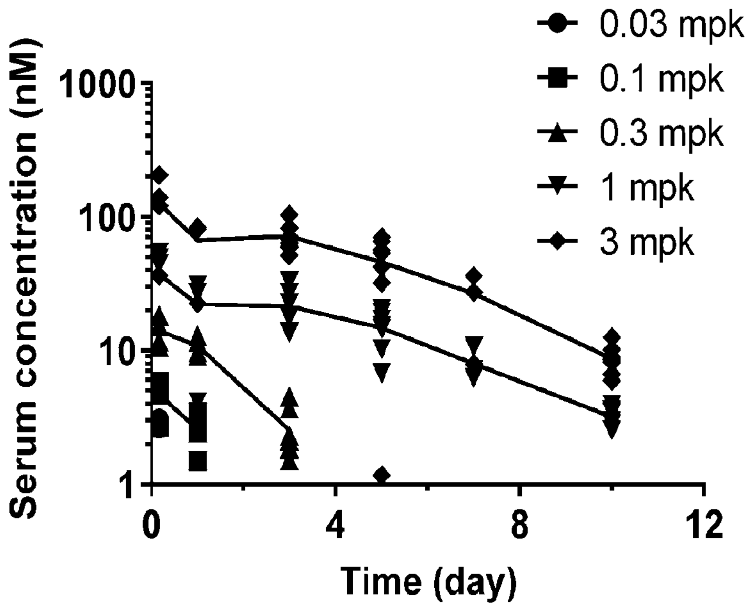

A single IP dose of anti-CCR8-mIgG2a demonstrates non-linear PK in the dosing range of 0.03 to 3 mg/kg indicating target-mediated drug disposition (TMDD). Compared with 0.3 mg/kg dosing, the $T_{1/2}$ increases by approximately three-fold compared to the $T_{1/2}$ for the 1 and 3 mg/kg doses (FIG. 24D).

Example 27

Anti-CCR8 and Anti-PD-1 MAbs Synergistically Reduce Tumor Growth in MB49 Mouse Bladder Carcinoma Tumor Model The anti-tumor activity of anti-CCR8-mIgG2a was measured as a single agent or in combination with an anti-mPD-1 Ab (clone 4H2) in the MB49 murine bladder carcinoma model, which is known to be less responsive to anti-mPD-1 monotherapy. Mice were also treated with a control mIgG2a Ab or with 4H2 alone. Anti-mPD-1 clone 4H2 is a chimeric rat-mouse anti-mPD-1 mAb constructed from a rat IgG2a anti-mouse PD-1 Ab in which the Fc-portion was replaced with an Fc-portion from a mouse IgG1 isotype to generate a mAb with reduced binding to mouse FcR's (Li et al., 2009). It blocks binding of mPD-L1 and mPD-L2 to mPD-1, stimulates a T cell response, and exhibits anti-tumor activity in mice, and was generated as previously described (Li et al., 2009) and expressed in CHO cells.

Fifteen-week-old male C57BL/6 Foxp3-IRES-EGFP mice were injected SC with $2\times10^5$ MB49 tumor cells and randomized into treatment groups of 10 mice/group 9 days post-tumor implantation. MAbs were administered at 200 μg/mouse via IP injections on Days 10, 13, and 18 post-implantation. Tumor measurements were recorded twice per week up to Day 39, after which the mice were euthanized.

For analysis of tumor-infiltrating lymphocytes, mouse tumors were harvested 17 days post-implantation. Tumors were digested with collagenase, dissociated mechanically using an OctoMacs dissociator (Miltenyi Biotech), and filtered through sterile 100-μM strainers. Samples were blocked for Fc receptors with FcR Blocking Reagent followed by surface staining for lymphocyte populations. Cells were then washed and processed through a flow cytometer. Analysis was performed using FlowJo software and graphed using GraphPad Prism.

As shown in FIG. 25A, single-agent anti-CCR8 and anti-PD-1 treatments induced partial anti-tumor activity in the mouse MB49 tumor model, with the anti-CCR8 mAb having a stronger effect that the anti-PD-1 mAb. However, administration of anti-CCR8 and anti-PD-1 mAbs in combination had a synergistic effect in almost completely inhibiting tumor growth, resulting in 8 out of 10 mice being tumor-free. This demonstrates that anti-PD-1 treatment can synergistically enhance the anti-tumor activity of anti-CCR8 in a less immunogenic tumor model. A combination of Abs is considered synergistic if the anti-tumor effect of the combination is greater than the sum of the level of inhibition exhibited by each Ab individually.

FIG. 25B shows the percentage of tumor-associated $CD4^+$ T cells that are Tregs following the various Ab treatments. Despite similar depletion levels of tumor Tregs in both the anti-CCR8 single agent and anti-$CCR^8$/anti-PD-1 combination treatments, the single-agent anti-CCR8 treatment arm was insufficient at inhibiting tumor growth.

FIG. 25C shows the percentage of tumor-associated $CD45^+$ T cells that are $CD8^+$ T cells following the various Ab treatments. $CD8^+$ T cell expansion levels were found to be similar for the single-agent and combination arms. However, the quality of the $CD8^+$ T cell responses may be improved with the combination treatment.

Example 28

Anti-CCR8 and Anti-PD-1 MAbs Synergistically Reduce Tumor Growth in 4T1 Murine Breast Cancer Model The anti-tumor activity of anti-CCR8-mIgG2a was measured as a single agent or in combination with an anti-PD-1 Ab (clone 4H2) in the 4T1 mammary carcinoma model, another mouse tumor model that is resistant to anti-mPD-1 monotherapy. Mice were also treated with 4H2 alone and with a combination of control mIgG2a and mIgG1-D265A Abs. Fifteen-week-old female Balb/C mice (Envigo, Indianapolis, IN) were injected SC with $10^6$ 4T1 tumor cells and randomized into treatment groups of 10 mice per group 7 days post-tumor implantation when tumors reached a median size of approximately 100 $mm^3$. Abs were administered at 200 μg/mouse via IP injections on Days 7, 10, and 14 post-implantation. Tumor measurements were recorded twice per week up to Day 27, after which the mice were euthanized. Data analysis and graphing was performed using GraphPad Prism.

As shown in FIG. 26, single agent anti-CCR8 treatment induced partial anti-tumor activity in the mouse 4T1 tumor model whereas anti-PD-1 treatment alone did not exhibit any anti-tumor efficacy in this model. Notwithstanding the absence of tumor growth inhibition by anti-PD-1, the combination of this Ab and the anti-CCR8 Ab produced a strong synergistic interaction, evidenced by a massive enhancement of the anti-tumor activity observed with antiCCR8, with 7 out of 10 mice having tumor volumes below 20 $mm^3$, compared to mean volumes of about 1,500 $mm^3$ for tumors showing uninhibited growth. Together with the MB49 data (Example 27), this demonstrates that in anti-PD-1-resistant tumor models, anti-CCR8 treatment can induce synergistic anti-tumor effects when combined with anti-PD-1 treatment.

Example 29

Anti-CCR8 MAbs Reduce Tumor Growth in SA1N Fibrosarcoma Mouse Model

The anti-tumor activity of anti-CCR8-mIgG2a was measured and compared to that of CCR8-mIgG1-D265A, a variant with the Fc-inert mIgG1-D265A heavy chain, in the SA1N fibrosarcoma mouse model. Female A/J mice were each injected SC with $10^6$ SA1N tumor cells and randomized into treatment groups of 9 mice per group 5 days post-tumor implantation. Abs (anti-CCR8-mIgG2a, anti-CCR8-mIgG1-D265A or a control mIgG2a Ab) were administered at 200 μg/mouse in a volume of 200 μl via IP injections at Days 5, 8, and 12 post-implantation. Tumor measurements were recorded twice per week for up to 57 days post-implantation, after which the mice were euthanized. Data analysis and graphing was performed using GraphPad Prism.

For analysis of tumor-infiltrating lymphocytes, mice tumors were harvested 16 days post-implantation. Tumors were dissociated mechanically and filtered through sterile 100-μM strainers. Samples were blocked for Fc receptors with FcR Blocking Reagent followed by surface staining for lymphocyte populations, fixation, permeablization and intracellular staining for Foxp3. Cells were then washed and processed through a flow cytometer. Analysis was performed using FlowJo software and graphed using GraphPad Prism.

The data show that anti-CCR8-mIgG2a potently reduced the rate of tumor growth, with 9 out of the 9 mice tumor-free by Day 25 post-implantation, whereas treatment with a control mIgG2a mAb did not inhibit tumor growth (FIG. 27A). Measurements for the control-treated mice stopped after about 57 days post-tumor implantation, after which the remaining mice were euthanized. These data show that the anti-CCR8 Ab is highly effective in inhibiting tumor growth in this SA1N mouse model. Interestingly, treatment of mice with the non-depleting anti-CCR8 mAb (CCR8-mIgG1-D265A) resulted in partial inhibition of tumor growth (FIG. 27A), indicating that at least in the SA1N tumor model, CCR8 engagement by CCL1 may be enhancing immune suppression by Tregs in the tumor environment.

FIG. 27B shows the percentage of tumor-associated $CD4^+$ T cells that are Tregs following the various Ab treatments. Despite the anti-tumor activity observed with the non-depleting anti-CCR8-mIgG1-D265A treatment, only the depleting anti-CCR8-mIgG2a treatment resulted in tumor Treg depletion. Blockade of CCL1-mediated enhancement of Treg suppression may have resulted in increased pro-inflammatory and anti-tumor responses.

Example 30

Anti-Tumor Efficacy Requires an Fc-Engaging Isotype of Anti-CCR8

Figure 28E:
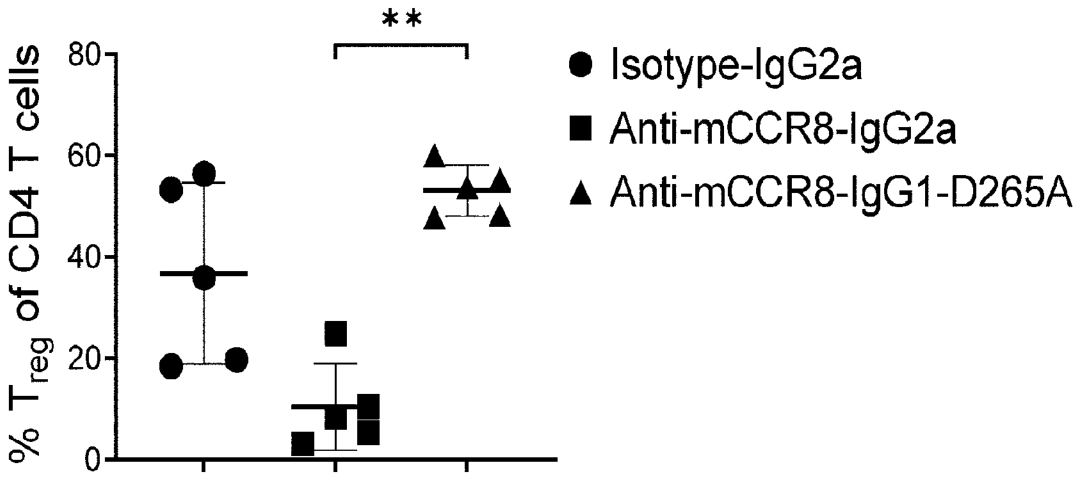
Figure 28F:
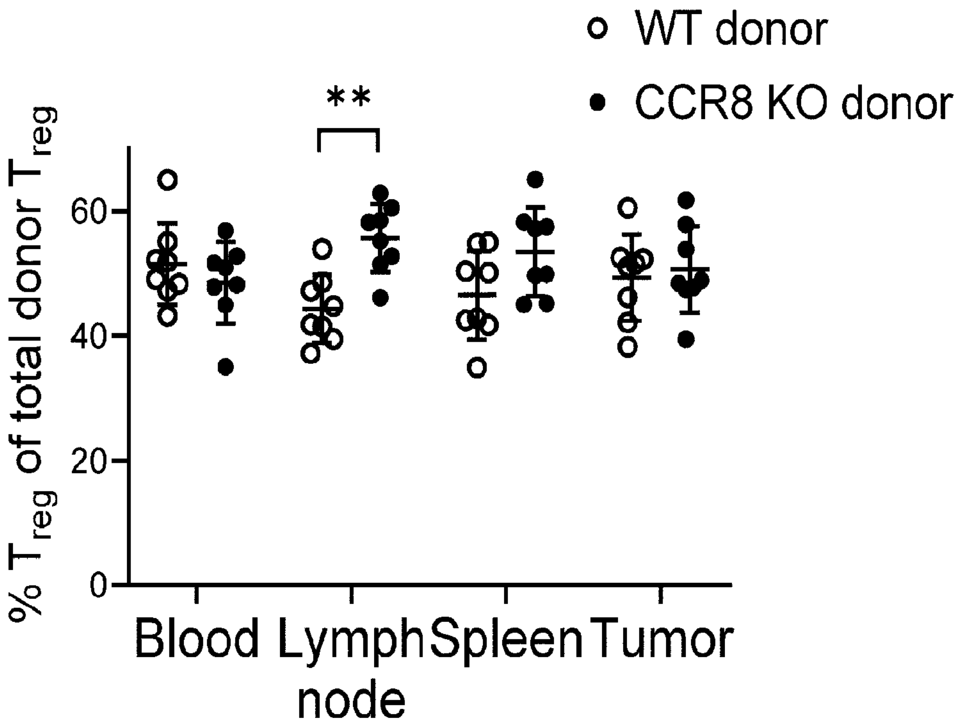

To further interrogate the relative contribution of CCR8 blockade versus Ab-mediated Treg cell depletion in anti-tumor immunity, an anti-mCCR8 Ab (Clone SA214G2 from BioLegend) was engineered into Fc-engaging (anti-CCR8-mIgG2a) and non-Fc-engaging or inert (anti-CCR8-mIgG1-D265A) isoforms, and MC38 tumor-bearing mice were treated with either anti-CCR8-mIgG2a or anti-CCR8-mIgG1-D265A. The mIgG2a isotype strongly engages Fc receptors to promote ADCC and ADCP, while the mIgG1-D265A version does not (Baudino et al., 2008; Nimmerjahn et al., 2010). Treatment with anti-CCR8-mIgG2a induced significant tumor regression (FIGS. 28A and D), whereas anti-CCR8-mIgG1-D265A treatment had no discernable effect on tumor growth in this MC38 model (FIGS. 28A and C), compared to treatment with the IgG2a isotype control (FIGS. 28A and B). Importantly, the frequency of Tregs in tumors was reduced by 75% following treatment with anti-CCR8-mIgG2a whereas anti-CCR8-mIgG1-D265A treatment did not cause a drop in the frequency of tumor Tregs (FIG. 28E). This mirrors the result of the in vitro experiments showing that whereas mAb 4A19 mediated depletion of tumor Tregs, an anti-CCR8 Ab with an inert backbone (anti-CCR8-inert) did not deplete Tregs, suggesting that target-mediated FcγR coengagement through the of backbone is required for Treg depletion (Example 22). It is also similar to the result observed with the SA1N tumor model where, although, treatment with anti-CCR8-mIgG1-D265A resulted in partial inhibition of tumor growth (Example 29), the immunosuppressive tumor Tregs were not depleted (FIG. 27B).

Indeed, despite similar binding characteristics, anti-CCR8-mIgG2a effectively cross-linked FcγRIV in the presence of CCR8-expressing target cells, while the CCR8-mIgG1-D265A isoform did not (data not shown; see Campbell et al., 2021). It was also verified that both the anti-CCR8-mIgG2a and anti-CCR8-mIgG1-D265A Abs blocked CCL1 binding to similar extents (data not shown; see Campbell et al., 2021).

It can be concluded that CCR8 blockade is not generally required for anti-tumor activity, but in certain highly immunogenic tumors, such as SA1N, blockade of CCL1 binding may result in partial inhibition of tumor growth due to an increase in pro-inflammatory cytokines. Greater tumor regression is produced by the depletion of immunosuppressive tumor Tregs, which requires an Fc-engaging anti-CCR8 Ab.

FOXP3$^+$ Treg Migration into Tumors Is CCR8-Independent

As an orthogonal approach, mixed bone marrow chimeras were conducted with congenic Ccr8$^{+/+}$ and Ccr8$^{-/-}$ donor bone marrow to determine whether CCR8 promotes chemotactic migration of Tregs into developing tumors.

Bone Marrow Chimera

Female recipient mice (WT-CD45.2-Thyl.1; Jackson Laboratory) were given 2 doses of 4.5 Gy 3 h apart, followed by intravenous delivery of congenic CCR8$^{+/+}$ (WT-CD45.1-Thyl1.2; Jackson Laboratory) and CCR8$^{-/-}$ (CCR8KO/B6N-CD45.2; Jackson Laboratory) bone marrow. Mice were maintained on antibiotic water, monitored for 8 weeks, and bled at 8 weeks post-transplant to assess donor cell reconstitution. $10^6$ MC38 cells were then implanted SC. Tumors, whole blood, lymph nodes, and splenocytes were harvested after 12 days for immune-monitoring.

Following the 8-week reconstitution phase, equivalent donor immune cell reconstitution was observed in the blood (data not shown). Recipient mice were then subcutaneously implanted with MC38 tumors. CCR8-deficient FOXP3$^+$ cells accumulated in tumors similarly to their wild-type counterparts (FIG. 28F), confirming that FOXP3$^+$ Treg migration into tumors is CCR8-independent.

Example 31

Anti-CCR8-Mediated Treg Depletion Enhances Memory Potential of Tumor-Specific CD8$^+$ T Cells The effect of Treg depletion on the generation of long-lived memory CD8$^+$ T cells recognizing the tumor antigen, AH1 (Huang et al., 1996), was measured.

BALB/c mice were subcutaneously injected with $10^6$ CT26 tumor cells and randomized when tumors reached a volume of 100-120 mm$^3$. Mice were treated retro-orbitally with 200 μg per dose of anti-CCR8-mIgG2a and anti-mCTLA-4-IgG2a treatment Abs or an IgG2a isotype control on Days 1, 4, and 8 after staging. Tumors were harvested on Day 9, and surgically resected on Day 11. After 3 months, mice were bled to quantify AH-1 specific CD8$^+$ T cells. Mice were challenged with $10^7$ CFU recombinant *Listeria monocytogenes* expressing the AH-1 peptide (LM-AH1A5) intravenously. *Listeria* was cultured in sterile Brain Heart Infusion Broth, Modified (Teknova Inc., Hollister, CA) overnight to achieve stationary phase culture of $10^9$ CFU/ml and then diluted with Hank's Balanced Salt solution (HBSS) to $10^8$ CFU/ml for immunization. Five days post-challenge, spleen and blood were harvested and processed for flow cytometry.

Figure 29A:
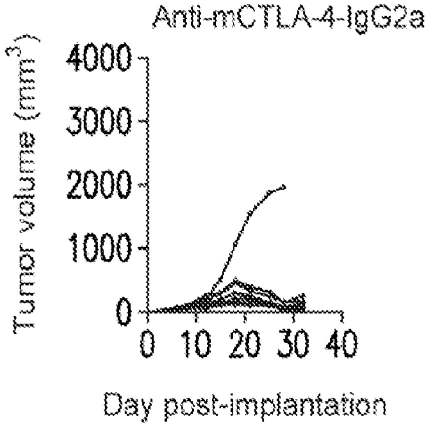
Figure 29B:
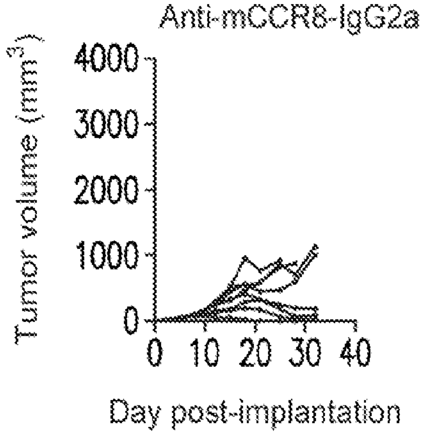
Figure 29C:
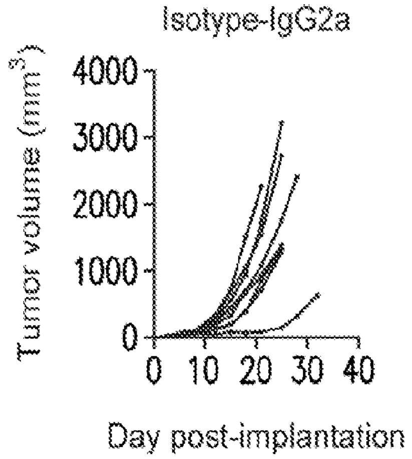
Figure 29D:
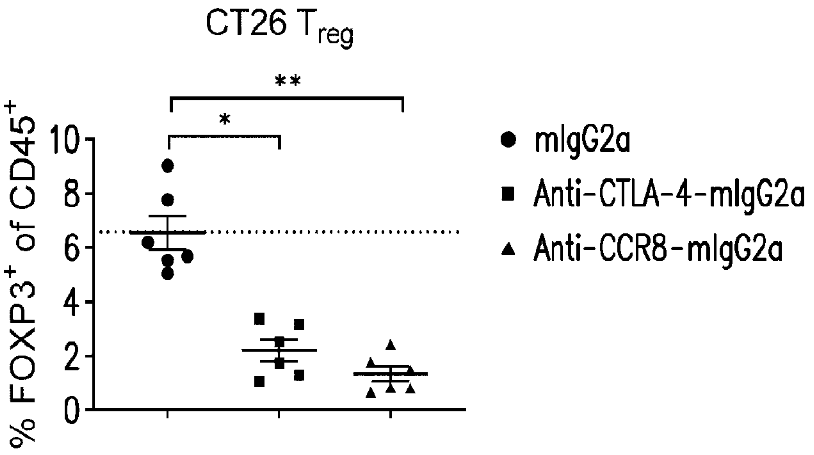
Figure 29E:
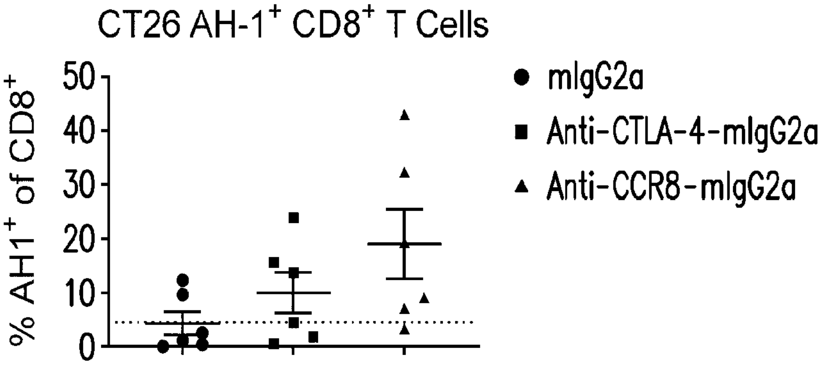
Figure 29F:
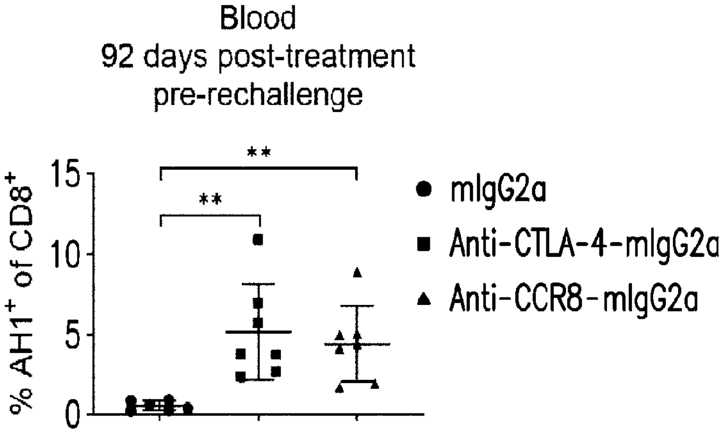
Figure 29G:
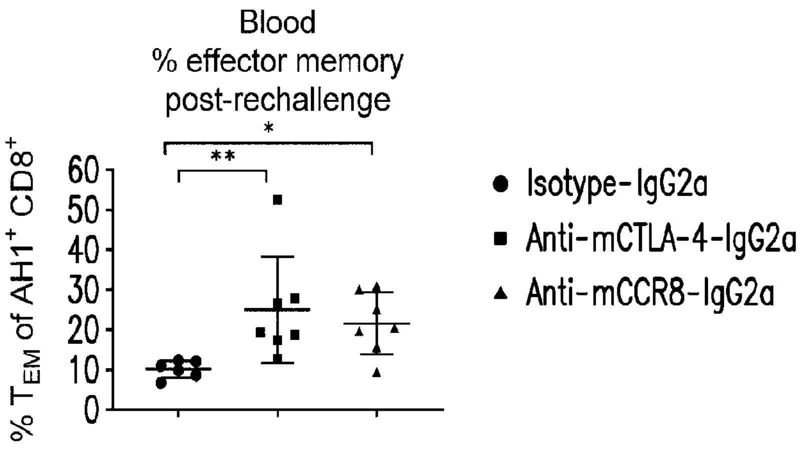
Figure 29H:
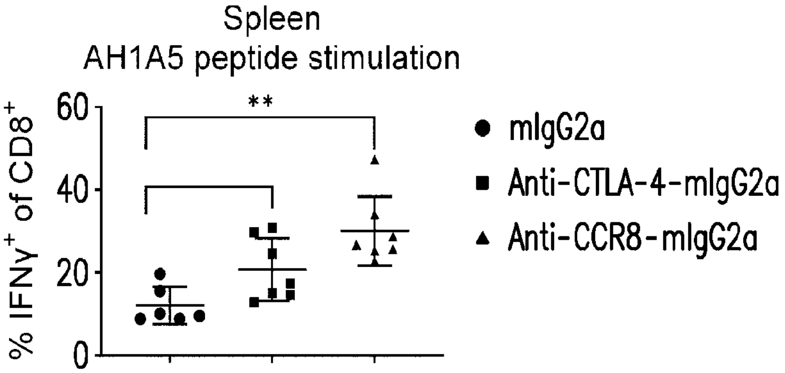
Figure 29I:
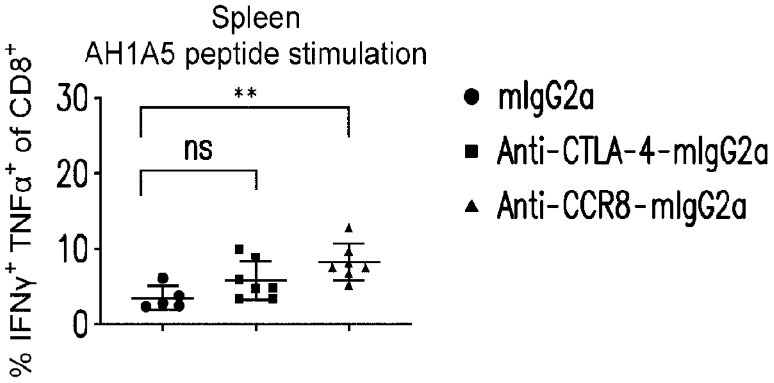

As expected, anti-mCTLA4-IgG2a and anti-CCR8-mIgG2a induced potent anti-tumor responses (FIGS. 29A and B) compared to the control (FIG. 29C), and Treg depletion (FIG. 29D). One day after the last treatment, the frequency of AH-1 tetramer$^+$ cells from resected tumors was trending higher in mice treated with either anti-mCTLA-4-IgG2a or anti-CCR8-mIgG2a relative to control treated mice (FIG. 29E), and AH-1 tetramer$^+$ cells remained elevated in the blood and spleen 3 months after resection (FIG. 29F). Upon challenge with a *Listeria monocytogenes* strain expressing AH-1 to assess AH-1 specific memory recall responses, mice initially treated with either anti-mCTLA-4-IgG2a or anti-CCR8-mIgG2a mounted larger recall expansions of AH-1 tetramer$^+$ effector memory cells compared to control mice (FIG. 29G).

Anti-CCR8 treated mice also had a significantly larger magnitude of IFNγ$^+$ and polyfunctional IFNγ$^+$TNFα$^+$ CD8$^+$ T cells in the spleen after AH1A5 peptide stimulation (FIGS. 29H and 29I), demonstrating that treatment of tumor-bearing mice with anti-CCR8-mIgG2a results in a boost in the frequency of tumor antigen-specific CD8$^+$ T cells with heightened effector functions.

Example 32

Differential Expression of CCR8 on Tumor Cells

Gene expression data for CCR8 and CD8A was used to prioritize tumor types that would benefit from treatment with an anti-CCR8 Ab. The RNA-seq gene expression data from bladder urothelial carcinoma (BLCA), breast invasive carcinoma (BRCA), cervical squamous cell carcinoma and endocervical adenocarcinoma (CESC), colon adenocarcinoma (COAD), esophageal carcinoma (ESCA), glioblastoma multiforme (GBM), Head and Neck squamous cell carcinoma (HNSC), kidney chromophobe (KICH), kidney renal clear cell carcinoma (KIRC), kidney renal papillary cell carcinoma (KIRP), acute myeloid leukemia (LAML), brain lower grade glioma (LGG), liver hepatocellular carcinoma (LIHC), lung adenocarcinoma (LUAD), lung squamous cell carcinoma (LUSC), mesothelioma (MESO), ovarian serous cystadenocarcinoma (OV), pancreatic adenocarcinoma (PAAD), pheochromocytoma and paraganglioma (PCPG), prostate adenocarcinoma (PRAD), rectum adenocarcinoma (READ), sarcoma (SARC), skin cutaneous melanoma (SKCM), stomach adenocarcinoma (STAD), THCA, UCEC and UVM were analyzed from data generated by the TCGA Research Network accessed at https://www.cancer.gov/tcga. The Therapeutically Applicable Research to Generate Effective Treatments (TARGET, https://ocg.cancer.gov/programs/target) initiative, data available at https://portal.gdc.cancer.gov/projects and M2GEN Oncology Research Information Exchange Network (ORIEN) https://www.oriencancer.org/ datasets were used to explore hematological tumors.

TMM normalized log 2 transformed CPM values from CCR8 and CD8A and the ratio of CCR8/CD8A were compared across tumor types. HNSC, LUAD, STAD, LUSC, PAAD, READ, ESCA, BRCA, COAD, CESC, follicular lymphoma acute lymphocytic leukemia and lymphoma were found to have the highest relative expression of CCR8 across the tumor types explored. KIRC, LUAD, LUSC, SKCM, STAD, CESC, MESO, HNSC, PAAD and BRCA express the highest relative expression of CD8A across tumor types. The ratio of CD8A/CCR8 was used to enrich for CD8A positive tumors that also have CCR8 expression. HNSC, STAD, LUAD BRCA, LUSC, PAAD, LAML, CESC, SKCM and MESO express the highest relative expression of CD8A/CCR8 across tumor types analyzed.

The relatively high expression of CCR8 and CD8A, and their high CCR8/CD8A ratio, identify HNSC, LUAD, STAD, LUSC, PAAD, READ, ESCA, BRCA, COAD, CESC, follicular lymphoma, acute lymphocytic leukemia and lymphoma as tumor types that are expected to be particularly amenable to treatment with an anti-CCR8 Ab.

Example 33

CCR8 Expression in Multiple Human Cancers

To profile CCR8 expression across multiple cancer types to support indication selection, with the underlying hypothesis that tumor types with higher levels of CCR8 expression are most likely to respond to CCR8 mAb therapy, immunohistochemistry (IHC) was conducted in 17 cancer types or subtypes from two sets of samples (TR-TP and MTB sets).

The TR-TP sample set comprised full-size formalin-fixed, paraffin-embedded (FFPE) slides of 6 tumor types/subtypes including colorectal adenocarcinoma (CRC), head and neck squamous cell carcinoma (HNSCC), non-small cell lung adenocarcinoma (NSCLC-AD), non-small cell lung squamous cell carcinoma (NSCLC-SQC), pancreatic carcinoma, and small cell lung carcinoma (SCLC), with 14-24 samples per tumor type, were studied. FFPE tissue samples were obtained from various commercial tissue vendors.

In addition, multi-tumor blocks (MTBs) containing 16 tumor types/subtypes including bladder, breast, cervical, CRC, endometrial, gastric, GBM, HNSCC, melanoma, NHL, NSCLC-AD, NSCLC-SQC, ovarian, RCC, prostate, and pancreatic carcinoma, with 20 cases/tumor types, were studied. Each MTB contained 5 cases of a single indication per FFPE block and 1 hyperplastic tonsil as positive control. The MTBs were custom made by Discovery Life Sciences.

To detect CCR8 tissue binding, an automated IHC assay was developed and validated with a commercial mouse anti-hCCR8 mAb, Clone 433H (BD Biosciences), and the Leica Bond RX System (Leica Biosystems, Buffalo Grove, IL). Slides were deparaffinized and rehydrated following routine histology procedures. Wet slides were loaded onto the Leica Bond RX automated IHC stainer for Heat Induced Epitope Retrieval (HIER) and staining. HIER was performed with the Leica Bond retrieval solution ER2 (pH 9) at 100° C. for 30 min, and CCR8 IHC staining was done with the Bond polymer refine detection system (Leica). Briefly, peroxidase blocking (Leica) was performed for 10 min followed by non-specific binding blocking using Dako serum-free protein block (Agilent, Santa Clara, CA) supplemented with 0.5% human gamma globulins (Sigma) for 20 min. The 433H primary Ab was incubated for 60 min at 0.25 μg/ml followed by rabbit anti-mouse linker and then anti-rabbit Poly-HRP-IgG (Leica) for 8 min each. Finally, slides were reacted with the DAB substrate-chromogen solution (Leica) for 10 min. Slides were then counterstained with hematoxylin (Leica) for 5 min and dehydrated, cleared, and coverslipped following routine histological procedures. Stained slides were scanned using a Leica AT Turbo scanner and whole-slide image analysis was performed using HALO® software (Indica Labs, Albuquerque, N.Mex.). CCR8 expression was reported as the percentage of positive cells out of total cells within the tumor region. In a small subset of samples, when image analysis score did not produce an accurate result as deemed by a Board-certified pathologist, manual visual scoring was performed by the pathologist.

Strong CCR8 positive staining was primarily distributed in a subset of immune cells showing both membranous and cytoplasmic patterns. Weak to moderate cytoplasmic staining in tumor cells was also observed in a small number of cases. Whole-slide image analysis of $CCR8^+$ cells in the TR-TP full-size tissue sections is shown in FIG. 30A, while whole-slide image analysis of $CCR8^+$ cells in the MTB set is shown in FIG. 30B. Both the TR-TP and the MTB data sets indicate that among the 17 tumor types evaluated, CCR8 expression was most abundant in HNSCC and least abundant in GBM. In order of highest to lowest CCR8 expression, the tumor cohorts ranked as follows: HNSCC, cervical, CRC, NSCLC-SCC, NSCLC-ADC, pancreatic, gastric, bladder, breast carcinomas, ovarian cancer and GBM. The RCC, prostate, melanoma, endometrial and NHL tumor cohorts showed similar levels of CCR8 expression and were lower than the expression observed in the breast cancer tumor cohort.

Based on the hypothesis that tumors with high CCR8 expression are more likely to respond to CCR8 mAb therapy, these tumor profiling data support the prioritization of indication selection to HNSCC, cervical, CRC, NSCLC-SCC, NSCLC-ADC, pancreatic, gastric, bladder, and breast cancers.

Example 34

Phase ½ Clinical Study of Anti-CCR8 in Treating Cancer

A phase ½ study of the 4A19 anti-CCR8 mAb administered as monotherapy and in combination with the anti-PD-1 mAb, nivolumab, is conducted in subjects having select advanced solid tumors patients, namely NSCLC, SCCHN, CRC, gastric/gastroesophageal (GE) junction, and cervical cancer, to assess, among other things, the safety, tolerability and preliminarily the efficacy of administering 4A19 as a single agent and as a combination therapy with nivolumab.

Study Design

This study is composed of 4 parts: 4A19 administered as monotherapy in dose escalation (Part 1A) and dose expansion (Part 2A), and 4A19 administered in combination with nivolumab in dose escalation (Part 1B) and expansion (Part 2B).

In the dose escalation stage, to identify suitable doses of anti-CCR8 a range of doses of 4A19 is administered to at least 3 subjects for each dose, except for the lowest 2 dose levels of 4A19 monotherapy consisting of at least 1 subject per dose level to minimize the number of participants receiving 4A19 at potentially sub-efficacious doses. In Part 1A, 4A19 is administered intravenously (IV) to subjects at a flat dose of 0.3, 1, 3, 10, 30, 100, 300 and 800 mg, once every 2 weeks (Q2W). The first-in-human (FIH) starting flat dose of 0.3 mg (4 μg/kg) IV Q2W for 4A19 was derived using the totality of data generated from a mix of pharmacology- and toxicology-based approaches with the goal of ensuring adequate safety while minimizing the participants' exposure to potentially sub-efficacious doses and risk of cytokine release.

In Part 1B, 4A19 is administered intravenously (IV) to subjects at the same flat doses in combination with nivolumab administered IV at the FDA-approved flat dose of 480 mg once every 4 weeks (Q4W).

For dose expansion, single-arm and randomized cohorts including different tumor types and dose levels from escalation are opened to administer monotherapy and combination therapy to at least 20 subjects per cohort.

All subjects complete up to 3 study periods:

(a) screening (up to 28 days), during which subjects are evaluated to verify they meet eligibility criteria and a fresh tumor biopsy is provided;

(b) treatment (up to 26 cycles of study therapy [104 weeks] from first treatment regardless of treatment delays, 28 days per cycle); and (c) follow-up, including safety and survival follow-up (up to 2 years following the end of treatment [EOT]) periods). The maximum duration of study participation is about 4 years (up to 28 days of screening, treatment of up to 2 years, and follow-up of up to 2 years).

The Ab drugs are administered to the subjects until progression, unacceptable toxicity, withdrawal of consent, completion of 26 cycles of study therapy (104 weeks), or the study ends, whichever occurs first.

TABLE 10

SEQ ID NOs. and Amino acid Sequence Summary

| SEQ ID NO. | Description of Sequence | Amino acid Sequence |
|---|---|---|
| 1 | Amino acid sequence of human CCR8 | MDYTLDLSVT TVTDYYYPDI FSSPCDAELI QTNGKLLLAV FYCLLFVFSL LGNSLVILVL VVCKKLRSIT DVYLLNLALS DLLFVFSFPF QTYYLLDQWV FGTVMCKVVS GFYYIGFYSS MFFITLMSVD RYLAVVHAVY ALKVRTIRMG TTLCLAVWLT AIMATIPLLV FYQVASEDGV LQCYSFYNQQ TLKWKIFTNF KMNILGLLIP FTIFMFCYIK ILHQLKRCQN HNKTKAIRLV LIVVIASLLF WVPFNVVLFL TSLHSMHILD GCSISQQLTY ATHVTEIISF THCCVNPVIY AFVGEKFKKH LSEIFQKSCS QIFNYLGRQM PRESCEKSSS CQQHSSRSSS VDYIL |
| 2 | Amino acid residues 15-21 of human CCR8 sequence | YYYPDIF |
| 3 | Amino Acid Sequence for $V_H$ in mAb 16B13 | EVQLVESGGG LVQPGGSLRL SCAASGFTFS SFNMNWVRQA PGKGLEWISY ISSGSTTIAH ADSVKGRFTI SRDNAKNSLY LQMNSLRDED TAVYYCVRRL KGSFDYWGQG TLVTVSS |
| 4 | Amino Acid Sequence for $N_H$ in mAb 14S15 | EVQLVEFGGG LVQPKGSLKL SCVVSGFRFN PYAMNWVRQA PGKGLEWLGR IRSKSNNYET YYADSVKDRF IISRDDSQKM VYLQMNNVKT EDTAMYYCVG YSDLYVLDYW GQGTSVTVSS |
| 5 | Amino Acid Sequence for $N_H$ in mAb 18Y12 | QVQLQQSGAE LVRPGASVTL SCKASGYTFT DYEMHWVKQT PVHGLEWIGA IDPKTGSTAY NQKFKGKAIM TADKSSSTAY MELRSLTSED SvvYYCTGLR RFVYWGQGTP VTVSA |
| 6 | Amino Acid Sequence for $V_H$ in mAb 4A19 | QVQLVQSGAE VKKPGASVKV SCKASGYTFT DSEMHWVRQA TGQGLEWMGA IQPETGGTAY NQKFKARVTM TRDTSISTAY MELSSLRSED TAVYYCARRR RNFDYWGQGT LVTVSS |
| 7 | Amino Acid Sequence for $V_H$ in mAb 2M18 | EVQLVESGGG LVQPGGSLRL SCVVSGFTFS NFNMIWVRQV PGKGLEWISH ISRGGTTINH ADSVKGRFTI SRDNAKNSLY LQMNSLRDED TAVYYCARRR LGVFDYWGQG TLVTVSS |
| 8 | Amino Acid Sequence for $V_H$ in mAb 15C17 | QVQLVESGGG LVQPGGSLRL SCAASGFTFS SYDMNWVRQA PGKGLEWISY ISSSNGNKHH ADSVKGRFTI SRDNAENSLY LQMNSLRDED TAVYYCARRR QGVFDIWGQG TLVTVSS |
| 9 | Amino Acid Sequence for $V_H$ in mAb 13T20 | QVQLVESGGG LVKPRGSLRL SCAASGFTFS VAWMHWVRQA PGKGLEWVGR IKSKTDGGTT DYATPVKGRF TISRDDSKNT LYLQMHSLKT EDTAVYYCTV VTMVRGVLYD FWGQGTLVTV SS |

TABLE 10-continued

SEQ ID NOs. and Amino acid Sequence Summary

| SEQ ID NO. | Description of Sequence | Amino acid Sequence |
|---|---|---|
| 10 | Amino Acid Sequence for $V_H$ in mAb 10R3 | QVQLVESGGG VVQPGRSLRL SCAASGFTFS SYAMHWVRQA PGKGLEWVGI ISYDGSNKYY ADSVKGRFTI SRDNSKNTLY LQMNSLRAED TALYSCARVP NWRGAFDIWG QGTMVTVSS |
| 11 | Amino Acid Sequence for $V_H$ in mAb 8D55 | QVQLVESGGG LVQPGGSLRL SCAASGFTFS NYNMIWVRQT PGKGLEWISY ISSSRSIISY ADSVKGRFTI SRDNAKNSLY LQMNSLRDED TAVYYCARRW KGVFDYWGQG TLVTVSS |
| 12 | Amino Acid Sequence for $V_H$ in mAb 1V11 | QVQLVESGGG VVQPGRSLRL SCAASGFTFS NYAMHWVRQA PGKGLDWLAV ISYDGSNKYH SDSVKGRFTI SRDNSKNTLY LQINSLRAED AAVYYCARRG ELGIGGFDYW GQGTLVTVSS |
| 13 | Amino Acid Sequence for $V_H$ in mAb 11K16 | QVQLVESGGG LVLPGGSLRL SCAASGFTFS SNNMIWVRQA PGKGLEWVSY ISSSSSTISY ADSVRGRFTI SRDNAKNSLF LQMNSLRDED TAVYYCARRW RGVFDYWGQG TLVTVSS |
| 14 | Amino Acid Sequence for $V_H$ in mAb 12F27 | QVQLVESGGG VVQPGRSLRL SCAASGFSFR SYGIHWVRQA PGKGLEWVAV ISYEGSNKRY ADSVKGRFTI SRDNSKSTLS LQMNSLRAED TAVYYCAKGR RPSGEGAFDI WGQGTMVTVS S |
| 15 | Amino Acid Sequence for $V_L$ in mAb 16B13 | DIQMTQSPSS LSASVGDRVT ITCRASQGIS SWLAWYQQKP EKAPKSLIYG ASRLQSGVPS RFSGSGSGTD FTLTISSLQP EDFATYYCQQ YNSYPPTFGQ GTKVEIK |
| 16 | Amino Acid Sequence for $V_L$ in mAb 14S15 | DIVMTQAAPS VPVTPGESVS ISCRSSKSLL HSNGNTFLYW FLQRPGQSPQ LLIYRMSNLA SGVPHRFSGS GSGTAFTLRI SRVEAEDVGV YYCMQHLEYP FTFGSGTKLE IK |
| 17 | Amino Acid Sequence for $V_L$ in mAb 18Y12 | DVVMTQTPLS LPVSLGDQAS ISCRSRQSLV HSSGYTYLHW YLQKPGQSPK LLIYRVSNRF SGVPDRFSGS GSGTDFTLKI SRVEAEDLGV YFCSQSTHVP FTFGSGTKLE IK |
| 18 | Amino Acid Sequence for $V_L$ in mAb 4A19 | DIVMTQTPLS LSVTPGQPAS ISCRSSQSLF HSSGNTYLHW YLQKPGQPPQ LLIYKVSNRF SGVPDRFSGS GSGTDFTLKI SRVEAEDVGV YYCSQSTHVP FTFGQGTKLE IK |
| 19 | Amino Acid Sequence for $V_L$ in mAb 2M18 | DIQMTQSPSS LSASVGDRVT ITCRASQGIS SWLAWYQQKP EKAPKSLIYA ASSLQSGVPS RFSGSGSGTD FTLTISSLQP EDFATYYCQQ YNSYPPTFGQ GTKVEIK |
| 20 | Amino Acid Sequence for $V_L$ in mAb 15C17 | DIVMTQSPSS LSASVGDRVT ITCRASQGIS RWLAWYQQKP EKAPKSLIYA ASSLQSGVPS RFSGSGSGTD FTLTISSLQP EDFATYYCQQ YNSYPPTFGG GTKVEIK |
| 21 | Amino Acid Sequence for $V_L$ in mAb 13T20 | DIVMTQSPGT LSLSPGERAT LSCRASQSVS SNYLAWYQQK PGQAPRLLIY GASSRATGIP DRFSGSGSGT DFTLTISRLE PEDFAVYYCQ QYGSSRTFGG GTKVEIK |
| 22 | Amino Acid Sequence for $V_L$ in mAb 10R3 | EIVLTQSPDF QSVTPKEKVT ITCRASQSIG SHLHWYQQKP DQSPKLLIKY ASQSFSGVPS RFSGSGSGTD FSLTINSLET EDAATYFCHQ SYSLPLTFGG GTKVEIK |
| 23 | Amino Acid Sequence for $V_L$ in mAb 8D55 | DIVMTQSPSS LSASVGDRVT ITCRASQGIS SWLAWYQQKP EKAPKSLIYA ASSLQSGVPS RFSGSGSGTD FTLTISSLQP EDFATYYCQQ YNSYPPTFGQ GTKVEIK |
| 24 | Amino Acid Sequence for $V_L$ in mAb 1V11 | DIVMTQTPLS SPVTLGRPAS ISCRSSRSLV HTDGNTYLNW LQQRPGQPPR LLIYKISNRF SGVPDRFSGS GAGTDFTLKI TRVEAEDVGV YYCMQATQFP LTFGPGTKVD IK |

TABLE 10-continued

| SEQ ID NOs. and Amino acid Sequence Summary | | |
|---|---|---|
| SEQ ID NO. | Description of Sequence | Amino acid Sequence |
| 25 | Amino Acid Sequence for $V_L$ in mAb 11K16 | DIVMTQSPSS LSASVGDRVT ITCRASQGIS SWLAWYQQKP EKAPKSLIYA ASSLQSGVPS RFSGSGSGTD FTLTISSLQP EDFATYYCQQ YNSYPPTFGQ GTKVEIK |
| 26 | Amino Acid Sequence for $V_L$ in mAb 12F27 | DIQMTQSPSS LSASVGDRVT ITCRASQGIS SWLAWYQQKP EKAPKSLIYA ASSLQSGVPS RFSGSGSGTD FTLTISSLQP EDFATYYCQQ YNSFPPTFGQ GTKVEIK |
| 27 | Amino Acid Sequence for $V_H$ CDR1 in mAb 16B13 | GFTFSSFNMN |
| 28 | Amino Acid Sequence for $V_H$ CDR2 in mAb 16B13 | YISSGSTTIA HADSVKG |
| 29 | Amino Acid Sequence for $V_H$ CDR3 in mAb 16B13 | RLKGSFDY |
| 30 | Amino Acid Sequence for $V_L$ CDR1 in mAb 16B13 | RASQGISSWL A |
| 31 | Amino Acid Sequence for $V_L$ CDR2in mAb 16B13 | GASRLQS |
| 32 | Amino Acid Sequence for $V_L$ CDR3 in mAb 16B13 | QQYNSYPPT |
| 33 | Amino Acid Sequence for $V_H$ CDR1 in mAb 14S15 | GFRFNPYAMN |
| 34 | Amino Acid Sequence for $V_H$ CDR2 in mAb 14S15 | RIRSKSNNYE TYYADSVKD |
| 35 | Amino Acid Sequence for $V_H$ CDR3 in mAb 14S15 | YSDLYVLDY |
| 36 | Amino Acid Sequence for $V_L$ CDR1 in mAb 14S15 | RSSKSLLHSN GNTFLY |
| 37 | Amino Acid Sequence for $V_L$ CDR2 in mAb 14S15 | RMSNLAS |
| 38 | Amino Acid Sequence for $V_L$ CDR3 in mAb 14S15 | MQHLEYPFT |
| 39 | Amino Acid Sequence for $V_H$ CDR1 in mAb 18Y12 | GYTFTDYEMH |
| 40 | Amino Acid Sequence for $V_H$ CDR2 in mAb 18Y12 | AIDPKTGSTA YNQKFKG |
| 41 | Amino Acid Sequence for $V_H$ CDR3 in mAb 18Y12 | LRRFVY |
| 42 | Amino Acid Sequence for $V_L$ CDR1 in mAb 18Y12 | RSSKSLLHSN GNTFLY |
| 43 | Amino Acid Sequence for $V_L$ CDR2 in mAb 18Y12 | RVSNRFS |
| 44 | Amino Acid Sequence for $V_L$ CDR3 in mAb 18Y12 | SQSTHVPFT |
| 45 | Amino Acid Sequence for $V_H$ CDR1 in mAb 4A19 | GYTFTDSEMH |
| 46 | Amino Acid Sequence for $V_H$ CDR2 in mAb 4A19 | AIQPETGGTA YNQKFKA |
| 47 | Amino Acid Sequence for $V_H$ CDR3 in mAb 4A19 | RRRNFDY |
| 48 | Amino Acid Sequence for $V_L$ CDR1 in mAb 4A19 | RSSQSLFHSS GNTYLH |

TABLE 10-continued

| SEQ ID NOs. and Amino acid Sequence Summary | | |
|---|---|---|
| SEQ ID NO. | Description of Sequence | Amino acid Sequence |
| 49 | Amino Acid Sequence for $V_L$ CDR2 in mAb 4A19 | KVSNRFS |
| 50 | Amino Acid Sequence for $V_L$ CDR3 in mAb 4A19 | SQSTHVPFT |
| 51 | Amino Acid Sequence for $V_H$ CDR1 in mAb 2M18 | GFTFSNFNMI |
| 52 | Amino Acid Sequence for $V_H$ CDR2 in mAb 2M18 | HISRGGTTIN HADSVKG |
| 53 | Amino Acid Sequence for $V_H$ CDR3 in mAb 2M18 | RLGVFDY |
| 54 | Amino Acid Sequence for $V_L$ CDR1 in mAb 2M18 | RASQGISSWL A |
| 55 | Amino Acid Sequence for $V_L$ CDR2 in mAb 2M18 | AASSLQS |
| 56 | Amino Acid Sequence for $V_L$ CDR3 in mAb 2M18 | QQYNSYPPT |
| 57 | Amino Acid Sequence for $V_H$ CDR1 in mAb 15C17 | GFTFSSYDMN |
| 58 | Amino Acid Sequence for $V_H$ CDR2 in mAb 15C17 | YISSSNGNKH HADSVKG |
| 59 | Amino Acid Sequence for $N_H$ CDR3 in mAb 15C17 | RQGVFDI |
| 60 | Amino Acid Sequence for $V_L$ CDR1 in mAb 15C17 | RASQGISRWL A |
| 61 | Amino Acid Sequence for $V_L$ CDR2 in mAb 15C17 | AASSLQS |
| 62 | Amino Acid Sequence for $V_L$ CDR3 in mAb 15C17 | QQYNSYPPT |
| 63 | Amino Acid Sequence for $V_H$ CDR1 in mAb 13T20 | GFTFSVAWMH |
| 64 | Amino Acid Sequence for $V_H$ CDR2 in mAb 13T20 | RIKSKTDGGT TDYATPVKG |
| 65 | Amino Acid Sequence for $V_H$ CDR3 in mAb 13T20 | VTMVRGVLYD F |
| 66 | Amino Acid Sequence for $V_L$ CDR1 in mAb 13T20 | RASQSVSSNY LA |
| 67 | Amino Acid Sequence for $V_L$ CDR2 in mAb 13T20 | GASSRAT |
| 68 | Amino Acid Sequence for $V_L$ CDR3 in mAb 13T20 | QQYGSSRT |
| 69 | Amino Acid Sequence for $V_H$ CDR1 in mAb 10R3 | GFTFSSYAMH |
| 70 | Amino Acid Sequence for $V_H$ CDR2 in mAb 10R3 | IISYDGSNKY YADSVKG |
| 71 | Amino Acid Sequence for $V_H$ CDR3 in mAb 10R3 | VPNWRGAFDI |
| 72 | Amino Acid Sequence for $V_L$ CDR1 in mAb 10R3 | RASQSIGSHL H |
| 73 | Amino Acid Sequence for $V_L$ CDR2 in mAb 10R3 | YASQSFS |

TABLE 10-continued

SEQ ID NOs. and Amino acid Sequence Summary

| SEQ ID NO. | Description of Sequence | Amino acid Sequence |
|---|---|---|
| 74 | Amino Acid Sequence for $V_L$ CDR3 in mAb 10R3 | HQSYSLPLT |
| 75 | Amino Acid Sequence for $V_H$ CDR1 in mAb 8D55 | GFTFSNYNMI |
| 76 | Amino Acid Sequence for $V_H$ CDR2 in mAb 8D55 | YISSSRSIIS YADSVKG |
| 77 | Amino Acid Sequence for $V_H$ CDR3 in mAb 8D55 | RWKGVFDY |
| 78 | Amino Acid Sequence for $V_L$ CDR1 in mAb 8D55 | RASQGISSWL A |
| 79 | Amino Acid Sequence for $V_L$ CDR2 in mAb 8D55 | AASSLQS |
| 80 | Amino Acid Sequence for $V_L$ CDR3 in mAb 8D55 | QQYNSYPPT |
| 81 | Amino Acid Sequence for $V_H$ CDR1 in mAb 1V11 | GFTFSNYAMH |
| 82 | Amino Acid Sequence for $V_H$ CDR2 in mAb 1V11 | YDGSNKYHSD SVKG |
| 83 | Amino Acid Sequence for $V_H$ CDR3 in mAb 1V11 | RGELGIGGFD Y |
| 84 | Amino Acid Sequence for $V_L$ CDR1 in mAb 1V11 | RSSRSLVHTD GNTYLN |
| 85 | Amino Acid Sequence for $V_L$ CDR2 in mAb 1V11 | KISNRFS |
| 86 | Amino Acid Sequence for $V_L$ CDR3 in mAb 1V11 | MQATQFPLT |
| 87 | Amino Acid Sequence for $V_H$ CDR1 in mAb 11K16 | GFTFSSNNMI |
| 88 | Amino Acid Sequence for $V_H$ CDR2 in mAb 11K16 | YISSSSSTIS YADSVRG |
| 89 | Amino Acid Sequence for $V_H$ CDR3 in mAb 11K16 | RWRGVFDY |
| 90 | Amino Acid Sequence for $V_L$ CDR1 in mAb 11K16 | RASQGISSWL A |
| 91 | Amino Acid Sequence for $V_L$ CDR2 in mAb 11K16 | AASSLQS |
| 92 | Amino Acid Sequence for $V_L$ CDR3 in mAb 11K16 | QQYNSYPPT |
| 93 | Amino Acid Sequence for $V_H$ CDR1 in mAb 12F27 | GFSFRSYGIH |
| 94 | Amino Acid Sequence for $V_H$ CDR2 in mAb 12F27 | VISYEGSNKR YADSVKG |
| 95 | Amino Acid Sequence for $V_H$ CDR3 in mAb 12F27 | GRRPSGEGAF DI |
| 96 | Amino Acid Sequence for $V_L$ CDR1 in mAb 12F27 | RASQGISSWL A |
| 97 | Amino Acid Sequence for $V_L$ CDR2 in mAb 12F27 | AASSLQS |
| 98 | Amino Acid Sequence for $V_L$ CDR3 in mAb 12F27 | QQYNSFPPT |

TABLE 10-continued

| SEQ ID NO. | Description of Sequence | Amino acid Sequence |
|---|---|---|
| | SEQ ID NOs. and Amino acid Sequence Summary | |
| 99 | Amino Acid Sequence for heavy chain mAb of 16B13 | EVQLVESGGG LVQPGGSLRL SCAASGFTFS SFNMNWVRQA PGKGLEWISY ISSGSTTIAH ADSVKGRFTI SRDNAKNSLY LQMNSLRDED TAVYYCVRRL KGSFDYWGQG TLVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APELLGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPGK |
| 100 | Amino Acid Sequence for heavy chain mAb of 14S15 | EVQLVEFGGG LVQPKGSLKL SCVVSGFRFN PYAMNWVRQA PGKGLEWLGR IRSKSNNYET YYADSVKDRF IISRDDSQKM VYLQMNNVKT EDTAMYYCVG YSDLYVLDYW GQGTSVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKRVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 101 | Amino Acid Sequence for heavy chain mAb of 18Y12 | QVQLQQSGAE LVRPGASVTL SCKASGYTFT DYEMHWVKQT PVHGLEWIGA IDPKTGGSTAY NQKFKGKAIM TADKSSSTAY MELRSLTSED SVVYYCTGLR RFVYWGQGTP VTVSAASTKG PSVFPLAPSS KSTSGGTAAL GCLVKDYFPE PVTVSWNSGA LTSGVHTFPA VLQSSGLYSL SSVVTVPSSS LGTQTYICNV NHKPSNTKVD KRVEPKSCDK THTCPPCPAP ELLGGPSVFL FPPKPKDTLM ISRTPEVTCV VVDVSHEDPE VKFNWYVDGV EVHNAKTKPR EEQYNSTYRV VSVLTVLHQD WLNGKEYKCK VSNKALPAPI EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPGK |
| 102 | Amino Acid Sequence for heavy chain mAb of 4A19 | QVQLVQSGAE VKKPGASVKV SCKASGYTFT DSEMHWVRQA TGQGLEWMGA IQPETGGTAY NQKFKARVTM TRDTSISTAY MELSSLRSED TAVYYCARRR RNFDYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKRVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPG |
| 103 | Amino Acid Sequence for $V_H$ CDR1 in mAb 14S15h | GFRFGPYAMN |
| 104 | Amino Acid Sequence for $V_H$ CDR2in mAb 14S15h | RIRSKSNNYE TYYADSVKD |
| 105 | Amino Acid Sequence for $V_H$ CDR3 in mAb 14S15h | YSDLYVLDY |

TABLE 10-continued

SEQ ID NOs. and Amino acid Sequence Summary

| SEQ ID NO. | Description of Sequence | Amino acid Sequence |
|---|---|---|
| 106 | Amino Acid Sequence for $V_L$ CDR1 in mAb 14S15h | RSSKSLLHSQ GNTFLY |
| 107 | Amino Acid Sequence for $V_L$ CDR2in mAb 14S15h | RMSNLAS |
| 108 | Amino Acid Sequence for $V_L$ CDR3 in mAb 14S15h | MQHLEYPFT |
| 109 | Amino acid residues 12-22 of human CCR8 sequence | VTDYYYPDIFS |
| 110 | Amino Acid Sequence for heavy chain of mAb 12F27 | QVQLVESGGG VVQPGRSLRL SCAASGFSFR SYGIHWVRQA PGKGLEWVAV ISYEGSNKRY ADSVKGRFTI SRDNSKSTLS LQMNSLRAED TAVYYCAKGR RPSGEGAFDI WGQGTMVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKRVE PKSCDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRE EMTKNQVSLT CLVKGFYPSD IAVEWESNGQ PENNYKTTPP VLDSDGSFFL YSKLTVDKSR WQQGNVFSCS VMHEALHNHY TQKSLSLSPG K |
| 111 | Amino Acid Sequence for light chain of mAb 16B13 | DIQMTQSPSS LSASVGDRVT ITCRASQGIS SWLAWYQQKP EKAPKSLIYG ASRLQSGVPS RFSGSGSGTD FTLTISSLQP EDFATYYCQQ YNSYPPTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 112 | Amino Acid Sequence for light chain of mAb 14S15 | DIVMTQAAPS VPVTPGESVS ISCRSSKSLL HSNGNTFLYW FLQRPGQSPQ LLIYRMSNLA SGVPHRFSGS GSGTAFTLRI SRVEAEDVGV YYCMQHLEYP FTFGSGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 113 | Amino Acid Sequence for light chain of mAb 18Y12 | DVVMTQTPLS LPVSLGDQAS ISCRSRQSLV HSSGYTYLHW YLQKPGQSPK LLIYRVSNRF SGVPDRFSGS GSGTDFTLKI SRVEAEDLGV YFCSQSTHVP FTFGSGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 114 | Amino Acid Sequence for light chain of mAb 4A19 | DIVMTQTPLS LSVTPGQPAS ISCRSSQSLF HSSGNTYLHW YLQKPGQPPQ LLIYKVSNRF SGVPDRFSGS GSGTDFTLKI SRVEAEDVGV YYCSQSTHVP FTFGQGTKLE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 115 | Amino Acid Sequence for $V_H$ in mAb 14S15h | EVQLVESGGG LVKPGGSLRL SCAASGFRFG PYAMNWVRQA PGKGLEWVGR IRSKSNNYET YYADSVKDRF TISRDDSKNT LYLQMNSLKT EDTAVYYCVG YSDLYVLDYW GQGTLVTVSS |
| 116 | Amino Acid Sequence for $V_L$ in mAb 14S15h | DIVMTQTPPS LPVNPGEPAS ISCRSSKSLL HSQGNTFLYW YLQKPGQSPQ LLIYRMSNLA SGVPDRFSGS GSGSDFTLKI SWVEAEDVGV YYCMQHLEYP FTFGPGTKVD IK |

TABLE 10-continued

SEQ ID NOs. and Amino acid Sequence Summary

| SEQ ID NO. | Description of Sequence | Amino acid Sequence |
|---|---|---|
| 117 | Amino Acid Sequence for heavy chain of mAb 14S15h | EVQLVESGGG LVKPGGSLRL SCAASGFRFG PYAMNWVRQA PGKGLEWVGR IRSKSNNYET YYADSVKDRF TISRDDSKNT LYLQMNSLKT EDTAVYYCVG YSDLYVLDYW GQGTLVTVSS ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKRVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPG |
| 118 | Amino Acid Sequence for light chain of mAb 14S15h | DIVMTQTPPS LPVNPGEPAS ISCRSSKSLL HSQGNTFLYW YLQKPGQSPQ LLIYRMSNLA SGVPDRFSGS GSGSDFTLKI SWVEAEDVGV YYCMQHLEYP FTFGPGTKVD IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 119 | Amino Acid Sequence for light chain mAb of 12F27 | DIQMTQSPSS LSASVGDRVT ITCRASQGIS SWLAWYQQKP EKAPKSLIYA ASSLQSGVPS RFSGSGSGTD FTLTISSLQP EDFATYYCQQ YNSFPPTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 120 | Amino acid sequence of mouse CCR8 | MDYTMEPNVT MTDYYPDFFT APCDAEFLLR GSMLYLAILY CVLFVLGLLG NSLVILVLVG CKKLRSITDI YLLNLAASDL LFVLSIPFQT HNLLDQWVFG TAMCKVVSGL YYIGFFSSMF FITLMSVDRY LAIVHAVYAI KVRTASVGTA LSLTVWLAAV TATIPLMVFY QVASEDGMLQ CFQFYEEQSL RWKLFTHFEI NALGLLLPFA ILLFCYVRIL QQLRGCLNHN RTRAIKLVLT VVIVSLLFWV PFNVALFLTS LHDLHILDGC ATRQRLALAI HVTEVISFTH CCVNPVIYAF IGEKFKKHLM DVFQKSCSHI FLYLGRQMPV GALERQLSSN QRSSHSSTLD DIL |

REFERENCES

Abhinandan K R, Martin A C (2008) Analysis and improvements to Kabat and structurally correct numbering of antibody variable domains. *Mol Immunol* 45:3832-3839.

Akinleye A, Rasool Z (2019) Immune checkpoint inhibitors of PD-L1 as cancer therapeutics. *J HematolOncol* 12(92).

Al-Lazikani, Lesk A M, Chothia C (1997) Standard conformations for the canonical structures of immunoglobulins. *J Mol Biol* 273(4):927-48.

Alvisi G, Brummelman J, Puccio S, Mazza E M C, Tomada E P, Losurdo A et al. (2020) IRF4 instructs effector Treg differentiation and immune suppression in human cancer. *J Clin Invest* 130(6):3137-50.

Arce Vargas F, Furness A J S, Solomon I, Joshi K, Mekkaoui L (2017) Fc-optimized anti-CD25 depletes tumor-infiltrating regulatory T cells and synergizes with PD-1 blockade to eradicate established tumors. Immunity 46(4):577-86.

Baitsch L, Legat A, Barba L, Fuertes Marraco S A, Rivals J P et al. (2012) Extended co-expression of inhibitory receptors by human CD8 T-cells depending on differentiation, antigen-specificity and anatomical localization. *PloS One* 7(2): e30852.

Barsheshet Y, Wildbaum G, Levy E, Vitenshtein A, Akinseye C et al. (2017) CCR8$^{+}$FOXp3$^{+}$ Treg cells as master drivers of immune regulation. *Proc Natl Acad Sci USA* 14(23):6086-91.

Baudino L, Shinohara Y, Nimmerjahn F, Furukawa J-I, Nakata M, Martinez-Soria E et al. (2008) Crucial role of aspartic acid at position 265 in the CH2 domain for murine IgG2a and IgG2b Fc-associated effector functions. *J Immunol* 181(9):6664-9.

Brahmer J R, Drake C G, Wollner I, Powderly J D, Picus J et al. (2010) Phase I study of single-agent anti-programmed death-1 (MDX-1106) in refractory solid tumors: safety, clinical activity, pharmacodynamics, and immunologic correlates. *J Clin Oncol* 28:3167-75.

Brahmer J R, Hammers H, Lipson E J (2015) Nivolumab: targeting PD-1 to bolster antitumor immunity. *Future Oncol* 11(9):1307-26.

Brahmer J R, Tykodi S S, Chow L Q, Hwu W J, Topalian S L et al. (2012) Safety and activity of anti-PD-L1 antibody in patients with advanced cancer. *N Engl J Med* 366:2455-65.

Callahan M, Postow M A, Wolchok J D (2016) Targeting T cell co-receptors for cancer therapy. *Immunity* 44(5): 1069-78.

Campbell J R, McDonald B R, Mesko P M, Siemers N O, Singh P B et al. (2021) Fc-optimized anti-CCR8 antibody depletes regulatory T cells in human tumor models. *Cancer Res* (in press).

Chakravarthi B V S K, Nepal S, Varambally S (2016) Genomic and epigenomic alterations in cancer. *Am J Pathol* 186(7): 1724-35.

Chothia C, Lesk A M (1987) Canonical structures for the hypervariable regions of immunoglobulins. *J Mol Biol* 196:901-17.

Chothia C, Lesk A M, Tramontano A, Levitt M, Smith-Gill J S et al. (1989) Conformations of immunoglobulin hypervariable regions. *Nature* 342:877-83.

Dall'Ozzo S, Tartas S, Paintaud G, Cartron G, Colombat P, et al. (2004) Rituximab-dependent cytotoxicity by natural killer cells: influence of FCGR3A polymorphism on the concentration-effect relationship. *Cancer Res* 64:4664-9.

Dépis F, Hu C, Weaver J, McGrath L, Klebanov B et al. (2020) Preclinical evaluation of JTX-1811, an anti-CCR8 antibody with enhanced ADCC activity, for preferential depletion of tumor-infiltrating regulatory T cells [abstract]. In: Proceedings of the Annual Meeting of the American Association for Cancer Research 2020; 2020 Apr. 27-28 and Jun. 22-24. Philadelphia (Pa.): AACR; *Cancer Res* 80(16 Suppl): Abstract nr 4532.

De Simone M, Arrigoni A, Rossetti G et al. (2016) Transcriptional landscape of human tissue lymphocytes unveils uniqueness of tumor-infiltrating T regulatory cells. *Immunity* 5:1135-47.

Drugs.com—Opdivo Approval History: https://www.drugs.com/history/opdivo.html, last accessed Mar. 23, 2020.

European Patent No. EP 1176195, granted May 22, 2013 to Kyowa Hakko Kirin Co.

Farkona et al. (2016) Cancer immunotherapy: the beginning of the end of cancer? *BMC Medicine* 14:73.

Fares C M, Van Allen E M, Drake C G, Allison J P, Hu-Lieskovan S (2019) Mechanisms of resistance to immune checkpoint blockade: why does checkpoint inhibitor immunotherapy not work for all patients? *ASCO Education Book* 39:147-64.

Finotello F, Trajanoski Z (2017) New strategies for cancer immunotherapy: targeting regulatory T cells. *Genome Medicine* 9:10.

Fontenot J D, Gavin M A, Rudensky A Y (2003) Foxp3 programs the development and function of $CD4^{+}CD25^{+}$ regulatory T cells. *Nature Immunol* 4(4):330-6.

Gennari R, Menard S, Fagnoni F, Ponchio L, Scelsi M et al. (2004) Pilot study of the mechanism of action of preoperative trastuzumab in patients with primary operable breast tumors overexpressing HER2. *Clin Cancer Res* 10:5650-5.

Goldman M, Craft B, Hastie M, Repečka K, McDade F et al. (2019) The UCSC Xena platform for public and private cancer genomics data visualization and interpretation. bioRxiv 326470; doi: https://doi.org/10.1101/326470.

Gorelik L, Avgerinos G, Kunes Y, Marasco W A (2017) Preclinical characterization of a novel fully human IgG1 anti-PD-L1 mAb CK-301. In: Proceedings of the American Association for Cancer Research (AACR) Annual Meeting, Apr. 1-5, 2017, *Cancer Res* 77(13 Suppl): Abstract No. 4606.

Guo L, Zhang H, Chen B (2017) Nivolumab as Programmed Death-1 (PD-1) inhibitor for targeted immunotherapy in tumor. *J Cancer* 8(3):410-416.

Hagemann U B, Gunnarsson L, Géraudie S, Scheffler U, Griep R A et al. (2014) Fully human antagonistic antibodies against CCR4 potently inhibit cell signaling and chemotaxis. PLoS ONE 9(7): e103776.

Han S, Toker A, Liu Z Q, Ohashi P S (2019) Turning the tide against regulatory T cells. *Front Oncol* 9: 279.

Harbour BioMed (2020) Harbour BioMed presented its newly discovered anti-human CCR8 novel monoclonal antibodies at the 16th PEGS Boston 2020. Sep. 2, 2020 press release, available at https://www.harbourbiomed.com/news/126.html# (last accessed Feb. 22, 2020).

Haslam A, Prasad V (2019) Estimation of the percentage of us patients with cancer who are eligible for and respond to checkpoint inhibitor immunotherapy drugs. *JAMA Netw Open* 2(5): e192535.

Herbst R S, Soria J C, Kowanetz M, Fine G D, Hamid O et al. (2014) Predictive correlates of response to the anti-PD-L1 antibody MPDL3280A in cancer patients. *Nature* 515: 563-7.

Hezareh M, Hessell A J, Jensen R C, van de Winkel J G, Parren P W (2001) Effector function activities of a panel of mutants of a broadly neutralizing antibody against human immunodeficiency virus type 1. J Virol 75(24): 12161-8.

Hollinger and Hudson (2005) Engineered antibody fragments and the rise of single domains. *Nature Biotech* 23(9):1126-36.

Huang A Y, Gulden P H, Woods A S, Thomas M C, Tong C D et al. (1996) The immunodominant major histocompatibility complex class I-restricted antigen of a murine colon tumor derives from an endogenous retroviral gene product. *Proc Natl Acad Sci USA* 3(18):9730-5.

Huttenhower C, Flamholz A I, Landis J N, Sahi S, Myers C L et al. (2007) Nearest neighbor networks: clustering expression data based on gene neighborhoods. *BMC Bioinformatics* 8:250.

Iida S (2006) Nonfucosylated therapeutic IgG1 antibody can evade the inhibitory effect of serum Immunoglobulin G on antibody-dependent cellular cytotoxicity through its high binding to Fc RIIIa. *Clin Cancer Res* 12(9):2879-87.

Ishida T, Joh T, Uike N, Yamamoto K, Utsunomiya A et al. (2012) Defucosylated anti-CCR4 monoclonal antibody (KW-0761) for relapsed adult T-cell leukemia-lymphoma: a multicenter phase II study. *J Clin Oncol* 30:837-42.

Jenkins R W, Barbie D A, Flaherty K T (2018) Mechanisms of resistance to immune checkpoint inhibitors. *Br J Cancer* 118(1):9-16.

Kabat E A, Wu T T, Bilofsky H, Reid-Miller M, Perry H (1983) Sequence of proteins of immunological interest. Bethesda: National Institute of Health; 1983. 323

Kabat E A, Wu T T, Perry H M, Gottesman K S, Foeller C (1991) Sequences of Proteins of Immunological Interest, $5^{th}$ edn. National Institutes of Health, Bethesda, MD.

Kamada T, Togashi Y, Tay C et al. (2019) $PD-1^{+}$ regulatory T cells amplified by PD-1 blockade promote hyperprogression of cancer. *Proc Natl Acad Sci USA* 116:9999-10008.

Kamta J, Chaar M, Ande A, Altomare D A, Ait-Oudhia S (2017) Advancing cancer therapy with present and emerging immuno-oncology approaches. *Front Oncol* 18(7):64.

Kaufman R J, Sharp P A (1982) Amplification and expression of sequences cotransfected with a modular dihydrofolate reductase complementary DNA gene. *Mol Biol* 159:601-21.
Kavanagh B, O'Brien S, Lee D, Hou Y, Weinberg V, Rini B et al. (2008) CTLA4 blockade expands $FoxP3^+$ regulatory and activated effector $CD4^+$ T cells in a dose-dependent fashion. Blood 112(4):1175-83.
Khattri R, Cox T, Yasayko S-A, Ramsdell F (2003) An essential role for Scurfin in $CD4^+CD25^+$ T regulatory cells. *Nature Immunol* 4(4):337-42.
Korman A J, Engelhardt J, Loffredo J, Valle J, Akter R et al. (2017) Next-generation anti-CTLA-4 antibodies [abstract]. In: Proceedings of the American Association for Cancer Research Annual Meeting 2017; Apr. 1-5, 2017; Washington, DC. Philadelphia (Pa.): AACR; *Cancer Res* 77(13 Suppl): Abstract nr SY09-01.
Kuehn H S, Ouyang W, Lo B, Deenick E K, Niemela J E, Avery D T et al. (2014) Immune dysregulation in human subjects with heterozygous germline mutations in CTLA4. *Science* 345(6204):1623-1627.
Kumar P, Bhattacharya P, Prabhakar B S (2018) A comprehensive review on the role of co-signaling receptors and Treg homeostasis in autoimmunity and tumor immunity. *J Autoimmun* 95:77-99.
Kurose K, Ohue Y, Wada H, Iida S, Ishida T, Kojima T et al. (2015) Phase Ia study of FoxP3+CD4 Treg depletion by infusion of a humanized anti-CCR4 antibody, KW-0761, in cancer patients. *Clin Cancer Res* 21(19):4327-36.
Lefranc M P, Pommie C, Ruiz M, Giudicelli V, Foulquier E et al. (2003) IMGT unique numbering for immunoglobulin and T cell receptor variable domains and Ig superfamily V-like domains. *Dev Comp Immunol* 27:55-77.
Li B, VanRoey M, Wang C, Chen T T, Korman A, Jooss K (2009) Anti-Programmed Death-1 synergizes with granulocyte macrophage colony-stimulating factor—secreting tumor cell immunotherapy providing therapeutic benefit to mice with established tumors. *Clin Cancer Res* 15(5): 1623-34.
Lipson E J, Sharfman W H, Drake C G, Wollner I, Taube J M et al. (2013) Durable cancer regression off-treatment and effective reinduction therapy with an anti-PD-1 antibody. *Clin Cancer Res* 19:462-8.
Liu S Y, Wu Y L (2017) Ongoing clinical trials of PD-1 and PD-L1 inhibitors for lung cancer in China. *J Hematol Oncol* 10(1):136.
Louis E, El Ghoul Z, Vermeire S, Dall'Ozzo S, Rutgeerts P et al. (2004) Association between polymorphism in IgG Fc receptor Ma coding gene and biological response to infliximab in Crohn's disease. *Aliment Pharmacol Ther* 19: 511-9.
Ludeman J P, Stone M J (2014) The structural role of receptor tyrosine sulfation in chemokine recognition. *Br J Pharmacol* 171:1167-79.
Luke J J, Zha Y, Matijevich K, Gajewski T F (2016) Single dose denileukin diftitox does not enhance vaccine-induced T cell responses or effectively deplete Tregs in advanced melanoma: immune monitoring and clinical results of a randomized phase II trial. *J Immunother Cancer* 4:35.
Martin A, Cheetham J C, Rees A R (1989) Modeling antibody hypervariable loops: a combined algorithm. *Proc Natl Acad Sci USA* 86(23):9268-72.
MacCallum R M., Martin A C R, Thornton J T (1996) Antibody-antigen interactions: contact analysis and binding site topography. *J Mol Biol* 262:732-745.
Mahvi D A, Liu R, Grinstaff M W, Colson Y L, Raut C P (2018) Local cancer recurrence: the realities, challenges, and opportunities for new therapies. *CA Cancer J Clin* 68(6):488-505.
Mehta A Y, Heimburg-Molinaro J, Cummings R D, Goth C K (2020) Emerging patterns of tyrosine sulfation and O-glycosylation cross-talk and co-localization. *Curr Opin Struct Biol* 62:102-11.
Mellman I, Coukos G, Dranoff (2011) Cancer immunotherapy comes of age. *Nature* 480: 480-9.
Miescher S, Spycher M O, Amstutz H, De Haas M, Kleijer M et al. (2004) A single recombinant anti-RhD IgG prevents RhD immunization: association of RhD-positive red blood cell clearance rate with polymorphisms in the FcγRIIA and FcγIIIA genes. *Blood* 103: 4028-35.
Moore K L. (2003) The biology and enzymology of protein tyrosine O-sulfation. *J Biol Chem* 278(27):24243-6.
Mössner E, Brunker P, Moser S, Püntener U, Schmidt C et al. (2010) Increasing the efficacy of CD20 antibody therapy through the engineering of a new type II anti-CD20 antibody with enhanced direct and immune effector cell-mediated B-cell cytotoxicity. *Blood* 115:4393-402.
Muroyama Y, Nirschl T R, Kochel C M et al. (2017) Stereotactic radiotherapy increases functionally suppressive regulatory T cells in the tumor microenvironment. *Cancer Immunol Res* 5:992-1004.
National Cancer Institute (2021). The Cancer Genome Atlas Program. https://www.cancer.gov/tcga. Last accessed Mar. 13, 2021.
Natsume A, Niwa R, Satoh M et al. (2009) Improving effector functions of antibodies for cancer treatment: Enhancing ADCC and CDC. Drug Des Devel Ther 3:7-16.
Ni X, Tao J, Barbi J, Chen Q, Park B V et al. (2018) YAP is essential for Treg-mediated suppression of antitumor immunity. *Cancer Discov* 8(8): 1026-43.
Nimmerjahn F, Lux A, Albert H, Woigk M, Lehmann C, Dudziak D et al. (2010) FcγRIV deletion reveals its central role for IgG2a and IgG2b activity in vivo. *Proc Natl Acad Sci USA* 107(45):19396-401.
Nimmerjahn F, Ravetch J V (2005) Divergent immunoglobulin g subclass activity through selective Fc receptor binding. *Science* 310:1510-2.
Olafsen and Wu (2010) Antibody vectors for imaging. *Semin Nucl Med* 40(3):167-81.
Pardoll D M (2012) The blockage of immune checkpoints in cancer immunotherapy. *Nat Rev Cancer* 12: 252-64.
PCT Publication No. WO 2007/044756, published Apr. 19, 2007 by ICOS Corp.
PCT Publication No. WO 2008/156712, published Dec. 24, 2008 by Organon N V.
PCT Publication No. WO 2012/145493, published Oct. 26, 2012 by Amplimmune, Inc.
PCT Publication No. WO 2013/173223, published Nov. 21, 2013 by Bristol-Myers Squibb Co.
PCT Publication No. WO 2014/179664, published Nov. 6, 2014 by AnaptysBio, Inc.
PCT Publication No. WO 2014/194302, published Dec. 4, 2014 by Sorrento Therapeutics, Inc.
PCT Publication No. WO 2014/206107, published Dec. 31, 2014 by Shanghai Junshi Biosciences Inc.
PCT Publication No. WO 2015/035606, published Mar. 19, 2015 by Beigene, Ltd.
PCT Publication No. WO 2015/085847, published Jun. 18, 2015 by Shanghai Hengrui Pharmaceutical Co., Ltd.
PCT Publication No. WO 2015/112800, published Jul. 30, 2015 by Regeneron Pharmaceuticals, Inc.

PCT Publication No. WO 2015/112900, published Jul. 30, 2015 by Dana-Farber Cancer Institute, Inc. and Novartis A G
PCT Publication No. WO 2016/106159, published Jun. 30, 2016 by Enumeral Biomedical Holdings, Inc.
PCT Publication No. WO 2016/149201, published Sep. 22, 2016 by Cytomx Therapeutics, Inc.
PCT Publication No. WO 2016/197367, published Dec. 15, 2016 by Wuxi Biologics (Shanghai) Co. Ltd.
PCT Publication No. WO 2017/020291, published Feb. 9, 2017 by Wuxi Biologics (Shanghai) Co. Ltd.
PCT Publication No. WO 2017/020858, published Feb. 9, 2017 by Wuxi Biologics (Shanghai) Co. Ltd.
PCT Publication No. WO 2017/024465, published by Feb. 16, 2017 Innovent Biologics (Suzhou) Co., Ltd.
PCT Publication No. WO 2017/024515, published Feb. 16, 2017 by Wuxi Biologics (Cayman) Inc.
PCT Publication No. WO 2017/025016, published Feb. 16, 2017 by Innovent Biologics (Suzhou) Co., Ltd.
PCT Publication No. WO 2017/025051, published Feb. 16, 2017 by Wuxi Biologics (Cayman) Inc.
PCT Publication No. WO 2017/034916, published Mar. 2, 2017 by Eli Lilly and Co.
PCT Publication No. WO 2017/040790, published Mar. 9, 2017 by Agenus Inc.
PCT Publication No. WO 2017/106061, published Jun. 22, 2017 by Macrogenics, Inc.
PCT Publication No. WO 2017/123557, published Jul. 20, 2017 by Armo Biosciences, Inc.
PCT Publication No. WO 2017/132827, published Aug. 10, 2017 by Innovent Biologics (Suzhou) Co., Ltd.
PCT Publication No. WO 2017/133540, published Aug. 10, 2017 by Innovent Biologics (Suzhou) Co., Ltd.
PCT Publication No. WO 2018/112033, published Jun. 21, 2018 by Harvard College.
PCT Publication No. WO 2019/157098, published Aug. 15, 2019 by Advaxis, Inc.
PCT Publication No. WO 2020/138489, published Jul. 2, 2020 by Shionogi & Co., Ltd.
Pianko M J, Liu Y, Bagchi S, Lesokhin A M (2017) Immune checkpoint blockade for hematologic malignancies: a review. *Stem Cell Investig* 4:32.
Plitas G, Konopacki C, Wu K et al. (2016) Regulatory T cells exhibit distinct features in human breast cancer. *Immunity* 5:1122-34.
Saleh R. Elkord E (2020) FoxP3$^{+}$ T regulatory cells in cancer: prognostic biomarkers and therapeutic targets. *Cancer Lett* 490:174-85.
Scortegagna M, Hockemeyer K, Dolgalev I, Poźniak J, Rambow F et al. (2020) Siah2 control of T-regulatory cells limits anti-tumor immunity. *Nat Commun* doi: 10.1038/s41467-019-13826-7.
Selby M J, Engelhardt J J, Quigley M, Henning K A, Chen T, Srinivasan M et al. (2013) Anti-CTLA-4 antibodies of IgG2a isotype enhance antitumor activity through reduction of intratumoral regulatory T cells. *Cancer Immunol Res* 1(1):32-42.
Shah W, Yan X, Jing L, Zhou Y, Chen H, Wang Y (2011) A reversed CD4/CD8 ratio of tumor-infiltrating lymphocytes and a high percentage of CD4$^{+}$FOXP3$^{+}$ regulatory T cells are significantly associated with clinical outcome in squamous cell carcinoma of the cervix. *Cell Mol Immunol* 8:59-66.
Sharma A, Subudhi S K, Blando J, Scutti J, Vence L, Wargo J, Allison J P et al. (2019a) Anti-CTLA-4 immunotherapy does not deplete FOXP3$^{+}$ regulatory T cells (Tregs) in human cancers. *Clin Cancer Res* 25(4):1233-8.
Sharma A, Subudhi S K, Blando J, Vence L, Wargo J, Allison J P et al. (2019b) Anti-CTLA-4 immunotherapy does not deplete foxp3+ regulatory t cells (tregs) in human cancers—Response. *Clin Cancer Res* 25(11):3469-3470.
Shitara K, Nishikawa H (2018) Regulatory T cells: a potential target in cancer immunotherapy. *Ann N Y Acad Sci* 1417(1):104-15.
Siemers N O, Holloway J L, Chang H, Chasalow S D, Ross-MacDonald P B et al. (2017) Genome-wide association analysis identifies genetic correlates of immune infiltrates in solid tumors. PLoS ONE 12(7): e0179726.
Simpson T R, Li F, Montalvo-Ortiz W, Sepulveda M A, Bergerhoff K, Arce F et al. (2013) Fc-dependent depletion of tumor-infiltrating regulatory T cells co-defines the efficacy of anti-CTLA-4 therapy against melanoma. *J Exp Med* 210(9):1695-710.
Tao H, Mimura Y, Aoe K et al. (2012) Prognostic potential of FOXP3 expression in non-small cell lung cancer cells combined with tumor-infiltrating regulatory T cells. *Lung Cancer* 75:95-101.
Teng M W L, Ngiow S F, von Scheidt B, McLaughlin N, Sparwasser T, Smyth M J (2010) Conditional regulatory T-cell depletion releases adaptive immunity preventing carcinogenesis and suppressing established tumor growth. *Cancer Research* 70(20):7800-9.
Tivol E A, Borriello F, Schweitzer A N, Lynch W P, Bluestone J A, Sharpe A H (1995) Loss of CTLA-4 leads to massive lymphoproliferation and fatal multiorgan tissue destruction, revealing a critical negative regulatory role of CTLA-4. *Immunity* 3(5):541-7.
U.S. Pat. No. 6,808,710, issued Oct. 26, 2004 to Wood et al.
U.S. Pat. No. 7,488,802, issued Feb. 10, 2009 to Collins et al.
U.S. Pat. No. 7,943,743, issued May 17, 2011 to Korman et al.
U.S. Pat. No. 7,767,429, issued Aug. 3, 2010 to Bookbinder et al.
U.S. Pat. No. 8,008,449, issued Aug. 30, 2011 to Korman et al.
U.S. Pat. No. 8,168,757, issued May 1, 2012 to Finnefrock et al.
U.S. Pat. No. 8,217,149, issued Jul. 10, 2012 to Irving et al.
U.S. Pat. No. 8,354,509, issued Jan. 15, 2013 to Carven et al.
U.S. Pat. No. 8,779,108, issued Jul. 15, 2014 to Queva et al.
U.S. Pat. No. 9,175,082, issued Nov. 3, 2015 to Zhou et al.
U.S. Pat. No. 9,205,148, issued Dec. 3, 2015 to Langermann et al.
U.S. Pat. No. 9,624,298, issued Apr. 18, 2017 to Nastri et al.
U.S. Pat. No. 10,087,259, issued Oct. 2, 2018 to Rudenski and Plitas
U.S. Pat. No. 10,550,191, issued Feb. 4, 2020 to Yoshida et al.
U.S. Publication No. 2004/0110704, published Jun. 10, 2004 by Yamane et al.
U.S. Publication No. 2015/0079109, published Mar. 19, 2015 by Li et al.
U.S. Publication No. 2016/0272708, published Sep. 22, 2016 by Chen et al.
Vila-Caballer M, Gonzalez-Granado J M, Zorita V, Abu Nabah Y N, Silvestre-Roig C et al. (2019) Disruption of the CCL1-CCR8 axis inhibits vascular Treg recruitment and function and promotes atherosclerosis in mice. *J Mol Cell Cardiol* 132:154-63.
Wang C, Thudium K B, Han M, Wang X T et al. (2014) In vitro characterization of the anti-PD-1 antibody nivolumab, BMS-936558, and in vivo toxicology in non-human primates. *Cancer Imm Res* 2(9):846-56.
Wang D D, Zhang S, Zhao H, Men A Y, Parivar K (2009) Fixed dosing versus body size-based dosing of monoclonal antibodies in adult clinical trials. *J Clin Pharmacol* 49:1012-24.
Wang L, Simons D L, Lu X et al. (2019) Connecting blood and intratumoral Treg cell activity in predicting future relapse in breast cancer. *Nature Immunol* 20:1220-30.
Wang S, Liu X (2019). The UCSCXenaTools R package: a toolkit for accessing genomics data from UCSC Xena platform, from cancer multi-omics to single-cell RNA-seq. *J Open Source Software* 4(40): 1627, https://doi.org/10.21105/joss.01627.
Weber J (2010) Immune checkpoint proteins: a new therapeutic paradigm for cancer-preclinical background: CTLA-4 and PD-1 blockade. *Semin Oncol* 37(5): 430-9.
Wolchok J D, Weber J S, Maio M, Neyns B, Harmankaya K et al. (2013) Four-year survival rates for patients with metastatic melanoma who received ipilimumab in phase II clinical trials. *Ann Oncol* 24(8):2174-80.
Wu T T, Kabat E A (1970) An analysis of the sequences of the variable regions of Bence Jones proteins and myeloma light chains and their implications for antibody complementarity. *J Exp Med* 132:211-250.
Xu K, He J, Zhang J, Liu T, Yang F, Ren T (2020) A novel prognostic risk score model based on immune-related genes in patients with stage IV colorectal cancer. *Biosci Rep* 40(10):BSR20201725.
Yagi H, Nomura T, Nakamura K, Yamazaki S, Kitawaki T, Hori S et al. (2004) Crucial role of FOXP3 in the development and function of human $CD25^{+}CD4^{+}$ regulatory T cells. *Int Immunol* 16(11):1643-56.
Yamane-Ohnuki N, Kinoshita S, Inoue-Urakubo M, Kusunoki M, Iida S et al. (2004) Establishment of FUT8 knockout Chinese hamster ovary cells: an ideal host cell line for producing completely defucosylated antibodies with enhanced antibody-dependent cellular cytotoxicity. *Biotechnol Bioeng* 87: 614-22.
Yao S, Zhu Y, Chen L (2013) Advances in targeting cell surface signalling molecules for immune modulation. *Nature Rev Drug Discov* 12:130-46.
Yi J, Jiang S-J. (2018) Dysregulation of CCL18/CCR8 axis predicts poor prognosis in patients with gastric cancer. *Eur J Inflamm* 16: 1-7.
Zhang F, Wei H, Wang X, Bai Y, Wang P et al. (2017) Structural basis of a novel PD-L1 nanobody for immune checkpoint blockade. *Cell Discov* 3:17004.
Zhao S, Jiang T, Zhang L, Yang H, Liu X et al. (2016) Clinicopathological and prognostic significance of regulatory T cells in patients with non-small cell lung cancer: a systematic review with meta-analysis. *Oncotarget* 7:36065-73.
Zheng C, Zheng L, Yoo J K, Guo H, Zhang Y et al. (2017) Landscape of infiltrating T cells in liver cancer revealed by single-cell sequencing. *Cell* 169(7):1342-56.
Zhu J Z, Millard C J, Ludeman J P, Simpson L S, Clayton D J et al. (2011) Tyrosine sulfation influences the chemokine binding selectivity of peptides derived from chemokine receptor CCR3. *Biochemistry* 50:1524-34.

What is claimed is:

1. An anti-hCCR8 monoclonal antibody or an antigen-binding portion thereof which specifically binds to human C-C Motif Chemokine Receptor 8 (hCCR8, the sequence of which is set forth as SEQ ID NO: 1) expressed on the surface of an activated human regulatory T cell (Treg) with an $EC_{50}$ of about 20 nM or lower as measured by a binding assay as described in Example 11 and mediates antibody-dependent cellular cytotoxicity (ADCC) killing of the activated human Treg, or a modified version of said anti-hCCR8 monoclonal antibody or an antigen-binding portion thereof which comprises a modified heavy chain constant region that binds with higher affinity to an Fcγ receptor and mediates enhanced ADCC compared to the unmodified anti-hCCR8 antibody, wherein the monoclonal antibody or the modified monoclonal antibody or the antigen-binding portion thereof comprises the following CDR domains as defined by the Kabat method:

(a) a heavy chain variable region CDR1 comprising consecutively linked amino acids having the sequence set forth as SEQ ID NO: 33; a heavy chain variable region CDR2 comprising consecutively linked amino acids having the sequence set forth as SEQ ID NO: 34; a heavy chain variable region CDR3 comprising consecutively linked amino acids having the sequence set forth as SEQ ID NO: 35; a light chain variable region CDR1 comprising consecutively linked amino acids having the sequence set forth as SEQ ID NO: 36; a light chain variable region CDR2 comprising consecutively linked amino acids having the sequence set forth as SEQ ID NO: 37; and a light chain variable region CDR3 comprising consecutively linked amino acids having the sequence set forth as SEQ ID NO: 38;

(b) a heavy chain variable region CDR1 comprising consecutively linked amino acids having the sequence set forth as SEQ ID NO: 39; a heavy chain variable region CDR2 comprising consecutively linked amino acids having the sequence set forth as SEQ ID NO: 40; a heavy chain variable region CDR3 comprising consecutively linked amino acids having the sequence set forth as SEQ ID NO: 41; a light chain variable region CDR1 comprising consecutively linked amino acids having the sequence set forth as SEQ ID NO: 42; a light chain variable region CDR2 comprising consecutively linked amino acids having the sequence set forth as SEQ ID NO: 43; and a light chain variable region CDR3 comprising consecutively linked amino acids having the sequence set forth as SEQ ID NO: 44;

(c) a heavy chain variable region CDR1 comprising consecutively linked amino acids having the sequence set forth as SEQ ID NO: 45; a heavy chain variable region CDR2 comprising consecutively linked amino acids having the sequence set forth as SEQ ID NO: 46; a heavy chain variable region CDR3 comprising consecutively linked amino acids having the sequence set forth as SEQ ID NO: 47; a light chain variable region CDR1 comprising consecutively linked amino acids having the sequence set forth as SEQ ID NO: 48; a light chain variable region CDR2 comprising consecutively linked amino acids having the sequence set forth as SEQ ID NO: 49; and a light chain variable region CDR3 comprising consecutively linked amino acids having the sequence set forth as SEQ ID NO: 50;

(d) a heavy chain variable region CDR1 comprising consecutively linked amino acids having the sequence set forth as SEQ ID NO: 69; a heavy chain variable region CDR2 comprising consecutively linked amino acids having the sequence set forth as SEQ ID NO: 70; a heavy chain variable region CDR3 comprising consecutively linked amino acids having the sequence set forth as SEQ ID NO: 71; a light chain variable region CDR1 comprising consecutively linked amino acids having the sequence set forth as SEQ ID NO: 72; a light chain variable region CDR2 comprising consecutively linked amino acids having the sequence set forth as SEQ ID NO: 73; and a light chain variable region CDR3 comprising consecutively linked amino acids having the sequence set forth as SEQ ID NO: 74;

(e) a heavy chain variable region CDR1 comprising consecutively linked amino acids having the sequence set forth as SEQ ID NO: 75; a heavy chain variable region CDR2 comprising consecutively linked amino acids having the sequence set forth as SEQ ID NO: 76; a heavy chain variable region CDR3 comprising consecutively linked amino acids having the sequence set forth as SEQ ID NO: 77; a light chain variable region CDR1 comprising consecutively linked amino acids having the sequence set forth as SEQ ID NO: 78; a light chain variable region CDR2 comprising consecutively linked amino acids having the sequence set forth as SEQ ID NO: 79; and a light chain variable region CDR3 comprising consecutively linked amino acids having the sequence set forth as SEQ ID NO: 80; or (f) a heavy chain variable region CDR1 comprising consecutively linked amino acids having the sequence set forth as SEQ ID NO: 103; a heavy chain variable region CDR2 comprising consecutively linked amino acids having the sequence set forth as SEQ ID NO: 104; a heavy chain variable region CDR3 comprising consecutively linked amino acids having the sequence set forth as SEQ ID NO: 105; a light chain variable region CDR1 comprising consecutively linked amino acids having the sequence set forth as SEQ ID NO: 106; a light chain variable region CDR2 comprising consecutively linked amino acids having the sequence set forth as SEQ ID NO: 107; and a light chain variable region CDR3 comprising consecutively linked amino acids having the sequence set forth as SEQ ID NO: 108.

2. The anti-hCCR8 monoclonal antibody or the modified monoclonal antibody or the antigen-binding portion thereof of claim 1, which comprises the following CDR domains as defined by the Kabat method: a heavy chain variable region CDR1 comprising consecutively linked amino acids having the sequence set forth as SEQ ID NO: 45; a heavy chain variable region CDR2 comprising consecutively linked amino acids having the sequence set forth as SEQ ID NO: 46; a heavy chain variable region CDR3 comprising consecutively linked amino acids having the sequence set forth as SEQ ID NO: 47; a light chain variable region CDR1 comprising consecutively linked amino acids having the sequence set forth as SEQ ID NO: 48; a light chain variable region CDR2 comprising consecutively linked amino acids having the sequence set forth as SEQ ID NO: 49; and a light chain variable region CDR3 comprising consecutively linked amino acids having the sequence set forth as SEQ ID NO: 50.

3. The modified anti-hCCR8 monoclonal antibody or the antigen-binding portion thereof of claim 1, comprising a modified IgG1 heavy chain constant region which exhibits reduced fucosylation and/or contains a mutation, or a multiplicity of mutations, that mediates enhanced ADCC.

4. The modified anti-hCCR8 monoclonal antibody or the antigen-binding portion thereof of claim 3, wherein the mutation or multiplicity of mutations is chosen from G236A; S239D; F243L; E333A; G236A/1332E; S239D/1332E; S267E/H268F; S267E/S324T; H268F/S324T; G236A/S239D/1332E; S239D/A330L/1332E; S267E/H268F/S324T; and G236A/S239D/A330L/1332E according to the EU numbering convention.

5. The monoclonal antibody or the modified monoclonal antibody or the antigen-binding portion thereof of claim 1, which (i) specifically binds to human CCR8-expressing Chinese Hamster Ovary cells with an $EC_{50}$, as measured by the binding assay described in Example 11, of:

(a) about 10 nM or lower;
(b) about 5 nM or lower;
(c) about 1.7 nM or lower;
(d) about 1 nM or lower;
(e) about 0.5 nM or lower;
(f) about 0.1 nM or lower;
(g) about 0.1 nM;
(h) about 1.7 nM;
(i) between about 0.1 nM and about 10 nM;

(j) between about 0.1 nM and about 2 nM;
(k) between about 0.5 nM and about 5 nM;
(l) between about 1 nM and about 2 nM; or
(m) between about 0.5 nM and about 1 nM;

and/or (ii) specifically binds to activated regulatory T cells (Tregs) with an $EC_{50}$, as measured by a binding assay as described in Example 11, of:
(a) about 14 nM or lower;
(b) about 5 nM or lower;
(c) about 2 nM or lower;
(d) about 0.5 nM or lower;
(e) about 0.3 nM or lower;
(f) about 0.1 nM or lower;
(g) about 0.03 nM or lower;
(h) about 1.7 nM;
(i) between about 0.03 nM and about 10 nM;
(j) between about 0.1 nM and about 5 nM; or
(k) between about 0.2 nM and about 2 nM;

and/or (iii) binds to a N-terminal peptide of human CCR8 comprising sulfated tyrosine-15 and tyrosine-17 residues with a $K_D$, as measured by surface plasmon resonance (SPR) as described in Example 11, of:
(a) about 100 nM or lower;
(b) about 50 nM or lower;
(c) about 10 nM or lower;
(d) about 5 nM or lower;
(e) about 1.6 nM;
(f) about 1.0 nM or lower;
(g) about 0.5 nM or lower;
(h) about 0.1 nM or lower;
(i) between about 100 nM and about 0.1 nM;
(j) between about 50 nM and about 0.5 nM;
(k) between about 10 nM and about 1 nM; or
(l) between about 2 nM and about 1 nM;

and/or (iv) binds to a N-terminal peptide of human CCR8 comprising a single sulfated residue, tyrosine-15, with a $K_D$, as measured by SPR as described in Example 11, of:
(a) about 100 nM or lower;
(b) about 50 nM or lower;
(c) about 25 nM or lower;
(d) about 10 nM or lower;
(f) about 1.0 nM or lower;
(e) about 20 nM;
(i) between about 100 nM and about 1 nM;
(j) between about 50 nM and about 10 nM; or
(k) between about 30 nM and about 20 nM.

6. The monoclonal antibody or the modified monoclonal antibody or the antigen-binding portion thereof of claim 1, which binds specifically to rare and scattered immune cells in the medulla of the thymus and dermis of the skin but does not bind to human cerebrum, cerebellum, heart, liver, lung, kidney, tonsil, spleen, thymus, colon, stomach, pancreas, adrenal, pituitary, skin, peripheral nerve, testis or uterus tissue, or peripheral blood mononuclear cells (PBMCs).

7. The monoclonal antibody or the modified monoclonal antibody or the antigen-binding portion thereof of claim 1, which (i) inhibits binding of C-C Motif Chemokine Ligand 1 (CCL1) to CCR8 and inhibits CCR8/CCL1 signaling with an $IC_{50}$, as measured by inhibition of calcium flux as described in Example 15, of:
(a) about 10 nM or lower;
(b) about 5 nM or lower;
(c) about 1 nM or lower;
(d) about 0.5 nM or lower;
(e) about 0.1 nM or lower;
(f) about 0.01 nM or lower;
(g) between about 0.01 nM and about 10 nM;
(h) between about 0.05 nM and about 5 nM;
(i) between about 0.1 nM and about 1 nM; or
(j) about 0.46 nM;

and/or (ii) mediates depletion of the activated human Treg with an $EC_{50}$, as measured by a CD16 cross-linking assay as described in Example 17, of:
(a) about 100 pM or lower;
(b) about 30 pM or lower;
(c) about 10 pM or lower;
(d) about 3 pM or lower;
(e) about 1 pM or lower;
(e) about 0.5 pM or lower;
(f) about 0.1 pM or lower;
(g) about 0.05 pM or lower;
(h) about 0.7 pM;
(i) between about 0.05 pM and about 50 pM;
(j) between about 0.1 pM and about 10 pM;
(k) between about 0.3 pM and about 7 pM; or
(l) between about 0.6 pM and about 3 pM;

and/or (iii) mediates depletion of the activated human Treg with an $EC_{50}$, as measured by an apoptosis assay as described in Example 19, of:
(a) about 500 pM or lower;
(b) about 100 pM or lower;
(c) about 30 pM or lower;
(d) about 15 pM or lower;
(e) about 5 pM or lower;
(f) about 1 pM or lower;
(g) about 13 pM;
(h) between about 1 pM and about 500 pM;
(i) between about 5 pM and about 100 pM; or
(j) between about 10 pM and about 50 pM.

8. The monoclonal antibody or the modified monoclonal antibody or the antigen-binding portion thereof of claim 1, which binds to an epitope located in the N-terminal domain of human CCR8 as determined by X-ray crystallography, wherein the epitope:

(a) comprises at least one amino acid within the peptide having the sequence $Y_{15}Y_{16}Y_{17}P_{18}D_{19}I_{20}F_{21}$ (SEQ ID NO: 2) and comprises a sulfated $Y_{15}$ or a sulfated $Y_{17}$ residue;
(b) comprises all 7 of the amino acids in the peptide having the sequence $Y_{15}Y_{16}Y_{17}P_{18}D_{19}I_{20}F_{21}$ (SEQ ID NO: 2) and comprises a sulfated Y15 or a sulfated $Y_{17}$ residue;
(c) consists of all 7 of the amino acids in the peptide having the sequence $Y_{15}Y_{16}Y_{17}P_{18}D_{19}I_{20}F_{21}$ (SEQ ID NO: 2) and comprises a sulfated Y15 or a sulfated $Y_{17}$ residue;
(d) comprises at least one amino acid within a peptide having the sequence $V_{12}T_{13}D_{14}Y_{15}Y_{16}Y_{17}P_{18}D_{19}I_{20}F_{21}S_{22}$ (SEQ ID NO: 109) and comprises sulfated Y15 and sulfated Y17 residues;
(e) comprises all 11 of the amino acids in the peptide having the sequence $V_{12}T_{13}D_{14}Y_{15}Y_{16}Y_{17}P_{18}D_{19}I_{20}F_{21}S_{22}$ (SEQ ID NO: 109) and comprises sulfated Y15 and sulfated Y17 residues; or (f) consists of all 11 of the amino acids in the peptide having the sequence $V_{12}T_{13}D_{14}Y_{15}Y_{16}Y_{17}P_{18}D_{19}I_{20}F_{21}S_{22}$ (SEQ ID NO: 109) and comprises sulfated Y15 and sulfated Y17 residues.

9. The monoclonal antibody or the modified monoclonal antibody or the antigen-binding portion thereof of claim 1, which (i) promotes depletion of human tumor-associated Tregs in vitro; and/or (ii) specifically induces depletion of tumor Tregs without depleting $CCR8^{+}$ T cells in non-tumor tissue; and/or (iii) inhibits growth of tumor cells in a subject when administered as monotherapy to the subject; and/or (iv) inhibits growth of tumor cells in a subject when administered to the subject in combination with an additional therapeutic agent for treating a cancer.

10. The monoclonal antibody or the modified monoclonal antibody or the antigen-binding portion thereof of claim 1, which comprises:

a $V_H$ comprising consecutively linked amino acids having a sequence that is at least 80% identical to the sequence set forth as SEQ ID NO: 6 and a $V_L$ comprising consecutively linked amino acids having a sequence that is at least 80% identical to the sequence set forth as SEQ ID NO: 18, and retains the functional properties of an antibody comprising $V_H$ and $V_L$ regions having the sequences set forth as SEQ ID NO: 6 and SEQ ID NO: 18, respectively.

11. An isolated nucleic acid encoding the monoclonal antibody or the modified monoclonal antibody or the antigen-binding portion thereof of claim 1.

12. A method for treating a cancer in a subject afflicted with the cancer, or for inhibiting growth of tumor cells in the subject, comprising administering to the subject a therapeutically effective amount of the monoclonal antibody or the modified monoclonal antibody or the antigen-binding portion thereof of claim 1 such that the cancer is treated or the growth of tumor cells is inhibited.

13. The method of claim 12, wherein the method further comprises administering to the subject a therapeutically effective amount of an additional therapeutic agent for treating a cancer.

14. The method of claim 12, wherein the cancer is a solid tumor or a hematological malignancy, or the tumor cells are cells of a solid tumor or of a hematological malignancy.

15. A method for potentiating an anti-tumor immune response elicited by a therapeutic agent in a subject afflicted with a cancer, comprising administering to the subject therapeutically effective amounts of the therapeutic agent and the monoclonal antibody or the modified monoclonal antibody or the antigen-binding portion thereof of claim 1, such that the subject experiences a stronger immune response against the cancer compared to the immune response elicited by the therapeutic agent alone.

16. A kit for treating a cancer in a subject afflicted with the cancer, the kit comprising:

(a) one or more dosages ranging from about 0.01 to about 20 mg/kg body weight of the anti-CCR8 monoclonal antibody or the modified monoclonal antibody or the antigen-binding portion thereof of claim 1; and (b) instructions for treating the cancer in the subject, wherein treating the cancer comprises administering to the subject a therapeutically effective amount of the monoclonal antibody or the modified monoclonal antibody or the antigen-binding portion thereof.

17. The method of claim 12, wherein the subject is a human.

18. The monoclonal antibody or the modified monoclonal antibody or the antigen-binding portion thereof of claim 8, which further binds to an epitope located in the N-terminal domain of human CCR8 with a $K_D$ of about 10 nM or lower, wherein the epitope comprises a peptide having the sequence $V_{12}T_{13}D_{14}Y_{15}Y_{16}Y_{17}P_{18}D_{19}I_{20}F_{21}S_{22}$ (SEQ ID NO: 109) and comprises sulfated $Y_{15}$ and $Y_{17}$ residues.

19. The monoclonal antibody or the modified monoclonal antibody or the antigen-binding portion thereof of claim 1, which exhibits at least one, two, three, four, five or six, or exhibits all, of the following properties:

(a) specifically binds to CCR8 expressed on the surface of a cell with an $EC_{50}$ of about 2 nM or lower;

(b) binds specifically to rare and scattered immune cells in the medulla of the thymus and dermis of the skin but does not bind to human cerebrum, cerebellum, heart, liver, lung, kidney, tonsil, spleen, thymus, colon, stomach, pancreas, adrenal, pituitary, skin, peripheral nerve, testis or uterus tissue, or peripheral blood mononuclear cells (PBMCs);

(c) inhibits binding of CCL1 to CCR8 and inhibits CCR8/CCL1 signaling with an $IC_{50}$ of about 5 nM or lower;

(d) when bound to CCR8 on the surface of a cell mediates depletion of the cell with an $EC_{50}$ of about 10 pM or lower;

(e) when bound to CCR8 on the surface of a cell does not cause internalization of CCR8 either in the presence or absence of a cross-linking antibody;

(f) promotes depletion of human tumor-associated Tregs in vitro using a Treg depletion assay as described in Example 22;

(g) promotes depletion of human tumor-associated Tregs in ex-vivo human tumor slice samples using a Treg depletion assay as described in Example 20;

(h) mediates depletion of tumor Tregs specifically while sparing $CCR8^{+}$ T cells in non-tumor tissues;

(i) inhibits growth of tumor cells in a subject when administered as monotherapy to the subject; and (j) inhibits growth of tumor cells in a subject when administered to the subject in combination with an additional therapeutic agent for treating a cancer.

20. The modified anti-hCCR8 monoclonal antibody or the antigen-binding portion thereof of claim 1, which mediates at least 2, 5 or 10 times enhanced ADCC compared to the unmodified monoclonal antibody or the antigen-binding portion thereof.

21. The monoclonal antibody or the modified monoclonal antibody or the antigen-binding portion thereof of claim 1, which is a chimeric antibody, a humanized antibody, a human antibody, a human IgG1 isotype, a human IgG3 isotype, or is an antibody comprising a modified IgG1 heavy chain constant region that mediates enhanced ADCC compared to the unmodified monoclonal antibody, or is an ADCC-mediating fragment of any of said antibodies.

22. The monoclonal antibody or the modified monoclonal antibody or antigen-binding portion thereof of claim 1, which comprises:

(a) a $V_H$ comprising consecutively linked amino acids having the sequence set forth as SEQ ID NO: 4 and a $V_L$ comprising consecutively linked amino acids having the sequence set forth as SEQ ID NO: 16;

(b) a $V_H$ comprising consecutively linked amino acids having the sequence set forth as SEQ ID NO: 5 and a $V_L$ comprising consecutively linked amino acids having the sequence set forth as SEQ ID NO: 17;

(c) a $V_H$ comprising consecutively linked amino acids having the sequence set forth as SEQ ID NO: 6 and a $V_L$ comprising consecutively linked amino acids having the sequence set forth as SEQ ID NO: 18;

(d) a $V_H$ comprising consecutively linked amino acids having the sequence set forth as SEQ ID NO: 10 and a $V_L$ comprising consecutively linked amino acids having the sequence set forth as SEQ ID NO: 22;

(e) a $V_H$ comprising consecutively linked amino acids having the sequence set forth as SEQ ID NO: 11 and a $V_L$ comprising consecutively linked amino acids having the sequence set forth as SEQ ID NO: 23; or (f) a $V_H$ comprising consecutively linked amino acids having the sequence set forth as SEQ ID NO: 115 and a $V_L$ comprising consecutively linked amino acids having the sequence set forth as SEQ ID NO: 116.

23. The monoclonal antibody or the modified monoclonal antibody or the antigen-binding portion thereof of claim 1, which comprises:

(a) a heavy chain comprising consecutively linked amino acids having the sequence set forth as SEQ ID NO: 100 and a light chain comprising consecutively linked amino acids having the sequence set forth as SEQ ID NO: 112;

(b) a heavy chain comprising consecutively linked amino acids having the sequence set forth as SEQ ID NO: 101 and a light chain comprising consecutively linked amino acids having the sequence set forth as SEQ ID NO: 113;

(c) a heavy chain comprising consecutively linked amino acids having the sequence set forth as SEQ ID NO: 102 and a light chain comprising consecutively linked amino acids having the sequence set forth as SEQ ID NO: 114; or (d) a heavy chain comprising consecutively linked amino acids having the sequence set forth as SEQ ID NO: 117 and a light chain comprising consecutively linked amino acids having the sequence set forth as SEQ ID NO: 118.

24. The monoclonal antibody or the modified monoclonal antibody or the antigen-binding portion thereof of claim 10, which comprises a $V_H$ comprising consecutively linked amino acids having the sequence set forth as SEQ ID NO: 6 and a $V_L$ comprising consecutively linked amino acids having the sequence set forth as SEQ ID NO: 18.

25. The monoclonal antibody or the modified monoclonal antibody or the antigen-binding portion thereof of claim 24, which comprises a heavy chain comprising consecutively linked amino acids having the sequence set forth as SEQ ID NO: 102 and a light chain comprising consecutively linked amino acids having the sequence set forth as SEQ ID NO: 114.

26. A modified monoclonal antibody comprising a heavy chain constant region that is hypofucosylated or nonfucosylated, which specifically binds to human C-C Motif Chemokine Receptor 8 (hCCR8) expressed on the surface of a cell and mediates depletion of the CCR8-expressing cell by antibody-dependent cellular cytotoxicity (ADCC), wherein said modified monoclonal antibody comprises a heavy chain comprising consecutively linked amino acids having the sequence set forth as SEQ ID NO: 102 and a light chain comprising consecutively linked amino acids having the sequence set forth as SEQ ID NO: 114.

27. An immunoconjugate comprising the monoclonal antibody or the modified monoclonal antibody or the antigen-binding portion thereof of claim 1, linked to a cytolytic agent.

28. The immunoconjugate of claim 27, wherein the cytolytic agent is a cytotoxin or a radioactive isotope.

29. A bispecific molecule comprising the monoclonal antibody or the modified monoclonal antibody or the antigen-binding portion thereof of claim 1, linked to a binding domain that has a different binding specificity than the monoclonal antibody or the modified monoclonal antibody or the antigen binding portion thereof.

30. A composition comprising the monoclonal antibody or the modified monoclonal antibody or the antigen-binding portion thereof of claim 1 and a pharmaceutically acceptable carrier.

31. A composition comprising the immunoconjugate of claim 27 and a pharmaceutically acceptable carrier.

32. A composition comprising the bispecific molecule of claim 29 and a pharmaceutically acceptable carrier.

33. An expression vector comprising the nucleic acid of claim 11.

34. A host cell comprising the expression vector of claim 33.

35. A method for preparing an anti-CCR8 monoclonal antibody or a modified monoclonal antibody or an antigen-binding portion thereof, which comprises expressing the monoclonal antibody or the modified monoclonal antibody or the antigen-binding portion thereof in the host cell of claim 34 and isolating the monoclonal antibody or the modified monoclonal antibody or the antigen-binding portion thereof from the host cell.

36. The method of claim 13, wherein the additional therapeutic agent is a compound that reduces inhibition, or increases stimulation, of the immune system.

* * * * *

SEQUENCE LISTING

```
<160> NUMBER OF SEQ ID NOS: 120

<210> SEQ ID NO 1
<211> LENGTH: 355
<212> TYPE: PRT
<213> ORGANISM: Homo Sapien

<400> SEQUENCE: 1

Met Asp Tyr Thr Leu Asp Leu Ser Val Thr Thr Val Thr Asp Tyr Tyr
1               5                   10                  15

Tyr Pro Asp Ile Phe Ser Ser Pro Cys Asp Ala Glu Leu Ile Gln Thr
            20                  25                  30

Asn Gly Lys Leu Leu Leu Ala Val Phe Tyr Cys Leu Leu Phe Val Phe
        35                  40                  45

Ser Leu Leu Gly Asn Ser Leu Val Ile Leu Val Leu Val Val Cys Lys
    50                  55                  60

Lys Leu Arg Ser Ile Thr Asp Val Tyr Leu Leu Asn Leu Ala Leu Ser
65                  70                  75                  80

Asp Leu Leu Phe Val Phe Ser Phe Pro Phe Gln Thr Tyr Tyr Leu Leu
                85                  90                  95

Asp Gln Trp Val Phe Gly Thr Val Met Cys Lys Val Val Ser Gly Phe
            100                 105                 110

Tyr Tyr Ile Gly Phe Tyr Ser Ser Met Phe Phe Ile Thr Leu Met Ser
        115                 120                 125

Val Asp Arg Tyr Leu Ala Val Val His Ala Val Tyr Ala Leu Lys Val
    130                 135                 140

Arg Thr Ile Arg Met Gly Thr Thr Leu Cys Leu Ala Val Trp Leu Thr
145                 150                 155                 160
```

-continued

```
Ala Ile Met Ala Thr Ile Pro Leu Leu Val Phe Tyr Gln Val Ala Ser
                165                 170                 175

Glu Asp Gly Val Leu Gln Cys Tyr Ser Phe Tyr Asn Gln Gln Thr Leu
            180                 185                 190

Lys Trp Lys Ile Phe Thr Asn Phe Lys Met Asn Ile Leu Gly Leu Leu
        195                 200                 205

Ile Pro Phe Thr Ile Phe Met Phe Cys Tyr Ile Lys Ile Leu His Gln
    210                 215                 220

Leu Lys Arg Cys Gln Asn His Asn Lys Thr Lys Ala Ile Arg Leu Val
225                 230                 235                 240

Leu Ile Val Val Ile Ala Ser Leu Leu Phe Trp Val Pro Phe Asn Val
                245                 250                 255

Val Leu Phe Leu Thr Ser Leu His Ser Met His Ile Leu Asp Gly Cys
            260                 265                 270

Ser Ile Ser Gln Gln Leu Thr Tyr Ala Thr His Val Thr Glu Ile Ile
        275                 280                 285

Ser Phe Thr His Cys Cys Val Asn Pro Val Ile Tyr Ala Phe Val Gly
    290                 295                 300

Glu Lys Phe Lys Lys His Leu Ser Glu Ile Phe Gln Lys Ser Cys Ser
305                 310                 315                 320

Gln Ile Phe Asn Tyr Leu Gly Arg Gln Met Pro Arg Glu Ser Cys Glu
                325                 330                 335

Lys Ser Ser Ser Cys Gln Gln His Ser Ser Arg Ser Ser Ser Val Asp
            340                 345                 350

Tyr Ile Leu
        355


<210> SEQ ID NO 2
<211> LENGTH: 7
<212> TYPE: PRT
<213> ORGANISM: Homo Sapien

<400> SEQUENCE: 2

Tyr Tyr Tyr Pro Asp Ile Phe
1               5


<210> SEQ ID NO 3
<211> LENGTH: 117
<212> TYPE: PRT
<213> ORGANISM: Homo Sapien

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Asn Met Asn Trp Val Arg Gln Ala Pro Gly Lys Gly Leu Glu Trp Ile
        35                  40                  45

Ser Tyr Ile Ser Ser Gly Ser Thr Thr Ile Ala His Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Val Arg Arg Leu Lys Gly Ser Phe Asp Tyr Trp Gly Gln Gly Thr Leu
            100                 105                 110
```

```
Val Thr Val Ser Ser
        115


<210> SEQ ID NO 4
<211> LENGTH: 120
<212> TYPE: PRT
<213> ORGANISM: Homo Sapien

<400> SEQUENCE: 4

Glu Val Gln Leu Val Glu Phe Gly Gly Gly Leu Val Gln Pro Lys Gly
1               5                   10                  15

Ser Leu Lys Leu Ser Cys Val Val Ser Gly Phe Arg Phe Asn Pro Tyr
            20                  25                  30

Ala Met Asn Trp Val Arg Gln Ala Pro Gly Lys Gly Leu Glu Trp Leu
        35                  40                  45

Gly Arg Ile Arg Ser Lys Ser Asn Asn Tyr Glu Thr Tyr Tyr Ala Asp
    50                  55                  60

Ser Val Lys Asp Arg Phe Ile Ile Ser Arg Asp Asp Ser Gln Lys Met
65                  70                  75                  80

Val Tyr Leu Gln Met Asn Asn Val Lys Thr Glu Asp Thr Ala Met Tyr
                85                  90                  95

Tyr Cys Val Gly Tyr Ser Asp Leu Tyr Val Leu Asp Tyr Trp Gly Gln
            100                 105                 110

Gly Thr Ser Val Thr Val Ser Ser
        115                 120


<210> SEQ ID NO 5
<211> LENGTH: 115
<212> TYPE: PRT
<213> ORGANISM: Homo Sapien

<400> SEQUENCE: 5

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Lys Thr Gly Ser Thr Ala Tyr Asn Gln Lys Phe
    50                  55                  60

Lys Gly Lys Ala Ile Met Thr Ala Asp Lys Ser Ser Ser Thr Ala Tyr
65                  70                  75                  80

Met Glu Leu Arg Ser Leu Thr Ser Glu Asp Ser Val Val Tyr Tyr Cys
                85                  90                  95

Thr Gly Leu Arg Arg Phe Val Tyr Trp Gly Gln Gly Thr Pro Val Thr
            100                 105                 110

Val Ser Ala
        115


<210> SEQ ID NO 6
<211> LENGTH: 116
<212> TYPE: PRT
<213> ORGANISM: Homo Sapien

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
```

20 25 30

Glu Met His Trp Val Arg Gln Ala Thr Gly Gln Gly Leu Glu Trp Met
35 40 45

Gly Ala Ile Gln Pro Glu Thr Gly Gly Thr Ala Tyr Asn Gln Lys Phe
50 55 60

Lys Ala Arg Val Thr Met Thr Arg Asp Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Arg Arg Arg Asn Phe Asp Tyr Trp Gly Gln Gly Thr Leu Val
100 105 110

Thr Val Ser Ser
115

<210> SEQ ID NO 7
<211> LENGTH: 117
<212> TYPE: PRT
<213> ORGANISM: Homo Sapien

<400> SEQUENCE: 7

Glu Val Gln Leu Val Glu Ser Gly Gly Gly Leu Val Gln Pro Gly Gly
1 5 10 15

Ser Leu Arg Leu Ser Cys Val Val Ser Gly Phe Thr Phe Ser Asn Phe
20 25 30

Asn Met Ile Trp Val Arg Gln Val Pro Gly Lys Gly Leu Glu Trp Ile
35 40 45

Ser His Ile Ser Arg Gly Gly Thr Thr Ile Asn His Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Asp Glu Asp Thr Ala Val Tyr Tyr Cys
85 90 95

Ala Arg Arg Arg Leu Gly Val Phe Asp Tyr Trp Gly Gln Gly Thr Leu
100 105 110

Val Thr Val Ser Ser
115

<210> SEQ ID NO 8
<211> LENGTH: 117
<212> TYPE: PRT
<213> ORGANISM: Homo Sapien

<400> SEQUENCE: 8

Gln Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Asp Met Asn Trp Val Arg Gln Ala Pro Gly Lys Gly Leu Glu Trp Ile
35 40 45

Ser Tyr Ile Ser Ser Ser Asn Gly Asn Lys His His Ala Asp Ser Val
50 55 60

Lys Gly Arg Phe Thr Ile Ser Arg Asp Asn Ala Glu Asn Ser Leu Tyr
65 70 75 80

Leu Gln Met Asn Ser Leu Arg Asp Glu Asp Thr Ala Val Tyr Tyr Cys
85 90 95

Ala Arg Arg Arg Gln Gly Val Phe Asp Ile Trp Gly Gln Gly Thr Leu

```
            100                 105                 110

Val Thr Val Ser Ser
        115


<210> SEQ ID NO 9
<211> LENGTH: 122
<212> TYPE: PRT
<213> ORGANISM: Homo Sapien

<400> SEQUENCE: 9

Gln Val Gln Leu Val Glu Ser Gly Gly Gly Leu Val Lys Pro Arg Gly
1               5                   10                  15

Ser Leu Arg Leu Ser Cys Ala Ala Ser Gly Phe Thr Phe Ser Val Ala
            20                  25                  30

Trp Met His Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Thr
    50                  55                  60

Pro Val Lys Gly Arg Phe Thr Ile Ser Arg Asp Asp Ser Lys Asn Thr
65                  70                  75                  80

Leu Tyr Leu Gln Met His Ser Leu Lys Thr Glu Asp Thr Ala Val Tyr
                85                  90                  95

Tyr Cys Thr Val Val Thr Met Val Arg Gly Val Leu Tyr Asp Phe Trp
            100                 105                 110

Gly Gln Gly Thr Leu Val Thr Val Ser Ser
        115                 120


<210> SEQ ID NO 10
<211> LENGTH: 119
<212> TYPE: PRT
<213> ORGANISM: Homo Sapien

<400> SEQUENCE: 10

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Gly Ile Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Ser Cys
                85                  90                  95

Ala Arg Val Pro Asn Trp Arg Gly Ala Phe Asp Ile Trp Gly Gln Gly
            100                 105                 110

Thr Met Val Thr Val Ser Ser
        115


<210> SEQ ID NO 11
<211> LENGTH: 117
<212> TYPE: PRT
<213> ORGANISM: Homo Sapien

<400> SEQUENCE: 11

Gln Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Tyr
            20                  25                  30

Asn Met Ile Trp Val Arg Gln Thr Pro Gly Lys Gly Leu Glu Trp Ile
        35                  40                  45

Ser Tyr Ile Ser Ser Ser Arg Ser Ile Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Arg Trp Lys Gly Val Phe Asp Tyr Trp Gly Gln Gly Thr Leu
            100                 105                 110

Val Thr Val Ser Ser
        115


<210> SEQ ID NO 12
<211> LENGTH: 120
<212> TYPE: PRT
<213> ORGANISM: Homo Sapien

<400> SEQUENCE: 12

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Asp Trp Leu
        35                  40                  45

Ala Val Ile Ser Tyr Asp Gly Ser Asn Lys Tyr His Ser Asp Ser Val
    50                  55                  60

Lys Gly Arg Phe Thr Ile Ser Arg Asp Asn Ser Lys Asn Thr Leu Tyr
65                  70                  75                  80

Leu Gln Ile Asn Ser Leu Arg Ala Glu Asp Ala Ala Val Tyr Tyr Cys
                85                  90                  95

Ala Arg Arg Gly Glu Leu Gly Ile Gly Gly Phe Asp Tyr Trp Gly Gln
            100                 105                 110

Gly Thr Leu Val Thr Val Ser Ser
        115                 120


<210> SEQ ID NO 13
<211> LENGTH: 117
<212> TYPE: PRT
<213> ORGANISM: Homo Sapien

<400> SEQUENCE: 13

Gln Val Gln Leu Val Glu Ser Gly Gly Gly Leu Val Leu Pro Gly Gly
1               5                   10                  15

Ser Leu Arg Leu Ser Cys Ala Ala Ser Gly Phe Thr Phe Ser Ser Asn
            20                  25                  30

Asn Met Ile Trp Val Arg Gln Ala Pro Gly Lys Gly Leu Glu Trp Val
        35                  40                  45

Ser Tyr Ile Ser Ser Ser Ser Ser Thr Ile Ser Tyr Ala Asp Ser Val
    50                  55                  60

Arg Gly Arg Phe Thr Ile Ser Arg Asp Asn Ala Lys Asn Ser Leu Phe
65                  70                  75                  80

Leu Gln Met Asn Ser Leu Arg Asp Glu Asp Thr Ala Val Tyr Tyr Cys
                85                  90                  95
```

```
Ala Arg Arg Trp Arg Gly Val Phe Asp Tyr Trp Gly Gln Gly Thr Leu
            100                 105                 110

Val Thr Val Ser Ser
        115


<210> SEQ ID NO 14
<211> LENGTH: 121
<212> TYPE: PRT
<213> ORGANISM: Homo Sapien

<400> SEQUENCE: 14

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Arg Ser Tyr
            20                  25                  30

Gly Ile His Trp Val Arg Gln Ala Pro Gly Lys Gly Leu Glu Trp Val
        35                  40                  45

Ala Val Ile Ser Tyr Glu Gly Ser Asn Lys Arg Tyr Ala Asp Ser Val
    50                  55                  60

Lys Gly Arg Phe Thr Ile Ser Arg Asp Asn Ser Lys Ser Thr Leu Ser
65                  70                  75                  80

Leu Gln Met Asn Ser Leu Arg Ala Glu Asp Thr Ala Val Tyr Tyr Cys
                85                  90                  95

Ala Lys Gly Arg Arg Pro Ser Gly Glu Gly Ala Phe Asp Ile Trp Gly
            100                 105                 110

Gln Gly Thr Met Val Thr Val Ser Ser
        115                 120


<210> SEQ ID NO 15
<211> LENGTH: 107
<212> TYPE: PRT
<213> ORGANISM: Homo Sapien

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Gly Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Val Glu Ile Lys
            100                 105


<210> SEQ ID NO 16
<211> LENGTH: 112
<212> TYPE: PRT
<213> ORGANISM: Homo Sapien

<400> SEQUENCE: 16

Asp Ile Val Met Thr Gln Ala Ala Pro Ser Val Pro Val Thr Pro Gly
1               5                   10                  15
```

```
Glu Ser Val Ser Ile Ser Cys Arg Ser Ser Lys Ser Leu Leu His Ser
            20                  25                  30

Asn Gly Asn Thr Phe Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

His Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110


<210> SEQ ID NO 17
<211> LENGTH: 112
<212> TYPE: PRT
<213> ORGANISM: Homo Sapien

<400> SEQUENCE: 17

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Ser Gly Tyr Thr Tyr Leu His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110


<210> SEQ ID NO 18
<211> LENGTH: 112
<212> TYPE: PRT
<213> ORGANISM: Homo Sapien

<400> SEQUENCE: 18

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Phe His Ser
            20                  25                  30

Ser Gly Asn Thr Tyr Leu His Trp Tyr Leu Gln Lys Pro Gly Gln Pro
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Phe Thr Phe Gly Gln Gly Thr Lys Leu Glu Ile Lys
            100                 105                 110


<210> SEQ ID NO 19
<211> LENGTH: 107
```

<212> TYPE: PRT
<213> ORGANISM: Homo Sapien

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Val Glu Ile Lys
            100                 105
```

<210> SEQ ID NO 20
<211> LENGTH: 107
<212> TYPE: PRT
<213> ORGANISM: Homo Sapien

<400> SEQUENCE: 20

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gly Gly Thr Lys Val Glu Ile Lys
            100                 105
```

<210> SEQ ID NO 21
<211> LENGTH: 107
<212> TYPE: PRT
<213> ORGANISM: Homo Sapien

<400> SEQUENCE: 21

```
Asp Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Arg
```

```
                85                  90                  95

Thr Phe Gly Gly Gly Thr Lys Val Glu Ile Lys
            100                 105


<210> SEQ ID NO 22
<211> LENGTH: 107
<212> TYPE: PRT
<213> ORGANISM: Homo Sapien

<400> SEQUENCE: 22

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser His
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Ser Leu Thr Ile Asn Ser Leu Glu Thr
65                  70                  75                  80

Glu Asp Ala Ala Thr Tyr Phe Cys His Gln Ser Tyr Ser Leu Pro Leu
                85                  90                  95

Thr Phe Gly Gly Gly Thr Lys Val Glu Ile Lys
            100                 105


<210> SEQ ID NO 23
<211> LENGTH: 107
<212> TYPE: PRT
<213> ORGANISM: Homo Sapien

<400> SEQUENCE: 23

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Val Glu Ile Lys
            100                 105


<210> SEQ ID NO 24
<211> LENGTH: 112
<212> TYPE: PRT
<213> ORGANISM: Homo Sapien

<400> SEQUENCE: 24

Asp Ile Val Met Thr Gln Thr Pro Leu Ser Ser Pro Val Thr Leu Gly
1               5                   10                  15

Arg Pro Ala Ser Ile Ser Cys Arg Ser Ser Arg Ser Leu Val His Thr
            20                  25                  30

Asp Gly Asn Thr Tyr Leu Asn Trp Leu Gln Gln Arg Pro Gly Gln Pro
        35                  40                  45
```

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Thr Arg Val Glu Ala Glu Asp Val Gly Val Tyr Tyr Cys Met Gln Ala
                85                  90                  95

Thr Gln Phe Pro Leu Thr Phe Gly Pro Gly Thr Lys Val Asp Ile Lys
            100                 105                 110

<210> SEQ ID NO 25
<211> LENGTH: 107
<212> TYPE: PRT
<213> ORGANISM: Homo Sapien

<400> SEQUENCE: 25

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Val Glu Ile Lys
            100                 105

<210> SEQ ID NO 26
<211> LENGTH: 107
<212> TYPE: PRT
<213> ORGANISM: Homo Sapien

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gln Gly Thr Lys Val Glu Ile Lys
            100                 105

<210> SEQ ID NO 27
<211> LENGTH: 10
<212> TYPE: PRT
<213> ORGANISM: Homo Sapien

<400> SEQUENCE: 27

Gly Phe Thr Phe Ser Ser Phe Asn Met Asn
1               5                   10

<210> SEQ ID NO 28
<211> LENGTH: 17
<212> TYPE: PRT
<213> ORGANISM: Homo Sapien

<400> SEQUENCE: 28

Tyr Ile Ser Ser Gly Ser Thr Thr Ile Ala His Ala Asp Ser Val Lys
1               5                   10                  15

Gly

<210> SEQ ID NO 29
<211> LENGTH: 8
<212> TYPE: PRT
<213> ORGANISM: Homo Sapien

<400> SEQUENCE: 29

Arg Leu Lys Gly Ser Phe Asp Tyr
1               5

<210> SEQ ID NO 30
<211> LENGTH: 11
<212> TYPE: PRT
<213> ORGANISM: Homo Sapien

<400> SEQUENCE: 30

Arg Ala Ser Gln Gly Ile Ser Ser Trp Leu Ala
1               5                   10

<210> SEQ ID NO 31
<211> LENGTH: 7
<212> TYPE: PRT
<213> ORGANISM: Homo Sapien

<400> SEQUENCE: 31

Gly Ala Ser Arg Leu Gln Ser
1               5

<210> SEQ ID NO 32
<211> LENGTH: 9
<212> TYPE: PRT
<213> ORGANISM: Homo Sapien

<400> SEQUENCE: 32

Gln Gln Tyr Asn Ser Tyr Pro Pro Thr
1               5

<210> SEQ ID NO 33
<211> LENGTH: 10
<212> TYPE: PRT
<213> ORGANISM: Homo Sapien

<400> SEQUENCE: 33

Gly Phe Arg Phe Asn Pro Tyr Ala Met Asn
1               5                   10

<210> SEQ ID NO 34
<211> LENGTH: 19
<212> TYPE: PRT
<213> ORGANISM: Homo Sapien

<400> SEQUENCE: 34

Arg Ile Arg Ser Lys Ser Asn Asn Tyr Glu Thr Tyr Tyr Ala Asp Ser
1 5 10 15

Val Lys Asp

<210> SEQ ID NO 35
<211> LENGTH: 9
<212> TYPE: PRT
<213> ORGANISM: Homo Sapien

<400> SEQUENCE: 35

Tyr Ser Asp Leu Tyr Val Leu Asp Tyr
1 5

<210> SEQ ID NO 36
<211> LENGTH: 16
<212> TYPE: PRT
<213> ORGANISM: Homo Sapien

<400> SEQUENCE: 36

Arg Ser Ser Lys Ser Leu Leu His Ser Asn Gly Asn Thr Phe Leu Tyr
1 5 10 15

<210> SEQ ID NO 37
<211> LENGTH: 7
<212> TYPE: PRT
<213> ORGANISM: Homo Sapien

<400> SEQUENCE: 37

Arg Met Ser Asn Leu Ala Ser
1 5

<210> SEQ ID NO 38
<211> LENGTH: 9
<212> TYPE: PRT
<213> ORGANISM: Homo Sapien

<400> SEQUENCE: 38

Met Gln His Leu Glu Tyr Pro Phe Thr
1 5

<210> SEQ ID NO 39
<211> LENGTH: 10
<212> TYPE: PRT
<213> ORGANISM: Homo Sapien

<400> SEQUENCE: 39

Gly Tyr Thr Phe Thr Asp Tyr Glu Met His
1 5 10

<210> SEQ ID NO 40
<211> LENGTH: 17
<212> TYPE: PRT
<213> ORGANISM: Homo Sapien

<400> SEQUENCE: 40

Ala Ile Asp Pro Lys Thr Gly Ser Thr Ala Tyr Asn Gln Lys Phe Lys
1 5 10 15

Gly

<210> SEQ ID NO 41
<211> LENGTH: 6
<212> TYPE: PRT
<213> ORGANISM: Homo Sapien

<400> SEQUENCE: 41

Leu Arg Arg Phe Val Tyr
1 5

<210> SEQ ID NO 42
<211> LENGTH: 16
<212> TYPE: PRT
<213> ORGANISM: Homo Sapien

<400> SEQUENCE: 42

Arg Ser Ser Lys Ser Leu Leu His Ser Asn Gly Asn Thr Phe Leu Tyr
1 5 10 15

<210> SEQ ID NO 43
<211> LENGTH: 7
<212> TYPE: PRT
<213> ORGANISM: Homo Sapien

<400> SEQUENCE: 43

Arg Val Ser Asn Arg Phe Ser
1 5

<210> SEQ ID NO 44
<211> LENGTH: 9
<212> TYPE: PRT
<213> ORGANISM: Homo Sapien

<400> SEQUENCE: 44

Ser Gln Ser Thr His Val Pro Phe Thr
1 5

<210> SEQ ID NO 45
<211> LENGTH: 10
<212> TYPE: PRT
<213> ORGANISM: Homo Sapien

<400> SEQUENCE: 45

Gly Tyr Thr Phe Thr Asp Ser Glu Met His
1 5 10

<210> SEQ ID NO 46
<211> LENGTH: 17
<212> TYPE: PRT
<213> ORGANISM: Homo Sapien

<400> SEQUENCE: 46

Ala Ile Gln Pro Glu Thr Gly Gly Thr Ala Tyr Asn Gln Lys Phe Lys
1 5 10 15

Ala

<210> SEQ ID NO 47
<211> LENGTH: 7
<212> TYPE: PRT
<213> ORGANISM: Homo Sapien

<400> SEQUENCE: 47

Arg Arg Arg Asn Phe Asp Tyr
1 5

<210> SEQ ID NO 48
<211> LENGTH: 16
<212> TYPE: PRT
<213> ORGANISM: Homo Sapien

<400> SEQUENCE: 48

Arg Ser Ser Gln Ser Leu Phe His Ser Ser Gly Asn Thr Tyr Leu His
1               5                   10                  15

<210> SEQ ID NO 49
<211> LENGTH: 7
<212> TYPE: PRT
<213> ORGANISM: Homo Sapien

<400> SEQUENCE: 49

Lys Val Ser Asn Arg Phe Ser
1               5

<210> SEQ ID NO 50
<211> LENGTH: 9
<212> TYPE: PRT
<213> ORGANISM: Homo Sapien

<400> SEQUENCE: 50

Ser Gln Ser Thr His Val Pro Phe Thr
1               5

<210> SEQ ID NO 51
<211> LENGTH: 10
<212> TYPE: PRT
<213> ORGANISM: Homo Sapien

<400> SEQUENCE: 51

Gly Phe Thr Phe Ser Asn Phe Asn Met Ile
1               5                   10

<210> SEQ ID NO 52
<211> LENGTH: 17
<212> TYPE: PRT
<213> ORGANISM: Homo Sapien

<400> SEQUENCE: 52

His Ile Ser Arg Gly Gly Thr Thr Ile Asn His Ala Asp Ser Val Lys
1               5                   10                  15

Gly

<210> SEQ ID NO 53
<211> LENGTH: 7
<212> TYPE: PRT
<213> ORGANISM: Homo Sapien

<400> SEQUENCE: 53

Arg Leu Gly Val Phe Asp Tyr
1               5

<210> SEQ ID NO 54
<211> LENGTH: 11
<212> TYPE: PRT
<213> ORGANISM: Homo Sapien

<400> SEQUENCE: 54

Arg Ala Ser Gln Gly Ile Ser Ser Trp Leu Ala
1               5                   10

<210> SEQ ID NO 55
<211> LENGTH: 7
<212> TYPE: PRT
<213> ORGANISM: Homo Sapien

<400> SEQUENCE: 55

Ala Ala Ser Ser Leu Gln Ser
1 5

<210> SEQ ID NO 56
<211> LENGTH: 9
<212> TYPE: PRT
<213> ORGANISM: Homo Sapien

<400> SEQUENCE: 56

Gln Gln Tyr Asn Ser Tyr Pro Pro Thr
1 5

<210> SEQ ID NO 57
<211> LENGTH: 10
<212> TYPE: PRT
<213> ORGANISM: Homo Sapien

<400> SEQUENCE: 57

Gly Phe Thr Phe Ser Ser Tyr Asp Met Asn
1 5 10

<210> SEQ ID NO 58
<211> LENGTH: 17
<212> TYPE: PRT
<213> ORGANISM: Homo Sapien

<400> SEQUENCE: 58

Tyr Ile Ser Ser Ser Asn Gly Asn Lys His His Ala Asp Ser Val Lys
1 5 10 15

Gly

<210> SEQ ID NO 59
<211> LENGTH: 7
<212> TYPE: PRT
<213> ORGANISM: Homo Sapien

<400> SEQUENCE: 59

Arg Gln Gly Val Phe Asp Ile
1 5

<210> SEQ ID NO 60
<211> LENGTH: 11
<212> TYPE: PRT
<213> ORGANISM: Homo Sapien

<400> SEQUENCE: 60

Arg Ala Ser Gln Gly Ile Ser Arg Trp Leu Ala
1 5 10

<210> SEQ ID NO 61
<211> LENGTH: 7
<212> TYPE: PRT
<213> ORGANISM: Homo Sapien

<400> SEQUENCE: 61

Ala Ala Ser Ser Leu Gln Ser
1 5

<210> SEQ ID NO 62
<211> LENGTH: 9
<212> TYPE: PRT
<213> ORGANISM: Homo Sapien

<400> SEQUENCE: 62

Gln Gln Tyr Asn Ser Tyr Pro Pro Thr
1 5

<210> SEQ ID NO 63
<211> LENGTH: 10
<212> TYPE: PRT
<213> ORGANISM: Homo Sapien

<400> SEQUENCE: 63

Gly Phe Thr Phe Ser Val Ala Trp Met His
1 5 10

<210> SEQ ID NO 64
<211> LENGTH: 19
<212> TYPE: PRT
<213> ORGANISM: Homo Sapien

<400> SEQUENCE: 64

Arg Ile Lys Ser Lys Thr Asp Gly Gly Thr Thr Asp Tyr Ala Thr Pro
1 5 10 15

Val Lys Gly

<210> SEQ ID NO 65
<211> LENGTH: 11
<212> TYPE: PRT
<213> ORGANISM: Homo Sapien

<400> SEQUENCE: 65

Val Thr Met Val Arg Gly Val Leu Tyr Asp Phe
1 5 10

<210> SEQ ID NO 66
<211> LENGTH: 12
<212> TYPE: PRT
<213> ORGANISM: Homo Sapien

<400> SEQUENCE: 66

Arg Ala Ser Gln Ser Val Ser Ser Asn Tyr Leu Ala
1 5 10

<210> SEQ ID NO 67
<211> LENGTH: 7
<212> TYPE: PRT
<213> ORGANISM: Homo Sapien

<400> SEQUENCE: 67

Gly Ala Ser Ser Arg Ala Thr
1 5

<210> SEQ ID NO 68
<211> LENGTH: 8
<212> TYPE: PRT
<213> ORGANISM: Homo Sapien

<400> SEQUENCE: 68

Gln Gln Tyr Gly Ser Ser Arg Thr
1 5

<210> SEQ ID NO 69
<211> LENGTH: 10
<212> TYPE: PRT
<213> ORGANISM: Homo Sapien

<400> SEQUENCE: 69

Gly Phe Thr Phe Ser Ser Tyr Ala Met His
1 5 10

<210> SEQ ID NO 70
<211> LENGTH: 17
<212> TYPE: PRT
<213> ORGANISM: Homo Sapien

<400> SEQUENCE: 70

Ile Ile Ser Tyr Asp Gly Ser Asn Lys Tyr Tyr Ala Asp Ser Val Lys
1 5 10 15

Gly

<210> SEQ ID NO 71
<211> LENGTH: 10
<212> TYPE: PRT
<213> ORGANISM: Homo Sapien

<400> SEQUENCE: 71

Val Pro Asn Trp Arg Gly Ala Phe Asp Ile
1 5 10

<210> SEQ ID NO 72
<211> LENGTH: 11
<212> TYPE: PRT
<213> ORGANISM: Homo Sapien

<400> SEQUENCE: 72

Arg Ala Ser Gln Ser Ile Gly Ser His Leu His
1 5 10

<210> SEQ ID NO 73
<211> LENGTH: 7
<212> TYPE: PRT
<213> ORGANISM: Homo Sapien

<400> SEQUENCE: 73

Tyr Ala Ser Gln Ser Phe Ser
1 5

<210> SEQ ID NO 74
<211> LENGTH: 9
<212> TYPE: PRT
<213> ORGANISM: Homo Sapien

<400> SEQUENCE: 74

His Gln Ser Tyr Ser Leu Pro Leu Thr
1 5

<210> SEQ ID NO 75
<211> LENGTH: 10
<212> TYPE: PRT
<213> ORGANISM: Homo Sapien

<400> SEQUENCE: 75

Gly Phe Thr Phe Ser Asn Tyr Asn Met Ile
1 5 10

<210> SEQ ID NO 76
<211> LENGTH: 17
<212> TYPE: PRT
<213> ORGANISM: Homo Sapien

<400> SEQUENCE: 76

Tyr Ile Ser Ser Ser Arg Ser Ile Ile Ser Tyr Ala Asp Ser Val Lys
1 5 10 15

Gly

<210> SEQ ID NO 77
<211> LENGTH: 8
<212> TYPE: PRT
<213> ORGANISM: Homo Sapien

<400> SEQUENCE: 77

Arg Trp Lys Gly Val Phe Asp Tyr
1 5

<210> SEQ ID NO 78
<211> LENGTH: 11
<212> TYPE: PRT
<213> ORGANISM: Homo Sapien

<400> SEQUENCE: 78

Arg Ala Ser Gln Gly Ile Ser Ser Trp Leu Ala
1 5 10

<210> SEQ ID NO 79
<211> LENGTH: 7
<212> TYPE: PRT
<213> ORGANISM: Homo Sapien

<400> SEQUENCE: 79

Ala Ala Ser Ser Leu Gln Ser
1 5

<210> SEQ ID NO 80
<211> LENGTH: 9
<212> TYPE: PRT
<213> ORGANISM: Homo Sapien

<400> SEQUENCE: 80

Gln Gln Tyr Asn Ser Tyr Pro Pro Thr
1 5

<210> SEQ ID NO 81
<211> LENGTH: 10
<212> TYPE: PRT
<213> ORGANISM: Homo Sapien

<400> SEQUENCE: 81

Gly Phe Thr Phe Ser Asn Tyr Ala Met His
1 5 10

<210> SEQ ID NO 82
<211> LENGTH: 14
<212> TYPE: PRT
<213> ORGANISM: Homo Sapien

<400> SEQUENCE: 82

Tyr Asp Gly Ser Asn Lys Tyr His Ser Asp Ser Val Lys Gly
1 5 10

<210> SEQ ID NO 83
<211> LENGTH: 11
<212> TYPE: PRT
<213> ORGANISM: Homo Sapien

<400> SEQUENCE: 83

Arg Gly Glu Leu Gly Ile Gly Gly Phe Asp Tyr
1               5                   10

<210> SEQ ID NO 84
<211> LENGTH: 16
<212> TYPE: PRT
<213> ORGANISM: Homo Sapien

<400> SEQUENCE: 84

Arg Ser Ser Arg Ser Leu Val His Thr Asp Gly Asn Thr Tyr Leu Asn
1               5                   10                  15

<210> SEQ ID NO 85
<211> LENGTH: 7
<212> TYPE: PRT
<213> ORGANISM: Homo Sapien

<400> SEQUENCE: 85

Lys Ile Ser Asn Arg Phe Ser
1               5

<210> SEQ ID NO 86
<211> LENGTH: 9
<212> TYPE: PRT
<213> ORGANISM: Homo Sapien

<400> SEQUENCE: 86

Met Gln Ala Thr Gln Phe Pro Leu Thr
1               5

<210> SEQ ID NO 87
<211> LENGTH: 10
<212> TYPE: PRT
<213> ORGANISM: Homo Sapien

<400> SEQUENCE: 87

Gly Phe Thr Phe Ser Ser Asn Asn Met Ile
1               5                   10

<210> SEQ ID NO 88
<211> LENGTH: 17
<212> TYPE: PRT
<213> ORGANISM: Homo Sapien

<400> SEQUENCE: 88

Tyr Ile Ser Ser Ser Ser Ser Thr Ile Ser Tyr Ala Asp Ser Val Arg
1               5                   10                  15

Gly

<210> SEQ ID NO 89
<211> LENGTH: 8
<212> TYPE: PRT
<213> ORGANISM: Homo Sapien

<400> SEQUENCE: 89

Arg Trp Arg Gly Val Phe Asp Tyr
1               5

<210> SEQ ID NO 90
<211> LENGTH: 11
<212> TYPE: PRT
<213> ORGANISM: Homo Sapien

<400> SEQUENCE: 90

Arg Ala Ser Gln Gly Ile Ser Ser Trp Leu Ala
1 5 10

<210> SEQ ID NO 91
<211> LENGTH: 7
<212> TYPE: PRT
<213> ORGANISM: Homo Sapien

<400> SEQUENCE: 91

Ala Ala Ser Ser Leu Gln Ser
1 5

<210> SEQ ID NO 92
<211> LENGTH: 9
<212> TYPE: PRT
<213> ORGANISM: Homo Sapien

<400> SEQUENCE: 92

Gln Gln Tyr Asn Ser Tyr Pro Pro Thr
1 5

<210> SEQ ID NO 93
<211> LENGTH: 10
<212> TYPE: PRT
<213> ORGANISM: Homo Sapien

<400> SEQUENCE: 93

Gly Phe Ser Phe Arg Ser Tyr Gly Ile His
1 5 10

<210> SEQ ID NO 94
<211> LENGTH: 17
<212> TYPE: PRT
<213> ORGANISM: Homo Sapien

<400> SEQUENCE: 94

Val Ile Ser Tyr Glu Gly Ser Asn Lys Arg Tyr Ala Asp Ser Val Lys
1 5 10 15

Gly

<210> SEQ ID NO 95
<211> LENGTH: 12
<212> TYPE: PRT
<213> ORGANISM: Homo Sapien

<400> SEQUENCE: 95

Gly Arg Arg Pro Ser Gly Glu Gly Ala Phe Asp Ile
1 5 10

<210> SEQ ID NO 96
<211> LENGTH: 11
<212> TYPE: PRT
<213> ORGANISM: Homo Sapien

<400> SEQUENCE: 96

Arg Ala Ser Gln Gly Ile Ser Ser Trp Leu Ala
1 5 10

<210> SEQ ID NO 97
<211> LENGTH: 7
<212> TYPE: PRT
<213> ORGANISM: Homo Sapien

<400> SEQUENCE: 97

Ala Ala Ser Ser Leu Gln Ser
1 5

<210> SEQ ID NO 98
<211> LENGTH: 9
<212> TYPE: PRT
<213> ORGANISM: Homo Sapien

<400> SEQUENCE: 98

Gln Gln Tyr Asn Ser Phe Pro Pro Thr
1 5

<210> SEQ ID NO 99
<211> LENGTH: 447
<212> TYPE: PRT
<213> ORGANISM: Homo Sapien

<400> SEQUENCE: 99

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Phe
20 25 30

Asn Met Asn Trp Val Arg Gln Ala Pro Gly Lys Gly Leu Glu Trp Ile
35 40 45

Ser Tyr Ile Ser Ser Gly Ser Thr Thr Ile Ala His Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Asp Glu Asp Thr Ala Val Tyr Tyr Cys
85 90 95

Val Arg Arg Leu Lys Gly Ser Phe Asp Tyr Trp Gly Gln Gly Thr Leu
100 105 110

Val Thr Val Ser Ser Ala Ser Thr Lys Gly Pro Ser Val Phe Pro Leu
115 120 125

Ala Pro Ser Ser Lys Ser Thr Ser Gly Gly Thr Ala Ala Leu Gly Cys
130 135 140

Leu Val Lys Asp Tyr Phe Pro Glu Pro Val Thr Val Ser Trp Asn Ser
145 150 155 160

Gly Ala Leu Thr Ser Gly Val His Thr Phe Pro Ala Val Leu Gln Ser
165 170 175

Ser Gly Leu Tyr Ser Leu Ser Ser Val Val Thr Val Pro Ser Ser Ser
180 185 190

Leu Gly Thr Gln Thr Tyr Ile Cys Asn Val Asn His Lys Pro Ser Asn
195 200 205

Thr Lys Val Asp Lys Arg Val Glu Pro Lys Ser Cys Asp Lys Thr His
210 215 220

Thr Cys Pro Pro Cys Pro Ala Pro Glu Leu Leu Gly Gly Pro Ser Val
225 230 235 240

Phe Leu Phe Pro Pro Lys Pro Lys Asp Thr Leu Met Ile Ser Arg Thr
245 250 255

Pro Glu Val Thr Cys Val Val Val Asp Val Ser His Glu Asp Pro Glu
260 265 270

Val Lys Phe Asn Trp Tyr Val Asp Gly Val Glu Val His Asn Ala Lys
275 280 285

Thr Lys Pro Arg Glu Glu Gln Tyr Asn Ser Thr Tyr Arg Val Val Ser

```
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 100
<211> LENGTH: 450
<212> TYPE: PRT
<213> ORGANISM: Homo Sapien

<400> SEQUENCE: 100

Glu Val Gln Leu Val Glu Phe Gly Gly Gly Leu Val Gln Pro Lys Gly
1               5                   10                  15

Ser Leu Lys Leu Ser Cys Val Val Ser Gly Phe Arg Phe Asn Pro Tyr
            20                  25                  30

Ala Met Asn Trp Val Arg Gln Ala Pro Gly Lys Gly Leu Glu Trp Leu
        35                  40                  45

Gly Arg Ile Arg Ser Lys Ser Asn Asn Tyr Glu Thr Tyr Tyr Ala Asp
    50                  55                  60

Ser Val Lys Asp Arg Phe Ile Ile Ser Arg Asp Asp Ser Gln Lys Met
65                  70                  75                  80

Val Tyr Leu Gln Met Asn Asn Val Lys Thr Glu Asp Thr Ala Met Tyr
                85                  90                  95

Tyr Cys Val Gly Tyr Ser Asp Leu Tyr Val Leu Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220
```

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Glu Glu Met Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 101
<211> LENGTH: 445
<212> TYPE: PRT
<213> ORGANISM: Homo Sapien

<400> SEQUENCE: 101

Gln Val Gln Leu Gln Gln Ser Gly Ala Glu Leu Val Arg Pro Gly Ala
1 5 10 15

Ser Val Thr Leu Ser Cys Lys Ala Ser Gly Tyr Thr Phe Thr Asp Tyr
20 25 30

Glu Met His Trp Val Lys Gln Thr Pro Val His Gly Leu Glu Trp Ile
35 40 45

Gly Ala Ile Asp Pro Lys Thr Gly Ser Thr Ala Tyr Asn Gln Lys Phe
50 55 60

Lys Gly Lys Ala Ile Met Thr Ala Asp Lys Ser Ser Ser Thr Ala Tyr
65 70 75 80

Met Glu Leu Arg Ser Leu Thr Ser Glu Asp Ser Val Val Tyr Tyr Cys
85 90 95

Thr Gly Leu Arg Arg Phe Val Tyr Trp Gly Gln Gly Thr Pro Val Thr
100 105 110

Val Ser Ala Ala Ser Thr Lys Gly Pro Ser Val Phe Pro Leu Ala Pro
115 120 125

Ser Ser Lys Ser Thr Ser Gly Gly Thr Ala Ala Leu Gly Cys Leu Val
130 135 140

```
Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Arg Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 102
<211> LENGTH: 445
<212> TYPE: PRT
<213> ORGANISM: Homo Sapien

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Glu Met His Trp Val Arg Gln Ala Thr Gly Gln Gly Leu Glu Trp Met
        35                  40                  45

Gly Ala Ile Gln Pro Glu Thr Gly Gly Thr Ala Tyr Asn Gln Lys Phe
    50                  55                  60

Lys Ala Arg Val Thr Met Thr Arg Asp Thr Ser Ile Ser Thr Ala Tyr
```

```
65                  70                  75                  80

Met Glu Leu Ser Ser Leu Arg Ser Glu Asp Thr Ala Val Tyr Tyr Cys
                85                  90                  95

Ala Arg Arg Arg Arg Asn Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445
```

<210> SEQ ID NO 103
<211> LENGTH: 10
<212> TYPE: PRT
<213> ORGANISM: Homo Sapien

<400> SEQUENCE: 103

```
Gly Phe Arg Phe Gly Pro Tyr Ala Met Asn
1               5                   10


<210> SEQ ID NO 104
<211> LENGTH: 19
<212> TYPE: PRT
<213> ORGANISM: Homo Sapien

<400> SEQUENCE: 104

Arg Ile Arg Ser Lys Ser Asn Asn Tyr Glu Thr Tyr Tyr Ala Asp Ser
1               5                   10                  15

Val Lys Asp


<210> SEQ ID NO 105
<211> LENGTH: 9
<212> TYPE: PRT
<213> ORGANISM: Homo Sapien

<400> SEQUENCE: 105

Tyr Ser Asp Leu Tyr Val Leu Asp Tyr
1               5


<210> SEQ ID NO 106
<211> LENGTH: 16
<212> TYPE: PRT
<213> ORGANISM: Homo Sapien

<400> SEQUENCE: 106

Arg Ser Ser Lys Ser Leu Leu His Ser Gln Gly Asn Thr Phe Leu Tyr
1               5                   10                  15


<210> SEQ ID NO 107
<211> LENGTH: 7
<212> TYPE: PRT
<213> ORGANISM: Homo Sapien

<400> SEQUENCE: 107

Arg Met Ser Asn Leu Ala Ser
1               5


<210> SEQ ID NO 108
<211> LENGTH: 9
<212> TYPE: PRT
<213> ORGANISM: Homo Sapien

<400> SEQUENCE: 108

Met Gln His Leu Glu Tyr Pro Phe Thr
1               5


<210> SEQ ID NO 109
<211> LENGTH: 11
<212> TYPE: PRT
<213> ORGANISM: Homo Sapien

<400> SEQUENCE: 109

Val Thr Asp Tyr Tyr Tyr Pro Asp Ile Phe Ser
1               5                   10


<210> SEQ ID NO 110
<211> LENGTH: 451
<212> TYPE: PRT
<213> ORGANISM: Homo Sapien

<400> SEQUENCE: 110
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Arg Ser Tyr
            20                  25                  30

Gly Ile His Trp Val Arg Gln Ala Pro Gly Lys Gly Leu Glu Trp Val
        35                  40                  45

Ala Val Ile Ser Tyr Glu Gly Ser Asn Lys Arg Tyr Ala Asp Ser Val
    50                  55                  60

Lys Gly Arg Phe Thr Ile Ser Arg Asp Asn Ser Lys Ser Thr Leu Ser
65                  70                  75                  80

Leu Gln Met Asn Ser Leu Arg Ala Glu Asp Thr Ala Val Tyr Tyr Cys
                85                  90                  95

Ala Lys Gly Arg Arg Pro Ser Gly Glu Gly Ala Phe Asp Ile Trp Gly
            100                 105                 110

Gln Gly Thr Met Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
```

```
            420                 425                 430

His Glu Ala Leu His Asn His Tyr Thr Gln Lys Ser Leu Ser Leu Ser
        435                 440                 445

Pro Gly Lys
    450


<210> SEQ ID NO 111
<211> LENGTH: 214
<212> TYPE: PRT
<213> ORGANISM: Homo Sapien

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Gly Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 112
<211> LENGTH: 219
<212> TYPE: PRT
<213> ORGANISM: Homo Sapien

<400> SEQUENCE: 112

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Phe Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

His Arg Phe Ser Gly Ser Gly Ser Gly Thr Ala Phe Thr Leu Arg Ile
```

```
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 113
<211> LENGTH: 219
<212> TYPE: PRT
<213> ORGANISM: Homo Sapien

<400> SEQUENCE: 113

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Leu Val His Ser
            20                  25                  30

Ser Gly Tyr Thr Tyr Leu His Trp Tyr Leu Gln Lys Pro Gly Gln Ser
        35                  40                  45

Pro Lys Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Ser Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 114
<211> LENGTH: 219
<212> TYPE: PRT
<213> ORGANISM: Homo Sapien

<400> SEQUENCE: 114

Asp Ile Val Met Thr Gln Thr Pro Leu Ser Leu Ser Val Thr Pro Gly
1 5 10 15

Gln Pro Ala Ser Ile Ser Cys Arg Ser Ser Gln Ser Leu Phe His Ser
20 25 30

Ser Gly Asn Thr Tyr Leu His Trp Tyr Leu Gln Lys Pro Gly Gln Pro
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Ser
85 90 95

Thr His Val Pro Phe Thr Phe Gly Gln Gly Thr Lys Leu Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 115
<211> LENGTH: 120
<212> TYPE: PRT
<213> ORGANISM: Homo Sapien

<400> SEQUENCE: 115

Glu Val Gln Leu Val Glu Ser Gly Gly Gly Leu Val Lys Pro Gly Gly
1 5 10 15

Ser Leu Arg Leu Ser Cys Ala Ala Ser Gly Phe Arg Phe Gly Pro Tyr
20 25 30

Ala Met Asn Trp Val Arg Gln Ala Pro Gly Lys Gly Leu Glu Trp Val
35 40 45

Gly Arg Ile Arg Ser Lys Ser Asn Asn Tyr Glu Thr Tyr Tyr Ala Asp
50 55 60

Ser Val Lys Asp Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Val Gly Tyr Ser Asp Leu Tyr Val Leu Asp Tyr Trp Gly Gln
100 105 110

Gly Thr Leu Val Thr Val Ser Ser
115 120

<210> SEQ ID NO 116
<211> LENGTH: 112
<212> TYPE: PRT
<213> ORGANISM: Homo Sapien

<400> SEQUENCE: 116

Asp Ile Val Met Thr Gln Thr Pro Pro Ser Leu Pro Val Asn Pro Gly
1 5 10 15

Glu Pro Ala Ser Ile Ser Cys Arg Ser Ser Lys Ser Leu Leu His Ser
20 25 30

Gln Gly Asn Thr Phe Leu Tyr Trp Tyr Leu Gln Lys Pro Gly Gln Ser
35 40 45

Pro Gln Leu Leu Ile Tyr Arg Met Ser Asn Leu Ala Ser Gly Val Pro
50 55 60

Asp Arg Phe Ser Gly Ser Gly Ser Gly Ser Asp Phe Thr Leu Lys Ile
65 70 75 80

Ser Trp Val Glu Ala Glu Asp Val Gly Val Tyr Tyr Cys Met Gln His
85 90 95

Leu Glu Tyr Pro Phe Thr Phe Gly Pro Gly Thr Lys Val Asp Ile Lys
100 105 110

<210> SEQ ID NO 117
<211> LENGTH: 449
<212> TYPE: PRT
<213> ORGANISM: Homo Sapien

<400> SEQUENCE: 117

Glu Val Gln Leu Val Glu Ser Gly Gly Gly Leu Val Lys Pro Gly Gly
1 5 10 15

Ser Leu Arg Leu Ser Cys Ala Ala Ser Gly Phe Arg Phe Gly Pro Tyr
20 25 30

Ala Met Asn Trp Val Arg Gln Ala Pro Gly Lys Gly Leu Glu Trp Val
35 40 45

Gly Arg Ile Arg Ser Lys Ser Asn Asn Tyr Glu Thr Tyr Tyr Ala Asp
50 55 60

Ser Val Lys Asp Arg Phe Thr Ile Ser Arg Asp Asp Ser Lys Asn Thr
65 70 75 80

Leu Tyr Leu Gln Met Asn Ser Leu Lys Thr Glu Asp Thr Ala Val Tyr
85 90 95

Tyr Cys Val Gly Tyr Ser Asp Leu Tyr Val Leu Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

```
Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 118
<211> LENGTH: 219
<212> TYPE: PRT
<213> ORGANISM: Homo Sapien

<400> SEQUENCE: 118

Asp Ile Val Met Thr Gln Thr Pro Pro Ser Leu Pro Val Asn Pro Gly
1               5                   10                  15

Glu Pro Ala Ser Ile Ser Cys Arg Ser Ser Lys Ser Leu Leu His Ser
            20                  25                  30

Gln Gly Asn Thr Phe Leu Tyr Trp Tyr Leu Gln Lys Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Ser Asp Phe Thr Leu Lys Ile
65                  70                  75                  80

Ser Trp Val Glu Ala Glu Asp Val Gly Val Tyr Tyr Cys Met Gln His
                85                  90                  95

Leu Glu Tyr Pro Phe Thr Phe Gly Pro Gly Thr Lys Val Asp Ile Lys
            100                 105                 110

Arg Thr Val Ala Ala Pro Ser Val Phe Ile Phe Pro Pro Ser Asp Glu
        115                 120                 125
```

```
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 119
<211> LENGTH: 214
<212> TYPE: PRT
<213> ORGANISM: Homo Sapien

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 120
<211> LENGTH: 353
<212> TYPE: PRT
<213> ORGANISM: Homo Sapien

<400> SEQUENCE: 120

Met Asp Tyr Thr Met Glu Pro Asn Val Thr Met Thr Asp Tyr Tyr Pro
1               5                   10                  15
```

-continued

```
Asp Phe Phe Thr Ala Pro Cys Asp Ala Glu Phe Leu Leu Arg Gly Ser
            20                  25                  30

Met Leu Tyr Leu Ala Ile Leu Tyr Cys Val Leu Phe Val Leu Gly Leu
        35                  40                  45

Leu Gly Asn Ser Leu Val Ile Leu Val Leu Val Gly Cys Lys Lys Leu
    50                  55                  60

Arg Ser Ile Thr Asp Ile Tyr Leu Leu Asn Leu Ala Ala Ser Asp Leu
65                  70                  75                  80

Leu Phe Val Leu Ser Ile Pro Phe Gln Thr His Asn Leu Leu Asp Gln
                85                  90                  95

Trp Val Phe Gly Thr Ala Met Cys Lys Val Val Ser Gly Leu Tyr Tyr
            100                 105                 110

Ile Gly Phe Phe Ser Ser Met Phe Phe Ile Thr Leu Met Ser Val Asp
        115                 120                 125

Arg Tyr Leu Ala Ile Val His Ala Val Tyr Ala Ile Lys Val Arg Thr
    130                 135                 140

Ala Ser Val Gly Thr Ala Leu Ser Leu Thr Val Trp Leu Ala Ala Val
145                 150                 155                 160

Thr Ala Thr Ile Pro Leu Met Val Phe Tyr Gln Val Ala Ser Glu Asp
                165                 170                 175

Gly Met Leu Gln Cys Phe Gln Phe Tyr Glu Glu Gln Ser Leu Arg Trp
            180                 185                 190

Lys Leu Phe Thr His Phe Glu Ile Asn Ala Leu Gly Leu Leu Leu Pro
        195                 200                 205

Phe Ala Ile Leu Leu Phe Cys Tyr Val Arg Ile Leu Gln Gln Leu Arg
    210                 215                 220

Gly Cys Leu Asn His Asn Arg Thr Arg Ala Ile Lys Leu Val Leu Thr
225                 230                 235                 240

Val Val Ile Val Ser Leu Leu Phe Trp Val Pro Phe Asn Val Ala Leu
                245                 250                 255

Phe Leu Thr Ser Leu His Asp Leu His Ile Leu Asp Gly Cys Ala Thr
            260                 265                 270

Arg Gln Arg Leu Ala Leu Ala Ile His Val Thr Glu Val Ile Ser Phe
        275                 280                 285

Thr His Cys Cys Val Asn Pro Val Ile Tyr Ala Phe Ile Gly Glu Lys
    290                 295                 300

Phe Lys Lys His Leu Met Asp Val Phe Gln Lys Ser Cys Ser His Ile
305                 310                 315                 320

Phe Leu Tyr Leu Gly Arg Gln Met Pro Val Gly Ala Leu Glu Arg Gln
                325                 330                 335

Leu Ser Ser Asn Gln Arg Ser Ser His Ser Ser Thr Leu Asp Asp Ile
            340                 345                 350

Leu
```